US012734225B2

(12) United States Patent
Lisziewicz et al.

(10) Patent No.: US 12,734,225 B2
(45) Date of Patent: *Sep. 15, 2026

(54) FUSION PEPTIDE VACCINES

(71) Applicant: Treos Bio Limited, London (GB)

(72) Inventors: Julianna Lisziewicz, Balatonalmádi (HU); Levente Molnár, Felsopakony (HU); Eniko Toke, Felsopakony (HU); József Toth, Gyor (HU); Orsolya Lorincz, Budapest (HU); Zsolt Csiszovszki, Budapest (HU); Eszter Somogyi, Balatonalmádi (HU); Katalin Pántya, Budapest (HU); Mónika Megyesi, Mezokeresztes (HU)

(73) Assignee: Treos Bio Limited, London (GB)

( * ) Notice: Subject to any disclaimer, the term of this patent is extended or adjusted under 35 U.S.C. 154(b) by 574 days.

This patent is subject to a terminal disclaimer.

(21) Appl. No.: 18/311,117

(22) Filed: May 2, 2023

(65) Prior Publication Data

US 2024/0000911 A1 Jan. 4, 2024

Related U.S. Application Data

(63) Continuation of application No. 17/250,725, filed as application No. PCT/EP2019/073476 on Sep. 3, 2019, now Pat. No. 11,666,644.

(30) Foreign Application Priority Data

| | | |
|---|---|---|
| Sep. 4, 2018 | (GB) | 1814364 |
| Sep. 4, 2018 | (GB) | 1814365 |
| Sep. 4, 2018 | (GB) | 1814366 |
| Sep. 4, 2018 | (GB) | 1814367 |

(51) Int. Cl.

| | |
|---|---|
| ***A61K 39/00*** | (2006.01) |
| ***A61K 45/06*** | (2006.01) |
| ***A61P 1/00*** | (2006.01) |
| ***A61P 35/00*** | (2006.01) |

(52) U.S. Cl.

CPC ................ *A61K 39/001184* (2018.08); *A61K 39/0011* (2013.01); *A61K 39/00115* (2018.08); *A61K 39/001166* (2018.08); *A61K 39/001186* (2018.08); *A61K 39/001189* (2018.08); *A61K 45/06* (2013.01); *A61P 1/00* (2018.01); *A61P 35/00* (2018.01); *A61K 2039/545* (2013.01); *A61K 2039/70* (2013.01); *A61K 2039/828* (2018.08)

(58) Field of Classification Search

CPC ........................... A61P 35/00; C07K 14/4748

See application file for complete search history.

(56) References Cited

U.S. PATENT DOCUMENTS

| | | | |
|---|---|---|---|
| 4,235,877 | A | 11/1980 | Fullerton |
| 6,287,756 | B1 | 9/2001 | Tureci et al. |
| 6,346,389 | B1 | 2/2002 | Altieri |
| 7,227,002 | B1 | 6/2007 | Kufer et al. |
| 7,619,058 | B2 | 11/2009 | Kuzushima |
| 7,632,925 | B2 | 12/2009 | Kufer et al. |
| 7,820,786 | B2 | 10/2010 | Thomson et al. |
| 7,842,294 | B2 | 11/2010 | Andersen et al. |
| 7,846,651 | B2 | 12/2010 | Kuzushima |
| 7,892,559 | B2 | 2/2011 | Straten et al. |
| 7,993,638 | B2 | 8/2011 | Cai et al. |
| 8,124,408 | B2 | 2/2012 | Cai et al. |
| 8,129,184 | B2 | 3/2012 | Yu |
| 8,268,964 | B2 | 9/2012 | Scholler et al. |
| 8,309,096 | B2 | 11/2012 | Blais et al. |
| 8,318,174 | B2 | 11/2012 | Straten et al. |
| 8,487,076 | B1 | 7/2013 | Miyakawa et al. |
| 8,647,629 | B2 | 2/2014 | Rammensee et al. |
| 8,956,878 | B2 | 2/2015 | Griffiths et al. |
| 9,353,151 | B2 | 5/2016 | Miyakawa et al. |
| 9,498,512 | B2 | 11/2016 | Rammensee et al. |
| 9,534,030 | B2 | 1/2017 | Straten et al. |
| 9,687,539 | B2 | 6/2017 | Wang et al. |
| 9,790,562 | B2 | 10/2017 | Al-Hendy et al. |
| 10,172,925 | B2 | 1/2019 | Nishimura |

(Continued)

FOREIGN PATENT DOCUMENTS

| | | | |
|---|---|---|---|
| CA | 2511775 | A1 | 6/2004 |
| CA | 2665816 | A1 | 3/2008 |

(Continued)

OTHER PUBLICATIONS

Wang, X-F., et al., Comprehensive analysis of HLA-DR- and HLA-DP4-restricted CD4+ T cell response specific for the tumor-shared antigen survivin in healthy donors and cancer patients, J Immunol, 181(1): 431-439 (2008).
New Zealand Examination Report dated Oct. 9, 2025, 8 pages.
U.S. Appl. No. 17/250,725, filed Feb. 24, 2021, U.S. Pat. No. 11,666,644, Jun. 6, 2023, Issued.
Futami, J., et al., Sensitive Multiplexed Quantitative Analysis of Autoantibodies to Cancer Antigens with Chemically S-Cationized Full-Length and Water-Soluble Denatured Proteins, Bioconjugate Chem, 26(10): 2076-2084 (2015).
U.S. Appl. No. 15/910,965, filed Mar. 2, 2018, Abandoned.

(Continued)

*Primary Examiner* — Elly-Gerald Stoica
(74) *Attorney, Agent, or Firm* — Goodwin Procter LLP

(57) ABSTRACT

The disclosure relates to polypeptides and pharmaceutical compositions comprising polypeptides that find use in the prevention or treatment of cancer, in particular gastric cancer, lung cancer, melanoma and bladder cancer. The disclosure also relates to methods of inducing a cytotoxic T cell response in a subject or treating cancer by administering pharmaceutical compositions comprising the peptides, and companion diagnostic methods of identifying subjects for treatment. The peptides comprise T cell epitopes that are immunogenic in a high percentage of patients.

7 Claims, 47 Drawing Sheets

Specification includes a Sequence Listing.

(56) References Cited

U.S. PATENT DOCUMENTS

| | | | |
|---|---|---|---|
| 10,213,497 B2 | 2/2019 | Lisziewicz et al. | |
| 10,336,808 B2 | 7/2019 | Scholler et al. | |
| 10,434,136 B2 | 10/2019 | Rammensee et al. | |
| 10,973,909 B1 | 4/2021 | Csiszovszki et al. | |
| 11,090,332 B2 | 8/2021 | Koos et al. | |
| 11,628,211 B2 | 4/2023 | Lisziewicz et al. | |
| 2002/0131960 A1 | 9/2002 | Sadelain et al. | |
| 2004/0053822 A1 | 3/2004 | Fikes et al. | |
| 2004/0054137 A1 | 3/2004 | Thomson et al. | |
| 2004/0209324 A1 | 10/2004 | Koren et al. | |
| 2005/0100883 A1 | 5/2005 | Wang et al. | |
| 2006/0127408 A1 | 6/2006 | Young et al. | |
| 2006/0257852 A1 | 11/2006 | Rappuoli et al. | |
| 2007/0055049 A1 | 3/2007 | Grey et al. | |
| 2008/0206270 A1 | 8/2008 | Minev | |
| 2009/0004214 A1 | 1/2009 | Wang et al. | |
| 2009/0010951 A1 | 1/2009 | Kuzushima | |
| 2009/0012004 A1 | 1/2009 | Sette et al. | |
| 2009/0028888 A1 | 1/2009 | Bergeron et al. | |
| 2009/0280138 A1 | 11/2009 | Harrop et al. | |
| 2009/0285843 A1 | 11/2009 | Simard et al. | |
| 2010/0074925 A1 | 3/2010 | Carmon | |
| 2010/0099613 A1 | 4/2010 | Buyse et al. | |
| 2010/0226854 A1 | 9/2010 | Scholler et al. | |
| 2011/0091489 A1 | 4/2011 | Andersen | |
| 2011/0097343 A1 | 4/2011 | Atanackovic et al. | |
| 2012/0244145 A1 | 9/2012 | Sampson et al. | |
| 2013/0029358 A1 | 1/2013 | Valmori et al. | |
| 2013/0189291 A1 | 7/2013 | Tsunoda et al. | |
| 2014/0094586 A1 | 4/2014 | Miyakawa et al. | |
| 2016/0074489 A1 | 3/2016 | Ichim et al. | |
| 2016/0161486 A1 | 6/2016 | Parenteau et al. | |
| 2016/0193314 A1 | 7/2016 | Nishimura | |
| 2016/0199469 A1 | 7/2016 | Georges et al. | |
| 2017/0032082 A1 | 2/2017 | Nguyen et al. | |
| 2017/0039314 A1 | 2/2017 | Bremel et al. | |
| 2017/0096455 A1 | 4/2017 | Baric et al. | |
| 2018/0264094 A1 | 9/2018 | Lisziewicz et al. | |
| 2018/0264095 A1 | 9/2018 | Lisziewicz et al. | |
| 2019/0240302 A1 | 8/2019 | Lisziewicz et al. | |
| 2020/0061173 A1 | 2/2020 | Bouzidi et al. | |
| 2020/0069786 A1 | 3/2020 | Molnar et al. | |
| 2020/0326340 A1 | 10/2020 | Delcommenne | |
| 2021/0236611 A1 | 8/2021 | Molnar et al. | |
| 2022/0031823 A1 | 2/2022 | Lisziewicz et al. | |
| 2022/0072114 A1 | 3/2022 | Lisziewicz et al. | |
| 2022/0111024 A1 | 4/2022 | Lisziewicz et al. | |

FOREIGN PATENT DOCUMENTS

| | | | | | |
|---|---|---|---|---|---|
| CN | 1824678 | A | | 8/2006 | |
| CN | 105219723 | A | | 1/2016 | |
| CN | 110713546 | A | | 1/2020 | |
| EP | 2042600 | A1 | | 4/2009 | |
| EP | 2329840 | A1 | | 6/2011 | |
| EP | 3369431 | A1 | | 9/2018 | |
| EP | 3370065 | A1 | | 9/2018 | |
| JP | 2016521128 | A | | 7/2016 | |
| WO | WO-9733602 | A1 | | 9/1997 | |
| WO | WO-0018238 | A1 | | 4/2000 | |
| WO | WO-0056365 | A1 | | 9/2000 | |
| WO | 2001042267 | A1 | | 6/2001 | |
| WO | WO-0190197 | A1 | | 11/2001 | |
| WO | 2004093808 | A2 | | 11/2004 | |
| WO | 2005068632 | A1 | | 7/2005 | |
| WO | WO2006081826 | | * | 8/2006 | ............ A61K 39/00 |
| WO | WO-2006081826 | A2 | | 8/2006 | |
| WO | 2007036638 | A1 | | 4/2007 | |
| WO | WO-2007039716 | A1 | | 4/2007 | |
| WO | WO-2008035350 | A1 | | 3/2008 | |
| WO | 2008039874 | A2 | | 4/2008 | |
| WO | WO-2008102557 | A1 | | 8/2008 | |
| WO | WO-2009040674 | A2 | | 4/2009 | |
| WO | 2009138236 | A1 | | 11/2009 | |
| WO | 2010037513 | A1 | | 4/2010 | |
| WO | WO-2010037395 | A2 | | 4/2010 | |
| WO | WO-2011040978 | A2 | | 4/2011 | |
| WO | 2011113872 | A1 | | 9/2011 | |
| WO | WO-2012051282 | A2 | | 4/2012 | |
| WO | WO2012141201 | | * | 10/2012 | ............ A61K 39/00 |
| WO | WO2013033961 | | * | 3/2013 | ............ A61P 35/00 |
| WO | WO-2014020357 | A1 | | 2/2014 | |
| WO | WO-2014127276 | A1 | | 8/2014 | |
| WO | WO-2014127296 | A1 | | 8/2014 | |
| WO | WO-2014153636 | A1 | | 10/2014 | |
| WO | WO2014168874 | | * | 10/2014 | ............ A61K 39/39 |
| WO | WO-2014178018 | A1 | | 11/2014 | |
| WO | WO-2014180490 | A1 | | 11/2014 | |
| WO | WO-2015014375 | A1 | | 2/2015 | |
| WO | WO-2015018805 | A1 | | 2/2015 | |
| WO | WO-2015033140 | A1 | | 3/2015 | |
| WO | WO-2015164798 | A1 | | 10/2015 | |
| WO | WO-2016040900 | A1 | | 3/2016 | |
| WO | WO-2016090177 | A1 | | 6/2016 | |
| WO | WO-2016102272 | A1 | | 6/2016 | |
| WO | WO-2016107740 | A1 | | 7/2016 | |
| WO | WO-2016109880 | A1 | | 7/2016 | |
| WO | WO-2016146751 | A1 | | 9/2016 | |
| WO | WO-2016156202 | A1 | | 10/2016 | |
| WO | WO-2016156230 | A1 | | 10/2016 | |
| WO | WO-2016170139 | A1 | | 10/2016 | |
| WO | WO-2016172722 | A1 | | 10/2016 | |
| WO | WO-2016176761 | A1 | | 11/2016 | |
| WO | WO-2016177784 | A1 | | 11/2016 | |
| WO | WO-2017001491 | A2 | | 1/2017 | |
| WO | WO-2017005733 | A2 | | 1/2017 | |
| WO | WO-2017011804 | A1 | | 1/2017 | |
| WO | WO-2017021527 | A2 | | 2/2017 | |
| WO | WO-2017083963 | A1 | | 5/2017 | |
| WO | WO-2017097699 | A1 | | 6/2017 | |
| WO | WO-2017157972 | A1 | | 9/2017 | |
| WO | WO-2017162501 | A1 | | 9/2017 | |
| WO | WO-2017174645 | A1 | | 10/2017 | |
| WO | WO-2018067869 | A1 | | 4/2018 | |
| WO | WO-2018/102585 | A1 | | 6/2018 | |
| WO | WO-2018138257 | A1 | | 8/2018 | |
| WO | WO-2018158455 | A1 | | 9/2018 | |
| WO | WO-2018158456 | A1 | | 9/2018 | |
| WO | WO-2018158457 | A1 | | 9/2018 | |
| WO | WO-2019010560 | A1 | | 1/2019 | |
| WO | WO-2019090411 | A1 | | 5/2019 | |
| WO | WO-2019094607 | A2 | | 5/2019 | |
| WO | WO-2019133853 | A1 | | 7/2019 | |
| WO | WO-2019222760 | A1 | | 11/2019 | |
| WO | WO-2019222762 | A1 | | 11/2019 | |
| WO | WO-2020048990 | A1 | | 3/2020 | |
| WO | WO-2020048992 | A1 | | 3/2020 | |
| WO | WO-2020048995 | A1 | | 3/2020 | |
| WO | WO-2020104923 | A1 | | 5/2020 | |
| WO | WO-2020146431 | A1 | | 7/2020 | |
| WO | WO-2020146434 | A2 | | 7/2020 | |
| WO | WO-2021072535 | A1 | | 4/2021 | |

OTHER PUBLICATIONS

U.S. Appl. No. 17/454,225, filed Nov. 9, 2021, Pending.
U.S. Appl. No. 15/910,930, filed Mar. 2, 2018, Abandoned.
U.S. Appl. No. 17/448,020, filed Sep. 17, 2021, Pending.
U.S. Appl. No. 16/244,497, filed Jan. 10, 2019, U.S. Pat. No. 11,213,578, Jan. 4, 2022, Issued.
U.S. Appl. No. 17/645,737, filed Dec. 22, 2021, U.S. Pat. No. 11,426,452, Aug. 30, 2022, Issued.
U.S. Appl. No. 17/645,741, filed Dec. 22, 2021, U.S. Pat. No. 11,628,211, Apr. 18, 2023, Issued.
U.S. Appl. No. 18/166,420, filed Feb. 8, 2023, Pending.
U.S. Appl. No. 16/559,430, filed Sep. 3, 2019, Abandoned.
U.S. Appl. No. 17/249,362, filed Feb. 26, 2021, Abandoned.
U.S. Appl. No. 17/650,360, filed Feb. 8, 2022, Pending.
U.S. Appl. No. 17/250,725, filed Feb. 24, 2021, Allowed.
Ahmed, S.F., et al., Preliminary identification of potential vaccine targets for the COVID-19 coronavirus (SARS-CoV-2) based on SARS-CoV Immunological studies, Viruses, 12: 254 (2020).

(56) References Cited

OTHER PUBLICATIONS

Ali-Khan, N., et al., Overview of proteome analysis, Curr Protoc Protein Sci, Chapter 22: Unit 22.1.1-22.1.19 (2002).
Andersen, M.H., et al., HLA-A24 and survivin: possibilities in therapeutic vaccination against cancer, J Transl Med, 4:38, 2 pages (2006).
Antigenic peptides search results for EpCAM, 1 page, retrieved on Apr. 16, 2021 from <caped.icp.ucl.ac.be/Peptide/search>.
Asahara, S., et al., Phase I/II clinical trial using HLA-A24-restricted peptide vaccine derived from KIF20A for patients with advanced pancreatic cancer, J Transl Med, 11: 291 (2013).
Bachinsky, M.M., et al., Mapping and binding analysis of peptides derived from the tumor-associated antigen survivin for eight HLA alleles, Cancer Immun, 5:6, pp. 1-9 (2005).
Bagarazzi, M., et al., Immunotherapy Against HPV16/18 Generates Potent $T_H1$ and Cytotoxic Cellular Immune Responses, Sci Transl Med, 4(155): 155ra138 (2012).
Batra, S.K., et al., Epidermal Growth Factor Ligand-independent, Unregulated, Cell-transforming Potential of a Naturally Occurring Human Mutant EGFRvIII Gene, Cell Growth Differ, 6:1251-1259 (1995).
Beatty, G.L., et al., Immune escape mechanisms as a guide for cancer immunotherapy, Clin Cancer Res, 21(4): 687-692 (2014).
Berger, T.G., et al., Circulation and homing of melanoma-reactive T cells to both cutaneous and visceral metastases after vaccination with monocyte-derived dendritic cells, Int J Cancer, 111: 229-237 (2004).
Bigner, S.H., et al., Characterization of the Epidermal Growth Factor Receptor in Human Glioma Cell Lines and Xenografts, Cancer Res, 50: 8017-8022 (1990).
Bioley, G., et al., HLA Class I—Associated Immunodominance Affects CTL Responsiveness to an ESO Recombinant Protein Tumor Antigen Vaccine, Clin Cancer Res, 15(1): 299-306 (2009).
Buonaguro, L., et al., Translating tumor antigens into cancer vaccines, Clin Vaccine Immunol, 18(1): 23-34 (2011).
Butts, C., et al., Randomized Phase IIB Trial of BLP25 Liposome Vaccine in Stage IIIB and IV Non-Small-Cell Lung Cancer, J Clin Oncol, 23(27): 6674-6681 (2005).
Cao, Q-H, et al., Testes-specific protease 50 (TSP50) promotes invasion and metastasis by inducing EMT in gastric cancer, BMC Cancer, 18(1): 94 (2018).
Carmon, L., et al., Phase I/II study exploring ImMucin, a pan-major histocompatibility complex, anti-MUC1 signal peptide vaccine, in multiple myeloma patients, Br J Hematol, 169(1):44-56 (2014).
Cathcart, K., et al., A multivalent bcr-abl fusion peptide vaccination trial in patients with chronic Myeloid Leukemia, Blood, 103:1037-1042 (2004).
Celis, E., et al., Identification of potential CTL epitopes of tumor-associated antigen MAGE-1 for five common HLA-A alleles, Mol Immunol, 31(18): 1423-1430 (1994).
Celis, E., et al., Induction of anti-tumor cytotoxic T lymphocytes in normal humans using primary cultures and synthetic peptide epitopes, PNAS USA, 91: 2105-2109 (1994).
Chapuis, A.G., et al., Transferred WT1-reactive CD8+ T cells can mediate antileukemic activity and persist in post-transplant patients, Sci Transl Med, 5(174): 174ra27 (2013).
Chen, J., et al., Clinical and prognostic significance of HIF-1a, PTEN, CD44v6, and survivin for gastric cancer: a meta-analysis, PLoS One, 9(3): e91842 (2014).
Chen, Y., et al., Multiple Cancer/Testis Antigens Are Preferentially Expressed in Hormone-Receptor Negative and High-Grade Breast Cancers, PLoS One, 6(3):e17876 (2011).
Chiriva-Internati, M., et al., Identification of AKAP-4 as a New Cancer/Testis Antigen for Detection and Immunotherapy of Prostate Cancer, Prostate, 72(1):12-23 (2012).
Choi, J., et al., The Expression of MAGE and SSX, and Correlation of COX2, VEGF, and Survivin in Colorectal Cancer, Anticancer Res, 32(2): 559-564 (2012).
Chowell, D., et al., Patient HLA class I genotype influences cancer response to checkpoint blockade immunotherapy, Science, 359(6375): 582-587 (2018).
Chu, C.T., et al., Receptor dimerization is not a factor in the signalling activity of a transforming variant epidermal growth factor receptor (EGFRvIII), Biochem J, 324: 855-861 (1997).
Ciesielski, M.J., et al., Therapeutic effect of a T helper cell supported CTL response induced by a survivin peptide vaccine against murine cerebral glioma, Cancer Immunol Immunother, 57(12): 1827-1835 (2008).
Cusi, M.G., et al., Phase I trial of the thymidylate synthase poly-epitope (TSPP) vaccine in advance cancer patients, Cancer Immunol Immunother, 64:1159-1173 (2015).
Dangi, M., et al., Advanced In Silico Tools for Designing of Antigenic Epitope as Potential Vaccine Candidates Against Coronavirus, In: Bioinformatics: Sequences, Structures, Phylogeny, Springer Nature Singapore Pte Ltd.: 329-357 (2018).
Durie, BGM, et al., International uniform response criteria for multiple myeloma, Leukemia, 20:1467-1473 (2006).
Eisenhauer, E.A., et al., New response evaluation criteria in solid tumours: Revised RECIST guideline (version 1.1), Euro J Cancer, 45: 228-247 (2009).
Engelhard, V.H., Structure of peptides associated with MHC class I molecules, Curr Opin Immunol, 6(1): 13-23 (1994).
Fenoglio, D., et al., A multi-peptide, dual-adjuvant telomerase vaccine (GX301) is highly immunogenic in patients with prostate and renal cancer, Cancer Immunol Immunother, 62:1041-1052 (2013).
Fujiwara, Y., et al., Multiple therapeutic peptide vaccines for patients with advanced gastric cancer, Int J Oncol, 50(5): 1655-1662 (2017).
Futawatari, N., et al., Early gastric cancer frequently has high expression of KK-LC-1, a cancer-testis antigen, World J Gastroenterol, 23(46): 8200-8206 (2017).
Gerdts, V., et al., Vaccines for porcine epidemic diarrhea virus and other swine coronaviruses, Vet Microbiol, 206: 45-51 (2017).
Goel, S., et al., CDK4/6 inhibition triggers anti-tumor immunity, Nature, 548(7668): 471-475 (2017).
Goossens-Beumer, J., et al., Clinical prognostic value of combined analysis of Aldh1, Survivin, and EpCAM expression in colorectal cancer, Br J Cancer, 110(12): 2935-2944 (2014).
Greenfield, W.W., et al., A phase I dose-escalation clinical trial of a peptide-based human papillomavirus therapeutic vaccine adjuvant for treating with women with biopsy-proven cervical intraepithelial neoplasia 2/3, Oncoimmunol, 10:e1031439 (2015).
Gross, S., et al., Short Peptide Vaccine Induces CD4+ T Helper Cells in Patients with Different Solid Cancers, Cancer Immunol Res, 4(1): 18-25 (2016).
Gudmundsdotter, L., et al., Amplified antigen-specific immune responses in HIV-1 infected individuals in a double blind DNA immunization and therapy interruption trial, Vaccine, 29(33):5558-5566 (2011).
Guo, H., et al., Different length peptides bind to HLA-Aw68 similarity at their ends but bulge out in the middle, Nature, 360: 364-366 (1992).
Hartmaier, R.J., et al., Genomic analysis of 63,220 tumors reveals insights into tumor uniqueness and targeted cancer immunotherapy strategies, Genome Med, 9:16 (2017).
Hirohashi, Y., et al., The functioning antigens: beyond just as the immunological targets, Cancer Sci 100(5): 798-806 (2009).
HLA Genetics and Nomenclature, 10th International Summer School on Immunogenetics, Stintino, Sardinia: 34 pages (2013).
HLA Nomenclature, (2015) retrieved from http://hla.alleles.org/nomenclature/stats.html on Mar. 17, 2015.
Hodi, F.S., et al., Improved Survival with Ipilimumab in Patients with Metastatic Melanoma, N Engl J Med, 363(8): 711-723 (2010).
Hondowitz, B.D., et al., Discovery of T cell antigens by high-throughput screening of synthetic minigene libraries, PLoS One, 7(1): e29949 (2012).
Hou. S., et al., Expressions of MAGE-A9 and MAGE-A11 in breast cancer and their expression mechanism, Arch Med Res, 45(1): 44-51 (2014).

(56) References Cited

OTHER PUBLICATIONS

Humphrey, P.A., et al., Anti-synthetic peptide antibody reacting at the fusion junction of deletion-mutant epidermal growth factor receptors in human glioblastoma, PNAS, 87: 4207-4211 (1990).
Jung, E.J., et al., Expression of family A melanoma antigen in human gastric carcinoma, Anticancer Res, 25(3B): 2105-2111 (2005).
Kaida, M., et al., Phase 1 Trial of Wilms Tumor 1 (WT1) Peptide Vaccine and Gemcitabine Combination Therapy in Patients With Advanced Pancreatic or Biliary Tract Cancer, J Immunother, 34: 92-99 (2011).
Kakimi, K., et al., A phase I study of vaccination with NY-ESO-1f peptide mixed with Picibanil OK-432 and Montanide ISA-51 in patients with cancers expressing the NY-ESO-1 antigen, Int J Cancer, 129(12): 2836-2846 (2011).
Kalos, M., et al., Adoptive T cell transfer for cancer immunotherapy in the era of synthetic biology, Immunity, 39:49-60 (2013).
Kanojia, D., et al., Sperm-Associated Antigen 9, a Novel Biomarker for Early Detection of Breast Cancer, Cancer Epidemiol Biomarkers Prev, 18(2): 630-639 (2009).
Kantoff, P.W., et al., Overall Survival Analysis of a Phase II Randomized Controlled Trial of a Poxviral-Based PSA-Targeted Immunotherapy in Metastatic Castration-Resistant Prostate Cancer, J Clin Oncol, 28(7): 1099-1105 (2010).
Karkada, M., et al., Therapeutic vaccines and cancer: focus on DPX-0907, Biologics, 8: 27-38 (2014).
Keilholz, U., et al., A clinical and immunologic phase 2 trial of Wilms tumor gene product 1 (WT1) peptide vaccination in patients with AML and MDS, Blood, 113(26): 6541-6548 (2009).
Kenter, G.G., et al., Vaccination against HPV-16 Oncoproteins for Vulvar Intraepithelial Neoplasia, N Engl J Med, 361(19): 1838-1847 (2009).
Kenter, G.K., et al., Phase I immunotherapeutic trial with long peptides spanning the E6 and E7 sequences of high-risk human papillomavirus 16 in end-stage cervical cancer patients shows low toxicity and robust immunogenicity, Clin Cancer Res, 14(1): 169-177 (2008).
Kerkar, S.P., et al., Cellular constituents of immune escape within the tumor microenvironment, Cancer Res, 72(13): 3125-3130 (2012).
Khallouf, H., et al., Therapeutic vaccine strategies against human papillomavirus, Vaccines (Basel), 2(2): 422-462 (2014).
Kissler, S.M., et al. Projecting the transmission dynamics of SARS-CoV-2 through the post-pandemic period, Available at http://nrs.harvard.edu/um-3:HUL.InstRepos:42639308 (31 pgs) (2020).
Kobayashi, J., et al., Comparative study on the immunogenicity between an HLA-A24-restricted cytotoxic T-cell epitope derived from survivin and that from its splice variant survivin-2B in oral cancer patients, J Transl Med, 7:1, pp. 1-11 (2009).
Kovjazin, R., et al., ImMucin: A novel therapeutic vaccine with promiscuous MHC binding for the treatment of MUC1-expressing tumors, Vaccine, 29(29-30): 4676-4686 (2011).
Krug, L.M., et al., WT1 peptide vaccinations induce CD4 and CD8 T cell Immune responses in patients with mesothelioma and non-small cell lung cancer, Cancer Immunol Immunother, 59(10): 1467-1479 (2010).
Krüger, T., et al., Lessons to be learned from primary renal cell carcinomas: novel tumor antigens and HLA ligands for immunotherapy, Cancer Immunol Immunother, 54: 826-836 (2005).
Lammering, G., et al., Inhibition of the Type III epidermal growth factor receptor variant mutant receptor by dominant-negative EGFR-CD533 enhances malignant glioma cell radiosensitivity, Clin Cancer Res, 10: 6732-6743 (2004).
Lammering, G., et al., Radiation-induced activation of a common variant of EGFR confers enhanced radioresistance, Radiother Oncol, 72: 267-273 (2004).
Lee, et al., In silico identification of vaccine targets for 2019-nCOV, F1000Res, 9:145, pp. 1-14 (2020).
Lee, S., et al., Immunomic analysis of human sarcoma, PNAS, 100(5): 2651-2656 (2003).
Li, J., et al., Thrombocytopenia caused by the development of antibodies to thrombopoietin, Blood, 96(12): 3241-3248 (2001).
Li, M., et al., Expression profile of cancer-testis genes in 121 human colorectal cancer tissue and adjacent normal tissue, Clin Cancer Res, 11(5): 1809-1814 (2005).
Lian, Y., et al., MAGE-A family is involved in gastric cancer progression and indicates poor prognosis of gastric cancer patients, Pathol Res Pract, 213(8): 943-948 (2017).
Libermann, T.A., et al., Amplification, enhanced expression and possible rearrangement of EGF receptor gene in primary human brain tumors of glial origin, Nature, 313: 144-147 (1985).
Liu, F., et al., Overexpression of Testes-Specific Protease 50 (TSP50) Predicts Poor Prognosis in Patients with Gastric Cancer, Gastroenterol Res Pract, 2014: 498246 (2014).
Liu, J., et al., Major histocompatibility complex: interaction with peptides, in: eLS, John Wiley & Sons, Ltd: Chichester, a0000922.pub2, pp. 1-12 (2011).
Liu, X., et al., Expression of hiwi gene in human gastric cancer was associated with proliferation of cancer cells, Int J Cancer, 118(8): 1922-1929 (2006).
Lladser, A., et al., Intradermal DNA electroporation induces survivin-specific CTLs, suppresses angiogenesis and confers protection against mouse melanoma, Cancer Immunol Immunother, 59(1): 81-92 (2010).
Mashino, K., et al., Expression of multiple cancer-testis antigen genes in gastrointestinal and breast carcinomas, Br J Cancer, 85(5): 713-720 (2001).
MHC-I binding prediction results, IEDB Analysis Resource, pp. 1/1-1/3 retrieved on Apr. 22, 2021 from <tools.iedb.org/mhci/result/>.
Montgomery, R.B., et al., Expression of oncogenic epidermal growth factor receptor family kinases induces paclitaxel resistance and alters ß-tubulin isotype expression, J Biol Chem, 275(23): 17358-17363 (2000).
Nagane, M., et al., A common mutant epidermal growth factor receptor confers enhanced tumorigenicity on human glioblastoma cells by increasing proliferation and reducing apoptosis, Cancer Res, 56: 5079-5086 (1996).
Nicosia, G., et al., Artificial Immune Systems, Third International Conference, ICARIS 2004, Catania, Sicily, Italy, Sep. 13-16, 2004. Lecture Notes in Computer Science, New York: Springer, 3236:189-196 (2004).
Nishikawa, R., et al., A mutant epidermal growth factor receptor common in human glioma confers enhanced tumorgenicity, PNAS USA, 91: 7727-7731 (1994).
Ochoa-Garay, J., et al., The ability of peptides to induce cytotoxic T cells in vitro does not strongly correlate with their affinity for the H-2L$^d$ molecule: implications for vaccine design and immunotherapy, Mol Immunol, 34(3): 273-281 (1997).
Okuno, K., et al., Clinical trial of a 7-peptide cocktail vaccine with oral chemotherapy for patients with metastatic colorectal cancer, Anticancer Res, 34: 3045-3052 (2014).
Padron-Regalado, E., et al., Vaccines for SARS-CoV-2: lessons from other coronavirus strains, Infect Dis Ther, 9: 255-274 (2020).
Paoletti, L.C., Potency of clinical group B streptococcal conjugate vaccines, Vaccine, 19: 2118-2126 (2001).
Pardi, N., et al., mRNA vaccines—a new era in vaccinology, Nat Rev Drug Discov, 19 pages (2018).
Pasini, E., et al., Undifferentiated nasopharyngeal carcinoma from a nonendemic area: Protective role of HLA allele products presenting conserved EBV epitopes, Int J Cancer, 125(6): 1358-1364 (2009).
PCT/EP2018/055230 International Search Report and Written Opinion dated Jun. 8, 2018.
PCT/EP2018/055231 International Search Report and Written Opinion dated Apr. 5, 2018.
PCT/EP2018/055232 International Search Report and Written Opinion dated May 9, 2018.
PCT/EP2019/073476 International Search Report and Written Opinion dated Jan. 23, 2020.
PCT/EP2019/073478 International Search Report and Written Opinion dated Sep. 20, 2019.
PCT/EP2019/073481 International Search Report and Written Opinion dated Dec. 20, 2019.

(56) References Cited

OTHER PUBLICATIONS

Phuphanich, S., et al., Phase I trial of a multi-epitope-pulsed dendritic call vaccine for patients with newly diagnosed glioblastoma, Cancer Immunol Immunother, 62(1): 125-135 (2013).
Rahman Oany, et al., Design of an epitope-based peptide vaccine against spike protein of human coronavirus: an in silico approach, Drug Des Devel Ther, 8: 1139-1149 (2014).
Ramakrishnan, R., et al., Chemotherapy enhances tumor cell susceptibility to CTL-mediated killing during cancer immunotherapy in mice, J Clin Invest, 120(4): 1111-1124 (2010).
Rapoport, A.P., et al., Combination immunotherapy after ASCT for multiple myeloma using MAGE-A3/Poly-ICLC immunizations followed by adoptive transfer of vaccine-primed and costimulated autologous T cells, Clin Cancer Res, 20(5): 1355-1365 (2014).
Reche, P.A., et al., Definition of MHC supertypes through clustering of MHC peptide binding repertoires, in Nicosia, G., et al., Eds. ICARIS 2004, LNCS 3239: 189-196( (2004).
Repana, D., et al., The network of cancer genes (NCG): a comprehensive catalogue of known and candidate cancer genes from cancer sequencing screens, Genome Biol, 20(1): 1-12 (2019).
Rosa, D.S., et al., Multiple approaches for increasing the immunogenicity of an epitope-based anti-HIV vaccine, AIDS Res Hum Retroviruses, 31(11): 1077-1088 (2015).
Saini, S., et al., A novel cancer testis antigen, a-kinase anchor protein 4 (AKAP4) is a potential biomarker for breast cancer, PLoS One, 8(2): e57095 (2013).
Sampson, J.H., et al., Immunologic escape after prolonged progression-free survival with epidermal growth factor receptor variant ill peptide vaccination in patients with newly diagnosed glioblastoma, J Clin Oncol, 28(31): 4722-4729 (2010).
Schmitz, M., et al., Generation of survivin-specific CD8+ T effector cells by dendritic cells pulsed with protein or selected peptides, Cancer Res, 60(17): 4845-4849 (2000).
Schumacher, T.N., et al., Neoantigens in cancer immunotherapy, Science, 348(6230): 69-74 (2015).
Seliger, B., et al., Molecular mechanisms of HLA class I antigen abnormalities following viral infection and transformation, Int J Cancer, 118(1): 129-138 (2006).
Shabestarian, H., et al., DPPA2 Protein Expression is Associated with Gastric Cancer Metastasis, Asian Pac J Cancer Prev, 16(18): 8461-8465 (2015).
Shi, R., et al., The immunogenicity of a novel cytotoxic T lymphocyte epitope from tumor antigen PL2L60 could be enhanced by 4-chlorophenylalanine substitution at position 1, Cancer Immunol Immunother, 62(11): 1723-1732 (2013).
Singh, S.P., et al., Major histocompatibility complex linked databases and prediction tools for designing vaccines, Hum Immunol, 77(3): 295-306 (2015).
Slingluff, C.L., et al., Clinical and Immunologic results of a randomized phase II trial of vaccination using four melanoma peptides either administered in granulocyte-macrophage colony-stimulating factor in adjuvant of pulsed on dendritic cells, J Clin Oncol, 21(21): 4016-4026 (2003).
Slingluff, C.L., et al., Randomized multicenter trial of the effects of melanoma-associated helper peptides and cyclophosphamide on the immunogenicity of a multipeptide melanoma vaccine, J Clin Oncol, 29(21): 2924-2932 (2011).
Smyth, L.J.C., et al., CD8 T-cell recognition of human 5T4 oncofetal antigen, Int J Cancer, 119(7): 1638-1647 (2006).
Snyder, A.S., et al., Genetic basis for clinical response to CTLA-4 blockade in melanoma, N Engl J Med, 371(23): 2189-2199 (2014).
Somogyi, E., et al., HIV vaccine to induce cytotoxic T cells recognizing conserved HIV-1/2-epitopes derived from the most frequent HLA types of the human population, Immunotherapy, 5(8): 825-828 (2013).
Somogyi, E., et al., Peptide vaccine candidate mimics the heterogeneity of natural SARS-CoV-2 immunity in convalescent humans and induces broad T cell responses in mice models, bioRxiv, pp. 1-39, Oct. 2020.
Song, M., et al., Cancer/testis antigen NT-SAR-35 enhances cell proliferation, migration, and invasion, Int J Oncol, 48(2):569-576 (2016).
Spranger, S., Mechanisms of tumor escape in the context of the T-cell-inflamed and the non-T-cell-inflamed tumor microenvironment, Int Immunol, 28(8): 383-391 (2016).
Tagawa, S.T., et al., Phase I study of intranodal delivery of a plasmid DNA vaccine for patients with stage IV melanoma, Cancer, 98(1):144-154 (2003).
Takedatsu, H., et al., Determination of thrombopoietin-derived peptides recognized by both cellular and humoral immunities in healthy donors and patients with thrombocytopenia, Stem Cells, 23(7): 975-982 (2005).
Tantigen search results for EpCAM T cell epitopes, 1 page, retrieved on Apr. 19, 2021 from <http://projects.met-hilab.org/tadb/cgi/searchT.pl>.
Tantigen search results for HILI/PIWIL-2, 1 page, retrieved on Apr. 16, 2021 from <http://projects.met-hilab.org/tadb/cgi/searchT.pl>.
The UniProt Consortium, UniProt: the universal protein knowledgebase, UniProtKB-Q8NOW7, Nucleic Acids Res. 46:2699 (2018).
Therasse, P., et al., New guidelines to evaluate the response to treatment in solid tumors, J Natl Cancer Inst, 92(3): 205-216 (2000).
Trimble, C.L., et al., Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial, Lancet, 386(10008): 2078-2088 (2015).
Tsuchida, Y., et al., Response evaluation criteria in solid tumors (RECIST): new guidelines, Med Pediatr Oncol, 37:1-3 (2001).
U.S. Appl. No. 15/910,930 Office Action dated Mar. 25, 2021.
U.S. Appl. No. 15/910,965 Office Action dated May 12, 2021.
U.S. Appl. No. 15/910,988 Office Action dated May 18, 2018.
U.S. Appl. No. 16/244,497 Office Action dated Aug. 18, 2021.
U.S. Appl. No. 16/559,430 Office Action dated Apr. 27, 2020.
U.S. Appl. No. 16/559,430 Office Action dated Aug. 27, 2020.
U.S. Appl. No. 17/249,362 Office Action dated Apr. 27, 2021.
U.S. Appl. No. 17/249,362 Office Action dated Sep. 8, 2021.
U.S. Appl. No. 17/645,741 Office Action dated Mar. 2, 2022.
Valmori, D., et al., Epitope clustering in regions undergoing efficient proteasomal processing defines immunodominant CTL regions of a tumor antigen, Clin Immunol, 122: 163-172 (2007).
Valmori, D., et al., Vaccination with NY-ESO-1 protein and CpG in montanide induces integrated antibody/Th1 responses and CD8 T cells through cross-priming, PNAS USA, 104(21): 8947-8952 (2007).
Van Allen, E.M., et al., Genomic correlates of response to CTLA-4 blockade in metastatic melanoma, Science, 350(6257): 207-211 (2015).
Vitale, M., et al., Effect of tumor cells and tumor microenvironment on NK-cell function, Eur J Immunol, 44: 1582-1592 (2014).
Voutsas, I.F., et al., Unraveling the role of preexisting immunity in prostate cancer patients vaccinated with a HER-2/neu hybrid peptide, J Immunother Cancer, 4:75, pp. 1-15 (2016).
Wada, H., et al., Vaccination with NY-ESO-1 overlapping peptides mixed with picibanil OK-432 and montanide ISA-51 in patients with cancers expressing the NY-ESO-1 antigen, J Immunother, 37(2): 84-92 (2014).
Walter, S., et al., Multipeptide immune response to cancer vaccine IMA901 after single-dose cyclophosphamide associates with longer patient survival, Nat Med, 18(8): 1254-1261 (2012).
Wang, Y-Q., et al., Enhancement of survivin-specific anti-tumor immunity by adenovirus prime protein-boost immunity strategy with DDA/MPL adjuvant in a murine melanoma model, Int Immunopharmacol, 17(1): 9-17 (2013).
Wei, J., et al., Screening of Single-Chain Variable Fragments against TSP50 from a Phage Display Antibody Library and Their Expression as Soluble Proteins, J Biol Med Screen, 11(5): 546-552, (2006).
Weller, M., et al., Rindopepimut with temozolomide for patients with newly diagnosed, EGFRvIII-expressing glioblastoma (ACT IV): a randomised, double-blind, international phase 2 trial, Lancet Oncol, 18(10): 1373-1385 (2017).

(56) References Cited

OTHER PUBLICATIONS

Welters, M.J.P., et al., Induction of tumor-specific CD4+ and CD8+ T-cell immunity in cervical cancer patients by a human papillomavirus type 16 E6 and E7 long peptides vaccine, Clin Cancer Res, 14(1): 178-187 (2008).

Welters, M.J.P., et al., Success or failure of vaccination for HPV16-positive vulvar lesions correlates with kinetics and phenotype of induced T-cell responses, PNAS USA, 107(25): 11895-11899 (2010).

Wieczorek, M., et al., Major histocompatibility complex (MHC) class I and MHC class II proteins: conformational plasticity in antigen presentation, Front Immunol, 8: 292 (2017).

Woolhouse, M., et al., Human viruses: discovery and emergence, Philos Trans R Soc London B Biol Sci, 367(1604): 2864-71 (2012).

Wu, F., et al., Severe acute respiratory syndrome coronavirus 2 isolate Wuhan-Hu-1, complete genome, NCBI Reference Sequence: NC_045512.2, (2020).

Yoshitake, Y., et al., Phase II clinical trial of multiple peptide vaccination for advanced head and neck cancer patients revealed induction of immune responses and improved OS, Clin Cancer Res, 21(2): 312-321 (2015).

You, L., et al., Understanding Prediction Systems for HLA-Binding Peptides and T-Cell Epitope Identification. In: Rajapakse, J.C., Schmidt, B., Volkert, G. (Eds) Pattern Recognition in Bioinformatics, 4774: 337-348 (2007).

Yuan, J., et al., Integrated NY-ESO-1 antibody and CD8+ T-cell responses correlate with clinical benefit in advanced melanoma patients treated with ipilimumab, PNAS USA, 108(40): 16723-16728 (2011).

Yuan, J., et al., Safety and immunogenicity of a human and mouse gp100 DNA vaccine in a phase I trial of patients with melanoma, Cancer Immunity, 9:5 (2009).

Zajac, P., et al., MAGE-A antigens and cancer immunotherapy, Front Immunol, 4: 18 (2017).

Zhang, H., et al., DNA and adenovirus tumor vaccine expressing truncated survivin generates specific immune responses and anti-tumor effects in a murine melanoma model, Cancer Immunol Immunother, 61(10): 1857-1867 (2012).

Zhang. X.W., A combination of epitope prediction and molecular docking allows for good identification of MHC class I restricted T-cell epitopes, Comput Biol Chem, 45: 30-35 (2013).

Zheng, L., et al., High Expression of Testes-Specific Protease 50 is Associated with Poor Prognosis in Colorectal Carcinoma, PLoS One, 6(7):e22203 (2011).

* cited by examiner

| Patient ID | #PEPI / HPV-16 E6 Pools | | | | | | | | | | | | | | | #PEPI / HPV-16 E7 Pools | | | | | | | | |
|---|---|---|---|---|---|---|---|---|---|---|---|---|---|---|---|---|---|---|---|---|---|---|---|---|
| | 19-Jan | 29-Nov | 21-39 | 31-49 | 41-59 | 51-69 | 61-79 | 71-89 | 81-99 | 91-109 | 101-119 | 111-129 | 121-139 | 131-149 | 141-158 | 19-Jan | 29-Nov | 21-39 | 31-49 | 41-59 | 51-69 | 61-79 | 71-89 | 81-98 |
| 1 | TN | TN | TN | FN | TN | FP | TN | TN | TN | TN | FN | TN | TN | TN | TN | FP | TN | TN | TN | FP | TN | TN | TN | TN |
| 2 | FN | FN | TN | TN | TN | FP | TN | TN | TN | TN | TN | TN | TN | TN | TN | FP | TN | TN | TN | FP | TN | TN | TN | TN |
| 3 | TN | TN | TN | TN | TN | TP | TN | TN | TN | TN | TN | FN | TN | TN | TN | TN | TN | TN | TN | TN | TN | TN | TN | TN |
| 4 | TN | FN | TN | TN | TN | FN | TN | TN | TN | TN | TN | TN | TN | TN | TN | TN | TN | TN | TN | TN | TN | TN | TN | TN |
| 6 | TN | TN | TN | FN | TN | FP | TN | TN | TN | TN | FN | TN | TN | TN | TN | FP | TN | TN | TN | TN | TN | TN | TN | FP |
| 7 | TN | TN | TN | TN | TN | FN | TN | TN | TN | TN | TN | TN | TN | TN | TN | TN | TN | TN | TN | TN | TN | TN | TN | TN |
| 8 | TN | FN | TN | FN | TN | FN | TN | FP | TN | TN | FN | TN | TN | TN | FN | TN | TN | TN | TN | TP | TN | TN | TN | TN |
| 9 | TN | TN | TN | TN | FN | FN | TN | FP | TN | TN | TN | TN | TN | TN | TN | TN | TN | TN | TN | FP | TN | TN | TN | TN |
| 10 | TN | TN | TN | TN | TN | TP | TN | TN | TN | TN | TN | TN | TN | TN | TN | TN | TN | TN | TN | FP | TN | TN | FP | TN |
| 11 | TN | FN | TN | TN | TN | TN | TN | TN | FP | TN | TN | TN | TN | TN | TN | TN | TN | TN | TN | TN | TN | TN | TN | TN |
| 13 | TN | TN | TN | TN | TN | FN | TN | TN | TN | FN | TN | TN | TN | TN | TN | TN | TN | TN | TN | TN | TN | TN | TN | TN |
| 16 | TN | TN | TN | TN | TN | TP | TN | TN | TN | FN | TN | TN | TN | TN | TN | TN | TN | TN | TN | TN | TN | TN | TN | TN |
| 18 | TN | TN | TN | TN | TN | FP | TN | TN | TN | TN | TN | TN | TN | TN | TN | TN | TN | TN | TN | TP | TN | TN | TN | TN |
| 22 | TN | FN | TN | TN | TN | TP | TN | TN | TN | TN | TN | TN | TN | TN | TN | FP | TN | TN | TN | FP | TN | TN | TN | TN |
| 23 | TN | TN | TN | FN | TN | TN | TN | TN | TN | FN | TN | TN | TN | FN | TN | TN | TN | TN | TN | TN | TN | TN | TN | TN |
| 24 | TN | TN | TN | TN | TN | TP | TN | TN | TN | FN | TN | TN | TN | TN | TN | FP | TN | TN | TN | TN | TN | TN | FN | FP |
| 27 | TN | TN | TN | TN | TN | TN | TN | TN | TN | TN | TN | TN | TN | TN | TN | TN | TN | TN | TN | TN | TN | TN | TN | TN |
| 28 | TN | TN | TN | TN | TN | FP | TN | TN | TN | TN | TN | TN | TN | TN | TN | TN | TN | TN | TN | FP | TN | TN | TN | TN |
| 29 | FN | TN | FN | TN | TN | TN | TN | TN | TN | FN | TN | TN | TN | TN | TN | TN | TN | TN | TN | TN | TN | TN | TN | TN |
| 30 | TN | TN | TN | TN | TN | FP | TN | TN | TN | TN | TN | TN | TN | TN | TN | TN | TN | TN | TN | TN | TN | TN | TN | TN |
| 100 | TN | TN | TN | TN | TN | FN | TN | TN | TN | TN | TN | TN | TN | TN | TN | TN | TN | TN | TN | TN | TN | TN | TN | TN |
| 102 | TN | TN | TN | TN | TN | TP | TN | TN | FP | TN | TN | TN | TN | TN | TN | TN | TN | TN | TN | TN | FN | TN | TN | TN |
| 103 | TN | FN | TN | TN | TN | TN | TN | TN | TN | TN | TN | TN | TN | TN | TN | TN | TN | TN | TN | TN | TN | TN | TN | TN |
| 105 | TN | TN | TN | TN | TN | TP | FN | TN | TN | TN | TN | TN | TN | TN | TN | FP | TN | TN | TN | FP | TN | TN | TN | TN |
| 107 | TN | TN | TN | TN | TN | TN | TN | TN | TN | FN | TN | TN | TN | TN | TN | TN | TN | TN | TN | TN | TN | TN | FN | TN |

Figure 3A

| Patient ID | #epitope / HPV-16 E6 Pools | | | | | | | | | | | | | | | #epitope / HPV-16 E7 Pools | | | | | | | | |
|---|---|---|---|---|---|---|---|---|---|---|---|---|---|---|---|---|---|---|---|---|---|---|---|---|
| | 19-Jan | 29-Nov | 21-39 | 31-49 | 41-59 | 51-69 | 61-79 | 71-89 | 81-99 | 91-109 | 101-119 | 111-129 | 121-139 | 131-149 | 141-158 | 19-Jan | 29-Nov | 21-39 | 31-49 | 41-59 | 51-69 | 61-79 | 71-89 | 81-98 |
| 1 | TN | FP | FP | TP | FP | FP | FP | FP | FP | FP | TP | FP | TN | TN | FP | FP | FP | TN | TN | FP | FP | FP | FP | FP |
| 2 | TP | TP | FP | FP | FP | FP | FP | FP | FP | FP | TN | TN | FP | FP | FP | FP | FP | TN | TN | FP | FP | FP | FP | FP |
| 3 | FP | FP | TN | FP | FP | TP | TN | FP | FP | FP | FP | TP | TN | FP | FP | FP | TN | TN | TN | FP | TN | TN | FP | FP |
| 4 | FP | TP | TN | FP | FP | TP | TN | FP | FP | FP | FP | FP | FP | FP | FP | FP | FP | TN | TN | FP | TN | FP | FP | FP |
| 6 | FP | FP | FP | FN | FP | FP | FP | FP | FP | FP | FN | TN | TN | TN | TN | FP | FP | TN | FP | FP | TN | FP | FP | FP |
| 7 | FP | FP | FP | FP | FP | TP | TN | FP | FP | FP | FP | FP | TN | FP | FP | FP | TN | TN | TN | FP | TN | TN | FP | FP |
| 8 | FP | TP | TN | TP | FP | TP | FP | FP | FP | FP | TP | FP | FP | FP | TP | FP | FP | TN | TN | TP | TN | FP | FP | FP |
| 9 | FP | FP | TN | FP | TP | TP | TN | FP | FP | FP | FP | FP | FP | FP | FP | FP | FP | TN | TN | FP | TN | FP | FP | FP |
| 10 | FP | FP | TN | FP | FP | TP | FP | FP | FP | FP | FP | FP | TN | FP | FP | FP | TN | TN | TN | FP | TN | TN | FP | FP |
| 11 | FP | TP | FP | FP | FP | FP | FP | TN | FP | FP | FP | FP | TN | FP | FP | FP | FP | TN | TN | FP | TN | TN | FP | FP |
| 13 | FP | FP | FP | FP | FP | TP | FP | FP | FP | TP | FP | FP | TN | FP | FP | FP | FP | TN | TN | FP | FP | TN | FP | FP |
| 16 | FP | FP | FP | FP | FP | TP | TN | FP | TN | TP | FP | TN | FP | FP | FP | FP | FP | FP | FP | FP | TN | FP | FP | FP |
| 18 | FP | FP | FP | FP | FP | FP | FP | FP | FP | FP | FP | FP | TN | FP | FP | FP | FP | TN | TN | TP | FP | FP | FP | FP |
| 22 | FP | TP | FP | FP | FP | TP | FP | FP | FP | FP | FP | FP | TN | FP | FP | FP | FP | TN | TN | FP | TN | FP | FP | FP |
| 23 | TN | FP | FP | TP | FP | FP | FP | FP | FP | TP | FP | FP | TN | TP | FP | FP | FP | FP | FP | FP | FP | TN | FP | FP |
| 24 | TN | FP | FP | FP | FP | TP | FP | TN | FP | TP | TN | TN | FP | FP | FP | FP | FP | FP | FP | FP | TN | FP | TP | FP |
| 27 | FP | FP | FP | FP | FP | FP | FP | FP | FP | FP | FP | FP | TN | FP | FP | FP | FP | TN | TN | FP | TN | FP | FP | FP |
| 28 | FP | FP | TN | TN | FP | FP | FP | FP | FP | FP | TN | FP | TN | FP | FP | FP | TN | TN | TN | FP | FP | TN | FP | FP |
| 29 | TP | FP | TP | FP | FP | FP | FP | FP | FP | TP | FP | FP | FP | FP | FP | FP | FP | TN | FP | FP | FP | FP | FP | FP |
| 30 | FP | FP | FP | FP | FP | FP | FP | FP | FP | FP | FP | TN | TN | TN | FP | FP | FP | TN | TN | FP | FP | TN | FP | FP |
| 100 | FP | FP | FP | FP | FP | TP | FP | FP | FP | FP | TN | TN | FP | FP | FP | FP | FP | FP | FP | FP | FP | FP | FP | TN |
| 102 | FP | FP | FP | FP | FP | TP | FP | FP | FP | FP | TN | FP | FP | FP | FP | FP | FP | TN | TN | FP | FN | TN | FP | TN |
| 103 | FP | TP | FP | FP | FP | FP | FP | FP | FP | FP | FP | FP | TN | FP | FP | FP | FP | TN | TN | FP | TN | TN | FP | FP |
| 105 | FP | FP | FP | FP | FP | TP | TP | FP | FP | FP | TN | FP | TN | FP | FP | FP | FP | TN | TN | FP | TN | FP | FP | FP |
| 107 | FP | FP | FP | FP | FP | FP | FP | FP | FP | TP | TN | FP | FP | FP | FP | FP | FP | FP | FP | FP | TN | FP | TP | FP |

Figure 4:
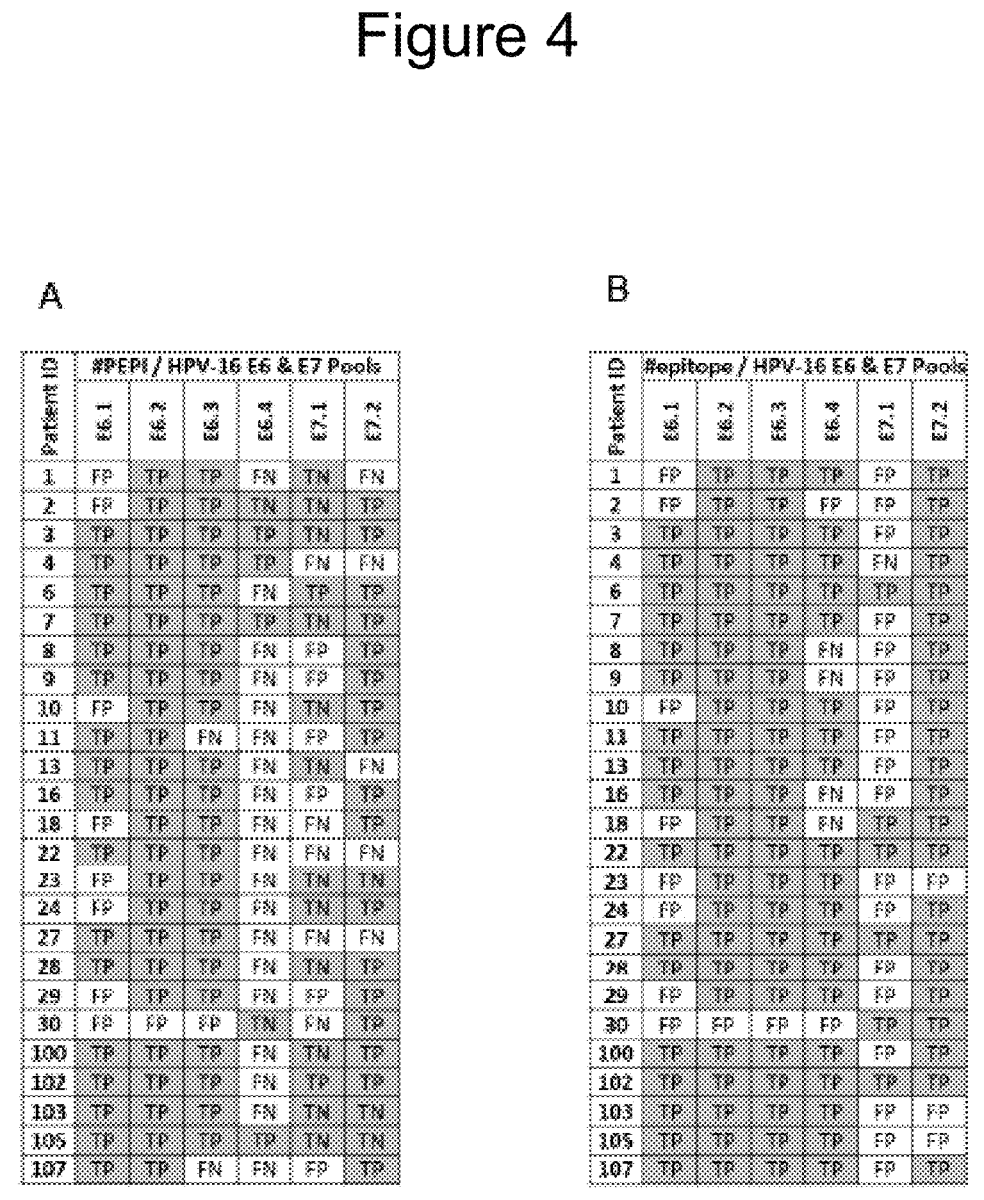

| Patient ID | #PEPI / HPV-16 E6 & E7 Pools | | | | | |
|---|---|---|---|---|---|---|
| | E6.1 | E6.2 | E6.3 | E6.4 | E7.1 | E7.2 |
| 1 | FP | TP | TP | FN | TN | FN |
| 2 | FP | TP | TP | TN | TN | TP |
| 3 | TP | TP | TP | TP | TN | TP |
| 4 | TP | TP | TP | TP | FN | FN |
| 6 | TP | TP | TP | FN | TP | TP |
| 7 | TP | TP | TP | TP | TN | TP |
| 8 | TP | TP | TP | FN | FP | TP |
| 9 | TP | TP | TP | FN | FP | TP |
| 10 | FP | TP | TP | FN | TN | TP |
| 11 | TP | TP | FN | FN | FP | TP |
| 13 | TP | TP | TP | FN | TN | FN |
| 16 | TP | TP | TP | FN | FP | TP |
| 18 | FP | TP | TP | FN | FN | TP |
| 22 | TP | TP | TP | FN | FN | FN |
| 23 | FP | TP | TP | FN | TN | TN |
| 24 | FP | TP | TP | FN | TN | TP |
| 27 | TP | TP | TP | FN | FN | FN |
| 28 | TP | TP | TP | FN | TN | TP |
| 29 | FP | TP | TP | FN | FP | TP |
| 30 | FP | FP | FP | TN | FN | TP |
| 100 | TP | TP | TP | FN | TN | TP |
| 102 | TP | TP | TP | FN | TP | TP |
| 103 | TP | TP | TP | FN | TN | TN |
| 105 | TP | TP | TP | TP | TN | TN |
| 107 | TP | TP | FN | FN | FP | TP |

B

| Patient ID | #epitope / HPV-16 E6 & E7 Pools | | | | | |
|---|---|---|---|---|---|---|
| | E6.1 | E6.2 | E6.3 | E6.4 | E7.1 | E7.2 |
| 1 | FP | TP | TP | TP | FP | TP |
| 2 | FP | TP | TP | FP | FP | TP |
| 3 | TP | TP | TP | TP | FP | TP |
| 4 | TP | TP | TP | TP | FN | TP |
| 6 | TP | TP | TP | TP | TP | TP |
| 7 | TP | TP | TP | TP | FP | TP |
| 8 | TP | TP | TP | FN | FP | TP |
| 9 | TP | TP | TP | FN | FP | TP |
| 10 | FP | TP | TP | TP | FP | TP |
| 11 | TP | TP | TP | TP | FP | TP |
| 13 | TP | TP | TP | TP | FP | TP |
| 16 | TP | TP | TP | FN | FP | TP |
| 18 | FP | TP | TP | FN | TP | TP |
| 22 | TP | TP | TP | TP | TP | TP |
| 23 | FP | TP | TP | TP | FP | FP |
| 24 | FP | TP | TP | TP | FP | TP |
| 27 | TP | TP | TP | TP | TP | TP |
| 28 | TP | TP | TP | TP | FP | TP |
| 29 | FP | TP | TP | TP | FP | TP |
| 30 | FP | FP | FP | FP | TP | TP |
| 100 | TP | TP | TP | TP | FP | TP |
| 102 | TP | TP | TP | TP | TP | TP |
| 103 | TP | TP | TP | TP | FP | FP |
| 105 | TP | TP | TP | TP | FP | FP |
| 107 | TP | TP | TP | TP | FP | TP |

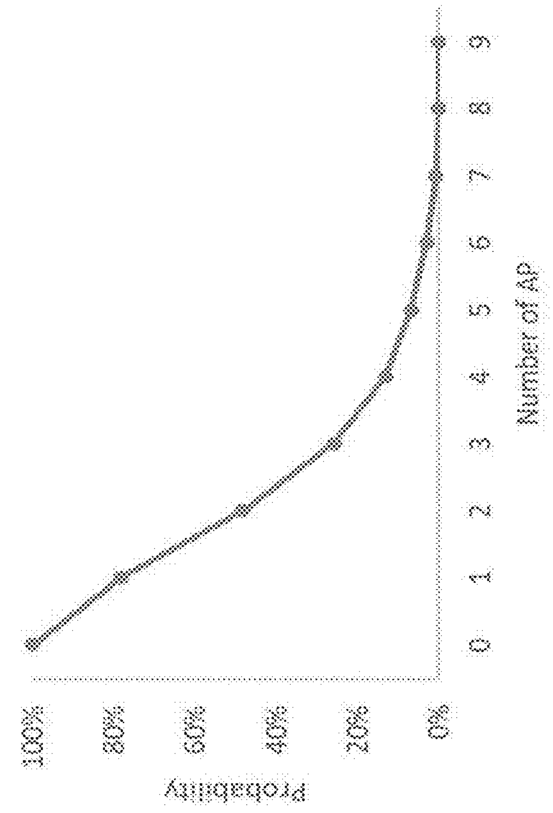
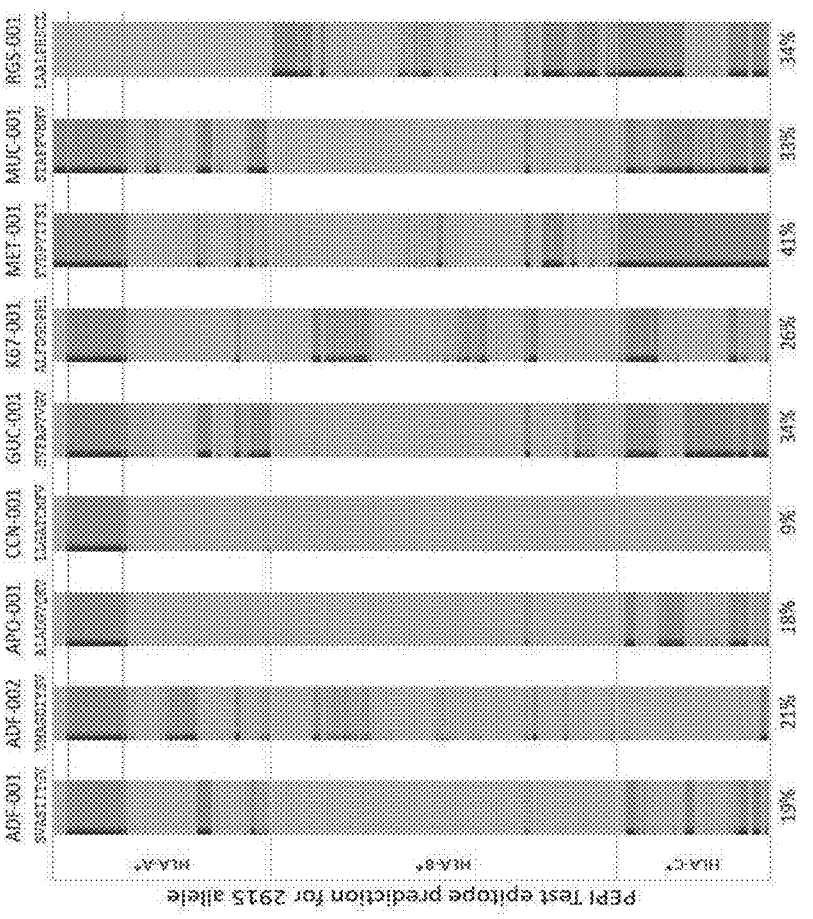
Figure 8

E F

| CRC Antigens targeted by PolyPEPI1018 | Expression Rate (2,391 CRC biopsies) |
|---|---|
| TSP50 | 89% |
| EpCAM | 88% |
| Survivin | 87% |
| CAGE1 | 74% |
| SPAG9 | 74% |
| MAGE-A8 | 44% |
| FBXO39 | 39% |

CRC_P3 peptide (30 aa)

EpCam (15 aa) MAGE-A8 (15 aa)

YVDEKAPEFSMQGLK DEKVAELVRFLLRKY

| PolyPEPI1018 vaccine antigens | Pre-clinical Immunogenicity | | Clinical Immunogenicity |
|---|---|---|---|
| | Model population (n=433) | CRC cohort (n=37) | OBERTO-101 (n=10) |
| TSP50 | 53% | 62% | 70% |
| EpCAM | 69% | 41% | 90% |
| Survivin | 36% | 32% | 70% |
| Cage | 68% | 81% | 50% |
| SPAG9 | 28% | 3% | 40% |
| FBXO39 | 90% | 100% | 60% |
| MAGE-A8 | 18% | 0% | 60% |
| Any antigen | 98% | 100% | 90% |
| Any 2 antigens | 92% | 92% | 90% |
| Any 3 antigens | 72% | 65% | 80% |

*Lorincz et al. *Journal of Clinical Oncology 37, 2019 (suppl; abstr e14298).*

Figure 13

Note: In the CAIRO3 trial the PFS1 was m8.5 month (95% CI 6.5-10.3)*

*CAIRO3 trial: Simkens et al. *The Lancet* 2015

| Antigen | Expression level |
|---|---|
| SURVIVIN | 100% |
| DPPA2 | 100% |
| KK-LC-1 | 80% |
| CAGE-1 | 77% |
| HIWI | 76% |
| TSP50 | 57% |
| 5T4 | 52% |
| MAGE-A3 | 37% |
| MAGE-A1 | 31% |
| MAGE-A2 | 31% |
| MAGE-A10 | 30% |
| PRAME | 20% |
| LAGE-1 | 14% |
| SSX1 | 13% |

Conclusion:

1. 99% of the tumor express ≥3 antigens
2. No biopsy is needed

Figure 17
A
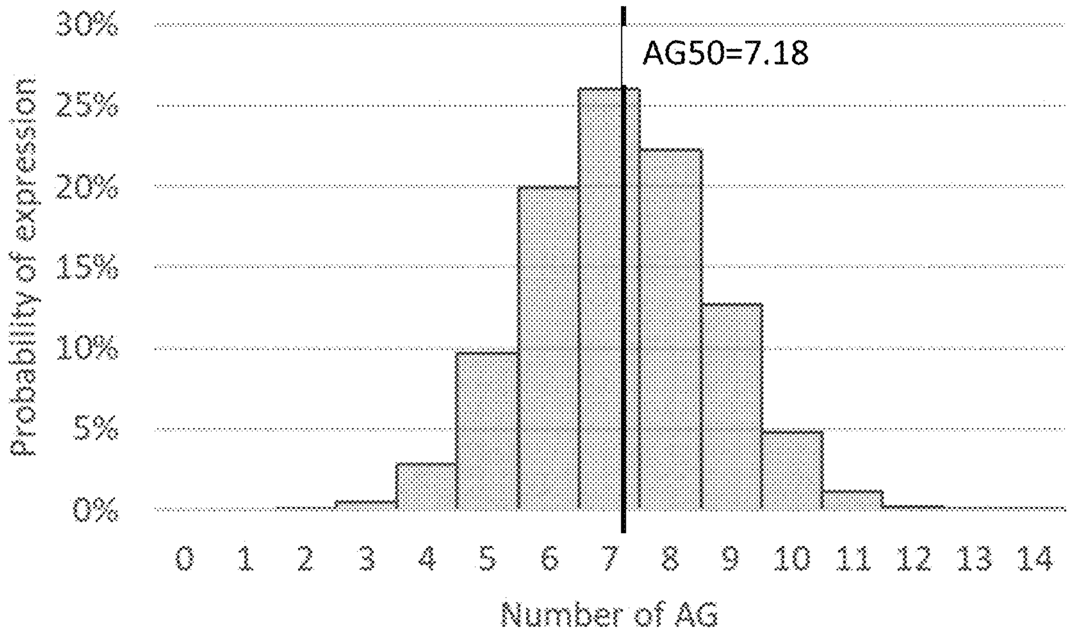
B
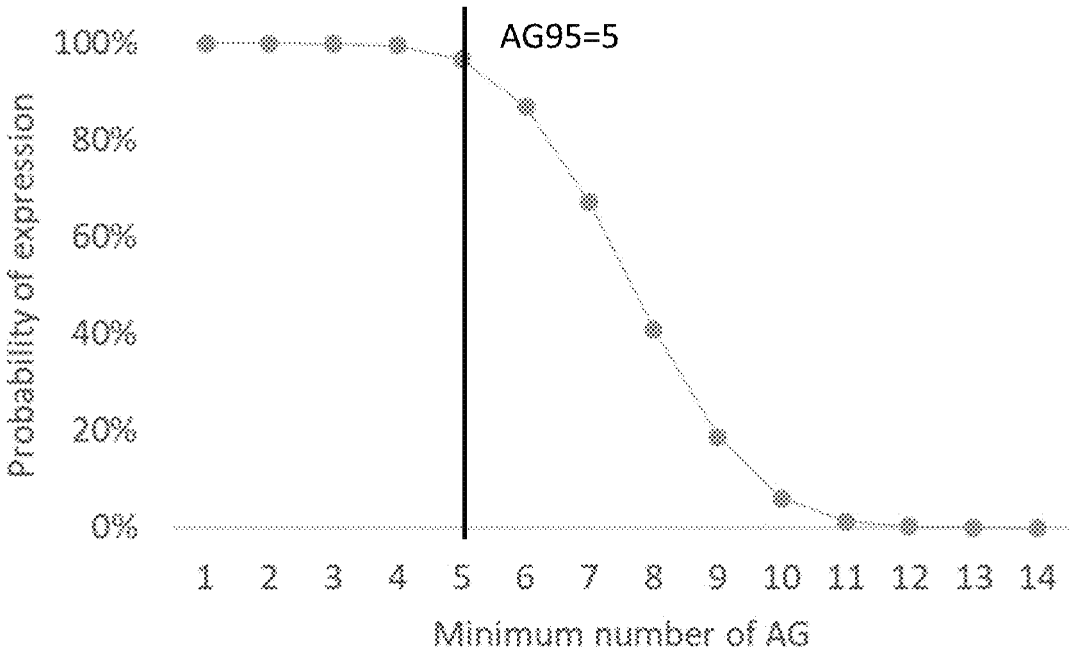

Figure 18
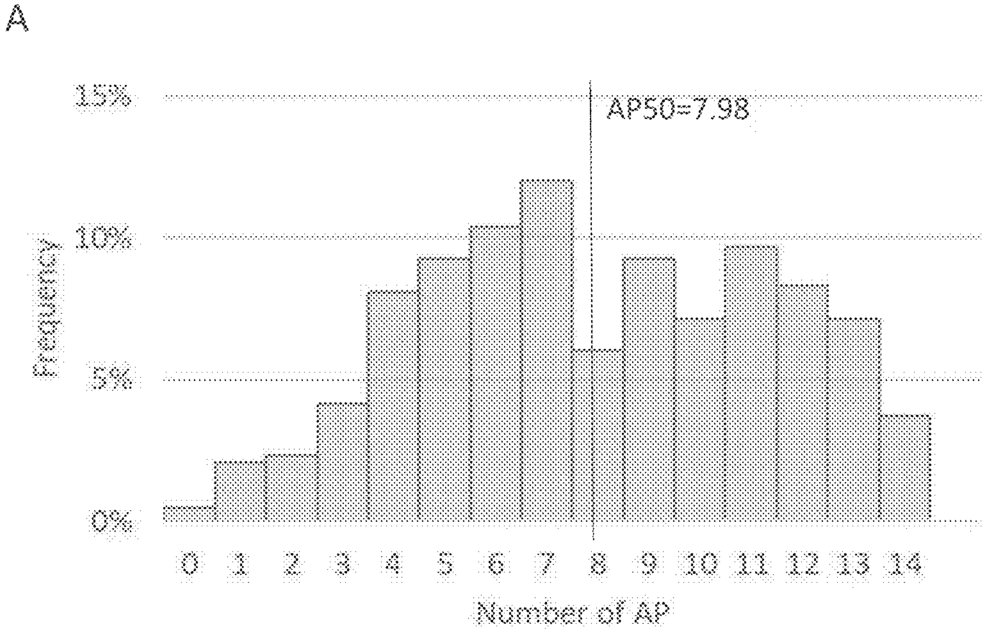
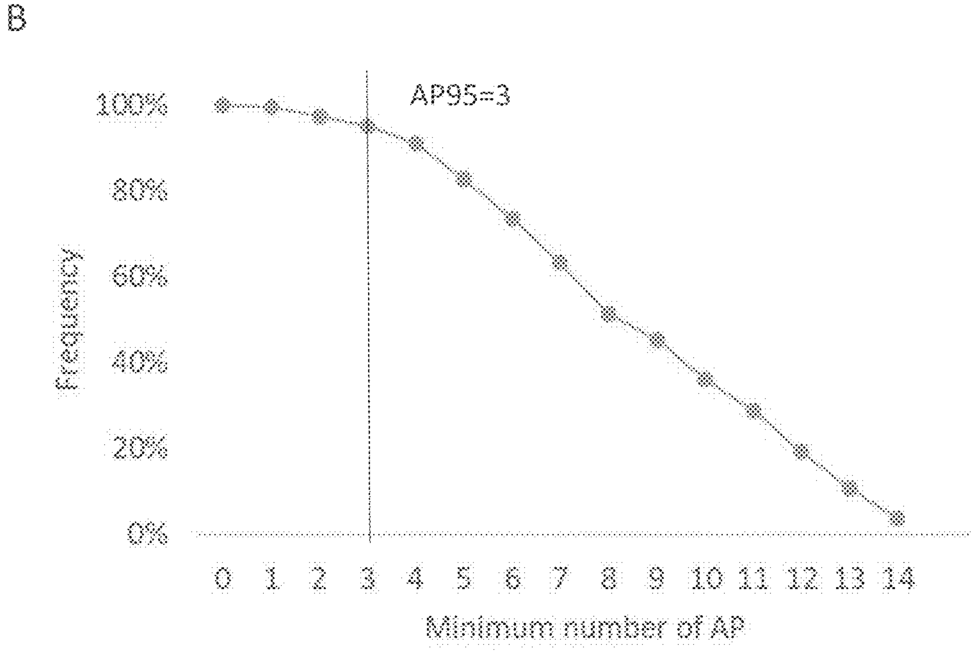

Figure 19
A
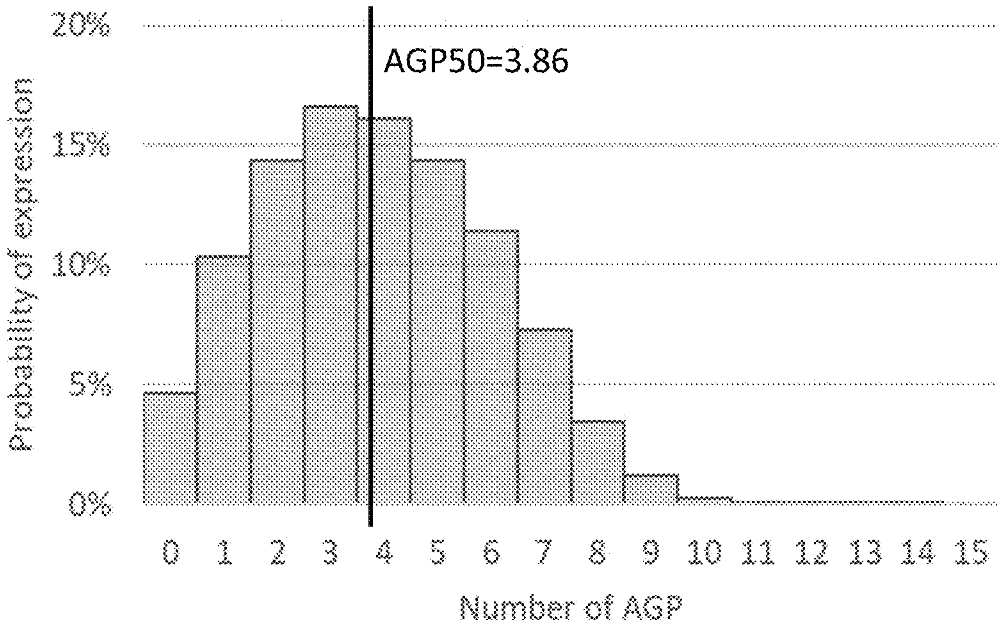
B
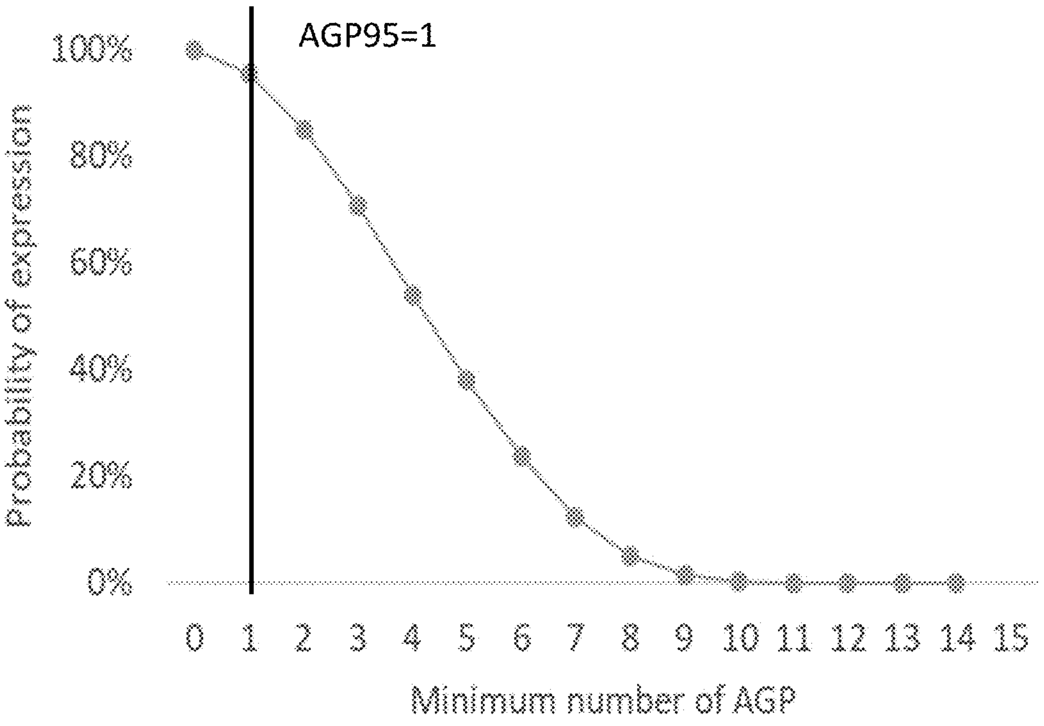

| Antigen | Expression level |
|---|---|
| BRDT | 48% |
| PRAME | 63% |
| NALP4 | 38% |
| MAGE-C2 | 24% |
| MAGE-A12 | 36% |
| NY-SAR-35 | 28% |
| DPPA2 | 30% |
| KK-LC-1 | 35% |
| SURVIVIN | 57% |
| MAGE-A2 | 27% |
| LDHC | 29% |
| MAGE-A3 | 33% |
| MAGE-A1 | 28% |

Conclusion:

1. 99% of the tumor express ≥3 antigens
2. No biopsy is needed

| Antigen | Expression level |
|---|---|
| Survivin | 96% |
| PRAME | 90% |
| MAGE-A6 | 62% |
| MAGE-A2 | 61% |
| MAGE-A3 | 59% |
| MAGE-A11 | 54% |
| MAGE-A12 | 45% |
| MAGE-C1 | 45% |
| MAGE-C2 | 45% |
| MAGE-A10 | 44% |
| Ny-ESO-1 | 38% |
| MAGE-A1 | 37% |
| LAGE-1 | 35% |
| BORIS | 27% |
| SSX-1 | 25% |

Conclusion:

1. 99% of the tumor express ≥3 antigens
2. No biopsy is needed

Figure 25
A
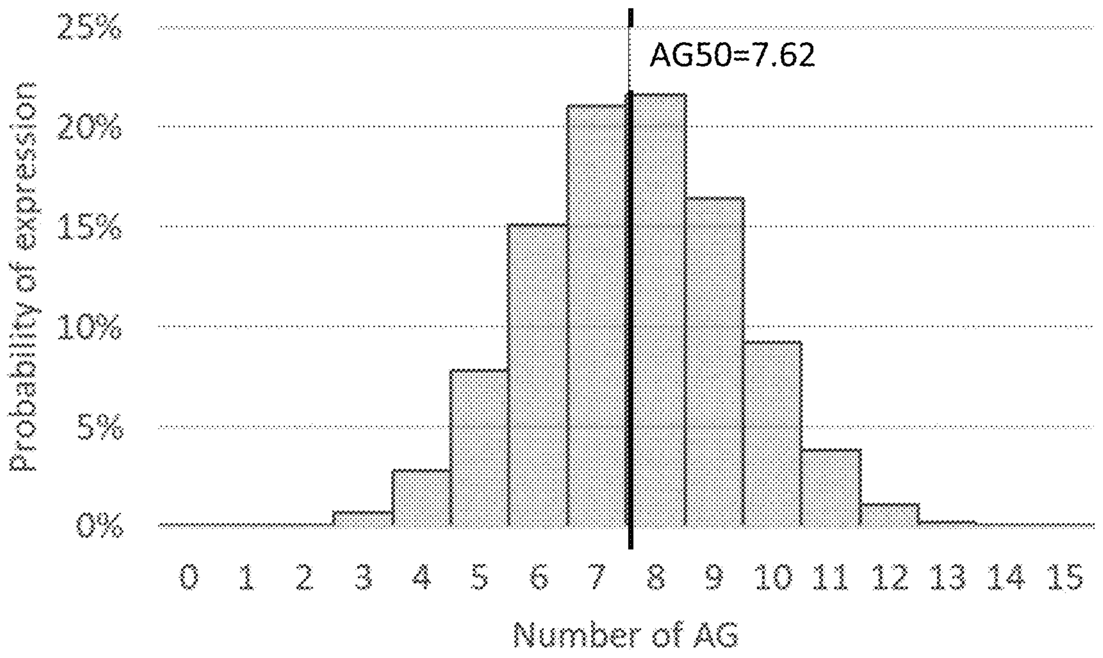
B
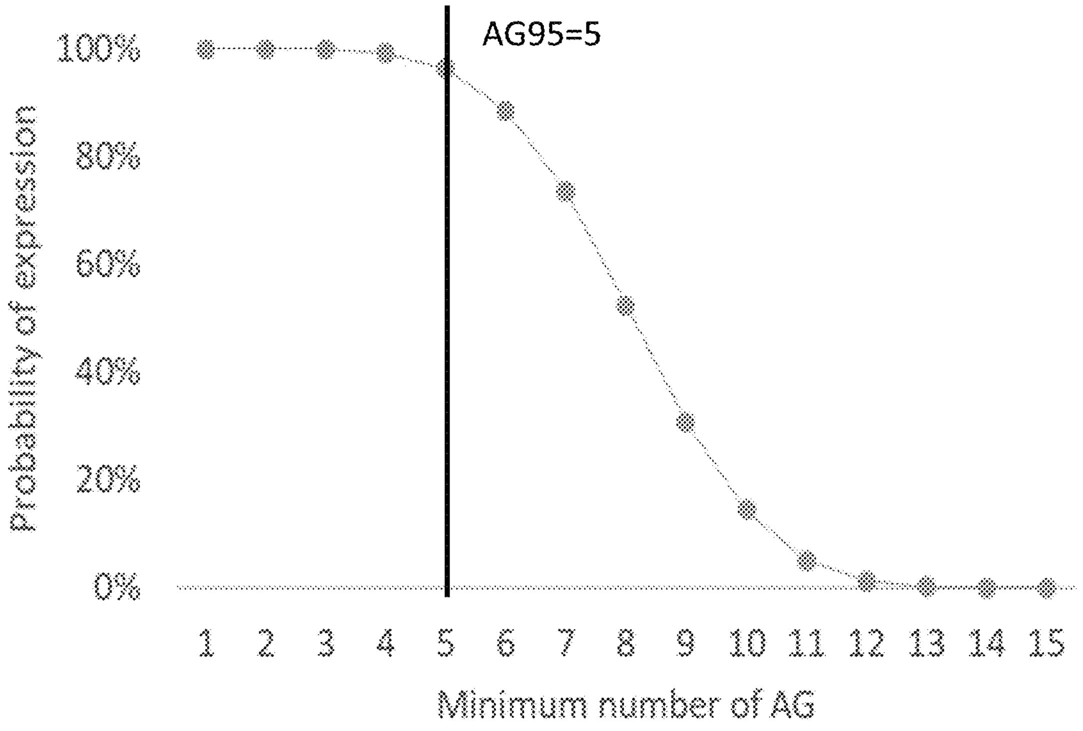

Figure 26
A
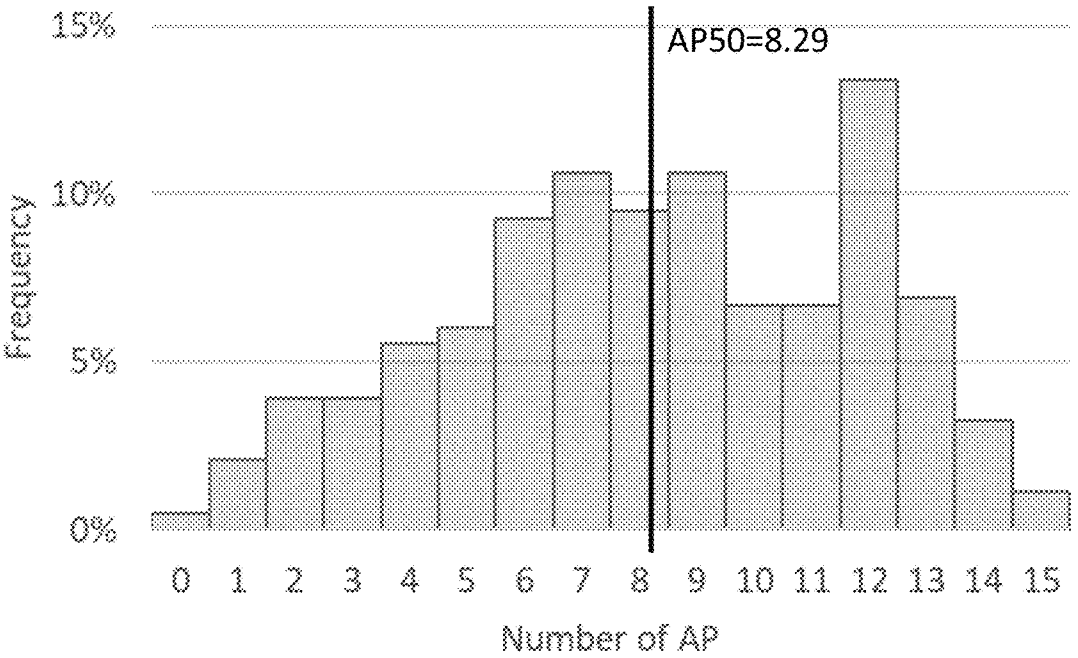
B
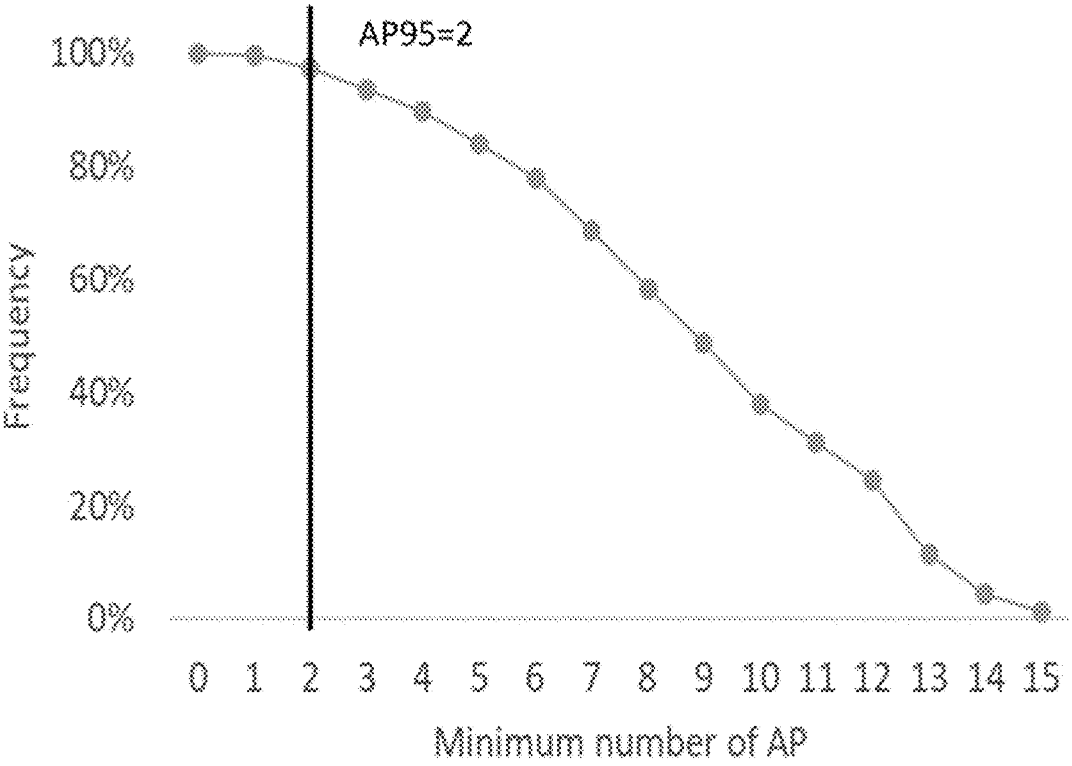

| Antigen | Expression level |
|---|---|
| PIWIL2 | 82% |
| SURVIVIN | 62% |
| MAGE-A9 | 61% |
| MAGE-A8 | 57% |
| EpCAM | 54% |
| CTAGE1 | 53% |
| MAGE-A3 | 42% |
| MAGE-A1 | 34% |
| NY-ESO-1 | 31% |
| LAGE-1 | 30% |
| MAGE-A12 | 29% |
| OY-TES-1 | 28% |
| MAGE-A10 | 28% |
| MAGE-C1 | 27% |
| MAGE-A2 | 25% |
| HAGE | 24% |
| MAGE-C2 | 19% |

Conclusion:

1. 99% of the tumor express ≥3 antigens
2. No biopsy is needed

Figure 30
A
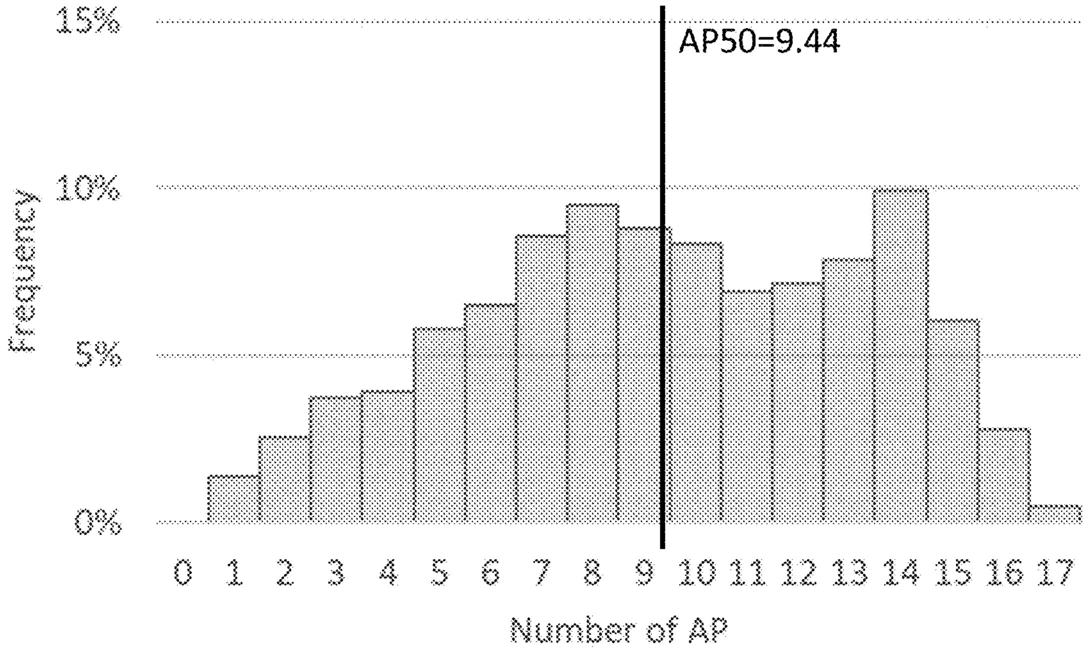
B
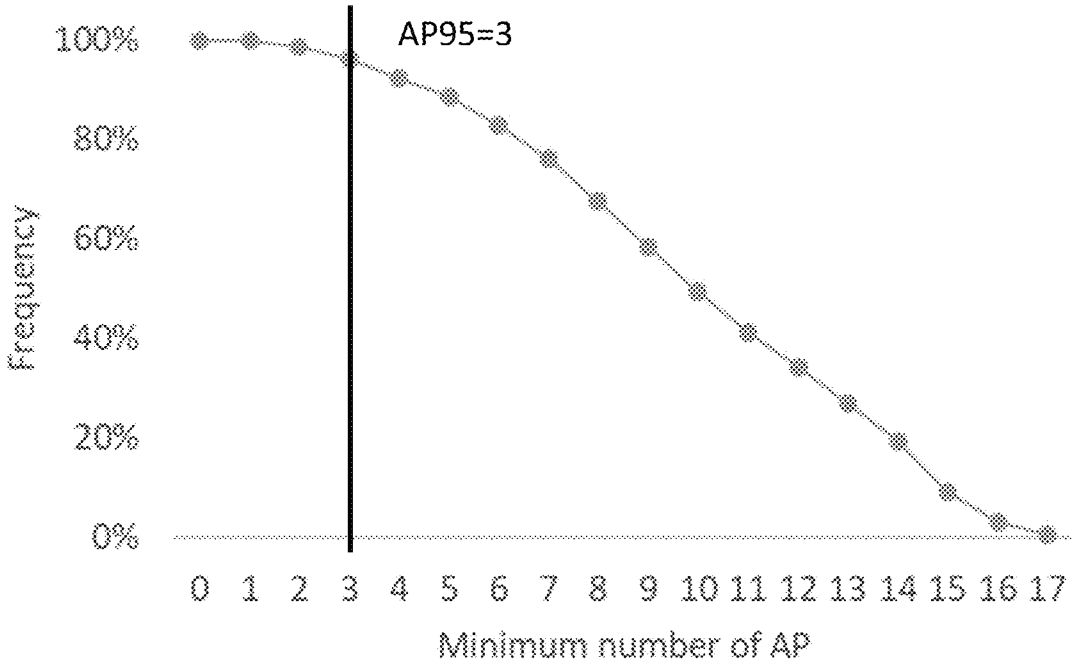

Figure 31
A
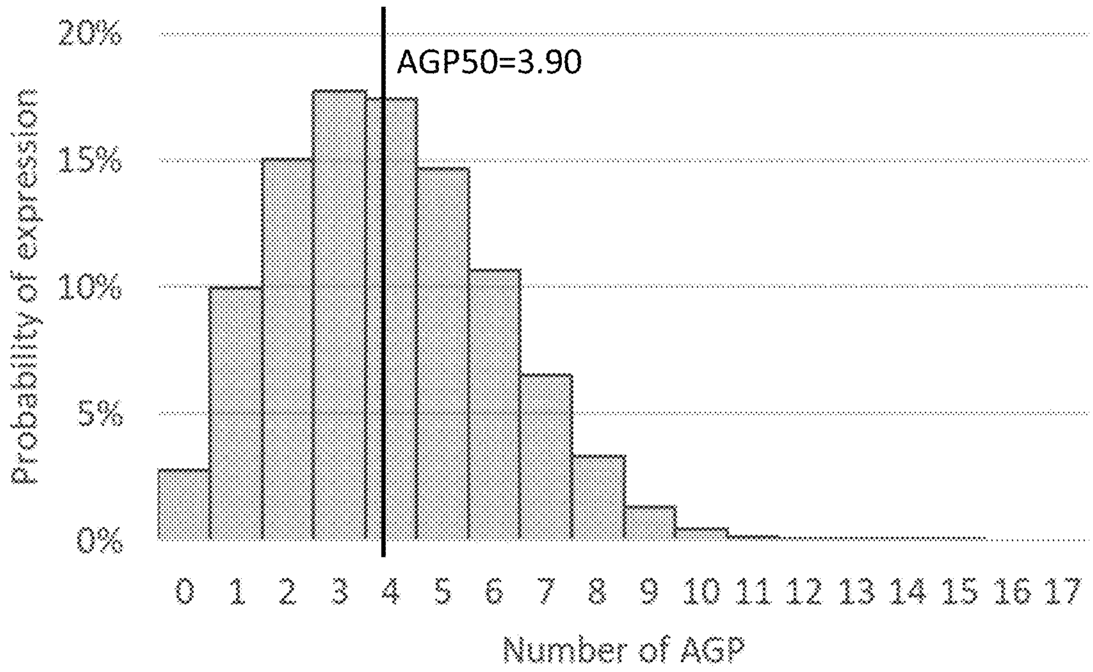
B
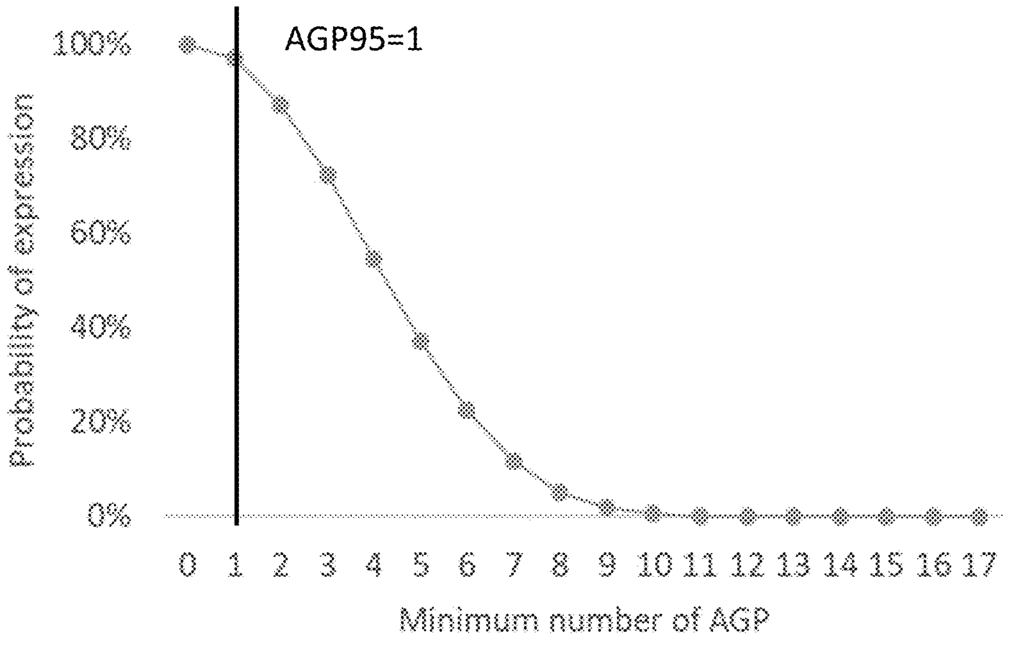

Predicted Immunogenicity, PEPI = 13 : 10 CI95% [9,13] (antigen specific T cell responses)

Detected Immunogenicity: 13 (20-mers) & 13 (9-mers) antigen specific T cell responses Positive T cell responses: >5 fold above control or >3 fold above control and >50 spots Vaccine peptide-specific T cell responses (20-mers)

CD8+ cytotoxic T cell responses (9-mers)

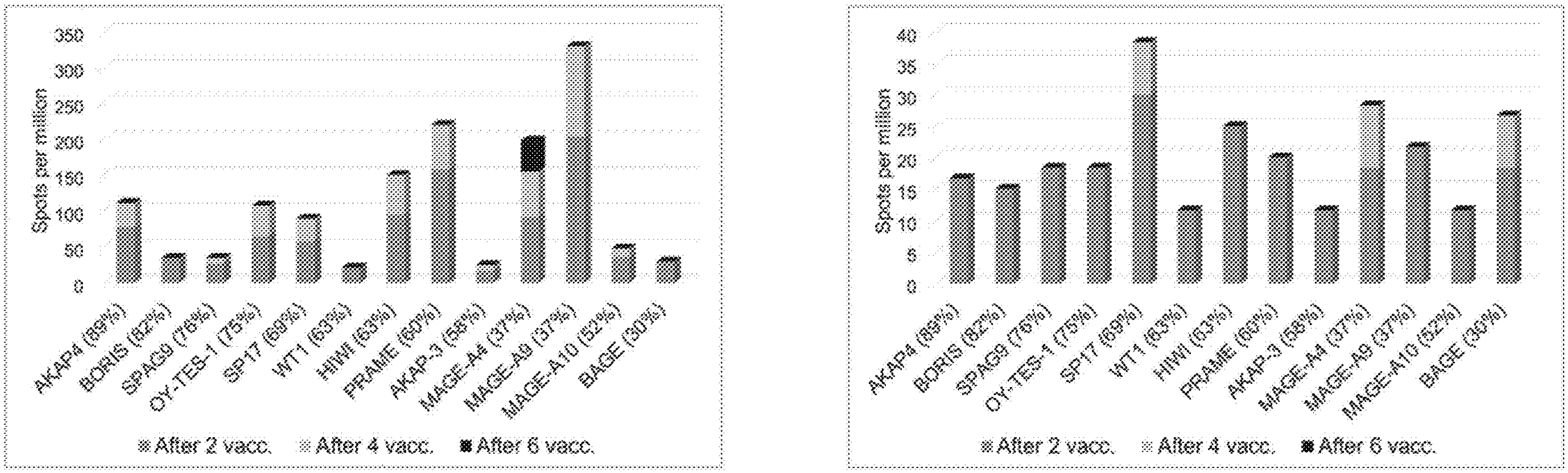

Horizontal axes: Target antigens (expression rate in ovarian cancer)

Figure 34

FUSION PEPTIDE VACCINES

CROSS-REFERENCE

This application is a continuation of U.S. application Ser. No. 17/250,725, filed Feb. 24, 2021, now issued as U.S. Pat. No. 11,666,644 on Jun. 6, 2023, which is the U.S. National Stage entry of International Application No. PCT/EP2019/073476, filed on Sep. 3, 2019, which claims the benefit of and priority to UK Application No. 1814367.7, filed on Sep. 4, 2018, UK Application No. 1814366.9, filed Sep. 4, 2018, UK Application No. 1814365.1, filed Sep. 4, 2018, UK Application No. 1814364.4, filed Sep. 4, 2018, each of which are incorporated herein by reference in their entireties.

REFERENCE TO A SEQUENCE LISTING XML

This application contains a Sequence Listing which has been submitted electronically in XML format. The Sequence Listing XML is incorporated herein by reference. Said XML file, created on Aug. 31, 2023, is named TBL-007C1_SL.xml and is 421,142 bytes in size.

FIELD

The disclosure relates to polypeptides and vaccines that find use in the prevention or treatment of cancer, in particular cancers that express certain antigens expressed in gastric cancers, lung cancers, melanomas and bladder cancers.

BACKGROUND

Cancer is killing millions of people worldwide, because existing drugs do not enable effective prevention or treatment. Current checkpoint inhibitor immunotherapies that re-activate existing immune responses can provide clinical benefit for a fraction of cancer patients. Current cancer vaccines that induce new immune responses are poorly immunogenic and fail to benefit most patients.

Recent analyses of 63,220 unique tumors revealed that cancer vaccines need to be generated specifically for each patient because extensive inter-individual tumor genomic heterogeneity (Hartmaier et al. *Genome Medicine* 2017 9:16). Using state of art technologies it is currently not feasible to scale HLA-specific cancer vaccines to large populations.

SUMMARY

In antigen presenting cells (APC) protein antigens, including tumour associated antigens (TAA), are processed into peptides. These peptides bind to HLA molecules and are presented on the cell surface as peptide-HLA complexes to T cells. Different individuals express different HLA molecules, and different HLA molecules present different peptides. The inventors have demonstrated that an epitope that binds to a single HLA class I allele expressed in a subject is essential, but not sufficient to induce tumor specific T cell responses. Instead tumour specific T cell responses are optimally activated when an epitope is recognised and presented by the HLA molecules encoded by at least three HLA class I genes of an individual (WO/2018/158456, WO/2018/158457, WO/2018/158455, EP 3370065 and EP 3369431).

Based on this discovery the inventors have identified the T cell epitopes from certain gastric and/or lung and/or melanoma and/or bladder cancer associated-polypeptide antigens (tumor specific antigens (TSA) and/or cancer testis antigens (CTA)) that are capable of binding to at least three class I HLA in a high proportion of individuals. These T cell epitopes, or fragments of the antigens comprising the T cell epitopes, are useful for inducing specific immune responses against tumor cells expressing these antigens and for treating or preventing cancer.

In a first aspect the disclosure provides a polypeptide that comprises a fragment of up to 50 consecutive amino acids of (a) a gastric cancer-associated antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein the fragment comprises an amino acid sequence selected from any one of SEQ ID NOs: 1 to 30;

(b) a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119;

(c) a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207; and/or (d) a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297.

In some specific cases the disclosure provides a polypeptide that (a) is a fragment of a gastric cancer-associated antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein the fragment comprises an amino acid sequence selected from any one of SEQ ID NOs: 1 to 30; or (b) comprises or consists of two or more fragments of one or more gastric cancer associated antigens selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein each fragment comprises a different amino acid sequence selected from any one of SEQ ID NOs: 1 to 30, optionally wherein the fragments overlap or are arranged end to end in the polypeptide; or (c) is a fragment of a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119; or (d) comprises or consists of two or more fragments of one or more lung cancer associated antigens selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein each fragment comprises a different amino acid sequence selected from any one of SEQ ID NOs: 90 to 119, optionally wherein the fragments overlap or are arranged end to end in the polypeptide; or (e) is a fragment of a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207; or (f) comprises or consists of two or more fragments of one or more melanoma associated antigens selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein each fragment comprises a different amino acid sequence selected from any one of SEQ ID NOs: 178 to 207, optionally wherein the fragments overlap or are arranged end to end in the polypeptide; or (g) is a fragment of a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297; or (h) comprises or consists of two or more fragments of one or more bladder cancer associated antigens selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein each fragment comprises a different amino acid sequence selected from any one of SEQ ID NOs: 268 to 297, optionally wherein the fragments overlap or are arranged end to end in the polypeptide.

In some specific cases the polypeptide comprises or consists of fragments of at least two different cancer-associated antigens, wherein the cancer-associated antigens are selected from (a) DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1 and wherein each fragment comprises a different amino acid sequence selected from SEQ ID NOs: 1 to 30; and/or (b) BRDT, PRAME, NALP4, MAGE-A12, MAGE-A2, SURVIVIN, DPPA2, NY-SAR-LDHC, MAGE-C2, MAGE-A3, KK-LC-1 and MAGE-A1; and wherein each fragment comprises a different amino acid sequence selected from SEQ ID NOs: 90 to 119; and/or (c) PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1; and wherein each fragment comprises a different amino acid sequence selected from SEQ ID NOs: 178 to 207 and/or (d) PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12; and wherein each fragment comprises a different amino acid sequence selected from SEQ ID NOs: 268 to 297.

In some cases the polypeptide comprises or consists of one or more amino acid sequences selected from SEQ ID NOs: 31 to 60, 90 to 119, 178 to 207 and/or 268 to 297.

In some cases the polypeptide comprises or consists of one or more amino acid sequences selected from SEQ ID NOs: 61 to 75, 120 to 149, 208 to 237, and/or 298 to 327.

In a further aspect the disclosure provides a panel of two or more polypeptides as described above, wherein each peptide comprises or consists of a different amino acid sequence selected from SEQ ID NOs: 1 to 30; and/or SEQ ID NOs: 31 to 60; and/or SEQ ID NOs: 61 to 75; or selected from SEQ ID NOs: 90 to 119; and/or SEQ ID NOs: 120 to 149; and/or SEQ ID NOs: 150 to 164; or selected from SEQ ID NOs: 178 to 207; and/or SEQ ID NOs: 208 to 237; and/or SEQ ID NOs: 238 to 252; or selected from SEQ ID NOs: 268 to 297; and/or SEQ ID NOs: 298 to 327; and/or SEQ ID NOs: 328 to 342.

In a further aspect the disclosure provides a pharmaceutical composition or kit having one or more polypeptides or panels of peptides as described above as active ingredients, or having a polypeptide comprising at least two amino acid sequences selected from SEQ ID NOs: 1 to 30; SEQ ID NOs: 31 to 60; and/or SEQ ID NOs: 61-75; and/or SEQ ID NOs: 90 to 119; SEQ ID NOs: 120 to 149; and/or SEQ ID NOs: 150 to 164; and/or SEQ ID NOs: 178 to 207; and/or SEQ ID NOs: 208 to 237; and/or SEQ ID NOs: 238 to 252; and/or SEQ ID NOs: 268 to 297; and/or SEQ ID NOs: 298 to 327; and/or SEQ ID NOs: 328 to 342 as an active ingredient.

In a further aspect the disclosure provides a method of inducing immune responses, (e.g. vaccination, providing immunotherapy or inducing a CD8+ T cell response in a subject), the method comprising administering to the subject a pharmaceutical composition, kit or the panel of polypeptides as described above. The method may be a method of treating cancer, such as gastric cancer, lung cancer, melanoma and bladder cancer.

In further aspects, the disclosure provides the pharmaceutical composition, kit or panel of polypeptides described above for use in a method of inducing immune responses or for use in a method of treating cancer, optionally gastric cancer, lung cancer, melanoma and bladder cancer; and use of a peptide or a panel of peptides as described above in the manufacture of a medicament for inducing immune responses or for treating cancer, optionally gastric cancer, lung cancer, melanoma and bladder cancer.

In a further aspect the disclosure provides a method of identifying a human subject who will likely have a CD8+ T cell response to administration of a pharmaceutical composition as described above, the method comprising (i) determining that the active ingredient polypeptide(s) of the pharmaceutical composition comprise a sequence that is a T cell epitope capable of binding to at least three HLA class I of the subject; and (ii) identifying the subject as likely to have a CD8+ T cell response to administration of the pharmaceutical composition.

In a further aspect the disclosure provides a method of identifying a subject who will likely have a clinical response to a method of treatment as described above, the method comprising (i) determining that the active ingredient polypeptide(s) comprise two or more different amino acid sequences each of which is a. a T cell epitope capable of binding to at least three HLA class I of the subject; and b. a fragment of a cancer-associated antigen expressed by cancer cells of the subject; and (ii) identifying the subject as likely to have a clinical response to the method of treatment.

In a further aspect the disclosure provides a method of determining the likelihood that a specific human subject will have a clinical response to a method of treatment described above, wherein one or more of the following factors corresponds to a higher likelihood of a clinical response:

(a) presence in the active ingredient polypeptide(s) of a higher number of amino acid sequences and/or different amino acid sequences that are each a T cell epitope capable of binding to at least three HLA class I of the subject;
(b) a higher number of target polypeptide antigens, comprising at least one amino acid sequence that is both
   A. comprised in an active ingredient polypeptide; and
   B. a T cell epitope capable of binding to at least three HLA class I of the subject; optionally wherein the target polypeptide antigens are expressed in the subject, further optionally wherein the target polypeptides antigens are in one or more samples obtained from the subject;
(c) a higher probability that the subject expresses target polypeptide antigens, optionally a threshold number of the target polypeptide antigens and/or optionally target polypeptide antigens that have been determined to comprise at least one amino acid sequence that is both
   A. comprised in in an active ingredient polypeptide; and
   B. a T cell epitope capable of binding to at least three HLA class I of the subject; and/or
(d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
   A. comprised in in an active ingredient polypeptide; and
   B. a T cell epitope capable of binding to at least three HLA class I of the subject.

In some cases the cancer-associated antigens may be a gastric cancer antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1, SSX1, a lung cancer antigen selected from BRDT, PRAME, NALP4, MAGE-A12, MAGE-A2, SURVIVIN, DPPA2NY-SAR-35, LDHC, MAGE-C2, MAGE-A3, KK-LC-1, MAGE-A1, a melanoma antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10, MAGE-A1, and/or a bladder cancer antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8 and HAGE, MAGE-A1, MAGE-C2, MAGE-A10 and MAGE A12. In some cases the methods above comprise the step of determining that one or more cancer-associated antigens is expressed by cancer cells of the subject. The cancer-associated antigen(s) may be present in one or more samples obtained from the subject.

In some cases administration of the pharmaceutical composition or the active ingredient polypeptides of the kit may then be selected as a method of treatment for the subject. The subject may further be treated by administration of the pharmaceutical composition or the active ingredient polypeptides.

In a further aspect the disclosure provides a method of treatment as described above, wherein the subject has been identified as likely to have a clinical response or as having above a threshold minimum likelihood of having a clinical response to the treatment by the method described above.

In a further aspect the disclosure provides a method of identifying a human subject who will likely not have a clinical response to a method of treatment as described above, the method comprising (i) determining that the active ingredient polypeptide(s) of the pharmaceutical composition do not comprise two or more different amino acid sequences each of which is a T cell epitope capable of binding to at least three HLA class I of the subject; and
(ii) identifying the subject as likely not to have a clinical response to the method of treatment.

The methods described above may comprise the step of determining the HLA class I and/or class II genotype of the subject.

The present disclosure includes methods of treating a human subject likely to respond to a polypeptide(s) or pharmaceutical composition comprising the polypeptide(s) of the current disclosure comprising: (a) determining that a polypeptide(s) or pharmaceutical composition comprising the polypeptide(s) comprises an amino acid sequence that is a T cell epitope capable of binding to at least three HLA class I molecules of the human subject; and (b) administering to the human subject the polypeptide or pharmaceutical composition. In certain embodiments, the method further comprises using population expression data for each antigen to determine the likelihood that the human subject will have a CD8+ T cell response that targets one or more polypeptide antigens that are expressed by cancer cells of the human subject, wherein the antigen: (a) is selected from gastric cancer antigens DPPA2, CAGE-1, TSP50, HIWI, SURVIVIN, 5T4, PRAME, KK-LC-1, MAGE-A2, MAGE-A3, LAGE-1, MAGE-A10, MAGE-A1 SSX1, and/or lung cancer antigens BRDT, PRAME, NALP4, MAGE-A12, MAGE-A2, SURVIVIN, DPPA2, NY-SAR-35, LDHC, MAGE-C2, MAGE-A3, KK-LC-1, MAGE-A1, and/or melanoma cancer antigens PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10, MAGE-A1, and/or bladder cancer antigens PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8 and HAGE, MAGE-A1, MAGE-C2, MAGE-A10 and MAGE-A12; and (b) comprises an amino acid sequence that is a fragment of an active ingredient peptide of the pharmaceutical composition, and a T cell epitope capable of binding to at least three HLA class I molecules of the human subject.

The present disclosure includes methods of treating a human subject likely to respond to a polypeptide(s) or pharmaceutical composition comprising the polypeptide(s) of the current disclosure comprising: (a) determining that a polypeptide(s) or pharmaceutical composition comprising the polypeptide(s) comprise two or more different amino acid sequences each of which is a T cell epitope capable of binding to at least three HLA class I molecules of the human subject; and a fragment of a cancer-associated antigen expressed by cancer cells of the human subject, optionally wherein the cancer-associated antigen is present in a sample obtained from the human subject; and (b) administering to the human subject the polypeptide or pharmaceutical composition.

The present disclosure includes methods of treating a human subject likely to respond to a polypeptide(s) or pharmaceutical composition comprising the polypeptide(s) of the current disclosure comprising determining any one of the following: (a) presence in a polypeptide(s) or pharmaceutical composition comprising the polypeptide(s) of a higher number of amino acid sequences and/or different amino acid sequences that are each a T cell epitope capable of binding to at least three HLA class I of the human subject; (b) a higher number of target polypeptide antigens in the human subject or a sample from the human subject, comprising at least one amino acid sequence that is both comprised in an active ingredient polypeptide, and a T cell epitope capable of binding to at least three HLA class I of the human subject; (c) a higher probability that the human subject expresses target polypeptide antigens, optionally a threshold number of the target polypeptide antigens and/or optionally target polypeptide antigens that have been determined to comprise at least one amino acid sequence that is both comprised in in an active ingredient polypeptide, and a T cell epitope capable of binding to at least three HLA class I of the human subject; and/or (d) a higher number of target polypeptide antigens that the human subject is predicted to express, optionally a higher number of target polypeptide antigens that the human subject expresses with a threshold probability, and/or optionally the target polypeptide antigens that have been determined to comprise at least one amino acid sequence that is both comprised in in an active ingredient polypeptide, and a T cell epitope capable of binding to at least three HLA class I of the human subject; and (e) administering to the human subject the polypeptide or pharmaceutical composition. In certain embodiments, the method further comprises identifying which polypeptide antigens targeted by the polypeptide(s) or pharmaceutical composition comprising the polypeptide(s) comprise an amino acid sequence that is both comprised in an active ingredient polypeptide, and a T cell epitope capable of binding to at least three HLA class I of the human subject using population expression data for each antigen identified to determine the probability that the human subject expresses one or more of the antigens identified that together comprise at least two different amino acid sequences; and administering to the human subject the polypeptide or pharmaceutical composition. In certain embodiments, the at least two different amino acid sequences are comprised in the amino acid sequence of two different polypeptide antigens targeted by the active ingredient polypeptide(s).

The disclosure will now be described in more detail, by way of example and not limitation, and by reference to the accompanying drawings. Many equivalent modifications and variations will be apparent, to those skilled in the art when given this disclosure. Accordingly, the exemplary embodiments of the disclosure set forth are considered to be illustrative and not limiting. Various changes to the described embodiments may be made without departing from the scope of the disclosure. All documents cited herein, whether supra or infra, are expressly incorporated by reference in their entirety.

The present disclosure includes the combination of the aspects and preferred features described except where such a combination is clearly impermissible or is stated to be expressly avoided. As used in this specification and the appended claims, the singular forms “a”, “an”, and “the” include plural referents unless the content clearly dictates otherwise. Thus, for example, reference to “a peptide” includes two or more such peptides.

Section headings are used herein for convenience only and are not to be construed as limiting in any way.

Figure 1:
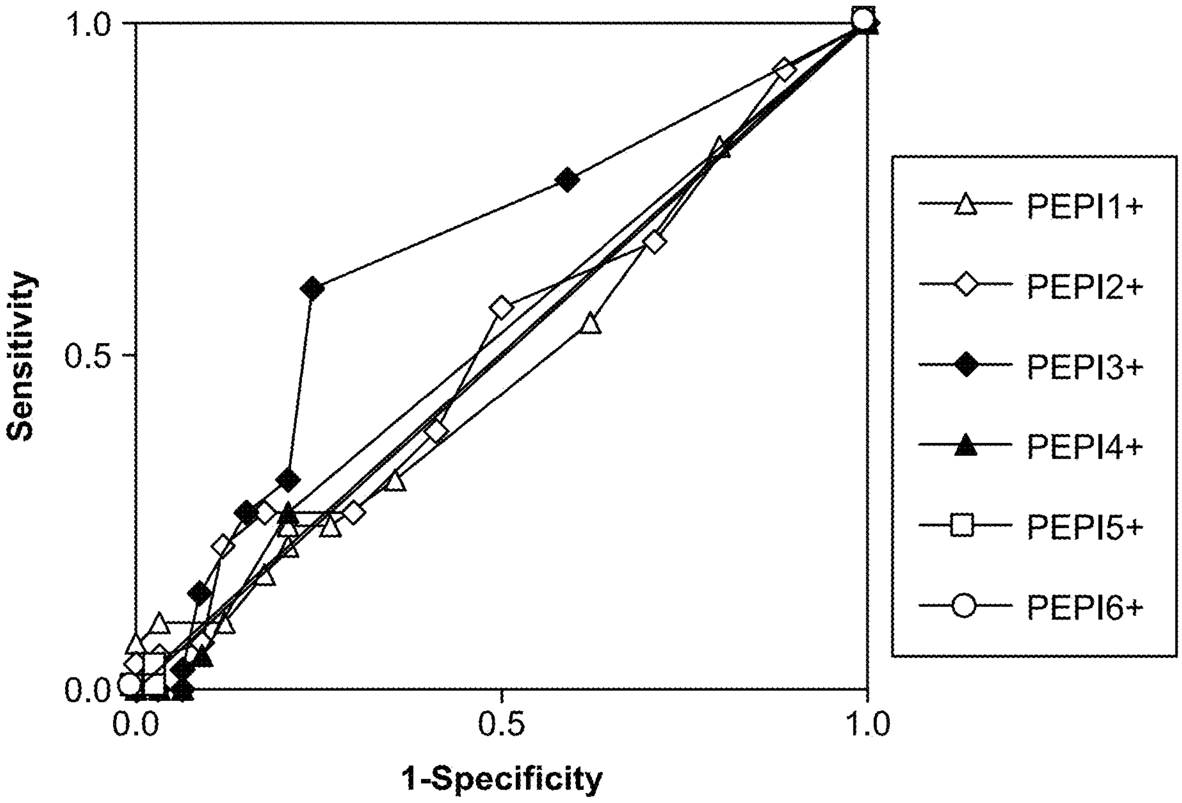
FIG. 1

ROC curve of HLA restricted PEPI biomarkers.

FIG. 2

ROC curve of ≥1 PEPI3+ Test for the determination of the diagnostic accuracy. AUC=0.73 classifies a fair diagnostic value for the PEPI biomarker.

FIGS. 3A-B

Distribution of HLA class I PEPI3+ compared to CD8+ T cell responses measured by a state of art assay among peptide pools used in the CD8+ T cell response assays. 3A: HLA class I restricted PEPI3+s. The 90% Overall Percent of Agreement (OPA) among the T cell responses and PEPI3+ peptides demonstrate the utility of the invented peptides for prediction of vaccine induced T cell response set of individuals ($p<0.001$). 3B: Class I HLA restricted epitopes (PEPI1+). The OPA between predicted epitopes and CD8+ T cell responses was 25% (not statistically significant). True positive (TP), both peptide and T cell responses were detected (shaded); True negative (TN): neither peptides nor T cell responses were detected (shaded); False negative (FN), only T cell responses were detected; False positive (FP), only peptide were detected.

FIG. 4

Correlation between PEPI Test predicted CD4 peptides and T-cell reactivity measured with peptide pools in patients treated with SLP vaccine. A: ≥HLA class II allele-binding PEPIs; B: single HLA class II allele-binding epitopes. Gray: true positive (TP) and true negative (TN) responses; White: false negative (FN) and false positive (FP) responses. TP: both peptide and T cell responses were detected; TN: neither peptides nor T cell responses were detected; FN: only T cell responses were detected; FP: only peptides were detected.

FIG. 5

Multiple HLA binding peptides that define the HPV-16 LPV vaccine specific T cell response set of 20 VIN-3 and 5 cervical cancer patients. PEPI counts were compared to clinical responses after treatment with LPV. Predicted CD8+ T cell responders according to HLA class I PEPIs (A) and CD4+ T cell responders according to HLA class II PEPIs (B). Correlation between HLA class I (C) and class II (D) PEPI count and clinical response at 3 months follow-up in VIN-3 patients. Predicted T cell responders: PEPI count≥1. Gray column, patient with HPV16 E6- and/or E7-specific T cell response; Dashed column, patient without T cell responses. CR, complete clinical responder; PR, partial clinical responder; NR, clinical non-responder.

FIG. 6

The multiple HLA class I binding peptides that define the HPV vaccine specific T cell response set of 2 patients. A: Four HPV antigens in the HPV vaccine. Boxes represent the length of the amino acid sequences from the N terminus to the C terminus. B: Process to identify the multiple HLA binding peptides of two patients: HLA sequences of the patients labelled as 4-digit HLA genotype right from the patient’s ID. The location of the $1^{st}$ amino acid of the 54 and 91 epitopes that can bind to the patient 12-11 and patient 14-5 HLAs (PEPI1+) respectively are depicted with lines. PEPI2 represents the peptides selected from PEPI1+s that can bind to multiple HLAs of a patient (PEPI2+). PEPI3 represent peptides that can bind to ≥3 HLAs of a patient (PEPI3+). PEPI4 represent peptides that can bind to ≥4 HLAs of a patient (PEPI4+). PEPI5 represent peptides that can bind to ≥5 HLAs of a patient (PEPI5+). PEPI6 represent peptides that can bind to 6 HLAs of a patient (PEPI6). C: The DNA vaccine specific PEPI3+ set of two patients characterizes their vaccine specific T cell responses.

FIG. 7

TSA expression probability targeted by IMA901 vaccine.

FIG. 8

HLA Class I allele binding properties of TUMAPs of IMA901 peptide vaccine for 2,915 common alleles. (A) and for the Class I genotype (6 alleles) of 51 HLA-A*02+ RCC patients. Percentages at the bottom indicate the proportion of HLAs the TUMAPs can bind to. Lines in darker grey indicate binding HLA alleles. (B) Probability indicates the proportion of patients who can present the indicated number of TUMAPs with their three or more HLAs. AP indicates number of antigens which can generate at least one PEPI. In this case, since both the antigens and the predicted PEPIs are 9mers, AP=TUMAP=PEPI.

FIG. 9

Correlation between immune response measured for any TUMAP and immune response against expressed antigen on the tumor (AGP)

FIG. 10

Correlation study between immune response rates (IRR) and PEPI Score, between objective response rates (ORR) and MultiPEPI Scores and between objective response rates (ORR) and MultiAg PEPI Scores. A: Preliminary experiment to explore the relationship between PEPI Score and immune response rate of therapeutic vaccines ($r^2$=0.7, p=0.001) B: IRR—PEPI Score plot. ($r^2$=0.47, p=0.001). C: MultiPEPI Score and clinical response rate of therapeutic vaccines ($r^2$=0.75, p=0.001). D: ORRs plotted against the MultiPEPI Score ($r^2$=0.12, p=0.124). E: ORRs plotted against the MultiAg PEPI Score for vaccines with multiple antigens ($r^2$=0.64; p=0.009). F: ORRs plotted against the MultiPEPI Score for vaccines with multiple antigens ($r^2$=0.87; p=0.0002). G: ORRs plotted against the MultiPEPI Score in patients with target antigen positive disease ($r^2$=0.56 and p=0.005). Dark grey dashed lines indicate the 95% confidence interval; grey dashed line indicates the trendline.

FIG. 11

OBERTO trial design (NCT03391232)

FIG. 12

Antigen expression in CRC cohort of OBERTO trial (n=10). A: Expression frequencies of PolyPEPI1018 source antigens determined based on 2391 biopsies. B: PolyPEPI1018 vaccine design specified as 3 out of 7 TSAs are expressed in CRC tumors with above 95% probability. C: In average, 4 out of the 10 patients had pre-existing immune responses against each target antigens, referring to the real expression of the TSAs in the tumors of the patients. D: 7 out of the patients had pre-existing immune responses against minimum of 1 TSA, in average against 3 different TSAs.

FIG. 13

Immunogenicity of PolyPEPI1018 in CRC patients confirms proper target antigen and target peptide selection. Upper part: target peptide selection and peptide design of PolyPEPI1018 vaccine composition. Two 15mers from CRC specific CTA (TSA) selected to contain 9mer PEPI3+ predominant in representative Model population. Table: PolyPEPI1018 vaccine has been retrospectively tested during a preclinical study in a CRC cohort and was proven to be immunogenic in all tested individuals for at least one antigen by generating PEPI3+s. Clinical immune responses were measured specific for at least one antigen in 90% of patients, and multi-antigen immune responses were also found in 90% of patients against at least 2, and in 80% of patients against at least 3 antigens as tested with IFNy fluorospot assay specifically measured for the vaccine-comprising peptides. FIG. 13 discloses SEQ ID NO: 385.

FIGS. 14A-C

Clinical response for PolyPEPI1018 treatment. 14A: Swimmer plot of clinical responses of OBERTO trial (NCT03391232). 14B: Association progression free survival (PFS) and AGP count. 14C: Association tumour volume and AGP count.

FIG. 15

Peptide hotspot analysis example: PRAME antigen hotspot on 433 patients of the Model Population. On the y axis are the 433 patients of the Model Population, on the x axis is the amino acid sequence of the PRAME antigen (CTA). Each data point represents a PEPI presented by HLA class I of one patient starting at the specified amino acid position. The two most frequent PEPIs (called bestEPIs) of the PRAME antigen are highlighted in dark gray (peptide hotspots=PEPI Hotspots).

FIG. 16

CTA Expression Curve calculated by analyzing expression frequency data of tumor specific antigens (CTAs) in human gastric cancer tissues. (No cell line data were included.)

FIG. 17

Antigen expression distribution for gastric cancer based on the calculation of multi-antigen responses from expression frequencies of the selected 14 different CTAs. A: non-cumulative distribution to calculate the expected value for the number of expressed antigens (AG50). This value shows that probably 7.18 vaccine antigens will be expressed by gastric tumor cells. B: cumulative distribution curve of the minimum number of expressed antigens (CTA expression curve). This shows that minimum 5 vaccine antigens will be expressed with 95% probability in gastric cancer cell (AG95).

FIG. 18

PEPI representing antigens: gastric cancer vaccine-specific CTA antigens with ≥1 PEPI, called as "AP") distribution within the Model Population (n=433) for gastric cancer vaccine. A: non-cumulative distribution of AP where the average number of APs is: AP50=7.98, meaning that in average almost 8 CTAs will have PEPIs in the Model Population. B: cumulative distribution curve of the minimum number of APs in the Model Population (n=433). This shows that at least three vaccine antigen will have PEPIs in 95% of the Model Population (n=433) (AP95=3).

FIG. 19

PEPI represented expressed antigen (gastric cancer vaccine-specific CTA antigens expressed by the tumor, for which ≥1 PEPI is predicted, called as "AGP") distribution within the model population (n=433) calculated with CTA expression rates for gastric cancer. A: non-cumulative distribution of AGP where the expected value for number expressed CTAs represented by PEPI is AGP50=3.86. AGP50 is a measure of the effectiveness of the disclosed gastric cancer vaccine in attacking gastric tumor in an unselected patient population. AGP50=3.86 means that at least 3 CTAs from the vaccine will probably be expressed by the gastric tumor cells and present PEPIs in the Model Population. B: cumulative distribution curve of the minimum number of AGPs in the Model Population (n=433) shows that at least 1 of the vaccine CTAs will present PEPIs in 95% of the population and the remaining 5% of the population will likely have no AGP at all (AGP95=1).

FIG. 20

CTA Expression Curve calculated by analyzing expression frequency data of tumor specific antigens (CTAs) in human lung cancer tissues. (No cell line data were included.)

FIG. 21

Antigen expression distribution for lung cancer based on the calculation of multi-antigen responses from expression frequencies of the selected 13 different CTAs. A: non-cumulative distribution to calculate the expected value for the number of expressed antigens (AG50). This value shows that probably 4.76 vaccine antigens will be expressed by lung tumor cells. B: cumulative distribution curve of the minimum number of expressed antigens (CTA expression curve). This shows that minimum 2 vaccine antigens will be expressed with 95% probability in lung cancer cell (AG95).

FIG. 22

PEPI representing antigens: lung cancer vaccine-specific CTA antigens with ≥1 PEPI, called as "AP") distribution within the Model Population (n=433) for lung cancer vaccine. A: non-cumulative distribution of AP where the average number of APs is: AP50=7.6, meaning that in average almost 8 CTAs will have PEPIs in the Model Population. B: cumulative distribution curve of the minimum number of APs in the Model Population (n=433). This shows that at least two vaccine antigen will have PEPIs in 95% of the Model Population (n=433) (AP95=2).

FIG. 23

PEPI represented expressed antigen (lung cancer vaccine-specific CTA antigens expressed by the tumor, for which ≥1 PEPI is predicted, called as "AGP") distribution within the model population (n=433) calculated with CTA expression rates for lung cancer. A: non-cumulative distribution of AGP where the expected value for number expressed CTAs represented by PEPI is AGP50=2.77. AGP50 is a measure of the effectiveness of the disclosed lung cancer vaccine in attacking lung tumor in an unselected patient population. AGP50=2.77 means that at least 3 CTAs from the vaccine will probably be expressed by the lung tumor cells and present PEPIs in the Model Population. B: cumulative distribution curve of the minimum number of AGPs in the Model Population (n=433) shows that at least 1 of the vaccine CTAs will present PEPIs in 91% of the population and the remaining 9% of the population will likely have no AGP at all (AGP95=0).

FIG. 24

CTA Expression Curve calculated by analyzing expression frequency data of tumor specific antigens (CTAs) in human melanoma. (No cell line data were included.)

FIG. 25

Antigen expression distribution for melanoma based on the calculation of multi-antigen responses from expression frequencies of the selected 15 different CTAs. A: non-cumulative distribution to calculate the expected value for the number of expressed antigens (AG50). This value shows that probably 7.62 vaccine antigens will be expressed by gastric tumor cells. B: cumulative distribution curve of the minimum number of expressed antigens (CTA expression curve). This shows that minimum 5 vaccine antigens will be expressed with 95% probability in melanoma cell (AG95).

FIG. 26

PEPI representing antigens: melanoma vaccine-specific CTA antigens with ≥1 PEPI, called as "AP") distribution within the Model Population (n=433) for melanoma vaccine. A: non-cumulative distribution of AP where the average number of APs is: AP50=8.29, meaning that in average 8 CTAs will have PEPIs in the Model Population. B: cumulative distribution curve of the minimum number of APs in the Model Population (n=433). This shows that at least three vaccine antigen will have PEPIs in 95% of the Model Population (n=433) (AP95=2).

FIG. 27

PEPI represented expressed antigen (melanoma vaccine-specific CTA antigens expressed by the tumor, for which ≥1 PEPI is predicted, called as "AGP") distribution within the model population (n=433) calculated with CTA expression rates for melanoma. A: non-cumulative distribution of AGP where the expected value for number expressed CTAs represented by PEPI is AGP50=4.22. AGP50 is a measure of the effectiveness of the disclosed melanoma vaccine in attacking gastric tumor in an unselected patient population. AGP50=4.22 means that at least 3 CTAs from the vaccine will probably be expressed by the gastric tumor cells and present PEPIs in the Model Population. B: cumulative distribution curve of the minimum number of AGPs in the Model Population (n=433) shows that at least 1 of the vaccine CTAs will present PEPIs in 95% of the population and the remaining 5% of the population will likely have no AGP at all (AGP95=1).

FIG. 28

CTA Expression Curve calculated by analyzing expression frequency data of tumor specific antigens (CTAs) in human bladder cancer tissues. (No cell line data were included.)

FIG. 29

Antigen expression distribution for bladder cancer based on the calculation of multi-antigen responses from expression frequencies of the selected 17 different CTAs. A: non-cumulative distribution to calculate the expected value for the number of expressed antigens (AG50). This value shows that probably 8.85 vaccine antigens will be expressed by bladder tumor cells. B: cumulative distribution curve of the minimum number of expressed antigens (CTA expression curve). This shows that minimum 4 vaccine antigens will be expressed with 95% probability in bladder cancer cell (AG95).

FIG. 30

PEPI representing antigens: bladder cancer vaccine-specific CTA antigens with ≥1 PEPI, called as "AP") distribution within the Model Population (n=433) for bladder cancer vaccine. A: non-cumulative distribution of AP where the average number of APs is: AP50=9.44, meaning that in average almost 8 CTAs will have PEPIs in the Model Population. B: cumulative distribution curve of the minimum number of APs in the Model Population (n=433). This shows that at least three vaccine antigen will have PEPIs in 95% of the Model Population (n=433) (AP95=3).

FIG. 31

PEPI represented expressed antigen (bladder cancer vaccine-specific CTA antigens expressed by the tumor, for which ≥1 PEPI is predicted, called as "AGP") distribution within the model population (n=433) calculated with CTA expression rates for bladder cancer. A: non-cumulative distribution of AGP where the expected value for number expressed CTAs represented by PEPI is AGP50=3.90. AGP50 is a measure of the effectiveness of the disclosed bladder cancer vaccine in attacking bladder tumor in an unselected patient population. AGP50=3.90 means that at least 3 CTAs from the vaccine will probably be expressed by the bladder tumor cells and present PEPIs in the Model Population. B: cumulative distribution curve of the minimum number of AGPs in the Model Population (n=433) shows that at least 1 of the vaccine CTAs will present PEPIs in 95% of the population and the remaining 5% of the population will likely have no AGP at all (AGP95=1).

FIG. 32

Probability of vaccine antigen expression in the Patient-A's tumor cells. There is over 95% probability that 5 out of the 13 target antigens in the vaccine regimen is expressed in the patient's tumor. Consequently, the 13 peptide vaccines together can induce immune responses against at least 5 ovarian cancer antigens with 95% probability (AGP95). It has 84% probability that each peptide will induce immune responses in the Patient-A. AGP50 is the mean (expected value)=7.9 (it is a measure of the effectiveness of the vaccine in attacking the tumor of Patient-A).

FIG. 33

Treatment schedule of Patient-A.

FIG. 34

T cell responses of patient-A. A. Left: Vaccine peptide-specific T cell responses (20-mers). right: CD8+ cytotoxic T cell responses (9-mers). Predicted T cell responses are confirmed by bioassay.

FIG. 35

MRI findings of Patient-A treated with personalised (PIT) vaccine. This late stage, heavily pretreated ovarian cancer patient had an unexpected objective response after the PIT vaccine treatment. These MRI findings suggest that PIT vaccine in combination with chemotherapy significantly reduced her tumor burden.

FIG. 36

Probability of vaccine antigen expression in the Patient-B's tumor cells and treatment schedule of Patient-B. A: There is over 95% probability that 4 out of the 13 target antigens in the vaccine is expressed in the patient's tumor. B: Consequently, the 12 peptide vaccines together can induce immune responses against at least 4 breast cancer antigens with 95% probability (AGP95). It has 84% probability that each peptide will induce immune responses in the Patient-B. AGP50=6.45; it is a measure of the effectiveness of the vaccine in attacking the tumor of Patient-B. C: Treatment schedule of Patient-B.

FIG. 37

T cell responses of Patient-A. Left: Vaccine peptide-specific T cell responses (20-mers) of P. Right: Kinetic of vaccine-specific CD8+ cytotoxic T cell responses (9-mers). Predicted T cell responses are confirmed by bioassay.

FIG. 38

Treatment schedule of Patient-C.

FIG. 39

T cell responses of Patient-C. A: Vaccine peptide-specific T cell responses (20-mers). B: Vaccine peptide-specific CD8+ T cell responses (9-mers). C-D: Kinetics of vaccine-specific CD4+ T cells and CD8+ cytotoxic T cell responses (9-mers), respectively. Long lasting immune responses both CD4 and CD 8 T cell specific are present after 14 months.

FIG. 40

Treatment schedule of Patient-D.

FIG. 41

Immune responses of Patient-D for PIT treatment. A: CD4+ specific T cell responses (20mer) and B: CD8+ T cell specific T cell responses (9mer). 0.5-4 months refer to the timespan following the last vaccination until PBMC sample collection.

FIG. 42

Schematic showing exemplary positions of amino acids in overlapping HLA class I- and HLA class-II binding epitopes in a 30-mer peptide.

DESCRIPTION OF THE SEQUENCES

SEQ ID NOs: 1 to 30 set forth 9 mer T cell epitopes described in Table 20a.

SEQ ID NOs: 31 to 60 set forth 15 mer T cell epitopes described in Table 20a.

SEQ ID NOs: 61 to 75 set forth gastric cancer vaccine peptides described in Table 21a.

SEQ ID NOs: 76 to 89 set forth gastric cancer associated antigens.

SEQ ID NOs: 90 to 119 set forth 9 mer T cell epitopes described in Table 20b.

SEQ ID NOs: 120 to 149 set forth 15 mer T cell epitopes described in Table 20b.

SEQ ID NOs: 150 to 164 set forth lung cancer vaccine peptides described in Table 21b.

SEQ ID NOs: 165 to 177 set forth lung cancer associated antigens.

SEQ ID NOs: 178 to 207 set forth 9 mer T cell epitopes described in Table 20c.

SEQ ID NOs: 208 to 237 set forth 15 mer T cell epitopes described in Table 20c.

SEQ ID NOs: 238 to 252 set forth melanoma vaccine peptides described in Table 21c.

SEQ ID NOs: 253 to 267 set forth melanoma associated antigens.

SEQ ID NOs: 268 to 297 set forth 9 mer T cell epitopes described in Table 20d.

SEQ ID NOs: 298 to 327 set forth 15 mer T cell epitopes described in Table 20d.

SEQ ID NOs: 328 to 342 set forth bladder cancer vaccine peptides described in Table 21d.

SEQ ID NOs: 343 to 359 set forth bladder cancer associated antigens.

SEQ ID NOs: 360 to 372 set forth sequences of personalized vaccine of Patient-A and are described in Table 22.

SEQ ID NOs: 373 to 384 set forth sequences of personalized vaccine of Patient-B and are described in Table 24.

SEQ ID NO: 385 sets forth the 30 amino acid CRC P3 peptide, FIG. 13.

SEQ ID NOs: 386 to 394 set forth the 9mer sequences shown in FIG. 8.

DETAILED DESCRIPTION

HLA Genotypes

HLAs are encoded by the most polymorphic genes of the human genome. Each person has a maternal and a paternal allele for the three HLA class I molecules (HLA-A*, HLA-B*, HLA-C*) and four HLA class II molecules (HLA-DP*, HLA-DQ*, HLA-DRB1*, HLA-DRB3*/4*/5*). Practically, each person expresses a different combination of 6 HLA class I and 8 HLA class II molecules that present different epitopes from the same protein antigen. The function of HLA molecules is to regulate T cell responses.

The nomenclature used to designate the amino acid sequence of the HLA molecule is as follows: gene name*allele:protein number, which, for instance, can look like: HLA-A*02:25. In this example, "02" refers to the allele. In most instances, alleles are defined by serotypes—meaning that the proteins of a given allele will not react with each other in serological assays. Protein numbers ("25" in the example above) are assigned consecutively as the protein is discovered. A new protein number is assigned for any protein with a different amino acid sequence determining the binding specificity to non-self antigenic peptides (e.g. even a one amino acid change in sequence is considered a different protein number). Further information on the nucleic acid sequence of a given locus may be appended to the HLA nomenclature, but such information is not required for the methods described herein.

The HLA class I genotype or HLA class II genotype of an individual may refer to the actual amino acid sequence of each class I or class II HLA of an individual, or may refer to the nomenclature, as described above, that designates, minimally, the allele and protein number of each HLA gene. In some embodiments, the HLA genotype of an individual is obtained or determined by assaying a biological sample from the individual. The biological sample typically contains subject DNA. The biological sample may be, for example, a blood, serum, plasma, saliva, urine, expiration, cell or tissue sample. In some embodiments the biological sample is a saliva sample. In some embodiments the biological sample is a buccal swab sample. An HLA genotype may be obtained or determined using any suitable method. For example, the sequence may be determined via sequencing the HLA gene loci using methods and protocols known in the art. In some embodiments, the HLA genotype is determined using sequence specific primer (SSP) technologies. In some embodiments, the HLA genotype is determined using sequence specific oligonucleotide (SSO) technologies. In some embodiments, the HLA genotype is determined using sequence based typing (SBT) technologies. In some embodiments, the HLA genotype is determined using next generation sequencing. Alternatively, the HLA set of an individual may be stored in a database and accessed using methods known in the art.

Some subjects may have two HLA alleles that encode the same HLA molecule (for example, two copies for HLA-A*02:25 in case of homozygosity). The HLA molecules encoded by these alleles bind all of the same T cell epitopes. For the purposes of this disclosure "binding to at least two HLA molecules of the subject" as used herein includes binding to the HLA molecules encoded by two identical HLA alleles in a single subject. In other words, "binding to at least two HLA molecules of the subject" and the like could otherwise be expressed as "binding to the HLA molecules encoded by at least two HLA alleles of the subject".

HLA-Epitope Binding

A given HLA of a subject will only present to T cells a limited number of different peptides produced by the processing of protein antigens in an APC. As used herein, "display" or "present", when used in relation to HLA, references the binding between a peptide (epitope) and an HLA. In this regard, to "display" or "present" a peptide is synonymous with "binding" a peptide.

As used herein, the term "epitope" or "T cell epitope" refers to a sequence of contiguous amino acids contained within a protein antigen that possess a binding affinity for (is capable of binding to) one or more HLAs. An epitope is HLA- and antigen-specific (HLA-epitope pairs, predicted with known methods), but not subject specific. An epitope, a T cell epitope, a polypeptide, a fragment of a polypeptide or a composition comprising a polypeptide or a fragment thereof is "immunogenic" for a specific human subject if it is capable of inducing a T cell response (a cytotoxic T cell response or a helper T cell response) in that subject. In some cases the helper T cell response is a Th1-type helper T cell response. In some cases an epitope, a T cell epitope, a polypeptide, a fragment of a polypeptide or a composition comprising a polypeptide or a fragment thereof is "immunogenic" for a specific human subject if it is more likely to induce a T cell response or immune response in the subject than a different T cell epitope (or in some cases two different T cell epitopes each) capable of binding to just one HLA molecule of the subject.

The terms "T cell response" and "immune response" are used herein interchangeably, and refer to the activation of T cells and/or the induction of one or more effector functions following recognition of one or more HLA-epitope binding pairs. In some cases an "immune response" includes an antibody response, because HLA class II molecules stimulate helper responses that are involved in inducing both long lasting CTL responses and antibody responses. Effector functions include cytotoxicity, cytokine production and proliferation. According to the present disclosure, an epitope, a T cell epitope, or a fragment of a polypeptide is immunogenic for a specific subject if it is capable of binding to at least two, or in some cases at least three, class I or at least two, or in some cases at least three or at least four class II HLAs of the subject.

The term "personal epitope", or "PEPI" as used herein distinguishes a subject-specific epitope from an HLA specific epitope. A "PEPI" is a fragment of a polypeptide consisting of a sequence of contiguous amino acids of the polypeptide that is a T cell epitope capable of binding to one or more HLA class I molecules of a specific human subject. In other cases a "PEPI" is a fragment of a polypeptide consisting of a sequence of contiguous amino acids of the polypeptide that is a T cell epitope capable of binding to one or more HLA class II molecules of a specific human subject. In other words a "PEPI" is a T cell epitope that is recognised by the HLA set of a specific individual, and is consequently specific to the subject in addition to the HLA and the antigen. In contrast to an "epitope", which is specific only to HLA and the antigen, PEPIs are specific to an individual because different individuals have different HLA molecules which each bind to different T cell epitopes. This subject specificity of the PEPIs allows to make personalized cancer vaccines.

"PEPI1" as used herein refers to a peptide, or a fragment of a polypeptide, that can bind to one HLA class I molecule (or, in specific contexts, HLA class II molecule) of an individual. "PEPI1+" refers to a peptide, or a fragment of a polypeptide, that can bind to one or more HLA class I (or II) molecule of an individual.

"PEPI2" refers to a peptide, or a fragment of a polypeptide, that can bind to two HLA class I (or II) molecules of an individual. "PEPI2+" refers to a peptide, or a fragment of a polypeptide, that can bind to two or more HLA class I (or II) molecules of an individual, i.e. a fragment identified according to a method of the disclosure.

"PEPI3" refers to a peptide, or a fragment of a polypeptide, that can bind to three HLA class I (or II) molecules of an individual. "PEPI3+" refers to a peptide, or a fragment of a polypeptide, that can bind to three or more HLA class I (or II) molecules of an individual.

"PEPI4" refers to a peptide, or a fragment of a polypeptide, that can bind to four HLA class I (or II) molecules of an individual. "PEPI4+" refers to a peptide, or a fragment of a polypeptide, that can bind to four or more HLA class I (or II) molecules of an individual.

"PEPI5" refers to a peptide, or a fragment of a polypeptide, that can bind to five HLA class I (or II) molecules of an individual. "PEPI5+" refers to a peptide, or a fragment of a polypeptide, that can bind to five or more HLA class I (or II) molecules of an individual.

"PEPI6" refers to a peptide, or a fragment of a polypeptide, that can bind to all six HLA class I (or six HLA class II) molecules of an individual.

Generally speaking, epitopes presented by HLA class I molecules are about nine amino acids long and epitopes presented by HLA class II molecules are about fifteen amino acids long. For the purposes of this disclosure, however, an epitope may be more or less than nine (for HLA Class I) or fifteen (for HLA Class II) amino acids long, as long as the epitope is capable of binding HLA. For example, an epitope that is capable of binding to class I HLA may be between 7, or 8 or 9 and 9 or 10 or 11 amino acids long. An epitope that is capable of binding to a class II HLA may be between 13, or 14 or 15 and 15 or 16 or 17 amino acids long.

Using techniques known in the art, it is possible to determine the epitopes that will bind to a known HLA. Any suitable method may be used, provided that the same method is used to determine multiple HLA-epitope binding pairs that are directly compared. For example, biochemical analysis may be used. It is also possible to use lists of epitopes known to be bound by a given HLA. It is also possible to use predictive or modelling software to determine which epitopes may be bound by a given HLA. Examples are provided in Table 1. In some cases a T cell epitope is capable of binding to a given HLA if it has an IC50 or predicted IC50 of less than 5000 nM, less than 2000 nM, less than 1000 nM, or less than 500 nM.

TABLE 1

Example software for determining epitope-HLA binding

| EPITOPE PREDICTION TOOLS | WEB ADDRESS |
|---|---|
| BIMAS, NIH | bimas.cit.nih.gov/molbio/hla_bind/ |
| PPAPROC, Tubingen Univ. | |
| MHCPred, Edward Jenner Inst, of Vaccine Res. | |
| EpiJen, Edward Jenner Inst, of Vaccine Res. | ddg-pharmfac.net/epijen/EpiJen/EpiJen.htm |
| NetMHC, Center for Biological Sequence Analysis | cbs.dtu.dk/services/NetMHC/ |
| SVMHC, Tubingen Univ. | abi.inf.uni-tuebingen.de/Services/SVMHC/ |
| SYFPEITHI, Biomedical Informatics, Heidelberg | syfpeithi.de/bin/MHCServer.dll/EpitopePrediction.htm |
| ETK EPITOOLKIT, Tubingen Univ. | etk.informatik.uni-tuebingen.de/epipred/ |
| PREDEP, Hebrew Univ. Jerusalem | margalit.huji.ac.il/Teppred/mhc-bind/index.html |
| RANKPEP, MIF Bioinformatics | bio.dfci.harvard.edu/RANKPEP/ |
| IEDB, Immune Epitope Database | tools.immuneepitope.org/main/html/tcell_tools.html |
| **EPITOPE DATABASES** | **WEB ADDRESS** |
| MHCBN, Institute of Microbial Technology, Chandigarh, INDIA | imtech.res.in/raghava/mhcbn/ |
| SYFPEITHI, Biomedical Informatics, Heidelberg | syfpeithi.de/ |
| AntiJen, Edward Jenner Inst, of Vaccine Res. | ddg-pharmfac.net/antijen/AntiJen/antijenhomepage.htm |
| EPIMHC database of MHC ligands, MIF Bioinformatics | immunax.dfci.harvard.edu/epimhc/ |
| IEDB, Immune Epitope Database | iedb.org/ |

HLA molecules regulate T cell responses. Until recently, the triggering of an immune response to individual epitopes was thought to be determined by recognition of the epitope by the product of single HLA allele, i.e. HLA-restricted epitopes. However, HLA-restricted epitopes induce T cell responses in only a fraction of individuals. Peptides that activate a T cell response in one individual are inactive in others despite HLA allele matching. Therefore, it was previously unknown how an individual's HLA molecules present the antigen-derived epitopes that positively activate T cell responses.

The inventors discovered that multiple HLA expressed by an individual need to present the same peptide in order to trigger a T cell response. Therefore the fragments of a polypeptide antigen (epitopes) that are immunogenic for a specific individual (PEPIs) are those that can bind to multiple class I (activate CD8+ T cells eg, cytotoxic T cells) or class II (activate CD4+ T cells, eg. helper T cells or CD4+ killer cells) HLAs expressed by that individual. This discovery is described in PCT/EP2018/055231, PCT/EP2018/055232, PCT/EP2018/055230, EP 3370065 and EP 3369431.

Polypeptides

The disclosure relates to polypeptides that are derived from CTAs and that are immunogenic for a high proportion of the human population.

As used herein, the term "polypeptide" refers to a full-length protein, a portion of a protein, or a peptide characterized as a string of amino acids. As used herein, the term "peptide" refers to a short polypeptide comprising between 2, or 3, or 4, or 5, or 6, or 7, or 8, or 9, or 10, or 11, or 12, or 13, or 14, or 15 and 10, or 11, or 12, or 13, or 14, or 15, or 20, or 25, or 30, or 35, or or 45, or 50 or 55 or 60 amino acids. The polypeptides are typically about 9 to 50 or 15 to 40 or 20 to 30 amino acids long.

The terms "fragment" or "fragment of a polypeptide" as used herein refer to a string of amino acids or an amino acid sequence typically of reduced length relative to the or a reference polypeptide and comprising, over the common portion, an amino acid sequence identical to the reference polypeptide. Such a fragment according to the disclosure may be, where appropriate, included in a larger polypeptide of which it is a constituent. In some cases the fragment may comprise the full length of the polypeptide, for example where the whole polypeptide, such as a 9 amino acid peptide, is a single T cell epitope. In some cases the fragments referred to herein may be between 2, or 3, or 4, or 5 or 6 or 7 or 8 or 9 and 20, or 25, or 30, or 35, or 40, or 45, or amino acids.

In some embodiments the peptides of the disclosure may comprise or consist of one or more fragments of one or more CTAs. CTAs are not typically expressed beyond embryonic development in healthy cells. In healthy adults, CTA expression is limited to male germ cells that do not express HLAs and cannot present antigens to T cells. Therefore, CTAs are considered expressional neoantigens when expressed in cancer cells.

CTAs are a good choice for cancer vaccine targets because their expression is (i) specific for tumor cells, (ii) more frequent in metastases than in primary tumors and (iii) conserved among metastases of the same patient (Gajewski ed. Targeted Therapeutics in Melanoma. Springer New York. 2012).

The peptides of the disclosure may comprise or consist of one or more fragments of one or more gastric cancer-associated antigens selected from DPPA2 (SEQ ID NO: 76, Q7Z7J5.1), CAGE-1 (SEQ ID NO: 77, Q8TC20.1), TSP50 (SEQ ID NO: 78, Q9UI38.1), HIWI (SEQ ID NO: 79, Q96J94.1), SURVIVIN (SEQ ID NO: 80, 015392.1), 5T4 (SEQ ID NO: 81, Q13641.1), PRAME (SEQ ID NO:82, P78395.1), KK-LC-1 (SEQ ID NO 83, Q5H943.1), MAGE-A2 (SEQ ID NO: 84, P43356.1), MAGE-A3 (SEQ ID NO: 85, P43357.1), LAGE-1 (SEQ ID NO: 86, 075638.1), MAGE-A10 (SEQ ID NO: 87, P43363.1), MAGE-A1 (SEQ ID NO: 88, P43355.1) and SSX1 (SEQ ID NO: 89, Q16384.1); and/or one or more lung cancer-associated antigens selected from BRDT (SEQ ID NO: 165, Q58F21.1), PRAME (SEQ ID NO: 166, P78395.1), NALP4 (SEQ ID NO: 167, Q96MN2.1), MAGE-A12 (SEQ ID NO: 168, P43365.1), MAGE-A2 (SEQ ID NO: 169, P43356.1), SURVIVIN (SEQ ID NO: 170, 015392.1), DPPA2 (SEQ ID NO:171, Q7Z7J5.1), NY-SAR-35 (SEQ ID NO 172, Q8NOW7.1), LDHC (SEQ ID NO: 173, P07864.1), MAGE-C2 (SEQ ID NO: 174, Q9UBF1.1), MAGE-A3 (SEQ ID NO: 175, P43357.1), KK-LC-1 (SEQ ID NO: 176, Q5H943.1) and MAGE-A1 (SEQ ID NO: 177, P43355.1); and/or one or more melanoma cancer-associated antigens selected from PRAME (SEQ ID NO: 253, P78395.1), MAGE-A2 (SEQ ID NO: 254, P43356.1), MAGE-C1 (SEQ ID NO: 255, P43355.1), SURVIVIN (SEQ ID NO: 256, 015392.1), MAGE-A12 (SEQ ID NO: 257, P43365.1), Ny-ESO-1 (SEQ ID NO: 258, P78358.1), MAGE-C2 (SEQ ID NO:259, Q9UBF1.1), MAGE-A6 (SEQ ID NO 260, P43360.1), BORIS (SEQ ID NO: 261, Q8NI51.1), LAGE-1 (SEQ ID NO: 262, 075638.1), MAGE-A11 (SEQ ID NO: 263, P43364.1), SSX-1 (SEQ ID NO: 264, Q16384.1), MAGE-A3 (SEQ ID NO: 265, P43357.1) MAGE-A10 (SEQ ID NO: 266, P43363.1) and MAGE-A1 (SEQ ID NO: 267, P43355.1); and/or one or more bladder cancer-associated antigens selected from PIWIL2 (SEQ ID NO: 343, Q8TC59.1), CTAGE1 (SEQ ID NO: 344, Q96RT6.1), MAGE-A9 (SEQ ID NO: 345, P43362.1), EpCAM (SEQ ID NO: 346, P16422.1), OY-TES-1 (SEQ ID NO: 347, Q8NEB7.1), NY-ESO-1 (SEQ ID NO: 348, P78358.1), SURVIVIN (SEQ ID NO:349, 015392.1), MAGE-C1 (SEQ ID NO 350, 060732.1), MAGE-A2 (SEQ ID NO: 351, P43356.1), LAGE-1 (SEQ ID NO: 352, 075638.1), MAGE-A3 (SEQ ID NO: 353, P43357.1), MAGE-A8 (SEQ ID NO: 354, P43361.1), HAGE (SEQ ID NO: 355, Q9NXZ2.1), MAGE-A1 (SEQ ID NO: 356, P43355.1), MAGE-C2 (SEQ ID NO: 357, Q9UBF1.1), MAGE-A10 (SEQ ID NO: 358, P43363.1), and MAGE-A12 (SEQ ID NO: 359, P43365.1).

In some cases the amino acid sequence is flanked at the N and/or C terminus by additional amino acids that are not part of the sequence of the target polypeptide antigen, in other words that are not the same sequence of consecutive amino acids found adjacent to the selected fragments in the target polypeptide antigen. In some cases the sequence is flanked by up to 41 or or 30 or 25 or 20 or 15 or 10, or 9 or 8 or 7 or 6 or 5 or 4 or 3 or 2 or 1 additional amino acid at the N and/or C terminus or between target polypeptide fragments. In other cases each polypeptide either consists of a fragment of a target polypeptide antigen, or consists of two or more such fragments arranged end to end (arranged sequentially in the peptide end to end) or overlapping in a single peptide (where two or more of the fragments comprise partially overlapping sequences, for example where two PEPIs in the same polypeptide are within 50 amino acids of each other). Typically each polypeptide may comprise at least one fragment of a target polypeptide antigen wherein the fragment comprises an amino acid sequence that is a T cell epitope capable of binding to at least three or at least four HLA class II alleles in some subjects or a high proportion of subjects or the maximum proportion of subjects.

Figure 42:
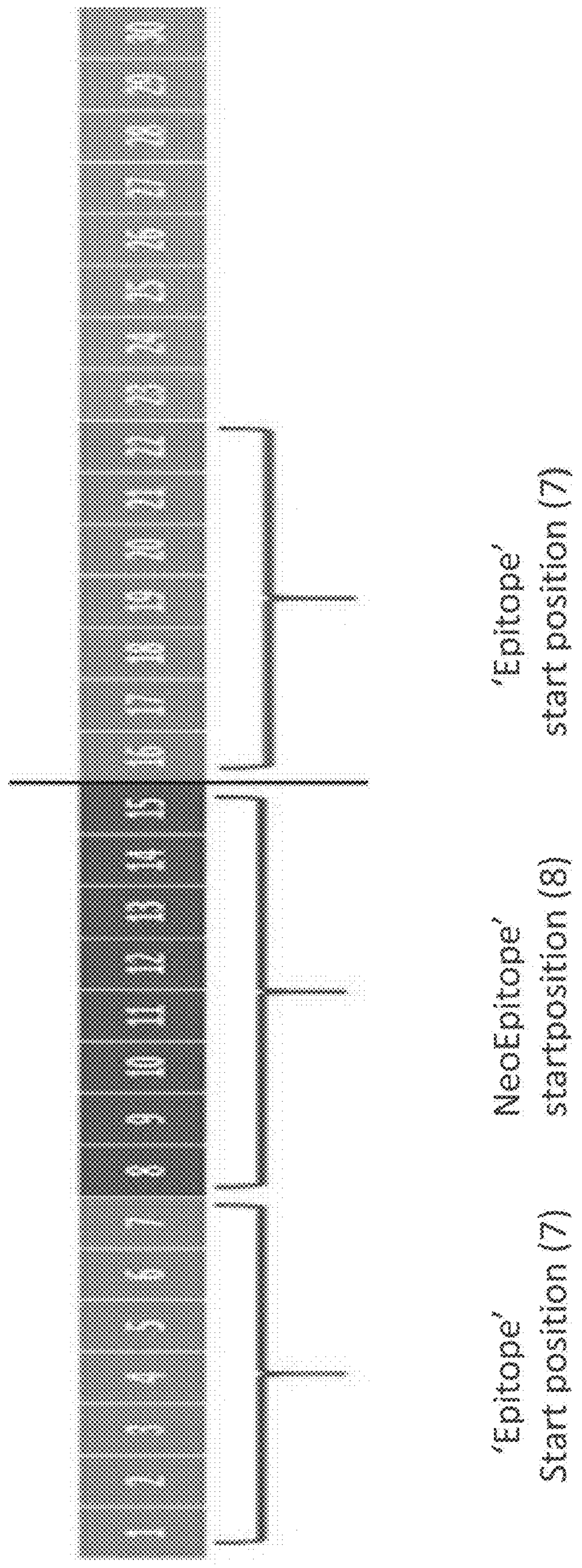

When fragments of different polypeptides or from different regions of the same polypeptide are joined together in an engineered peptide there is the potential for neoepitopes to be generated around the join or junction (FIG. 42). Such neoepitopes encompass at least one amino acid from each fragment on either side of the join or junction, and may be referred to herein as junctional amino acid sequences. The neoepitopes may induce undesired T cell responses against healthy cells (autoimmunity). The polypeptides may be designed, or the polypeptides may be screened, to avoid, eliminate or minimise neoepitopes that correspond to a fragment of a protein expressed in normal healthy human cells and/or neoepitopes that are capable of binding to at least two, or in some cases at least three, or at least four HLA class I molecules of the subject, or in some cases at least two, or at least three or four or five HLA class II molecules of the subject. In some cases the peptide is designed, or the polypeptide screened, to eliminate polypeptides having a junctional neoepitope that is capable of binding in more than a threshold percentage of human subjects in an intent-to-treat population, to at least two HLA class I molecules expressed by individual subjects of the population. In some cases the threshold is 20%, or 15%, or 10%, or 5%, or 2%, or 1%, or 0.5% of said population. Alignment may be determined using known methods such as BLAST algorithms. Software for performing BLAST analyses is publicly available through the National Center for Biotechnology Information (ncbi.nlm.nih.gov/).

The presence in a vaccine or immunotherapy composition of at least two polypeptide fragments (epitopes) that can bind to at least three HLA class I of an individual (≥2 PEPI3+) is predictive for a clinical response. In other words, if ≥2 PEPI3+ can be identified within the active ingredient polypeptide(s) of a vaccine or immunotherapy composition, then an individual is a likely clinical responder. The at least two multiple HLA-binding PEPIs of the composition polypeptides may both target a single antigen (e.g. a polypeptide vaccine comprising two multiple HLA-binding PEPIs derived from a single tumor associated antigen targeted by the vaccine) or may target different antigens (e.g. a polypeptide vaccine comprising one multiple HLA-binding PEPI derived from one tumor associated antigen and a second multiple HLA-binding PEPI derived from a different tumor associated antigen).

Without wishing to be bound by theory, the inventors believe that one reason for the increased likelihood of deriving clinical benefit from a vaccine/immunotherapy comprising at least two multiple-HLA binding PEPIs, is that diseased cell populations, such as cancer or tumor cells or cells infected by viruses or pathogens such as HIV, are often heterogenous both within and between effected subjects. A specific cancer patient, for example, may or may not express or overexpress a particular cancer associated target polypeptide antigen of a vaccine, or their cancer may comprise heterogeneous cell populations, some of which (over-)express the antigen and some of which do not. In addition, the likelihood of developing resistance is decreased when more multiple HLA-binding PEPIs are included or targeted by a vaccine/immunotherapy because a patient is less likely to develop resistance to the composition through mutation of the target PEPI(s).

Currently most vaccines and immunotherapy compositions target only a single polypeptide antigen. However according to the present disclosure it is in some cases beneficial to provide a pharmaceutical composition that targets two or more different polypeptide antigens. For example, most cancers or tumors are heterogeneous, meaning that different cancer or tumor cells of a subject (over-) express different antigens. The tumour cells of different cancer patients also express different combinations of tumour-associated antigens. The anti-cancer immunogenic compositions that are most likely to be effective are those that target multiple antigens expressed by the tumor, and therefore more cancer or tumor cells, in an individual human subject or in a population.

The beneficial effect of combining multiple best EPIs in a single treatment (administration of one or more pharmaceutical compositions that together comprise multiple PEPIs), can be illustrated by the personalised vaccine polypeptides described in Example 21 below. Exemplary CTA expression probabilities in ovarian cancer are as follows: BAGE: 30%; MAGE A9: 37%; MAGE A4: 34%; MAGE A10: 52%. If patient-A were treated with a vaccine comprising PEPIs in only BAGE and MAGE A9, then the probability of having a mAGP (multiple expressed antigens with PEPI) would be 11%. If patient-A were treated with a vaccine comprising only PEPIs for the MAGE A4 and MAGE A10 CTAs, then the probability of having a multi-AGP would be 19%. However if a vaccine contained all 4 of these CTAs (BAGE, MAGE A9, MAGE A4 and MAGE A10), then the probability of having a mAGP would be 50%. In other words the effect would be greater than the combined probabilities of mAGP for both two-PEPI treatments (probability mAGP for BAGE/MAGE+ probability mAGP for MAGE A4 and MAGE A10). Patient-A's PIT vaccine described in Example 21 contains a further 9 PEPIs, and thus, the probability of having a mAGP is over 99.95%.

Likewise exemplary CTA expression probabilities in breast cancer are as follows: MAGE C2: 21%; MAGE A1: 37%; SPC1: 38%; MAGE A9: 44%. Treatment of patient-B with a vaccine comprising PEPIs in only MAGE C2: 21% and MAGE A1 has a mAGP probability of 7%. Treatment of patient-B with a vaccine comprising PEPIs in only SPC1: 38%; MAGE A9 has a mAGP probability of 11%. Treatment of patient-B with a vaccine comprising PEPIs in MAGE C2: 21%; MAGE A1: 37%; SPC1: 38%; MAGE A9 has a mAGP probability of 44% (44>7+11). Patient's PIT vaccine described in Example 21 contains a further 8 PEPIs, and thus, the probability of having a mAGP is over 99.93%.

Accordingly in some cases, the polypeptide or panel of polypeptides of the disclosure or an active ingredient polypeptide of a pharmaceutical composition or kit of the disclosure may comprise or consist of any combination of at least 1, 2, 3, 4, 5, 6, 7, 8, 9, 10, 11, 12, 13, 14, 15, 16, 17, 18, 19, 20, 21, 22, 23, 24 or 25 fragments of at least 1, 2, 3, 4, 5, 6, 7, 8, 9, 10, 11, 12, 13, 14, 15, 16, 17, 18, 19, 20, 21, 22, 23, 24 or 25 or more of the cancer associated antigens, or CTAs, such as the CTA discussed above. In some cases each fragment may comprise or consist of a different target epitope having an amino acid sequence selected from SEQ ID NOs: 1-30, SEQ ID NOs: 31-60, SEQ ID NOs: 90 to 119, SEQ ID NOs: 120 to 149, SEQ ID NOs: 178 to 207, SEQ ID NOs: 208 to 237, SEQ ID NOs: 268 to 297, and/or SEQ ID NOs: 298 to 327; or selected from SEQ ID NOs: 1 to 2, or to 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29; or SEQ ID NOs: 31 to 32, or to 33, or 34, or 35, or 36, or 37, or 38, or 39, or 40, or 41 to 42, or to 43, or to 44, or to 45, or to 46, or to 47, or to 48, or to 49, or 50, or 51, or 52, or 53, or 54, or 55, or 56, or 57, or 58, or 59; or selected from SEQ ID NOs: 90 to 91, or to 92, or 93 or 94, or 95, or 96, or 97, or 98, or 99, or 100, or 101, or 102, or 103, or 104, or 105, or 106, or 107, or 108, or 109, or 110, or 111, or 112, or 113, or 114, or 115, or 116, or 117, or 118; or SEQ ID NOs: 120 to 121, or to 122, or 123, or 124, or 125, or 126, or 127, or 128, or 129; or 130; or 131; or 132; or 133; or 134; or 135; or 136; or 137; or 138; or 139; or 140; or 141; or 142; or 143; or 144; or 145; or 146; or 147; or 148; or 149; or selected from SEQ ID NOs: 178 to 179, or to 180, or 181, or 182, or 183, or 184, or 185, or 186, or 187, or 188, or 189, or 190, or 191, or 192, or 193, or 194, or 195, or 196, or 197, or 198, or 199, or 200, or 201, or 202, or 203, or 204, or 205, or 206; or SEQ ID NOs: 208 to 209, or 210, or 211, or 212, or 213, or 214, or 215, or 216, or 217, or 218, or 219, or 220, or 221, or 222, or 223, or 224, or 225, or 226, or 227, or 228, or 229, or 230, or 231, or 232, or 233, or 234, or 235, or 236; or selected from SEQ ID NOs: 268 to 269, or to 270, or 271, or 272, or 273, or 274, or 275, or 276, or 277, or 278, or 279, or 280, or 281, or 282, or 283, or 284, or 285, or 286, or 287, or 288, or 289, or 290, or 291, or 292, or 293, or 294, or 295, or 296; or selected from SEQ ID NOs: 298 to 299, or to 300, or 301, or 302, or 303, or 304, or 305, or 306, or 307, or 308, or 309, or 310, or 311, or 312, or 313, or 314, or 315, or 316, or 317, or 318, or 319, or 320, or 321, or 322, or 323, or 324, or 325, or 326; or selected from any of these groups of sequences but excluding any specific combinations of sequences that are within 50-60 amino acids of each other in any one or more of the antigens of SEQ ID NOs: 76 to 89, 165 to 177, 253 to 267 and/or 343 to 359, such as any combination of SEQ ID NOs: 3 and 8; SEQ ID NOs: 9 and 10; SEQ ID NOs: 12 and 16; SEQ ID NOs: 13, 18 and 25; SEQ ID NOs: 21 and 24; SEQ ID NOs: 23 and 30; SEQ ID NOs: 93 and 94; SEQ ID NOs: 99, 100 and 102; SEQ ID NOs: 109 and 111; SEQ ID NOs: 96, 101 and 113; SEQ ID NOs: 188 and 190; and/or SEQ ID NOs: 201 and 203; SEQ ID NOs: 268 and 270; SEQ ID NOs: 271 and 281; SEQ ID NOs: 272 and 275; and/or SEQ ID NOs: 288 and 291. In some cases each fragment may comprise or consist of a different amino acid sequence selected from SEQ ID NOs: 60 or 61 to 75; SEQ ID NOs: 150 to 164; SEQ ID NOs: 238 to 252; and/or SEQ ID NOs: 328 to 342.

In some cases the disclosure provides a panel of any two or more of the peptides or groups of peptides described above. For example the panel may comprise 2, 3, 4, 5, 6, 7, 8, 9, 11, 12, 13, 14, 15, 16, 17, 18, 19, 20, 21, 22, 23, 24, 25 or more such peptides.

Pharmaceutical Compositions, Methods of Treatment and Modes of Administration

In some aspects the disclosure relates to a pharmaceutical composition, kit, or panels of polypeptides as described above having one or more polypeptides as active ingredient(s). These may be for use in a method of inducing an immune response, treating, vaccinating or providing immunotherapy to a subject, and the pharmaceutical composition may be a vaccine or immunotherapy composition. Such a treatment comprises administering one or more polypeptides or pharmaceutical compositions that together comprise all of the active ingredient polypeptides of the treatment to the subject. Multiple polypeptides or pharmaceutical compositions may be administered together or sequentially, for example all of the pharmaceutical compositions or polypeptides may be administered to the subject within a period of 1 year, or 6 months, or 3 months, or 60 or 50 or 40 or 30 days.

The term "active ingredient" as used herein refers to a polypeptide that is intended to induce an immune response and may include a polypeptide product of a vaccine or immunotherapy composition that is produced in vivo after administration to a subject. For a DNA or RNA immunotherapy composition, the polypeptide may be produced in vivo by the cells of a subject to whom the composition is administered. For a cell-based composition, the polypeptide may be processed and/or presented by cells of the composition, for example autologous dendritic cells or antigen presenting cells pulsed with the polypeptide or comprising an expression construct encoding the polypeptide. The pharmaceutical composition may comprise a polynucleotide or cell encoding one or more active ingredient polypeptides.

The composition/kit may optionally further comprise at least one pharmaceutically acceptable diluent, carrier, or preservative and/or additional polypeptides that do not comprise any PEPIs. The polypeptides may be engineered or non-naturally occurring. The kit may comprise one or more separate containers each containing one or more of the active ingredient peptides. The composition/kit may be a personalised medicine to prevent, diagnose, alleviate, treat, or cure a disease of an individual, such as a cancer.

The immunogenic or pharmaceutical compositions or kits described herein may comprise, in addition to one or more immunogenic peptides, a pharmaceutically acceptable excipient, carrier, diluent, buffer, stabiliser, preservative, adjuvant or other materials well known to those skilled in the art. Such materials are preferably non-toxic and preferably do not interfere with the pharmaceutical activity of the active ingredient(s). The pharmaceutical carrier or diluent may be, for example, water containing solutions. The precise nature of the carrier or other material may depend on the route of administration, e.g. oral, intravenous, cutaneous or subcutaneous, nasal, intramuscular, intradermal, and intraperitoneal routes.

The pharmaceutical compositions of the disclosure may comprise one or more "pharmaceutically acceptable carriers". These are typically large, slowly metabolized macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The pharmaceutical compositions may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier (Gennaro, 2000, Remington: The Science and Practice of Pharmacy, 20th edition, ISBN:0683306472).

The pharmaceutical compositions of the disclosure may be lyophilized or in aqueous form, i.e. solutions or suspensions. Liquid formulations of this type allow the compositions to be administered direct from their packaged form, without the need for reconstitution in an aqueous medium, and are thus ideal for injection. The pharmaceutical compositions may be presented in vials, or they may be presented in ready filled syringes. The syringes may be supplied with or without needles. A syringe will include a single dose, whereas a vial may include a single dose or multiple doses.

Liquid formulations of the disclosure are also suitable for reconstituting other medicaments from a lyophilized form. Where a pharmaceutical composition is to be used for such extemporaneous reconstitution, the disclosure provides a kit, which may comprise two vials, or may comprise one ready-filled syringe and one vial, with the contents of the syringe being used to reconstitute the contents of the vial prior to injection.

The pharmaceutical compositions of the disclosure may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

The pharmaceutical compositions of the disclosure may comprise detergent e.g. Tween (polysorbate), DMSO (dimethyl sulfoxide), DMF (dimethylformamide). Detergents are generally present at low levels, e.g. <0.01%, but may also be used at higher levels, e.g. 0.01-50%.

The pharmaceutical compositions of the disclosure may include sodium salts (e.g. sodium chloride) and free phosphate ions in solution (e.g. by the use of a phosphate buffer).

In certain embodiments, the pharmaceutical composition may be encapsulated in a suitable vehicle either to deliver the peptides into antigen presenting cells or to increase the stability. As will be appreciated by a skilled artisan, a variety of vehicles are suitable for delivering a pharmaceutical composition of the disclosure. Non-limiting examples of suitable structured fluid delivery systems may include nanoparticles, liposomes, microemulsions, micelles, dendrimers and other phospholipid-containing systems. Methods of incorporating pharmaceutical compositions into delivery vehicles are known in the art.

In order to increase the immunogenicity of the composition, the pharmacological compositions may comprise one or more adjuvants and/or cytokines.

Suitable adjuvants include an aluminum salt such as aluminum hydroxide or aluminum phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL [3D-MPL], quil A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants.

In some embodiments, the compositions comprise an adjuvant selected from the group consisting of Montanide ISA-51 (Seppic, Inc., Fairfield, N.J., United States of America), QS-21 (Aquila Biopharmaceuticals, Inc., Lexington, Mass., United States of America), GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, oil emulsions, dinitrophenol, diphtheria toxin (DT).

By way of example, the cytokine may be selected from the group consisting of a transforming growth factor (TGF) such as but not limited to TGF-α and TGF-β; insulin-like growth factor-I and/or insulin-like growth factor-II; erythropoietin (EPO); an osteoinductive factor; an interferon such as but not limited to interferon-.α, β, and -γ; a colony stimulating factor (CSF) such as but not limited to macrophage-CSF (M-CSF); granulocyte-macrophage-CSF (GM-CSF); and granulocyte-CSF (G-CSF). In some embodiments, the cytokine is selected from the group consisting of nerve growth factors such as NGF-β; platelet-growth factor; a transforming growth factor (TGF) such as but not limited to TGF-α. and TGF-β; insulin-like growth factor-I and insulin-like growth factor-II; erythropoietin (EPO); an osteoinductive factor; an interferon (IFN) such as but not limited to IFN-α, IFN-β, and IFN-γ; a colony stimulating factor (CSF) such as macrophage-CSF (M-CSF); granulocyte-macrophage-CSF (GM-CSF); and granulocyte-CSF (G-CSF); an interleukin (Il) such as but not limited to IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18; LIF; kit-ligand or FLT-3; angiostatin; thrombospondin; endostatin; a tumor necrosis factor (TNF); and LT.

It is expected that an adjuvant or cytokine can be added in an amount of about 0.01 mg to about 10 mg per dose, preferably in an amount of about 0.2 mg to about 5 mg per dose. Alternatively, the adjuvant or cytokine may be at a concentration of about 0.01 to 50%, preferably at a concentration of about 2% to 30%.

In certain aspects, the pharmaceutical compositions of the disclosure are prepared by physically mixing the adjuvant and/or cytokine with the peptides of the disclosure under appropriate sterile conditions in accordance with known techniques to produce the final product.

Examples of suitable compositions of the invented polypeptide fragments and methods of administration are provided in Esseku and Adeyeye (2011) and Van den Mooter G. (2006). Vaccine and immunotherapy composition preparation is generally described in Vaccine Design ("The subunit and adjuvant approach" (eds Powell M. F. & Newman M. J. (1995) Plenum Press New York). Encapsulation within liposomes, which is also envisaged, is described by Fullerton, U.S. Pat. No. 4,235,877.

In some embodiments, the compositions disclosed herein are prepared as a nucleic acid vaccine. In some embodiments, the nucleic acid vaccine is a DNA vaccine. In some embodiments, DNA vaccines, or gene vaccines, comprise a plasmid with a promoter and appropriate transcription and translation control elements and a nucleic acid sequence encoding one or more polypeptides of the disclosure. In some embodiments, the plasmids also include sequences to enhance, for example, expression levels, intracellular targeting, or proteasomal processing. In some embodiments, DNA vaccines comprise a viral vector containing a nucleic acid sequence encoding one or more polypeptides of the disclosure. In additional aspects, the compositions disclosed herein comprise one or more nucleic acids encoding peptides determined to have immunoreactivity with a biological sample. For example, in some embodiments, the compositions comprise one or more nucleotide sequences encoding 1, 2, 3, 4, 5, 6, 7, 8, 9, 10, 11, 12, 13, 14, 15, 16, 17, 18, 19, 20, or more peptides comprising a fragment that is a T cell epitope capable of binding to at least three HLA class I molecules and/or at least three HLA class II molecules of a patient. In some embodiments, the peptides are derived from an antigen that is expressed in cancer. In some embodiments the DNA or gene vaccine also encodes immunomodulatory molecules to manipulate the resulting immune responses, such as enhancing the potency of the vaccine, stimulating the immune system or reducing immunosuppression. Strategies for enhancing the immunogenicity of DNA or gene vaccines include encoding of xenogeneic versions of antigens, fusion of antigens to molecules that activate T cells or trigger associative recognition, priming with DNA vectors followed by boosting with viral vector, and utilization of immunomodulatory molecules. In some embodiments, the DNA vaccine is introduced by a needle, a gene gun, an aerosol injector, with patches, via microneedles, by abrasion, among other forms. In some forms the DNA vaccine is incorporated into liposomes or other forms of nanobodies. In some embodiments, the DNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle. In some embodiments, the DNA vaccines is administered by inhalation or ingestion. In some embodiments, the DNA vaccine is introduced into the blood, the thymus, the pancreas, the skin, the muscle, a tumor, or other sites.

In some embodiments, the compositions disclosed herein are prepared as an RNA vaccine. In some embodiments, the RNA is non-replicating mRNA or virally derived, self-amplifying RNA. In some embodiments, the non-replicating mRNA encodes the peptides disclosed herein and contains 5' and 3' untranslated regions (UTRs). In some embodiments, the virally derived, self-amplifying RNA encodes not only the peptides disclosed herein but also the viral replication machinery that enables intracellular RNA amplification and abundant protein expression. In some embodiments, the RNA is directly introduced into the individual. In some embodiments, the RNA is chemically synthesized or transcribed in vitro. In some embodiments, the mRNA is produced from a linear DNA template using a T7, a T3, or an Sp6 phage RNA polymerase, and the resulting product contains an open reading frame that encodes the peptides disclosed herein, flanking UTRs, a 5' cap, and a poly(A) tail. In some embodiments, various versions of 5' caps are added during or after the transcription reaction using a vaccinia virus capping enzyme or by incorporating synthetic cap or anti-reverse cap analogues. In some embodiments, an optimal length of the poly(A) tail is added to mRNA either directly from the encoding DNA template or by using poly(A) polymerase. The RNA encodes one or more peptides comprising a fragment that is a T cell epitope capable of binding to at least three HLA class I and/or at least three HLA class II molecules of a patient. In some embodiments, the fragments are derived from an antigen that is expressed in cancer. In some embodiments, the RNA includes signals to enhance stability and translation. In some embodiments, the RNA also includes unnatural nucleotides to increase the half-life or modified nucleosides to change the immunostimulatory profile. In some embodiments, the RNAs is introduced by a needle, a gene gun, an aerosol injector, with patches, via microneedles, by abrasion, among other forms. In some forms the RNA vaccine is incorporated into liposomes or other forms of nanobodies that facilitate cellular uptake of RNA and protect it from degradation. In some embodiments, the RNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle; and/or naked mRNA; naked mRNA with in vivo electroporation; protamine-complexed mRNA; mRNA associated with a positively charged oil-in-water cationic nanoemulsion; mRNA associated with a chemically modified dendrimer and complexed with polyethylene glycol (PEG)-lipid; protamine-complexed mRNA in a PEG-lipid nanoparticle; mRNA associated with a cationic polymer such as polyethylenitnine (PEI); mRNA associated with a cationic polymer such as PET and a lipid component; mRNA associated with a polysaccharide (for example, chitosan) particle or gel; mRNA in a cationic lipid nanoparticle example, 1,2-dioleoyloxy-3-trimethylammoniumpropane (DOTAP) or dioleoylphosphaticlylethanolamine (DOPE) lipids); mRNA complexed with cationic lipids and cholesterol; or mRNA complexed with cationic lipids, cholesterol and PEG-lipid. In some embodiments, the RNA vaccine is administered by inhalation or ingestion. In some embodiments, the RNA is introduced into the blood, the thymus, the pancreas, the skin, the muscle, a tumor, or other sites, and/or by an intradermal, intramuscular, subcutaneous, intranasal, intranodal, intravenous, intrasplenic, intratumoral or other delivery route.

Polynucleotide or oligonucleotide components may be naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration.

Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

Administration is typically in a “prophylactically effective amount” or a “therapeutically effective amount” (as the case may be, although prophylaxis may be considered therapy), this being sufficient to result in a clinical response or to show clinical benefit to the individual, e.g. an effective amount to prevent or delay onset of the disease or condition, to ameliorate one or more symptoms, to induce or prolong remission, or to delay relapse or recurrence.

The dose may be determined according to various parameters, especially according to the substance used; the age, weight and condition of the individual to be treated; the route of administration; and the required regimen. The amount of antigen in each dose is selected as an amount which induces an immune response. A physician will be able to determine the required route of administration and dosage for any particular individual. The dose may be provided as a single dose or may be provided as multiple doses, for example taken at regular intervals, for example 2, 3 or 4 doses administered hourly. Typically peptides, polynucleotides or oligonucleotides are typically administered in the range of 1 pg to 1 mg, more typically 1 μg to μg for particle mediated delivery and 1 μg to 1 mg, more typically 1-100 more typically 5-50 μg for other routes. Generally, it is expected that each dose will comprise 0.01-3 mg of antigen. An optimal amount for a particular vaccine can be ascertained by studies involving observation of immune responses in subjects.

Examples of the techniques and protocols mentioned above can be found in Remington’s Pharmaceutical Sciences, 20th Edition, 2000, pub. Lippincott, Williams & Wilkins.

In some cases in accordance with the disclosure, more than one peptide or composition of peptides is administered. Two or more pharmaceutical compositions may be administered together/simultaneously and/or at different times or sequentially. Thus, the disclosure includes sets of pharmaceutical compositions and uses thereof. The use of combination of different peptides, optionally targeting different antigens, is important to overcome the challenges of genetic heterogeneity of tumors and HLA heterogeneity of individuals. The use of peptides of the disclosure in combination expands the group of individuals who can experience clinical benefit from vaccination. Multiple pharmaceutical compositions of peptides of the disclosure, manufactured for use in one regimen, may define a drug product.

Routes of administration include but are not limited to intranasal, oral, subcutaneous, intradermal, and intramuscular. The subcutaneous administration is particularly preferred. Subcutaneous administration may for example be by injection into the abdomen, lateral and anterior aspects of upper arm or thigh, scapular area of back, or upper ventrodorsal gluteal area.

The compositions of the disclosure may also be administered in one, or more doses, as well as, by other routes of administration. For example, such other routes include, intracutaneously, intravenously, intravascularly, intraarterially, intraperitnoeally, intrathecally, intratracheally, intracardially, intralobally, intramedullarly, intrapulmonarily, and intravaginally. Depending on the desired duration of the treatment, the compositions according to the disclosure may be administered once or several times, also intermittently, for instance on a monthly basis for several months or years and in different dosages.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

One or more compositions of the disclosure may be administered, or the methods and uses for treatment according to the disclosure may be performed, alone or in combination with other pharmacological compositions or treatments, for example chemotherapy and/or immunotherapy and/or vaccine. The other therapeutic compositions or treatments may for example be one or more of those discussed herein, and may be administered either simultaneously or sequentially with (before or after) the composition or treatment of the disclosure.

In some cases the treatment may be administered in combination with checkpoint blockade therapy, co-stimulatory antibodies, chemotherapy and/or radiotherapy, targeted therapy or monoclonal antibody therapy. It has been demonstrated that chemotherapy sensitizes tumors to be killed by tumor specific cytotoxic T cells induced by vaccination (Ramakrishnan et al. *J Clin Invest.* 2010; 120(4):1111-1124). Examples for checkpoint inhibitors are CTLA-4 inhibitor, Ipilimumab and programmed cell death-1/programmed cell death ligand-1 (PD-1/PD-L1) signaling inhibitors, Nibolumab, Pembrolizumab, Atezolizumab and Durvalumab. Examples of chemotherapy agents include alkylating agents including nitrogen mustards such as mechlorethamine (HN2), cyclophosphamide, ifosfamide, melphalan (L-sarcolysin) and chlorambucil; anthracyclines; epothilones; nitrosoureas such as carmustine (BCNU), lomustine (CCNU), semustine (methyl-CCNU) and streptozocin (streptozotocin); triazenes such as decarbazine (DTIC; dimethyltriazenoimidazole-carboxamide; ethylenimines/methylmelamines such as hexamethylmelamine, thiotepa; alkyl sulfonates such as busulfan; Antimetabolites including folic acid analogues such as methotrexate (amethopterin); alkylating agents, antimetabolites, pyrimidine analogs such as fluorouracil (5-fluorouracil; 5-FU), floxuridine (fluorodeoxyuridine; FUdR) and cytarabine (cytosine arabinoside); purine analogues and related inhibitors such as mercaptopurine (6-mercaptopurine; 6-MP), thioguanine (6-thioguanine; TG) and pentostatin (2'-deoxycoformycin); epipodophylotoxins; enzymes such as L-asparaginase; biological response modifiers such as IFNα, IL-2, G-CSF and GM-CSF; platinum coordination complexes such as cisplatin (cis-DDP), oxaliplatin and carboplatin; anthracenediones such as mitoxantrone and anthracycline; substituted urea such as hydroxyurea; methylhydrazine derivatives including procarbazine (N-methylhydrazine, MIH) and procarbazine; adrenocortical suppressants such as mitotane (o,p'-DDD) and aminoglutethimide; taxol and analogues/derivatives; hormones and agonists/antagonists including adrenocorticosteroid antagonists such as prednisone and equivalents, dexamethasone and aminoglutethimide, progestin such as hydroxyprogesterone caproate, medroxyprogesterone acetate and megestrol acetate, estrogen such as diethylstilbestrol and ethinyl estradiol equivalents, antiestrogen such as tamoxifen, androgens including testosterone propionate and fluoxymesterone/equivalents, antiandrogens such as flutamide, gonadotropin-releasing hormone analogs and leuprolide and non-steroidal antiandrogens such as flutamide; natural products including vinca alkaloids such as vinblastine (VLB) and vincristine, epipodophyllotoxins such as etoposide and teniposide, antibiotics such as dactinomycin (actinomycin D), daunorubicin (daunomycin; rubidomycin), doxorubicin, bleomycin, plicamycin (mithramycin) and mitomycin (mitomycin C), enzymes such as L-asparaginase, and biological response modifiers such as interferon alphenomes.

In some cases the method of treatment is a method of vaccination or a method of providing immunotherapy. As used herein, "immunotherapy" is the prevention or treatment of a disease or condition by inducing or enhancing an immune response in an individual. In certain embodiments, immunotherapy refers to a therapy that comprises the administration of one or more drugs to an individual to elicit T cell responses. In a specific embodiment, immunotherapy refers to a therapy that comprises the administration or expression of polypeptides that contain one or more PEPIs to an individual to elicit a T cell response to recognize and kill cells that display the one or more PEPIs on their cell surface in conjunction with a class I HLAs. In another specific embodiment, immunotherapy comprises the administration of one or more PEPIs to an individual to elicit a cytotoxic T cell response against cells that display tumor associated antigens (TAAs), tumor specific antigens (TSA) or cancer testis antigens (CTAs) comprising the one or more PEPIs on their cell surface. In another embodiment, immunotherapy refers to a therapy that comprises the administration or expression of polypeptides that contain one or more PEPIs presented by class II HLAs to an individual to elicit a CD4+T helper or CD4+ killer cell response to provide co-stimulation to cytotoxic T cells that recognize and kill diseased cells that display the one or more PEPIs on their cell surface in conjunction with a class I HLAs. In still another specific embodiment, immunotherapy refers to a therapy that comprises administration of one or more drugs to an individual that re-activate existing T cells to kill target cells. The theory is that the cytotoxic T cell response will eliminate the cells displaying the one or more PEPIs, thereby improving the clinical condition of the individual. In some instances, immunotherapy may be used to treat tumors. In other instances, immunotherapy may be used to treat intracellular pathogen-based diseases or disorders.

In some cases the disclosure relates to the treatment of cancer or the treatment of solid tumors. In some cases the treatment is of gastric cancer, lung cancer, melanoma and/or bladder cancer. In other cases the treatment may be of any other cancer or solid tumor that expresses a target tumor associated antigen of the present peptides as described herein, or any cancer in which such target polypeptide antigens are expressed in some or a high percentage of subjects. The treatment may be of cancers or malignant or benign tumors of any cell, tissue, or organ type. The cancer may or may not be metastatic. Exemplary cancers include carcinomas, sarcomas, lymphomas, leukemias, germ cell tumors, or blastomas. The cancer may or may not be a hormone related or dependent cancer (e.g., an estrogen or androgen related cancer). The cancer may or may not be one that is associated with or caused by a viral infection and/or viral TAAs.

Selection of Polypeptides and Patients

Specific polypeptide antigens, and particularly short peptides derived from such antigens that are commonly used in vaccination and immunotherapy, induce immune responses in only a fraction of human subjects. The polypeptides of the present disclosure are specifically selected to induce immune responses in a high proportion of the general population, but they may not be effective in all individuals due to HLA genotype heterogeneity. HLA genotype population heterogeneity means that the immune or clinical response rate to the vaccines described herein will differ between different human subpopulations. In some cases the vaccines described herein are for use to treat a specific or target subpopulation, for example an Asian population, or a Vietnamese, Chinese, and/or Japanese population.

The disclosure also provides a method of identifying a human subject who will likely have a CD8+ or cytotoxic T cell response to administration of a pharmaceutical composition comprising a peptide of the disclosure (likely responders), or of predicting the likelihood that a subject will have a cytotoxic T cell response.

As provided herein T cell epitope presentation by multiple HLAs of an individual is generally needed to trigger a T cell response. The best predictor of a cytotoxic T cell response to a given polypeptide, as determined by the inventors, is the presence of at least one T cell epitope that is presented by three or more HLA class I of an individual (≥1 PEPI3+). Accordingly the presence within the active ingredient peptides of a pharmaceutical composition of one or more T cell epitopes that is capable of binding to at least three HLA of a subject is predictive for the subject having a cytotoxic T cell response to administration of the pharmaceutical composition. The subject is a likely immune responder.

In some cases the T cell epitope that is capable of binding to at least three HLA class I of the subject has the amino acid sequence of any one of SEQ ID NOs: 1 to 30. In other cases the T cell epitope may have a different amino acid sequence within the one or more peptides of the pharmaceutical composition.

The inventors have further discovered that the presence in a vaccine or immunotherapy composition of at least two epitopes that can bind to at least three HLA of an individual is predictive for a clinical response. In other words, if an individual has a total of ≥2 PEPI3+ within the active ingredient polypeptide(s) of a vaccine or immunotherapy composition, and these PEPI3+s are derived from antigen sequences that are in fact expressed in the individual (for example, target tumor cells of the individual express the target tumor-associated antigens), then the individual is a likely clinical responder (i.e. a clinically relevant immune responder).

Accordingly some aspects of the disclosure relate to a method of identifying a subject who will likely have a clinical response to a method of treatment according to the disclosure, or of predicting the likelihood that a subject will have a clinical response. A "clinical response" or "clinical benefit" as used herein may be the prevention or a delay in the onset of a disease or condition, the amelioration of one or more symptoms, the induction or prolonging of remission, or the delay of a relapse or recurrence or deterioration, or any other improvement or stabilisation in the disease status of a subject. Where appropriate, a "clinical response" may correlate to "disease control" or an "objective response" as defined by the Response Evaluation Criteria In Solid Tumors (RECIST) guidelines.

In some embodiments the method comprises determining that one or more cancer-associated antigens selected from gastric cancer antigens DPPA2, CAGE-1, TSP50, HIWI, SURVIVIN, 5T4, PRAME, KK-LC-1, MAGE-A2, MAGE-A3, LAGE-1, MAGE-A10, MAGE-A1 SSX1, and/or lung cancer antigens BRDT, PRAME, NALP4, MAGE-A12, MAGE-A2, SURVIVIN, DPPA2, NY-SAR-35, LDHC, MAGE-C2, MAGE-A3, KK-LC-1, MAGE-A1, and/or melanoma cancer antigens PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10, MAGE-A1, and/or bladder cancer antigens PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8 and HAGE, MAGE-A1, MAGE-C2, MAGE-A10 and MAGE-A12 is expressed by a cancer. For example expression of the cancer associated antigen may be detected in a sample obtained from the subject, for example a tumor biopsy, using methods that are known in the art.

The inventors have discovered that it is not sufficient that a vaccine or immunotherapy composition targets an antigen that is expressed by cancer or tumor cells of a patient, nor that the target sequences of that antigen can bind to HLA class I of the patient (HLA restricted epitopes). The composition is likely effective only in patients that both express the target antigen and have three or more different HLA class I molecules that bind to the same sequence T cell epitope of the target antigen. Moreover, as described above, at least two epitopes that binds to at least 3 HLAs of the patient are generally needed to induce a clinically relevant immune response.

Therefore the method further comprises determining that the active ingredient peptide(s) of the pharmaceutical composition comprise two or more different amino acid sequences each of which is a) a fragment of a cancer-associated antigen expressed by cancer cells of the subject, determined as described above; and b) a T cell epitope capable of binding to at least three HLA class I molecules of the subject.

In some cases the likelihood that a subject will have a clinical response to a peptide vaccine or immunotherapy composition, such as those described herein, can be determined without knowing whether the target antigens are expressed in cancer or tumor cells of the subject and/or without determining the HLA class I genotype of the subject. Known antigen expression frequencies in the disease (e.g. MAGE-A3 in a tumor type like gastric cancer, lung cancer, melanoma or bladder cancer) and/or known frequencies for HLA class I and class II genotype of subjects in the target population (e.g. ethnic population, general population, diseased population) may be used instead. Moreover by combining peptides that target the most frequently presented PEPIs across the population (BestEPIs) in multiple frequently expressed target antigens in the disease, as identified and described herein, it is possible to design a cancer vaccine regime that is effective for a high proportion of patients. However, using the companion diagnostic methods described herein to pre-select patients who are most likely to have a clinical response will increase clinical response rates amongst treated patients.

The likelihood that a subject will respond to treatment is increased by (i) the presence of more multiple HLA-binding PEPIs in the active ingredient polypeptides; (ii) the presence of PEPIs in more target polypeptide antigens; and (iii) expression of the target polypeptide antigens in the subject or in diseased cells of the subject. In some cases expression of the target polypeptide antigens in the subject may be known, for example if target polypeptide antigens are in a sample obtained from the subject. In other cases, the probability that a specific subject, or diseased cells of a specific subject, (over-)express a specific or any combination of target polypeptide antigens may be determined using population expression frequency data, e.g. probability of expression of an antigen in gastric cancer, lung cancer, melanoma or bladder cancer. The population expression frequency data may relate to a subject- and/or disease-matched population or the intent-to-treat population. For example, the frequency or probability of expression of a particular cancer-associated antigen in a particular cancer or subject having a particular cancer, for example gastric cancer, can be determined by detecting the antigen in tumor, e.g. gastric cancer tumor samples. In some cases such expression frequencies may be determined from published figures and scientific publications. In some cases a method of the disclosure comprises a step of determining the expression frequency of a relevant target polypeptide antigen in a relevant population.

Disclosed is a range of pharmacodynamic biomarkers to predict the activity/effect of vaccines in individual human subjects as well as in populations of human subjects. These biomarkers expedite more effective vaccine development and also decrease the development cost and may be used to assess and compare different compositions. Exemplary biomarkers are as follows.

AG95 or AG50—potency of a vaccine: The number of antigens in a cancer vaccine that a specific tumor type expresses with 95% or 50% probability. AG95 and AG50 are indicators of the vaccine's potency, and are independent of the immunogenicity of the vaccine antigens. AG95 and AG50 are calculated from the tumor antigen expression rate data. Such data may be obtained from experiments published in peer reviewed scientific journals. Technically, AG95 and AG50 are determined from the binomial distribution of antigens in the vaccine, and takes into account all possible variations and expression rates.

PEPI3+ count—immunogenicity of a vaccine in a subject: Vaccine-derived PEPI3+ are personal epitopes that bind to at least 3 HLAs of a subject and induce T cell responses. PEPI3+ can be determined using the PEPI3+ Test in subjects whose complete 4-digit HLA genotype is known.

AP count—antigenicity of a vaccine in a subject: Number of vaccine antigens with PEPI3+. Vaccines contain sequences from target polypeptide antigens expressed by diseased cells. AP count is the number of antigens in the vaccine that contain PEPI3+, and the AP count represents the number of antigens in the vaccine that can induce T cell responses in a subject. AP count characterizes the vaccine-antigen specific T cell responses of the subject since it depends only on the HLA genotype of the subject and is independent of the subject's disease, age, and medication. The correct value is between 0 (no PEPI presented by the antigen) and maximum number of antigens (all antigens present PEPIs).

AP50—antigenicity of a vaccine in a population: The mean number of vaccine antigens with a PEPI in a population. The AP50 is suitable for the characterization of vaccine-antigen specific T cell responses in a given population since it depends on the HLA genotype of subjects in a population.

AGP count—effectiveness of a vaccine in a subject: Number of vaccine antigens expressed in the tumor with PEPI. The AGP count indicates the number of tumor antigens that vaccine recognizes and induces a T cell response against (hit the target). The AGP count depends on the vaccine-antigen expression rate in the subject's tumor and the HLA genotype of the subject. The correct value is between 0 (no PEPI presented by expressed antigen) and maximum number of antigens (all antigens are expressed and present a PEPI).

AGP50—effectiveness of a cancer vaccine in a population: The mean number of vaccine antigens expressed in the indicated tumor with PEPI (i.e., AGP) in a population. The AGP50 indicates the mean number of tumor antigens that the T cell responses induced by the vaccine can recognize. AGP50 is dependent on the expression rate of the antigens in the indicated tumor type and the immunogenicity of the antigens in the target population. AGP50 can estimate a vaccine's effectiveness in different populations and can be used to compare different vaccines in the same population. The computation of AGP50 is similar to that used for AG50, except the expression is weighted by the occurrence of the PEPI3+ in the subject on the expressed vaccine antigens. In a theoretical population, where each subject has a PEPI from each vaccine antigen, the AGP50 will be equal to AG50. In another theoretical population, where no subject has a PEPI from any vaccine antigen, the AGP50 will be 0. In general, the following statement is valid: $0 \leq AGP50 \leq AG50$.

mAGP—a candidate biomarker for the selection of likely responders: Likelihood that a cancer vaccine induces T cell responses against multiple antigens expressed in the indicated tumor. mAGP is calculated from the expression rates of vaccine-antigens in the tumor and the presence of vaccine derived PEPIs in the subject. Technically, based on the AGP distribution, the mAGP is the sum of probabilities of the multiple AGP (≥2 AGPs).

The results of a prediction as set out above may be used to inform a physician's decisions concerning treatment of the subject. Accordingly, in some cases the method of the disclosure predicts that a subject will have or is likely to have a T cell response and/or a clinical response to a treatment as described herein, and the method further comprises selecting the treatment for the human subject. In some cases a subject is selected for treatment if their likelihood of a response targeted at a predefined number of target polypeptide antigens, optionally wherein the target polypeptide antigens are (predicted to be) expressed, is above a predetermined threshold. In some cases the number of target polypeptide antigens or epitopes is two. In some cases the number of target polypeptide antigens or epitopes is three, or four, or five, or six, or seven, or eight, or nine, or ten. The method may further comprise administering the treatment to the human subject. Alternatively, the method may predict that the subject will not have an immune response and/or a clinical response and further comprise selecting a different treatment for the subject.

Further Embodiments of the Disclosure—(1A)—Gastric Cancer

1. A pharmaceutical composition comprising one or more peptides, wherein each peptide comprises a different one of the amino acid sequence of any one of SEQ ID NOs: 61 to 75.
2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
3. The pharmaceutical composition of item 1, further comprising at least one additional peptide comprising a fragment of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1.
4. The pharmaceutical composition of item 3, wherein the fragment of an antigen comprises an amino acid sequence selected from any one of SEQ ID NOs: 1 to 30.
5. The pharmaceutical composition of item 3, wherein the fragment of an antigen comprises an amino acid sequence selected from any one of SEQ ID NOs: 31-60.
6. The pharmaceutical composition of item 1, further comprising a pharmaceutically acceptable adjuvant, diluent, carrier, preservative, or combination thereof.
7. The pharmaceutical composition of item 6, wherein the adjuvant is selected from the group consisting of Montanide ISA-51, QS-21, GM-CSF, cyclophosamide, *bacillus* Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
8. A pharmaceutical composition comprising one or more nucleic acid molecules encoding one or more peptides, wherein each peptide comprises a different one of the amino acid sequence of any one of SEQ ID NOs:61 to 75.
9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
10. The pharmaceutical composition of item 8, wherein the one or more nucleic acid molecules encode at least one additional peptide comprising a fragment of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1.
11. The pharmaceutical composition of item 10, wherein the fragment of an antigen comprises an amino acid sequence selected from any one of SEQ ID NOs: 1 to 30.
12. The pharmaceutical composition of item 10, wherein the fragment of an antigen comprises an amino acid sequence selected from any one of SEQ ID NOs:31-60.
13. The pharmaceutical composition of item 8, further comprising a pharmaceutically acceptable adjuvant, diluent, carrier, preservative, or combination thereof.
14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof
15. A method of identifying and treating a human subject having cancer who will likely have a clinical response to administration of a pharmaceutical composition according to item 1, the method comprising
    - (i) assaying a biological sample of the subject to determine HLA genotype of the subject;
    - (ii) determining that the pharmaceutical composition comprises two or more sequences that are a T cell epitope capable of binding to at least three HLA class I molecules of the subject;
    - (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
    - (iv) administering the composition of item 1 to the identified subject.
16. The method of item 15, wherein the subject has gastric cancer.
17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
18. The method of item 15, wherein the pharmaceutical composition further comprises comprising at least one additional peptide comprising a fragment of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1.
19. The method of item 18, wherein the fragment of an antigen comprises an amino acid sequence selected from any one of SEQ ID NOs: 1 to 30.
20. The method of item 18, wherein the fragment of an antigen comprises an amino acid sequence selected from any one of SEQ ID NOs: 31-60.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof 23. The method of item 15, further comprising administering a chemotherapeutic agent, a checkpoint inhibitor, a targeted therapy, radiation therapy, another immunotherapy, neoadjuvant therapy or combination thereof to the identified subject.
24. The method of item 15, further comprising prior to the administering step,
    (i) assaying a tumor sample from the subject to determine that the three or more peptides of the pharmaceutical composition comprise two or more different amino acid sequences each of which is
        a. a fragment of a cancer-associated antigen expressed by cancer cells of the subject as determined in step (i); and
        b. a T cell epitope capable of binding to at least three HLA class I molecules of the subject; and
    (ii) confirming the subject as likely to have a clinical response to the method of treatment.
25. A method of identifying and treating a human subject having cancer who will likely have an immune response to administration of a pharmaceutical composition according to item 1, the method comprising
    (i) assaying a biological sample of the subject to determine HLA genotype of the subject;
    (ii) determining that the pharmaceutical composition comprises one or more sequences that are a T cell epitope capable of binding to at least three HLA class I molecules of the subject; and
    (iii) administering the composition of item 1 to the identified subject.
26. A kit comprising:
    a. a first pharmaceutical composition comprising one or more peptides, wherein each peptide comprises a different one of the amino acid sequence of any one of SEQ ID NOs: 61 to 75; and
    b. a second different pharmaceutical composition comprising one or more peptides, wherein each peptide comprises a different one of the amino acid sequence of any one of SEQ ID NOs: 61 to 75.
27. A pharmaceutical composition comprising: a nucleic acid molecule expressing two or more polypeptides, each polypeptide comprising a fragment of up to 50 consecutive amino acids of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein each fragment comprises a different amino acid sequence selected from any one of SEQ ID NOs: 1 to 30.

Further Embodiments of the Disclosure—(1B)—Lung Cancer

1. A pharmaceutical composition comprising one or more peptides, wherein each peptide comprises a different one of the amino acid sequence of any one of SEQ ID NOs: 150 to 164.
2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
3. The pharmaceutical composition of item 1, further comprising at least one additional peptide comprising a fragment of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1.
4. The pharmaceutical composition of item 3, wherein the fragment of an antigen comprises an amino acid sequence selected from any one of SEQ ID NOs: 90 to 119.
5. The pharmaceutical composition of item 3, wherein the fragment of an antigen comprises an amino acid sequence selected from any one of SEQ ID NOs: 120 to 149.
6. The pharmaceutical composition of item 1, further comprising a pharmaceutically acceptable adjuvant, diluent, carrier, preservative, or combination thereof.
7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof
8. A pharmaceutical composition comprising one or more nucleic acid molecules encoding one or more peptides, wherein each peptide comprises a different one of the amino acid sequence of any one of SEQ ID NOs: 150 to 164.
9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
10. The pharmaceutical composition of item 8, wherein the one or more nucleic acid molecules encode at least one additional peptide comprising a fragment of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1.
11. The pharmaceutical composition of item 10, wherein the fragment of an antigen comprises an amino acid sequence selected from any one of SEQ ID NOs: 90 to 119.
12. The pharmaceutical composition of item 10, wherein the fragment of an antigen comprises an amino acid sequence selected from any one of SEQ ID NOs: 120 to 149.
13. The pharmaceutical composition of item 8, further comprising a pharmaceutically acceptable adjuvant, diluent, carrier, preservative, or combination thereof.
14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof 15. A method of identifying and treating a human subject having cancer who will likely have a clinical response to administration of a pharmaceutical composition according to item 1, the method comprising
    (i) assaying a biological sample of the subject to determine HLA genotype of the subject;
    (ii) determining that the pharmaceutical composition comprises two or more sequences that are a T cell epitope capable of binding to at least three HLA class I molecules of the subject;
    (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
    (iv) administering the composition of item 1 to the identified subject.
16. The method of item 15, wherein the subject has lung cancer.
17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
18. The method of item 15, wherein the pharmaceutical composition further comprises comprising at least one additional peptide comprising a fragment of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1.
19. The method of item 18, wherein the fragment of an antigen comprises an amino acid sequence selected from any one of SEQ ID NOs: 90 to 119.
20. The method of item 18, wherein the fragment of an antigen comprises an amino acid sequence selected from any one of SEQ ID NOs: 120 to 149.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
23. The method of item 15, further comprising administering a chemotherapeutic agent, a checkpoint inhibitor, a targeted therapy, radiation therapy, another immunotherapy, neoadjuvant therapy or combination thereof to the identified subject.
24. The method of item 15, further comprising prior to the administering step,
    (i) assaying a tumor sample from the subject to determine that the three or more peptides of the pharmaceutical composition comprise two or more different amino acid sequences each of which is
        a. a fragment of a cancer-associated antigen expressed by cancer cells of the subject as determined in step (i); and
        b. a T cell epitope capable of binding to at least three HLA class I molecules of the subject; and
    (ii) confirming the subject as likely to have a clinical response to the method of treatment.
25. A method of identifying and treating a human subject having cancer who will likely have an immune response to administration of a pharmaceutical composition according to item 1, the method comprising
    (i) assaying a biological sample of the subject to determine HLA genotype of the subject;
    (ii) determining that the pharmaceutical composition comprises one or more sequences that are a T cell epitope capable of binding to at least three HLA class I molecules of the subject; and
    (iii) administering the composition of item 1 to the identified subject.
26. A kit comprising:
    a. a first pharmaceutical composition comprising one or more peptides, wherein each peptide comprises a different one of the amino acid sequence of any one of SEQ ID NOs: 150 to 164; and
    b. a second different pharmaceutical composition comprising one or more peptides, wherein each peptide comprises a different one of the amino acid sequence of any one of SEQ ID NOs: 150 to 164.
27. A pharmaceutical composition comprising: a nucleic acid molecule expressing two or more polypeptides, each polypeptide comprising a fragment of up to 50 consecutive amino acids of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein each fragment comprises a different amino acid sequence selected from any one of SEQ ID NOs: 90 to 119.

Further Embodiments of the Disclosure—(1C)—Melanoma

1. A pharmaceutical composition comprising one or more peptides, wherein each peptide comprises a different one of the amino acid sequence of any one of SEQ ID NOs: 238 to 252.
2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
3. The pharmaceutical composition of item 1, further comprising at least one additional peptide comprising a fragment of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1.
4. The pharmaceutical composition of item 3, wherein the fragment of an antigen comprises an amino acid sequence selected from any one of SEQ ID NOs: 178 to 207.
5. The pharmaceutical composition of item 3, wherein the fragment of an antigen comprises an amino acid sequence selected from any one of SEQ ID NOs: 208 to 237.

6. The pharmaceutical composition of item 1, further comprising a pharmaceutically acceptable adjuvant, diluent, carrier, preservative, or combination thereof.
7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof
8. A pharmaceutical composition comprising one or more nucleic acid molecules encoding one or more peptides, wherein each peptide comprises a different one of the amino acid sequence of any one of SEQ ID NOs:61 to 75.
9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
10. The pharmaceutical composition of item 8, wherein the one or more nucleic acid molecules encode at least one additional peptide comprising a fragment of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1.
11. The pharmaceutical composition of item 10, wherein the fragment of an antigen comprises an amino acid sequence selected from any one of SEQ ID NOs: 178 to 207.
12. The pharmaceutical composition of item 10, wherein the fragment of an antigen comprises an amino acid sequence selected from any one of SEQ ID NOs: 208 to 237.
13. The pharmaceutical composition of item 8, further comprising a pharmaceutically acceptable adjuvant, diluent, carrier, preservative, or combination thereof.
14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof
15. A method of identifying and treating a human subject having cancer who will likely have a clinical response to administration of a pharmaceutical composition according to item 1, the method comprising
   (i) assaying a biological sample of the subject to determine HLA genotype of the subject;
   (ii) determining that the pharmaceutical composition comprises two or more sequences that are a T cell epitope capable of binding to at least three HLA class I molecules of the subject;
   (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
   (iv) administering the composition of item 1 to the identified subject.
16. The method of item 15, wherein the subject has melanoma.
17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
18. The method of item 15, wherein the pharmaceutical composition further comprises comprising at least one additional peptide comprising a fragment of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1.
19. The method of item 18, wherein the fragment of an antigen comprises an amino acid sequence selected from any one of SEQ ID NOs:178 to 207.
20. The method of item 18, wherein the fragment of an antigen comprises an amino acid sequence selected from any one of SEQ ID NOs:208 to 237.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
23. The method of item 15, further comprising administering a chemotherapeutic agent, a checkpoint inhibitor, a targeted therapy, radiation therapy, another immunotherapy, neoadjuvant therapy or combination thereof to the identified subject.
24. The method of item 15, further comprising prior to the administering step,
   (iii) assaying a tumor sample from the subject to determine that the three or more peptides of the pharmaceutical composition comprise two or more different amino acid sequences each of which is
      c. a fragment of a cancer-associated antigen expressed by cancer cells of the subject as determined in step (i); and
      d. a T cell epitope capable of binding to at least three HLA class I molecules of the subject; and
   (iv) confirming the subject as likely to have a clinical response to the method of treatment.
25. A method of identifying and treating a human subject having cancer who will likely have an immune response to administration of a pharmaceutical composition according to item 1, the method comprising
   (i) assaying a biological sample of the subject to determine HLA genotype of the subject;

(ii) determining that the pharmaceutical composition comprises one or more sequences that are a T cell epitope capable of binding to at least three HLA class I molecules of the subject; and (iii) administering the composition of item 1 to the identified subject.

26. A kit comprising:

a. a first pharmaceutical composition comprising one or more peptides, wherein each peptide comprises a different one of the amino acid sequence of any one of SEQ ID NOs: 238 to 267; and b. a second different pharmaceutical composition comprising one or more peptides, wherein each peptide comprises a different one of the amino acid sequence of any one of SEQ ID NOs: 238 to 267.

27. A pharmaceutical composition comprising: a nucleic acid molecule expressing two or more polypeptides, each polypeptide comprising a fragment of up to 50 consecutive amino acids of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein each fragment comprises a different amino acid sequence selected from any one of SEQ ID NOs:178 to 207.

Further Embodiments of the Disclosure—(1D)—Bladder Cancer

1. A pharmaceutical composition comprising one or more peptides, wherein each peptide comprises a different one of the amino acid sequence of any one of SEQ ID NOs: 328 to 342.

2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

3. The pharmaceutical composition of item 1, further comprising at least one additional peptide comprising a fragment of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12.

4. The pharmaceutical composition of item 3, wherein the fragment of an antigen comprises an amino acid sequence selected from any one of SEQ ID NOs: 268 to 297.

5. The pharmaceutical composition of item 3, wherein the fragment of an antigen comprises an amino acid sequence selected from any one of SEQ ID NOs: 298 to 327.

6. The pharmaceutical composition of item 1, further comprising a pharmaceutically acceptable adjuvant, diluent, carrier, preservative, or combination thereof.

7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof 8. A pharmaceutical composition comprising one or more nucleic acid molecules encoding one or more peptides, wherein each peptide comprises a different one of the amino acid sequence of any one of SEQ ID NOs: 328 to 342.

9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

10. The pharmaceutical composition of item 8, wherein the one or more nucleic acid molecules encode at least one additional peptide comprising a fragment of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12.

11. The pharmaceutical composition of item 10, wherein the fragment of an antigen comprises an amino acid sequence selected from any one of SEQ ID NOs: 268 to 297.

12. The pharmaceutical composition of item 10, wherein the fragment of an antigen comprises an amino acid sequence selected from any one of SEQ ID NOs: 298 to 327.

13. The pharmaceutical composition of item 8, further comprising a pharmaceutically acceptable adjuvant, diluent, carrier, preservative, or combination thereof.

14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof 15. A method of identifying and treating a human subject having cancer who will likely have a clinical response to administration of a pharmaceutical composition according to item 1, the method comprising (i) assaying a biological sample of the subject to determine HLA genotype of the subject;

(ii) determining that the pharmaceutical composition comprises two or more sequences that are a T cell epitope capable of binding to at least three HLA class I molecules of the subject;

(iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and (iv) administering the composition of item 1 to the identified subject.

16. The method of item 15, wherein the subject has bladder cancer.

17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

18. The method of item 15, wherein the pharmaceutical composition further comprises comprising at least one additional peptide comprising a fragment of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12.
19. The method of item 18, wherein the fragment of an antigen comprises an amino acid sequence selected from any one of SEQ ID NOs: 268 to 297.
20. The method of item 18, wherein the fragment of an antigen comprises an amino acid sequence selected from any one of SEQ ID NOs: 298 to 327.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
23. The method of item 15, further comprising administering a chemotherapeutic agent, a checkpoint inhibitor, a targeted therapy, radiation therapy, another immunotherapy, neoadjuvant therapy or combination thereof to the identified subject.
24. The method of item 15, further comprising prior to the administering step,
    - (v) assaying a tumor sample from the subject to determine that the three or more peptides of the pharmaceutical composition comprise two or more different amino acid sequences each of which is
        - e. a fragment of a cancer-associated antigen expressed by cancer cells of the subject as determined in step (i); and
        - f. a T cell epitope capable of binding to at least three HLA class I molecules of the subject; and
    - (vi) confirming the subject as likely to have a clinical response to the method of treatment.
25. A method of identifying and treating a human subject having cancer who will likely have an immune response to administration of a pharmaceutical composition according to item 1, the method comprising
    - (i) assaying a biological sample of the subject to determine HLA genotype of the subject;
    - (ii) determining that the pharmaceutical composition comprises one or more sequences that are a T cell epitope capable of binding to at least three HLA class I molecules of the subject; and
    - (iii) administering the composition of item 1 to the identified subject.
26. A kit comprising:
    - a. a first pharmaceutical composition comprising one or more peptides, wherein each peptide comprises a different one of the amino acid sequence of any one of SEQ ID NOs: 328 to 342; and
    - b. a second different pharmaceutical composition comprising one or more peptides, wherein each peptide comprises a different one of the amino acid sequence of any one of SEQ ID NOs: 328 to 342.
27. A pharmaceutical composition comprising: a nucleic acid molecule expressing two or more polypeptides, each polypeptide comprising a fragment of up to 50 consecutive amino acids of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein each fragment comprises a different amino acid sequence selected from any one of SEQ ID NOs: 268 to 297.

Further Embodiments of the Disclosure—(2B)—Lung

1. A polypeptide that comprises a fragment of up to 50 consecutive amino acids of a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: to 119, optionally wherein the fragment is flanked at the N and/or C terminus by additional amino acids that are not part of the sequence of the lung cancer-associated antigen.
2. The polypeptide of item 1, wherein the polypeptide
    - a. is a fragment of a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119; or
    - b. comprises or consists of two or more fragments of one or more lung cancer associated antigens selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein each fragment comprises a different amino acid sequence selected from any one of SEQ ID NOs: 90 to 119, optionally wherein the fragments overlap or are arranged end to end in the polypeptide.
3. The polypeptide according to item 1 or item 2, wherein the polypeptide comprises or consists of fragments of at least two different cancer-associated antigens, wherein the cancer-associated antigens are selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1; and wherein each fragment comprises a different amino acid sequence selected from SEQ ID NOs: 90 to 119.
4. The polypeptide according to any one of items 1 to 3, comprising or consisting of one or more amino acid sequences selected from SEQ ID NOs: 120 to 149.
5. The polypeptide according to any one of items 1 to 4 comprising or consisting of the amino acid sequence of any one of SEQ ID NOs: 150 to 164.

6. A panel of two or more polypeptides according to any one of items 1 to 5, wherein each polypeptide comprises a different amino acid sequence selected from SEQ ID NOs: 90 to 119.
7. A pharmaceutical composition or kit comprising one or more polypeptides according to any one of items 1 to 5, or a panel of polypeptides according to item 6, or a polypeptide comprising at least two amino acid sequences selected SEQ ID NOs: 90 to 119, or one or more polynucleic acids or vectors encoding said one or more polypeptides.
8. A method of vaccination, providing immunotherapy or inducing a cytotoxic T cell response in a subject, the method comprising administering to the subject a pharmaceutical composition or the peptides, polynucleic acids or vectors of a kit according to item 7.
9. The method of item 8 that is a method of treating cancer, optionally lung cancer.
10. A method of identifying a human subject who will likely have a cytotoxic T cell response to administration of a pharmaceutical composition or the peptides, polynucleic acids or vectors of a kit according to item 7, the method comprising
    (i) determining that the active ingredient polypeptide(s) of the pharmaceutical composition or kit comprise a sequence that is a T cell epitope capable of binding to at least three HLA class I molecules of the subject; and
    (ii) identifying the subject as likely to have a cytotoxic T cell response to administration of the pharmaceutical composition or the peptides, polynucleic acids or vectors of the kit.
11. The method of item 10 further comprising using population expression data for each antigen that
    (a) is selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1; and
    (b) comprises an amino acid sequence that is
        i. a fragment of an active ingredient peptide of the pharmaceutical composition; and
        ii. a T cell epitope capable of binding to at least three HLA class I molecules of the subject;

to determine the likelihood that the subject will have a CD8+ T cell response that targets one or more polypeptide antigens that are expressed by cancer cells of the subject.
12. A method of identifying a subject who will likely have a clinical response to a method of treatment according to item 9, the method comprising
    (i) determining that the active ingredient polypeptide(s) of the pharmaceutical composition comprise two or more different amino acid sequences each of which is
        a. a T cell epitope capable of binding to at least three HLA class I molecules of the subject; and
        b. a fragment of a cancer-associated antigen expressed by cancer cells of the subject, optionally wherein the cancer-associated antigen is present in a sample obtained from the subject; and
    (ii) identifying the subject as likely to have a clinical response to the method of treatment.
13. A method of determining the likelihood that a specific human subject will have a clinical response to a method of treatment according to item 9, wherein one or more of the following factors corresponds to a higher likelihood of a clinical response:
    (a) presence in the active ingredient polypeptide(s) of a higher number of amino acid sequences and/or different amino acid sequences that are each a T cell epitope capable of binding to at least three HLA class I of the subject;
    (b) a higher number of target polypeptide antigens, comprising at least one amino acid sequence that is both
        A. comprised in an active ingredient polypeptide; and
        B. a T cell epitope capable of binding to at least three HLA class I of the subject; optionally wherein the target polypeptide antigens are expressed in the subject, further optionally wherein the target polypeptides antigens are in one or more samples obtained from the subject;
    (c) a higher probability that the subject expresses target polypeptide antigens, optionally a threshold number of the target polypeptide antigens and/or optionally target polypeptide antigens that have been determined to comprise at least one amino acid sequence that is both
        A. comprised in in an active ingredient polypeptide; and
        B. a T cell epitope capable of binding to at least three HLA class I of the subject; and/or
    (d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
        A. comprised in in an active ingredient polypeptide; and
        B. a T cell epitope capable of binding to at least three HLA class I of the subject.
14. The method of item 13, wherein the method comprises
    (i) identifying which polypeptide antigens targeted by the active ingredient polypeptide(s) comprise an amino acid sequence that is both
        A. comprised in an active ingredient polypeptide; and
        B. a T cell epitope capable of binding to at least three HLA class I of the subject;
    (ii) using population expression data for each antigen identified in step (i) to determine the probability that the subject expresses one or more of the antigens identified in step (i) that together comprise at least two different amino acid sequences of step (i); and
    (iii) determining the likelihood that the subject will have a clinical response to administration of the pharmaceutical composition, kit or panel of polypeptides, wherein a higher probability determined in step (ii) corresponds to a more likely clinical response.
15. The method of item 14, wherein the at least two different amino acid sequences are comprised in the amino acid sequence of two different polypeptide antigens targeted by the active ingredient polypeptide(s).
16. The method of any one of items 12 to 15 further comprising selecting or recommending administration of the pharmaceutical composition or the peptides, polynucleic acids or vectors of the kit as a method of treatment for the subject, and optionally further treating the subject by administering the pharmaceutical composition or the peptides, polynucleic acids or vectors of the kit.

17. A method of treatment according to item 9, wherein the subject has been identified as likely to have a clinical response or as having above a threshold minimum likelihood of having a clinical response to the treatment by a method according to any one of items 12 to 15.
18. The method of any one of items 8, 9, 16 and 17 wherein the treatment is administered in combination with chemotherapy, targeted therapy or a checkpoint inhibitor.
19. A method of identifying a human subject who will likely not have a clinical response to a method of treatment according to item 9, the method comprising
   (i) determining that the active ingredient peptide(s) of the pharmaceutical composition do not comprise two or more different amino acid sequences each of which is a T cell epitope capable of binding to at least three HLA class I molecules of the subject; and
   (ii) identifying the subject as likely not to have a clinical response to the method of treatment.

Further Embodiments of the Disclosure—(3B)—Melanoma

1. A polypeptide that comprises a fragment of up to 50 consecutive amino acids of a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207, optionally wherein the fragment is flanked at the N and/or C terminus by additional amino acids that are not part of the sequence of the melanoma-associated antigen.
2. The polypeptide of item 1, wherein the polypeptide
   c. is a fragment of a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207; or
   d. comprises or consists of two or more fragments of one or more melanoma associated antigens selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein each fragment comprises a different amino acid sequence selected from any one of SEQ ID NOs: 178 to 207, optionally wherein the fragments overlap or are arranged end to end in the polypeptide.
3. The polypeptide according to item 1 or item 2, wherein the polypeptide comprises or consists of fragments of at least two different cancer-associated antigens, wherein the cancer-associated antigens are selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1; and wherein each fragment comprises a different amino acid sequence selected from SEQ ID NOs: 178 to 207.
4. The polypeptide according to any one of items 1 to 3, comprising or consisting of one or more amino acid sequences selected from SEQ ID NOs: 208 to 237.
5. The polypeptide according to any one of items 1 to 4 comprising or consisting of the amino acid sequence of any one of SEQ ID NOs: 238 to 252.
6. A panel of two or more polypeptides according to any one of items 1 to 5, wherein each polypeptide comprises a different amino acid sequence selected from SEQ ID NOs: 178 to 207.
7. A pharmaceutical composition or kit comprising one or more polypeptides according to any one of items 1 to 5, or a panel of polypeptides according to item 6, or a polypeptide comprising at least two amino acid sequences selected SEQ ID NOs: 178 to 207, or one or more polynucleic acids or vectors encoding said one or more polypeptides.
8. A method of vaccination, providing immunotherapy or inducing a cytotoxic T cell response in a subject, the method comprising administering to the subject a pharmaceutical composition or the peptides, polynucleic acids or vectors of a kit according to item 7.
9. The method of item 8 that is a method of treating cancer, optionally melanoma.
10. A method of identifying a human subject who will likely have a cytotoxic T cell response to administration of a pharmaceutical composition or the peptides, polynucleic acids or vectors of a kit according to item 7, the method comprising
   (i) determining that the active ingredient polypeptide(s) of the pharmaceutical composition or kit comprise a sequence that is a T cell epitope capable of binding to at least three HLA class I molecules of the subject; and
   (iii) identifying the subject as likely to have a cytotoxic T cell response to administration of the pharmaceutical composition or the peptides, polynucleic acids or vectors of the kit.
11. The method of item 10 further comprising using population expression data for each antigen that
   (a) is selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1; and
   (b) comprises an amino acid sequence that is
      i. a fragment of an active ingredient peptide of the pharmaceutical composition; and
      ii. a T cell epitope capable of binding to at least three HLA class I molecules of the subject;
   to determine the likelihood that the subject will have a CD8+ T cell response that targets one or more polypeptide antigens that are expressed by cancer cells of the subject.
12. A method of identifying a subject who will likely have a clinical response to a method of treatment according to item 9, the method comprising
   (i) determining that the active ingredient polypeptide(s) of the pharmaceutical composition comprise two or more different amino acid sequences each of which is
      c. a T cell epitope capable of binding to at least three HLA class I molecules of the subject; and
      d. a fragment of a cancer-associated antigen expressed by cancer cells of the subject, optionally wherein the cancer-associated antigen is present in a sample obtained from the subject; and (ii) identifying the subject as likely to have a clinical response to the method of treatment.

13. A method of determining the likelihood that a specific human subject will have a clinical response to a method of treatment according to item 9, wherein one or more of the following factors corresponds to a higher likelihood of a clinical response:

(a) presence in the active ingredient polypeptide(s) of a higher number of amino acid sequences and/or different amino acid sequences that are each a T cell epitope capable of binding to at least three HLA class I of the subject;

(b) a higher number of target polypeptide antigens, comprising at least one amino acid sequence that is both A. comprised in an active ingredient polypeptide; and B. a T cell epitope capable of binding to at least three HLA class I of the subject; optionally wherein the target polypeptide antigens are expressed in the subject, further optionally wherein the target polypeptides antigens are in one or more samples obtained from the subject;

(c) a higher probability that the subject expresses target polypeptide antigens, optionally a threshold number of the target polypeptide antigens and/or optionally target polypeptide antigens that have been determined to comprise at least one amino acid sequence that is both A. comprised in in an active ingredient polypeptide; and B. a T cell epitope capable of binding to at least three HLA class I of the subject; and/or (d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both A. comprised in in an active ingredient polypeptide; and B. a T cell epitope capable of binding to at least three HLA class I of the subject.

14. The method of item 13, wherein the method comprises (iv) identifying which polypeptide antigens targeted by the active ingredient polypeptide(s) comprise an amino acid sequence that is both A. comprised in an active ingredient polypeptide; and B. a T cell epitope capable of binding to at least three HLA class I of the subject;

(v) using population expression data for each antigen identified in step (i) to determine the probability that the subject expresses one or more of the antigens identified in step (i) that together comprise at least two different amino acid sequences of step (i); and (vi) determining the likelihood that the subject will have a clinical response to administration of the pharmaceutical composition, kit or panel of polypeptides, wherein a higher probability determined in step (ii) corresponds to a more likely clinical response.

15. The method of item 14, wherein the at least two different amino acid sequences are comprised in the amino acid sequence of two different polypeptide antigens targeted by the active ingredient polypeptide(s).

16. The method of any one of items 12 to 15 further comprising selecting or recommending administration of the pharmaceutical composition or the peptides, polynucleic acids or vectors of the kit as a method of treatment for the subject, and optionally further treating the subject by administering the pharmaceutical composition or the peptides, polynucleic acids or vectors of the kit.

17. A method of treatment according to item 9, wherein the subject has been identified as likely to have a clinical response or as having above a threshold minimum likelihood of having a clinical response to the treatment by a method according to any one of items 12 to 15.

18. The method of any one of items 8, 9, 16 and 17 wherein the treatment is administered in combination with chemotherapy, targeted therapy or a checkpoint inhibitor.

19. A method of identifying a human subject who will likely not have a clinical response to a method of treatment according to item 9, the method comprising (i) determining that the active ingredient peptide(s) of the pharmaceutical composition do not comprise two or more different amino acid sequences each of which is a T cell epitope capable of binding to at least three HLA class I molecules of the subject; and (ii) identifying the subject as likely not to have a clinical response to the method of treatment.

Further Embodiments of the Disclosure—(4B)—Bladder

1. A polypeptide that comprises a fragment of up to 50 consecutive amino acids of a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297, optionally wherein the fragment is flanked at the N and/or C terminus by additional amino acids that are not part of the sequence of the bladder cancer-associated antigen.

2. The polypeptide of item 1, wherein the polypeptide e. is a fragment of a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297; or f. comprises or consists of two or more fragments of one or more bladder cancer associated antigens selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein each fragment comprises a different amino acid sequence selected from any one of SEQ ID NOs: 268 to 297, optionally wherein the fragments overlap or are arranged end to end in the polypeptide.

3. The polypeptide according to item 1 or item 2, wherein the polypeptide comprises or consists of fragments of at least two different cancer-associated antigens, wherein the cancer-associated antigens are selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12; and wherein each fragment comprises a different amino acid sequence selected from SEQ ID NOs: 268 to 297.

4. The polypeptide according to any one of items 1 to 3, comprising or consisting of one or more amino acid sequences selected from SEQ ID NOs: 298 to 327.

5. The polypeptide according to any one of items 1 to 4 comprising or consisting of the amino acid sequence of any one of SEQ ID NOs: 328 to 342.

6. A panel of two or more polypeptides according to any one of items 1 to 5, wherein each polypeptide comprises a different amino acid sequence selected from SEQ ID NOs: 268 to 297.

7. A pharmaceutical composition or kit comprising one or more polypeptides according to any one of items 1 to 5, or a panel of polypeptides according to item 6, or a polypeptide comprising at least two amino acid sequences selected SEQ ID NOs: 268 to 297, or one or more polynucleic acids or vectors encoding said one or more polypeptides.

8. A method of vaccination, providing immunotherapy or inducing a cytotoxic T cell response in a subject, the method comprising administering to the subject a pharmaceutical composition or the peptides, polynucleic acids or vectors of a kit according to item 7.

9. The method of item 8 that is a method of treating cancer, optionally bladder cancer.

10. A method of identifying a human subject who will likely have a cytotoxic T cell response to administration of a pharmaceutical composition or the peptides, polynucleic acids or vectors of a kit according to item 7, the method comprising (i) determining that the active ingredient polypeptide(s) of the pharmaceutical composition or kit comprise a sequence that is a T cell epitope capable of binding to at least three HLA class I molecules of the subject; and (iv) identifying the subject as likely to have a cytotoxic T cell response to administration of the pharmaceutical composition or the peptides, polynucleic acids or vectors of the kit.

11. The method of item 10 further comprising using population expression data for each antigen that (a) is selected PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12; and (b) comprises an amino acid sequence that is i. a fragment of an active ingredient peptide of the pharmaceutical composition; and ii. a T cell epitope capable of binding to at least three HLA class I molecules of the subject;

to determine the likelihood that the subject will have a CD8+ T cell response that targets one or more polypeptide antigens that are expressed by cancer cells of the subject.

12. A method of identifying a subject who will likely have a clinical response to a method of treatment according to item 9, the method comprising (i) determining that the active ingredient polypeptide(s) of the pharmaceutical composition comprise two or more different amino acid sequences each of which is e. a T cell epitope capable of binding to at least three HLA class I molecules of the subject; and f. a fragment of a cancer-associated antigen expressed by cancer cells of the subject, optionally wherein the cancer-associated antigen is present in a sample obtained from the subject; and (ii) identifying the subject as likely to have a clinical response to the method of treatment.

13. A method of determining the likelihood that a specific human subject will have a clinical response to a method of treatment according to item 9, wherein one or more of the following factors corresponds to a higher likelihood of a clinical response:

(a) presence in the active ingredient polypeptide(s) of a higher number of amino acid sequences and/or different amino acid sequences that are each a T cell epitope capable of binding to at least three HLA class I of the subject;

(b) a higher number of target polypeptide antigens, comprising at least one amino acid sequence that is both A. comprised in an active ingredient polypeptide; and B. a T cell epitope capable of binding to at least three HLA class I of the subject; optionally wherein the target polypeptide antigens are expressed in the subject, further optionally wherein the target polypeptides antigens are in one or more samples obtained from the subject;

(c) a higher probability that the subject expresses target polypeptide antigens, optionally a threshold number of the target polypeptide antigens and/or optionally target polypeptide antigens that have been determined to comprise at least one amino acid sequence that is both A. comprised in in an active ingredient polypeptide; and B. a T cell epitope capable of binding to at least three HLA class I of the subject; and/or (d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both A. comprised in in an active ingredient polypeptide; and B. a T cell epitope capable of binding to at least three HLA class I of the subject.

14. The method of item 13, wherein the method comprises (vii) identifying which polypeptide antigens targeted by the active ingredient polypeptide(s) comprise an amino acid sequence that is both A. comprised in an active ingredient polypeptide; and B. a T cell epitope capable of binding to at least three HLA class I of the subject;

(viii) using population expression data for each antigen identified in step (i) to determine the probability that the subject expresses one or more of the antigens identified in step (i) that together comprise at least two different amino acid sequences of step (i); and (ix) determining the likelihood that the subject will have a clinical response to administration of the pharmaceutical composition, kit or panel of polypeptides, wherein a higher probability determined in step (ii) corresponds to a more likely clinical response.

15. The method of item 14, wherein the at least two different amino acid sequences are comprised in the amino acid sequence of two different polypeptide antigens targeted by the active ingredient polypeptide(s).

16. The method of any one of items 12 to 15 further comprising selecting or recommending administration of the pharmaceutical composition or the peptides, polynucleic acids or vectors of the kit as a method of treatment for the subject, and optionally further treating the subject by administering the pharmaceutical composition or the peptides, polynucleic acids or vectors of the kit.

17. A method of treatment according to item 9, wherein the subject has been identified as likely to have a clinical response or as having above a threshold minimum likelihood of having a clinical response to the treatment by a method according to any one of items 12 to 15.

18. The method of any one of items 8, 9, 16 and 17 wherein the treatment is administered in combination with chemotherapy, targeted therapy or a checkpoint inhibitor.

19. A method of identifying a human subject who will likely not have a clinical response to a method of treatment according to item 9, the method comprising (i) determining that the active ingredient peptide(s) of the pharmaceutical composition do not comprise two or more different amino acid sequences each of which is a T cell epitope capable of binding to at least three HLA class I molecules of the subject; and (ii) identifying the subject as likely not to have a clinical response to the method of treatment.

EXAMPLES

Example 1—HLA-Epitope Binding Prediction Process and Validation

Predicted binding between particular HLA and epitopes (9 mer peptides) was based on the Immune Epitope Database tool for epitope prediction (iedb.org).

The HLA I-epitope binding prediction process was validated by comparison with HLA class I-epitope pairs determined by laboratory experiments. A dataset was compiled of HLA I-epitope pairs reported in peer reviewed publications or public immunological databases.

The rate of agreement with the experimentally determined dataset was determined (Table 2). The binding HLA I-epitope pairs of the dataset were correctly predicted with a 93% probability. Coincidentally the non-binding HLA I-epitope pairs were also correctly predicted with a 93% probability.

TABLE 2

Analytical specificity and sensitivity of the HLA-epitope binding prediction process.

| HLA-epitope pairs | True epitopes (n = 327) (Binder match) | False epitopes (n = 100) (Non-binder match) |
|---|---|---|
| HIV | 91% (32) | 82% (14) |
| Viral | 100% (35) | 100% (11) |
| Tumor | 90% (172) | 94% (32) |
| Other (fungi, bacteria, etc.) | 100% (65) | 95% (36) |
| All | 93% (304) | 93% (93) |

The accuracy of the prediction of multiple HLA binding epitopes was also determined (Table 3). Based on the analytical specificity and sensitivity using the 93% probability for both true positive and true negative prediction and 7% (=100%-93%) probability for false positive and false negative prediction, the probability of the existence of a multiple HLA binding epitope in a person can be calculated. The probability of multiple HLA binding to an epitope shows the relationship between the number of HLAs binding an epitope and the expected minimum number of real binding. Per PEPI definition three is the expected minimum number of HLA to bind an epitope (bold).

TABLE 3

Accuracy of multiple HLA binding epitopes predictions.

| Expected minimum number of real HLA binding | Predicted number of HLAs binding to an epitope: 0 | 1 | 2 | 3 | 4 | 5 | 6 |
|---|---|---|---|---|---|---|---|
| 1 | 35% | 95% | 100% | 100% | 100% | 100% | 100% |
| 2 | 6% | 29% | 90% | 99% | 100% | 100% | 100% |
| 3 | 1% | 4% | 22% | 84% | 98% | 100% | 100% |
| 4 | 0% | 0% | 2% | 16% | 78% | 96% | 99% |
| 5 | 0% | 0% | 0% | 1% | 10% | 71% | 94% |
| 6 | 0% | 0% | 0% | 0% | 0% | 5% | 65% |

The validated HLA-epitope binding prediction process was used to determine all HLA-epitope binding pairs described in the Examples below.

Example 2—Epitope Presentation by Multiple HLA Predicts Cytotoxic T Lymphocyte (CTL) Response This study investigates whether the presentation of one or more epitopes of a polypeptide antigen by one or more HLA class I molecule of an individual is predictive for a CTL response.

The study was carried out by retrospective analysis of six clinical trials, conducted on 71 cancer patients and 9 HIV-infected patients (Table 4). Patients from these studies were treated with an HPV vaccine, three different NY-ESO-1 specific cancer vaccines, one HIV-1 vaccine and a CTLA-4 specific monoclonal antibody (Ipilimumab) that was shown to reactivate CTLs against NY-ESO-1 antigen in melanoma patients. All of these clinical trials measured antigen specific CD8+ CTL responses (immunogenicity) in the study subjects after vaccination. In some cases, correlation between CTL responses and clinical responses were reported.

No patient was excluded from the retrospective study for any reason other than data availability. The 157 patient datasets (Table 4) were randomized with a standard random number generator to create two independent cohorts for training and evaluation studies. In some cases the cohorts contained multiple datasets from the same patient, resulting in a training cohort of 76 datasets from 48 patients and a test/validation cohort of 81 datasets from 51 patients.

TABLE 4

Summary of patient datasets

| Clinical trial | Immunotherapy | Target Antigen | Disease | # Patients* | #Data sets (#antigen × # patient) | Immunoassay performed in the clinical trials** | HLA genotyping method |
|---|---|---|---|---|---|---|---|
| 1 | VGX-3100 | HPV16-E6 HPV16-E7 HPV18-E6 HPV18-E7 HPV16/18 | Cervical cancer | 17/18 | 5 × 17 | IFN-γ ELISPOT | High Resolution SBT |
| 2 | HIVIS vaccine | HIV-1 Gag HIV-1 RT | AIDS | 9/12 | 2 × 9 | IFN-γ ELISPOT | Low-Medium Resolution SSO |
| 3 | rNY-ESO-1 | NY-ESO-1 | Breast-and ovarian cancers, melanoma and sarcoma | 18/18 | 1 × 18 | In vitro and Ex vivo IFN-γ ELISPOT | High Resolution SBT |
| 4 | Ipilimumab | NY-ESO-1 | Metastatic melanoma | 19/20 | 1 × 19 | ICS after T-cell stimulation | Low to medium resolution typing, SSP of genomic DNA, high resolution sequencing |
| 5 | NY-ESO-1f | NY-ESO-1 (91-110) | Esophageal-, non-small-cell lung- and gastric cancer | 10/10 | 1 × 10 | ICS after T-cell stimulation | SSO probing and SSP of genomic DNA |
| 6 | NY-ESO-1 overlapping peptides | NY-ESO-1 (79-173) | Esophageal- and lung cancer, malignant melanoma | 7/9 | 1 × 7 | ICS after T-cell stimulation | SSO probing and SSP of genomic DNA |
| Total | 6 | 7 | | 80 | 157 | | |

The reported CD8+ T cell responses of the training dataset were compared with the HLA class I restriction profile of epitopes (9 mers) of the vaccine antigens. The antigen sequences and the HLA class I genotype of each patient were obtained from publicly available protein sequence databases or peer reviewed publications and the HLA I-epitope binding prediction process was blinded to patients' clinical CD8+ T cell response data where CD8+ T cells are IFN-y producing CTL specific for vaccine peptides (9 mers). The number of epitopes from each antigen predicted to bind to at least 1 (PEPI1+), or at least 2 (PEPI2+), or at least 3 (PEPI3+), or at least 4 (PEPI4+), or at least 5 (PEPI5+), or all 6 (PEPI6) HLA class I molecules of each patient was determined and the number of HLA bound were used as classifiers for the reported CTL responses. The true positive rate (sensitivity) and true negative rate (specificity) were determined from the training dataset for each classifier (number of HLA bound) separately.

ROC analysis was performed for each classifier. In a ROC curve, the true positive rate (Sensitivity) was plotted in function of the false positive rate (1-Specificity) for different cut-off points (FIG. 1). Each point on the ROC curve represents a sensitivity/specificity pair corresponding to a particular decision threshold (epitope (PEPI) count). The area under the ROC curve (AUC) is a measure of how well the classifier can distinguish between two diagnostic groups (CTL responder or non-responder).

The analysis unexpectedly revealed that predicted epitope presentation by multiple class I HLAs of a subject (PEPI2+, PEPI3+, PEPI4+, PEPI5+, or PEPI6), was in every case a better predictor of the CD8+ T cell response or CTL response than epitope presentation by merely one or more HLA class I (PEPI1+, AUC=0.48, Table 5).

TABLE 5

Determination of diagnostic value of the PEPI biomarker by ROC analysis

| Classifiers | AUC |
|---|---|
| PEPI1+ | 0.48 |
| PEPI2+ | 0.51 |
| PEPI3+ | 0.65 |
| PEPI4+ | 0.52 |
| PEPI5+ | 0.5 |
| PEPI6+ | 0.5 |

The CTL response of an individual was best predicted by considering the epitopes of an antigen that could be presented by at least 3 HLA class I alleles of an individual (PEPI3+, AUC=0.65, Table 5). The threshold count of PEPI3+(number of antigen-specific epitopes presented by 3 or more HLA of an individual) that best predicted a positive CTL response was 1 (Table 6). In other words, at least one antigen-derived epitope is presented by at least 3 HLA class I of a subject (≥1 PEPI3+), then the antigen can trigger at least one CTL clone, and the subject is a likely CTL responder. Using the ≥1 PEPI3+ threshold to predict likely CTL responders ("≥1 PEPI3+ test") provided 76% true positive rate (diagnostic sensitivity) (Table 6).

TABLE 6

Determination of the ≥1 PEPI3+ threshold to predict likely CTL responders in the training dataset.

| | PEPI3+ Count | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Sensitivity: | 0.76 | 0.60 | 0.31 | 0.26 | 0.14 | 0.02 | 0 | 0 | 0 | 0 | 0 | 0 |
| 1-Specificity: | 0.59 | 0.24 | 0.21 | 0.15 | 0.09 | 0.06 | 0.06 | 0.03 | 0.03 | 0.03 | 0.03 | 0.03 |

Example 3—Retrospective Validation of the ≥1 PEPI3+ Threshold as Novel Biomarker for PEPI Test In a retrospective analysis, the test cohort of 81 datasets from 51 patients was used to validate the ≥1 PEPI3+ threshold to predict an antigen-specific CD8+ T cell response or CTL response. For each dataset in the test cohort it was determined whether the ≥1 PEPI3+ threshold was met (at least one antigen-derived epitope presented by at least three class I HLA of the individual). This was compared with the experimentally determined CD8+ T cell responses (CTL responses) reported from the clinical trials (Table 7).

The retrospective validation demonstrated that a PEPI3+ peptide induces CD8+ T cell response (CTL response) in an individual with 84% probability. 84% is the same value that was determined in the analytical validation of the PEPI3+ prediction, epitopes that binds to at least 3 HLAs of an individual (Table 3). These data provide strong evidences that immune responses are induced by PEPIs in individuals.

TABLE 7

Diagnostic performance characteristics of the ≥1 PEPI3+ test (n = 81).

| Performance characteristic | | Description | Result |
|---|---|---|---|
| Positive predictive value (PPV) | 100% [A/(A + B)] | The likelihood that an individual that meets the ≥1 PEPI3+ threshold has antigen-specific CTL responses after treatment with immunotherapy. | 84% |
| Sensitivity | 100% [A/(A + C)] | The proportion of subjects with antigen-specific CTL responses after treatment with immunotherapy who meet the ≥1 PEPI3+ threshold. | 75% |
| Specificity | 100% [D/(B + D)] | The proportion of subjects without antigen-specific CTL responses after treatment with immunotherapy who do not meet the ≥1 PEPI3+ threshold. | 55% |
| Negative predictive value (NPV) | 100% [D/(C + D)] | The likelihood that an individual who does not meet the ≥1 PEPI3+ threshold does not have antigen-specific CTL responses after treatment with immunotherapy. | 42% |
| Overall percent agreement (OPA) | 100% [(A + D)/N] | The percentage of predictions based on the ≥1 PEPI3+ threshold that match the experimentally determined result, whether positive or negative. | 70% |
| Fisher's exact (p) | | | 0.01 |

Figure 2:
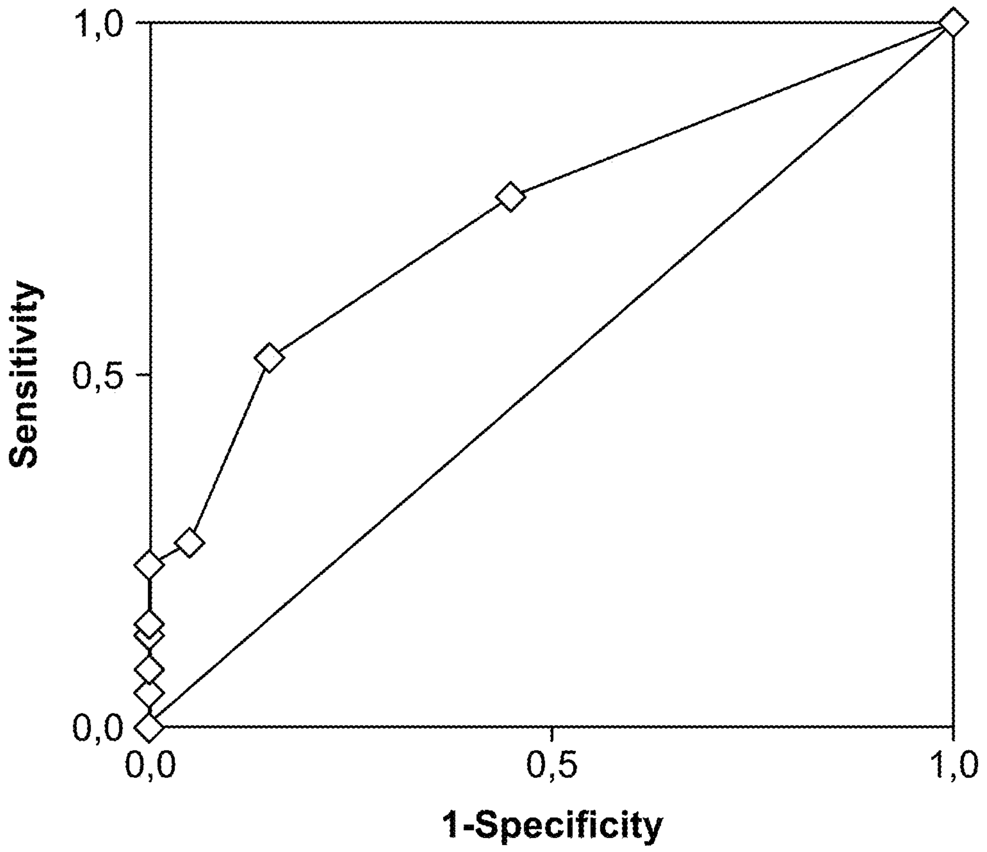

ROC analysis determined the diagnostic accuracy, using the PEPI3+ count as cut-off values (FIG. 2). The AUC value=0.73. For ROC analysis an AUC of 0.7 to 0.8 is generally considered as fair diagnostic value.

A PEPI3+ count of at least 1 (≥1 PEPI3+) best predicted a CTL response in the test dataset (Table 8). This result confirmed the threshold determined during the training (Table 5).

TABLE 8

Confirmation of the ≥1 PEPI3+ threshold to predict likely CTL responders in the test/validation dataset.

| | PEPI3+ Count | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Sensitivity: | 0.75 | 0.5 | 0.26 | 0.23 | 0.15 | 0.13 | 0.08 | 0.05 | 0 | 0 | 0 | 0 |
| 1-Specificity: | 0.45 | 0.15 | 0.05 | 0 | 0 | 0 | 0 | 0 | 0 | 0 | 0 | 0 |

Example 4—Clinical Validation of the ≥1 PEPI3+ Threshold as Novel Biomarker for PEPI Test The PEPI3+ biomarker-based vaccine design has been tested first time in a phase I clinical trial in metastatic colorectal cancer (mCRC) patients in the OBERTO phase I/II clinical trial (NCT03391232). In this study, we evaluated the safety, tolerability and immunogenicity of a single or multiple dose(s) of PolyPEPI1018 as an add-on to maintenance therapy in subjects with mCRC. PolyPEPI1018 is a peptide vaccine containing 12 unique epitopes derived from 7 conserved TSAs frequently expressed in mCRC (WO2018158455 A1). These epitopes were designed to bind to at least three autologous HLA alleles that are more likely to induce T-cell responses than epitopes presented by a single HLA (See Examples 2 & 3). mCRC patients in the first line setting received the vaccine (dose: 0.2 mg/peptide) just after the transition to maintenance therapy with a fluoropyrimidine and bevacizumab. Vaccine-specific T-cell responses were first predicted by identification of PEPI3+-s in silico (using the patient's complete HLA genotype and antigen expression rate specifically for CRC) and then measured by ELISpot after one cycle of vaccination (phase I part of the trial).

Seventy datasets from 10 patients (Phase 1 cohort and dataset of OBERTO trial) was used to prospectively validate that PEPI3+ biomarker predicts antigen-specific CTL responses. For each dataset, predicted PEPI3+-s were determined in silico and compared to the vaccine-specific immune responses measured by ELISPOT assay from the patients' blood. Diagnostic characteristics (positive predictive value, negative predictive value, overall percent agreement) determined this way were then compared with the retrospective validation results described in Example 3.

The overall percent agreement was 64%, with high positive predictive value of 79%, representing 79% probability that the patient with predicted PEPI3+ will produce CD8 T cell specific immune response against the analyzed antigen. Clinical trial data were significantly correlated with the retrospective trial results (p=0.01) and provides evidence for the PEPI3+ calculation with PEPI test to predict antigen-specific T cell responses based on the complete HLA-genotype of patients (Table 91.

TABLE 9

Prospective validation of the ≥1 PEPI3+ and PEPI test

| Parameter | Definition | Retrospective validation n = 81* | Prospective validation (OBERTO) n = 70** |
|---|---|---|---|
| PPV Positive Predictive Value | The likelihood that an individual with a positive PEPI test result has antigen-specific T cell responses | 84% | 79% |
| NPV Negative Predictive Value | The likelihood that an individual with a negative PEPI test result does not have antigen-specific T cell responses | 42% | 51% |
| OPA Overall Percent Agreement | The percentage of results that are true results, whether positive or negative | 70% | 64% |
| Fisher's exact probability test (p) | | 0.01 | 0.01 |

*51 patients; 6 clinical trials; 81 dataset

**10 patients; Treos phase I clinical trial (OBERTO); 70 datasets

Example 5—the ≥1 PEPI3+ Test Predicts CD8+ T Cell Reactivities

Supporting data were obtained to show that the ≥1 PEPI3+ correlates with clinical immunogenicity data but the state-of-art mono-HLA specific epitope determination does not show correlation with vaccine-specific immunogenicity.

The ≥1 PEPI3+ calculation was compared with a state-of-art method for predicting a specific human subject's CTL response to peptide antigens.

The HLA genotypes of 28 cervical cancer and VIN-3 patients that received HPV-16 synthetic long peptide vaccine (LPV) in two different clinical trials were determined from DNA samples. The LPV consists of long peptides covering the HPV-16 viral oncoproteins E6 and E7. The amino acid sequence of the LPV was obtained from M. J. Welters, et al. Induction of tumor-specific CD4+ and CD8+ T-cell immunity in cervical cancer patients by a human papillomavirus type 16 E6 and E7 long peptides vaccine. *Clin Cancer Res* 14, 178-187 (2008), G. G. Kenter, et al. Vaccination against HPV-16 oncoproteins for vulvar intraepithelial neoplasia. *N Engl J Med* 361, 1838-1847 (2009). M. J. Welters, et al. Success or failure of vaccination for HPV16-positive vulvar lesions correlates with kinetics and phenotype of induced T-cell responses. *Proc Natl Acad Sci USA* 107, 11895-11899 (2010). The publications also report the T cell responses of each vaccinated patient to pools of overlapping peptides of the vaccine. 25 (20 having VIN-3 and 5 having cervical cancer) patients had immune response data available, and 25 had clinical response data available.

For each patient, epitopes (9 mers) of the LPV that are presented by at least three patient class I HLA (PEPI3+s) were identified and their distribution among the peptide pools was determined. Peptides that comprised at least one PEPI3+(≥1 PEPI3+) were predicted to induce a CD8+ T cell response. Peptides that comprised no PEPI3+ were predicted not to induce a CD8+ T cell response.

The ≥1 PEPI3+ threshold correctly predicted 529 out of 555 negative CD8+ T cell responses (95% true negative (TN) rate) and 9 out of 45 positive CD8+ T cell responses (20% true positive (TP) rate) measured after vaccination (FIG. 3A). Overall, the agreement between the ≥1 PEPI3+ threshold and experimentally determined CD8+ T cell reactivity was 90% ($p<0.001$).

For each patient the distribution among the peptide pools of epitopes that are presented by at least one patient class I HLA (≥1 PEPI1+, HLA restricted epitope prediction, prior art method) was also determined. Forty-two HLA class I-binding epitopes predicted 45 CD8+T cell responses (93% TP rate). In contrast, of the 555 negative T cell responses, only 105 were ruled out by HLA-binding epitopes (19% TN rate) (FIG. 3B). Overall, the agreement between a single HLA class I allele-binding epitope and CD8+ T cell response was 25%, which was not statistically significant.

Example 6—Prediction of HLA Class II Restricted CD4+ Helper T Cell Epitopes

The 28 cervical cancer and VIN-3 patients that received the HPV-16 synthetic long peptide vaccine (LPV) in two different clinical trials (as detailed in Example 5) were investigated for CD4+T helper responses following LPV vaccination (FIG. 4). The TP rate of the prediction of HLA class II restricted epitopes was 95%, since the State of Art tool predicted 112 positive responses (positive CD4+ T cell reactivity to a peptide pool for a person's HLA class II alleles) out of 117. The TN rate was 0% since it could rule out 0 of 33 negative T cell responses. Overall, the agreement between HLA-restricted class II PEPI prediction and CD4+ T cell reactivity was 75% (not significant).

The HLA class II-binding PEPI3+–s predicted 86 of 117 positive CD4+ T-cell responses (73% TP rate) and ruled out 17 of 33 negative T cell responses (52% TN rate). Overall, the agreement between HLA class II PEPI3+–s and CD4+ T-cell response was 69% ($p=0.005$)(FIG. 4A).

Figure 5:
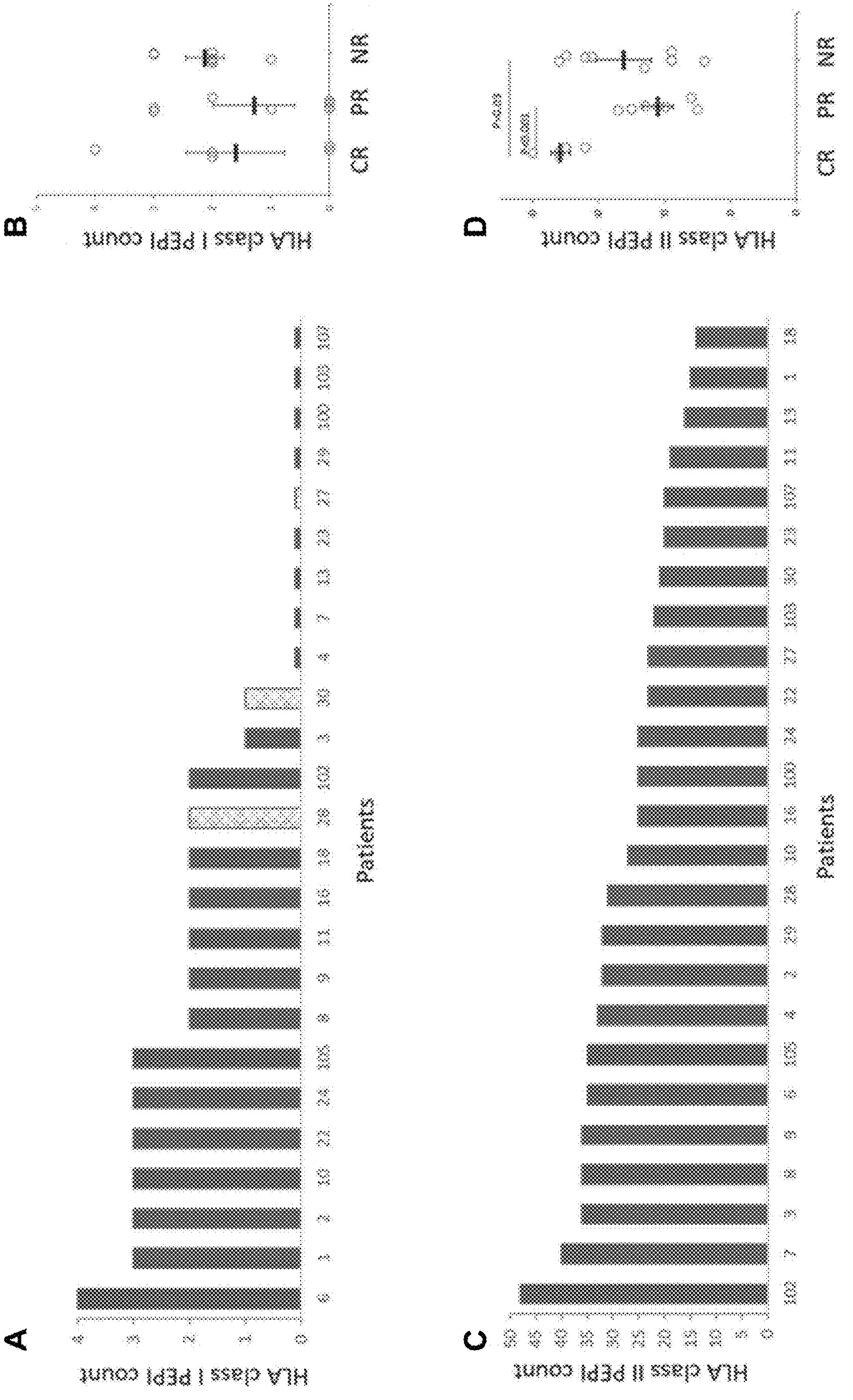

Example 7—the ≥1 PEPI3+ Test Predicts T Cell Responses to Full Length LPV Polypeptides Using the same studies reported in Examples 5 and 6, the ≥1 PEPI3+ test was used to predict patient CD8+ and CD4+ T cell responses to the full length E6 and E7 polypeptide antigens of the LPV vaccine. Results were compared to the experimentally determined responses reported. The test correctly predicted the CD8+ T cell reactivity (PEPI3+) of 11 out of 15 VIN-3 patients with positive CD8+ T cell reactivity test results (sensitivity 70%, PPV 85%) and of 2 out of 5 cervical cancer patients (sensitivity 40%, PPV 100%) (FIG. 5A). The CD4+ T cell reactivities (PEPI3+) were correctly predicted 100% both of VIN-3 and cervical cancer patients (FIG. 5B).

Class I and class II HLA restricted PEPI3+ count was also observed to correlate with the reported clinical benefit to LPV vaccinated patients. Patients with higher PEPI3+ counts had either complete or partial response already after 3 months. There was also a correlation between the number of PEPIs and clinical response in VIN-3 patients for HLA class II PEPIs but not HLA class I PEPIs, confirming the post-hoc analysis results from the clinical trial (FIGS. 5C and 5D).

Example 8—Case Study, PEPI3+ Correlation with Vaccine-Specific Immunogenicity

Figure 6:
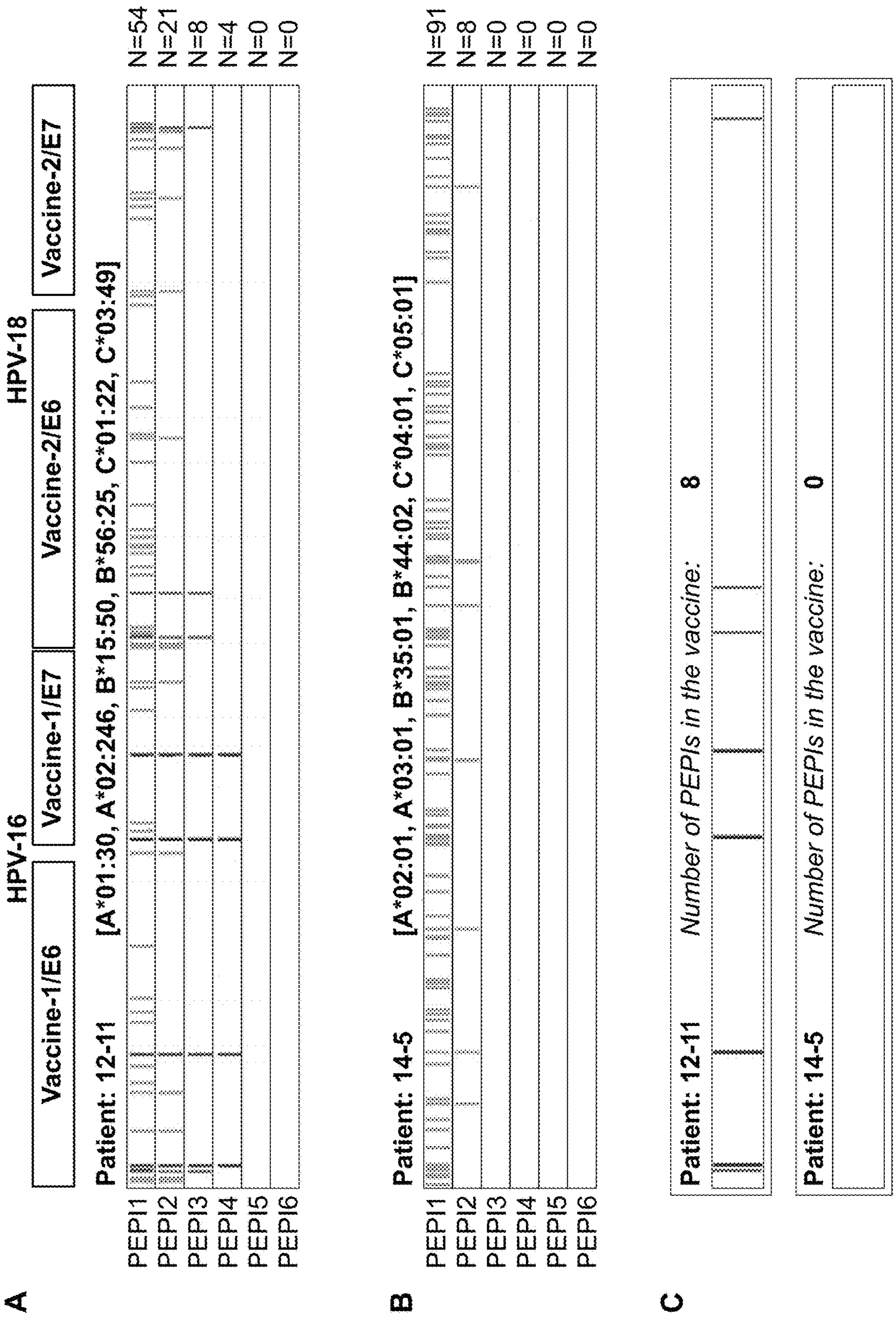

"Vaccine-1" is an HPV16 based DNA vaccine containing full length E6 and E7 antigens with a linker in between. "Vaccine-2" is an HPV18 based DNA vaccine containing full length E6 and E7 antigens with a linker in between (FIG. 6A). A Phase II clinical trial investigated the T cell responses of 17 HPV-infected patients with cervical cancer who were vaccinated with both Vaccine-1" and "Vaccine-2" ("Vaccine-3" vaccination, Bagarazzi et al. Science Translational Medicine. 2012; 4(155):155ra138).

FIG. 6B shows for two illustrative patients (patient 12-11 and patient 14-5) the position of each epitope (9 mer) presented by at least 1 (PEPI1+), at least 2 (PEPI2+), at least 3 (PEPI3+), at least 4 (PEPI4+), at least 5 (PEPI5+), or all 6 (PEPI6) class I HLA of these patients within the full length sequence of the two HPV-16 and two HPV-18 antigens.

Patient 12-11 had an overall PEPI1+ count of 54 for the combined vaccines (54 epitopes presented by one or more class I HLA). Patient 14-5 had a PEPI1+ count of 91. Therefore patient 14-5 has a higher PEPI1+ count than patient 12-11 with respect to the four HPV antigens. The PEPI1+s represent the distinct vaccine antigen specific HLA restricted epitope sets of patients 12-11 and 14-5. Only 27 PEPI1+s were common between these two patients.

For the PEPI3+ counts (number of epitopes presented by three or more patient class I HLA), the results for patients 12-11 and 14-5 were reversed. Patient 12-11 had a PEPI3+ count of 8, including at least one PEPI3+ in each of the four HPV16/18 antigens. Patient 14-5 had a PEPI3+ count of 0 (FIG. 6C).

The reported immune responses of these two patients matched the PEPI3+ counts, not the PEPI1+ counts. Patient 12-11 developed immune responses to each of the four antigens post-vaccination as measured by ELISpot, whilst patient 14-5 did not develop immune responses to any of the four antigens of the vaccines. A similar pattern was observed when the PEPI1+ and PEPI3+ sets of all 17 patients in the trial were compared. There was no correlation between the PEPI1+ count and the experimentally determined T cell responses reported from the clinical trial. However, correlation between the T cell immunity predicted by the ≥1 PEPI3+ test and the reported T cell immunity was observed. The ≥1 PEPI3+ test predicted the immune responders to HPV DNA vaccine.

Moreover, the diversity of the patient's PEPI3+ set resembled the diversity of T cell responses generally found in cancer vaccine trials. Patients 12-3 and 12-6, similar to patient 14-did not have PEPI3+s predicting that the HPV vaccine could not trigger T cell immunity. All other patients had at least one PEPI3 predicting the likelihood that the HPV vaccine can trigger T cell immunity. 11 patients had multiple PEPI3+ predicting that the HPV vaccine likely triggers polyclonal T cell responses. Patients 15-2 and 15-3 could mount high magnitude T cell immunity to E6 of both HPV, but poor immunity to E7. Other patients 15-1 and 12-11 had the same magnitude response to E7 of HPV18 and HPV16, respectively.

Example 9—Design of a Model Population for Conducting in Silico Trials and Identifying Candidate Precision Vaccine Targets for Large Population An in silico human trial cohort of 433 subjects with complete 4-digit HLA class I genotype (2×HLA-A*xx:xx; 2×HLA-B*xx:xx; 2×HLA-C*xx:xx) and demographic information was compiled. This Model Population has subjects with mixed ethnicity having a total of 152 different HLA alleles that are representative for >85% of presently known allele G-groups.

A database of a "Big Population" containing 7,189 subjects characterized with 4-digit HLA genotype and demographic information was also established. The Big Population has 328 different HLA class I alleles. The HLA allele distribution of the Model Population significantly correlated with the Big Population (Table 10) (Pearson $p<0.001$). Therefore the 433 patient Model Population is representative for a 16 times larger population.

The Model Population is representative for 85% of the human race as given by HLA diversity as well as HLA frequency.

TABLE 10

| Statistical analysis of HLA distributions in "Model Population" vs. "Big Population". | | | | |
|---|---|---|---|---|
| Group name 1 | Group name 2 | Pearson R value | Correlation | P Value |
| 433 Model Population | 7,189 Big Population | 0.89 | Strong | P < 0.001 |

Figure 7:
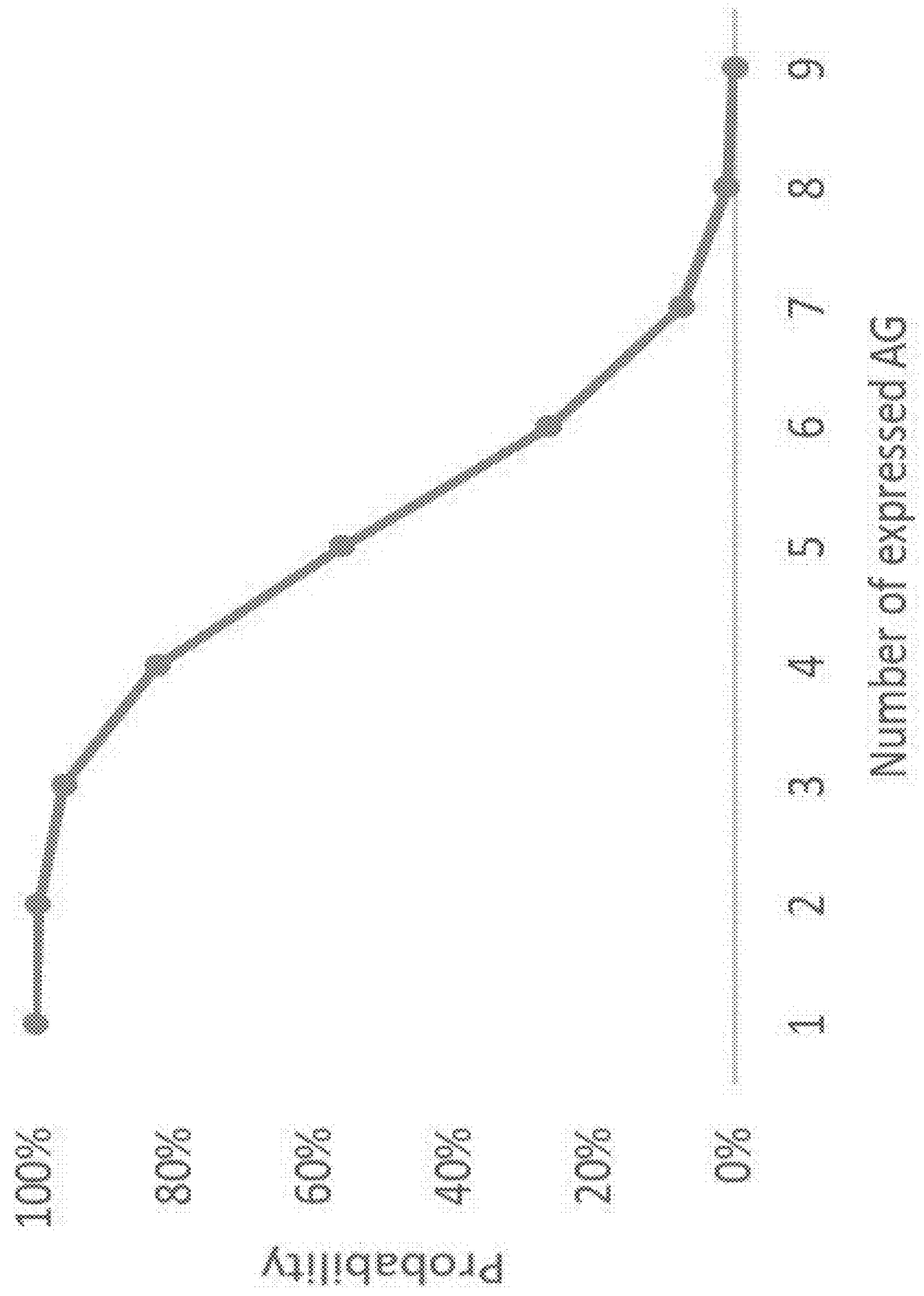

Example 10—in Silico Trial Based on the Identification of Multiple HLA Binding Epitopes in a Multi-Peptide Vaccine IMA901 Predict the Reported Clinical Trial Immune Response Rate Probability of Targeting Multiple Antigens in the Tumor of RCC Patients IMA901 is a therapeutic vaccine for renal cell cancer (RCC) comprising 9 peptides derived from tumor-associated antigens (TUMAPs). It was demonstrated that TUMAPs are naturally presented in human cancer tissue, they are over-expressed antigens shared by a subset of patients with the given cancer entity (Table 11). We estimated the probability that a TSA is expressed in a subject treated with IMA901 vaccine using available data from the scientific literature (FIG. 7). We used the Bayesian convention assuming that the expression probabilities follow a Beta-distribution.

We defined AG50 as the number of TSAs (AG) in the cancer vaccine that a specific tumor type expresses with 50% probability. The AG50 modelling of cancer vaccines assumes that each AG produces an effect proportional to the expression rate of the AG in the tumor type (if each AG in the vaccine is immunogenic).

For IMA901 vaccine targeting 9 antigens (9 TUMAPs), the AG50 value is 4.7, meaning that about half of the antigens are overexpressed in 50% of patients' tumor. Moreover, the probability of targeting 2 expressed antigens is 100% and 3 antigens is 96%. These results suggest high potency of IMA901 vaccine based on target antigen selection.

TABLE 11

| Overexpression of TAAs in RCC tumors selected for IMA901 vaccine | | |
|---|---|---|
| TAA (AG) | Published expression rate in RCC tumors* | Estimated expression rate (95% CI) |
| ADF-001 | 5/11[1] | 46% (21%, 72%) |
| ADF-002 | 5/11 | 46% (21%, 72%) |
| APO-001 | 9/11[1] | 77% (52%, 95%) |
| CCN-001 | 4/11 | 38% (15%, 65%) |
| GUC-001 | 0/2[2] | 25% (1%, 71%) |
| K67-001 | 2/2 | 75% (29%, 99%) |
| MET-001 | 11/11 | 92% (74%, 100%) |
| MUC-001 | 0/11 | 8% (0%, 26%) |
| RGS-001 | 7/11 | 62% (35%, 85%) |

*expression is defined as overexpression in tumors compared to healthy tissues provided in the source publications

[1]Walter S et al, Multipeptide immune response to cancer vaccine IMA901 after single-dose cyclophosphamide associates with longer patient survival, Nature Medicine, (2012), 18, 1254-1261

[2]Krüger T et al, Lessons to be learned from primary renal cell carcinomas, Cancer Immunol, Immunother, 2005, 54, 826-836

Probability of Inducing Immune Responses Against Multiple Antigens in the Tumor of RCC Patients A total of 96 HLA-A*02+ subjects with advanced RCC were treated with IMA901 in two independent clinical studies (Phase I and Phase II) (Walter S et al, Multipeptide immune response to cancer vaccine IMA901 after single-dose cyclophosphamide associates with longer patient survival, Nature Medicine, (2012), 18, 1254-1261). Each of the 9 peptides in IMA901 have been identified as HLA-A*02-restricted epitopes. Based on currently accepted standards, all 9 peptides are strong candidates to boost T cell responses against renal cancer since their presence has been detected in renal cancer patients, and because the trial patients were specifically selected to have at least one HLA molecule (HLA-A*02) capable of presenting each of the peptides. Despite this restriction the immune response rate of the phase I and phase II clinical trials measured for at least one peptide of the vaccine was 74% and 64%, respectively.

We analyzed by in silico prediction the HLA binding properties of each TUMAP in IMA901 and found that 8 out of the 9 TUMAPs can bind to many HLA-A*02 alleles confirming the identification process (FIG. 8). However, we found that each TUMAP can bind to many other HLA-B* and HLA-C* alleles (FIG. 8A).

Since the complete 4-digit HLA genotype of subjects who participated in IMA901 clinical trials were not available, we used the genotype data of 51 HLA-A*02 selected RCC subjects from another clinical trial, to characterize the immunogenicity of IMA901 vaccine (REF: Chowell D, Morris L G T, Grigg C M, Weber J K, Samstein R M, et al. Patient HLA class I genotype influences cancer response to checkpoint blockade immunotherapy. Science. 2018; 359 (6375): 582-587). As presented on FIG. 8B, only few TUMAPs are able to bind to multiple HLAs of the same subject. The most immunogenic peptide in this context turned to be MET-001 capable of generating PEPI in 35% of RCC patients. However, CCN-001 could not generate PEPI in any of the patients, in agreement with FIG. 8A; CCN-001 can bind only to HLA-A*02 alleles. Based on FIG. 8A, MUC-001 is theoretically able to bind other alleles, too (both HLA-B and HLA-C), however those alleles were not present in the patients of our model population, therefore this peptide could not generate PEPI, either.

The immunogenicity of IMA901 vaccine determined in the 2 clinical trials was compared with the PEPI response rate determined using the PEPI test in our RCC model population. We found 67% (CI95 53-78%) immune response to at least one peptide of the IMA901 vaccine. According to PEPI test, 33% (CI95 22-47%) of these HLA-A*02+ subjects did not have 3 HLAs binding to any TUMAPs. Interestingly, IMA901 did not induce T cell responses in 25% and 36% of HLA-A*02 selected subjects in the Phase I and Phase II clinical trials, respectively. Furthermore, PEPI test predicted 30% (CI95 19-43%) of subjects with 1 PEPI to one TUMAP, and 37% (CI95 25-51%) have 2 PEPIs to at least two IMA901 peptides, which is in agreement with the average 40% and 27% immune response to 1 or 2 TUMAPs in both clinical trials (Table 12). The differences between the immunogenicity found in the 3 cohorts can be explained by the differences in the HLA genotype of the study subjects as well as the potential errors in measuring T cell responses and in determining PEPIs with the PEPI test (see Example 1). The phase I and phase II study results show the variability of the immune response rates of the same vaccine in different trial cohorts. However, the agreements between PEPI response rates and immunogenicity of peptide vaccines are determined by the host HLA sequences.

TABLE 12

Immunogenicity of IMA901 vaccine is determined by the host HLA genotype (multiple HLAs)

| Immune responses to TUMAPs | Phase I (n = 27)* | Phase II (n = 61)* | Phase I + II (n = 88) | RCC model population (n = 51)** (CI95%) |
|---|---|---|---|---|
| No peptide | 25% | 36% | 33% | 33% (22-47%) |
| ≥1 peptide | 74% | 64% | 67% | 67% (53-78%) |
| 1 peptide | 44% | 38% | 40% | 30% (19-43%) |
| ≥2 peptides | 29% | 26% | 27% | 37% (25-51%) |

*reported immunological data for the trials conducted with IMA901 vaccine (REF: Walter Nat Med 2012);
**Predicted by PEPI test Similarly to the AG50, we defined AP50 as the average number of antigens with PEPI of a vaccine which shows how the vaccine can induce immune response against the antigens targeted by the composition (cancer vaccine specific immune response). AP, therefore is depending of the HLA heterogeneity of the analyzed population and is independent on the expression of the antigen on the tumor. The IMA901 composition can induce immune response against an average of 1.06 vaccine antigens (AP50=1.06) meaning that in the HLA-A*02 selected RCC model population it can induce immune response against at least one vaccine antigen. This result is far less compared to the designed intention of immunogenicity (HLA-matched patients treated with 9 peptides).

Comparison of Immunogenicity and Clinical Response of TUMAPs in the IMA901 Peptide Vaccine An immune response induced by a vaccine against a single antigen might not be sufficient for clinical activity, as the given antigen might not be expressed in the patient.

Therefore, we defined AGP as the immune response which targets an expressed antigen, taking into account both the immunogenicity and expression probability of the vaccine antigen on the tumor, presented above. AGP depends on the antigen (AG) expression rate in the indicated tumor and the HLA genotype of subjects capable to make PEPI (P) in the study population.

Figure 9:
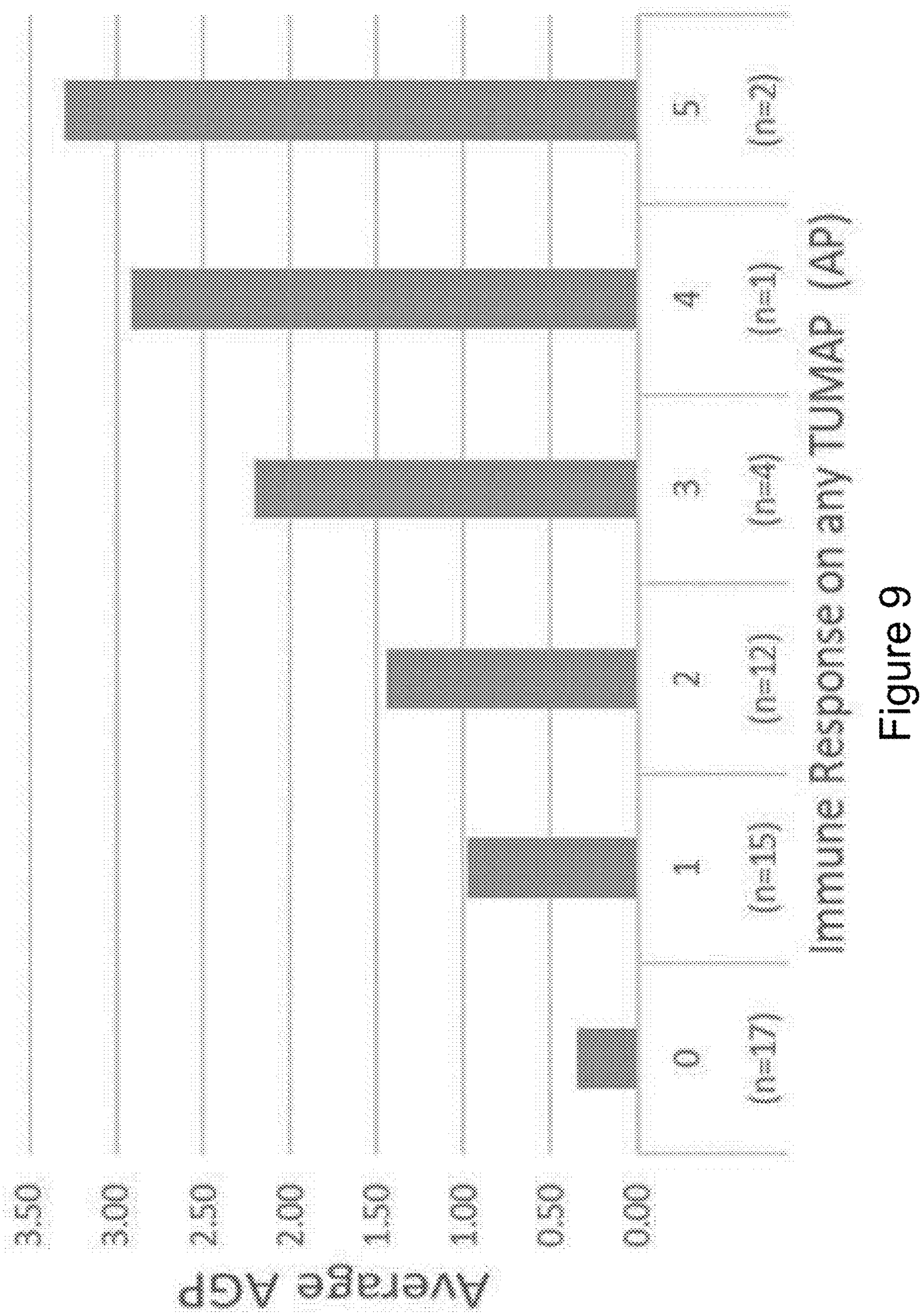

Therefore, we investigated the correlation between immune responses against different number of antigens (TUMAPs) and the immune responses against likely expressed antigens (AGP). We found that an immune response elicited by one peptide (1 TUMAP) corresponds to AGP, meaning that there is 98% probability that the immune response induced by any peptide of the IMA901 vaccine will target an expressed antigen on the tumor (FIG. 9). However, immune responses elicited by 2 or 3 TUMAPs correspond to only 1.44 and 2.21 AGP, respectively. 0.35 AGP corresponding to 0 TUMAP indicates the cumulated error of PEPI test prediction (see Example 1).

To characterize the potency of a cancer vaccine we defined AGP50, a parameter showing the number of antigens that the vaccine induced CTLs can recognize in a tumor with 50% probability. The computation is similar to the AG50 but in addition to the expression, the occurrence of the PEPI presentation on certain vaccine antigen is also considered. AGP50 for IMA901 vaccine for the RCC model population is 1.10.

In a retrospective analysis, IMA901 clinical trial investigators found that significantly more subjects who responded to multiple TUMAPs of IMA901 experienced disease control (DC, stable disease or partial response) compared with subjects who had no response or responded to only 1 TUMAP (Table 13). Since the presence of PEPIs accurately predicted the responders to TUMAPs, we investigated the relationship between disease control rate in the TUMAP responder subpopulation and AGP. Similarly, to the investigators we analyzed the percentage of patients who are likely to have immune response against an expressed antigen (i.e.: ≥1 AGP) for the subpopulations predicted to have immune response to 0, 1 or 2 TUMAPs using our RCC model population. Interestingly, percentage of patients with 1 AGP is similar to the percentage of patients with disease control in the subpopulations: i.e.: 33% of patients had disease control vs 47% (CI95 23-67%) had 1 AGP and considerably more patients had disease control and AGP in the subgroup with immune response to 2 TUMAPs 75% vs 90% (CI95 70, 97%), respectively. These results suggest that only those patients are likely to experience clinical benefit, who have immune response against at least one expressed tumor antigen. Moreover, the percentage of patients with 1 AGP in our RCC model population is similar to the disease control rate of the phase I and phase II trials conducted with IMA901 vaccine (Table 12).

TABLE 13

Correlation between clinical benefit and AGP

| Subpopulation | % of pts with DC in the clinical subpopulation | % pts with 1 AGP in the model subpopulation (CI95) |
|---|---|---|
| No IR | 14% | 5% (0%, 18%) |
| IR to 1TUMAP | 33% | 47% (23%, 67%) |
| IR to ≥2 TUMAPs | 75% | 90% (70%, 97%) |
| Phase I | 40% | 49% (35%, 61%) |
| Phase II | 31% | |

Analysis of IMA901 Vaccine Potency in Multiple Populations

As shown in Table 14, AG50 value of 4.7 was observed for IMA901 vaccine, suggesting high potency based on target antigen selection. However, AP50 for IMA901 in both the unselected general population and HLA-A*02 selected subjects were only 0.75 and 1.12, respectively. Similar results were obtained for unselected RCC model population and HLA-A*02 selected populations. This results demonstrate that HLA-A*02 enrichment improved the antigenicity of IMA901, however did not ensure the immunogenicity of the vaccine. Consequently, the AGP50 values describing the potency of the vaccine are low in each population.

TABLE 14

Potency of IMA901 vaccine in in unselected population and HLA-A*02 selected subjects

| Model Population | AG50 | AP50 | AGP50 |
|---|---|---|---|
| All Subjects (n = 433) | 4.7 | 0.75 | 0.49 |
| HLA-A*02 Subjects (n = 180) | 4.7 | 1.12 | 0.81 |
| RCC population (n = 129) | 4.7 | 0.61 | 0.70 |
| RCC subpopulation A*02 (n = 51) | 4.7 | 1.06 | 1.10 |

Example 11—in Silico Trials Based on the Identification of Multiple HLA Binding Epitopes Predict the Reported T Cell Response Rates of Clinical Trials The objective of this study was to determine whether a model population, such as the one described in Example 9, may be used to predict CTL reactivity rates of vaccines, i.e.

used in an in silico efficacy trial and to determine the correlation between the clinical outcome of vaccine trials and PEPI.

Published clinical trial results were collected from studies with therapeutic vaccines, which included 1,790 subjects in 64 clinical studies, treated with 42 therapeutic vaccines covering 61 different antigens (Table 15). The same vaccines used in those clinical trials were used to perform in silico trials with the model population of 433 human leukocyte antigen (HLA)-genotyped subjects (described in Example 9). No subjects were excluded for reasons other than data availability. IRR was defined as the proportion of subjects in the study population with T cell responses induced by the study vaccine. ORR was defined as the proportion of subjects in the study population with objective response (complete and partial response) after vaccination. The proportion of subjects with PEPIs (personal epitopes that bind to 3 HLA alleles of a subject), multiple PEPIs, and PEPIs in multiple antigens were computed in the in silico trials to obtain the PEPI Score, MultiPEPI Score, and MultiAgPEPI Score, respectively. The immune and objective response rates (IRR and ORR) from the published clinical trials were compared with the PEPI Score, MultiPEPI Score, and MultiAgPEPI Score. All reported and calculated scores are summarized in Table 16.

TABLE 15

Summary of patient demographics in the published clinical trials

| Characteristic | Count | Percentage |
|---|---|---|
| Total subjects | 1,790 | |
| Total studies | 64 | |
| Subjects with HIV infection | 12 | 1% |
| Subjects with neoplasia or dysplasia | 172 | 9% |
| Subjects with cancer | 1606 | 90% |
| Subjects with solid tumors | 1503 | 84% |
| Subjects with liquid tumors | 103 | 6% |
| Subjects with metastatic tumors | 788 | 44% |
| Subjects with non-metastatic tumors | 818 | 46% |
| HLA selected subjects | 918 | 51% |
| Non-HLA selected subjects | 872 | 49% |
| Trials with HLA selected subjects | 32 | 50% |
| Trials without HLA selected subjects | 32 | 50% |

TABLE 16

Response rates and PEPI Scores

| Immunotherapy | IRR | ORR | PEPI Score | Multi PEPI Score | MultiAg PEPI Score |
|---|---|---|---|---|---|
| PSMA-Survivin pulsed DC vaccine | — | 18% | 3% | 0% | 0% |
| Peptide vaccine | — | 3% | 10% | 0% | 0% |
| HPV-SLP | 83% | 60% | 73% | 70% | 34% |
| | 100% | 60% | 73% | 70% | 34% |
| VGX-3100 | 78% | 50% | 87% | 56% | 64% |
| Melanoma peptide vaccine | 52% | 12% | 42% | 6% | 6% |
| GAA peptides vaccine | 55% | 15% | 18% | 0% | 0% |
| KRM-20 peptide vaccine | 40% | 13% | 36% | 15% | 15% |
| Peptide vaccine | 100% | 25% | 81% | 3% | 1% |
| S-288310 peptide vaccine | 67% | 17% | 44% | 8% | 8% |
| KIF20A-66 peptide | 70% | 26% | 38% | 7% | — |
| PepCan | 65% | 52% | 62% | 26% | — |
| Iplilimumab (NYESO-1 specific response) | 72% | 25% | 84% | 65% | — |

TABLE 16-continued

Response rates and PEPI Scores

| Immunotherapy | IRR | ORR | PEPI Score | Multi PEPI Score | MultiAg PEPI Score |
|---|---|---|---|---|---|
| p53 SLP70-248 | 88% | 0% | 77% | 52% | — |
| | 100% | 0% | 77% | 52% | — |
| | 0% | — | 77% | 52% | — |
| p53 SLP70-235 | 21% | — | 75% | 52% | — |
| GVX301 | 64% | 0% | 65% | 7% | — |
| TroVax vaccine | 65% | 0% | 94% | 83% | — |
| (OXB-301) | 57% | 0% | 94% | 83% | — |
| StimuVax | 21% | — | 2% | — | — |
| IMA901 | 74% | — | 48% | 27% | 27% |
| | 64% | — | 48% | 27% | 27% |
| ICT107 | 33% | — | 52% | — | — |
| ProstVac | 67% | — | 50% | 23% | — |
| | 45% | — | 50% | 23% | — |
| | 76% | — | 50% | 23% | — |
| | 67% | — | 50% | 23% | — |
| | 50% | — | 50% | 23% | — |
| | 72% | — | 50% | 23% | — |
| Synchrotope TA2M | 46% | — | 24% | 7% | — |
| MELITAC 12 · 1 | 49% | — | 47% | 19% | — |
| HIVIS | 50% | — | 88% | — | — |
| | 80% | — | 93% | — | — |
| ImMucin | 90% | — | 95% | 70% | — |
| | 100% | 47% | 95% | 70% | — |
| NY-ESO-1 OLP | 71% | — | 84% | 65% | — |
| | 82% | 0% | 84% | 65% | — |
| WT1 vaccine | 83% | — | 80% | 77% | — |
| WT1 peptide vaccine | 72% | 6% | 86% | — | — |
| RHAMM-R3 peptide vaccine | 44% | 0% | 0% | — | — |
| GMMG-MM5 peptides | 35% | — | 86% | 21% | 21% |
| INGN-225 p53 vaccine | 58% | 4% | 82% | 61% | — |
| HR2822 | 8% | — | 3% | — | — |
| GV1001 | 17% | — | 3% | — | — |
| | 45% | — | 3% | — | — |
| Vx-001 | 51% | — | 33% | — | — |
| | 66% | 7% | 33% | — | — |
| | 58% | 4% | 33% | — | — |
| | 71% | 0% | 33% | — | — |
| NY-ESO-1f | 90% | 0% | 55% | 18% | — |
| GL-0817 | 33% | — | 29% | 3% | — |
| (MAGE-A3 Trojan) | 57% | 0% | 29% | 3% | — |
| | 0% | 0% | 29% | 3% | — |
| DPX0907 (per | 0% | — | 22% | — | — |
| peptide) | 11% | — | 18% | — | — |
| | 11% | — | 7% | — | — |
| | 11% | — | 39% | — | — |
| | 17% | — | 12% | — | — |
| | 17% | — | 5% | — | — |
| | 22% | — | 31% | — | — |
| CV9103 mRNA vaccine | 80% | — | 100% | — | — |
| TG4010 vaccine | 38% | 13% | 43% | 6% | — |
| | 26% | 0% | 43% | 6% | — |
| | 21% | — | 43% | 6% | — |
| | — | 0% | — | — | — |
| SVN-2B peptide vaccine | 60% | — | 35% | — | — |
| TSPP peptide vaccine | — | 5% | 72% | 31% | — |
| Her2/neu peptide vaccine (p369) | 62% | — | 4% | — | — |
| Her2/neu peptide vaccine (p688) | 31% | — | 1% | — | — |
| Her2/neu peptide vaccine (p971) | 54% | — | 0% | — | — |
| MART-1 Peptide Vaccine | 15% | — | 0% | — | — |

Figure 10:
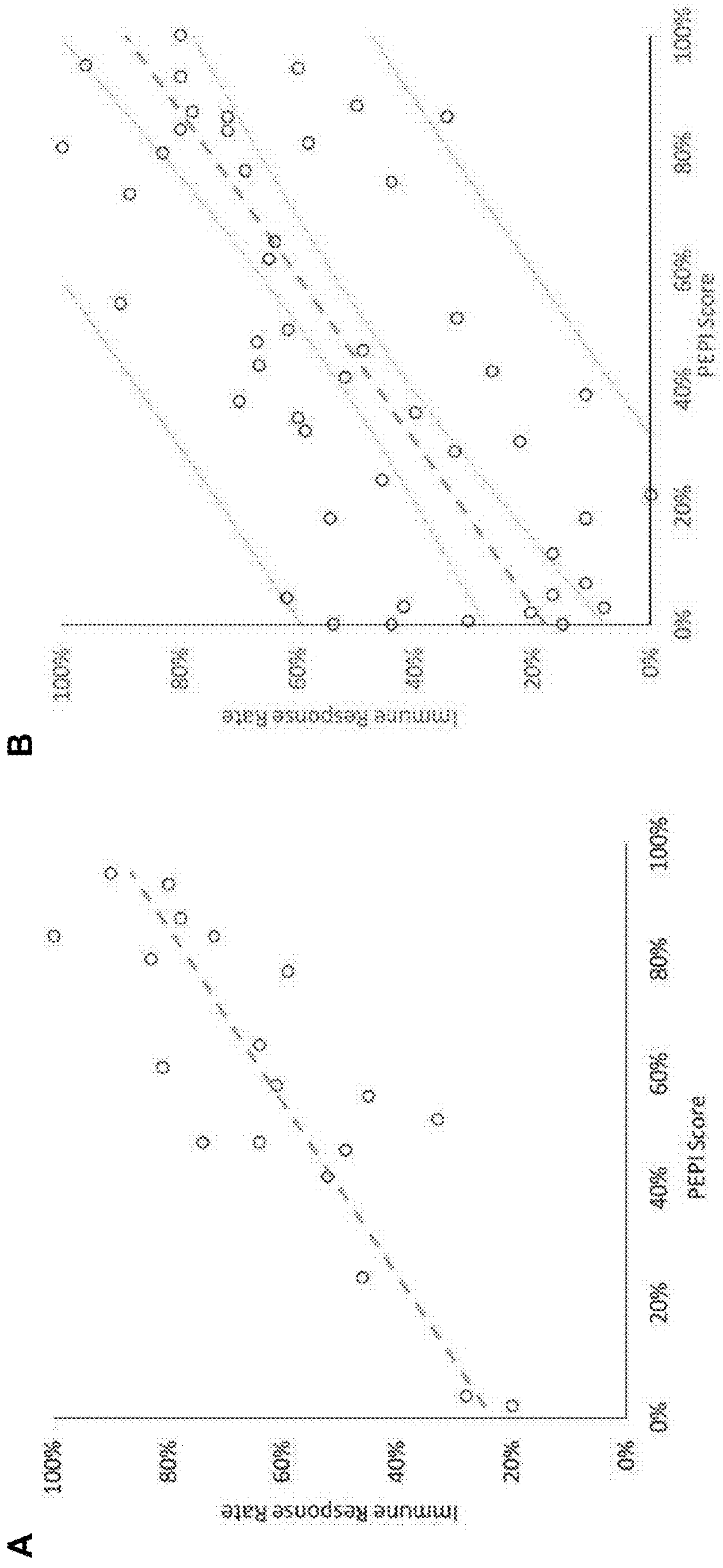
Figure 10:
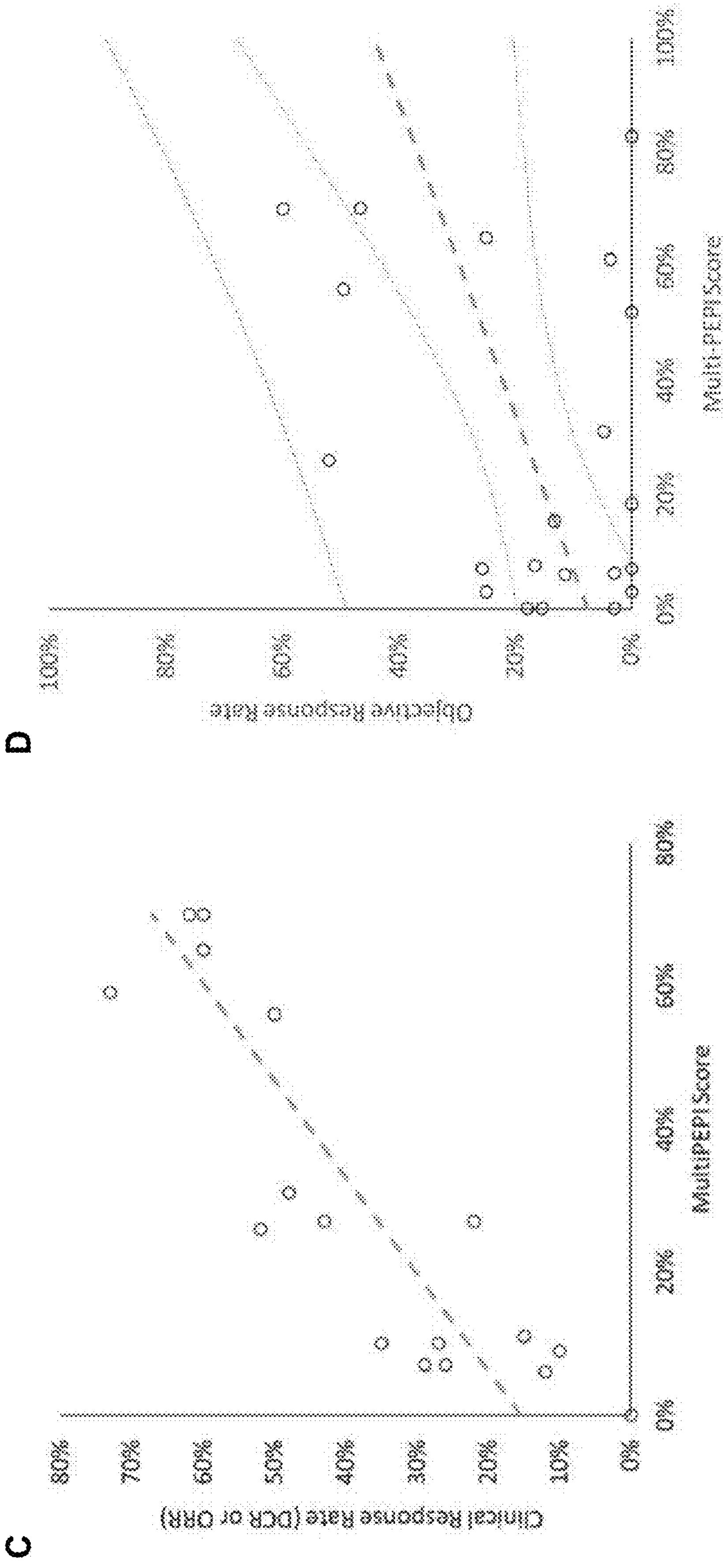
Figure 10:
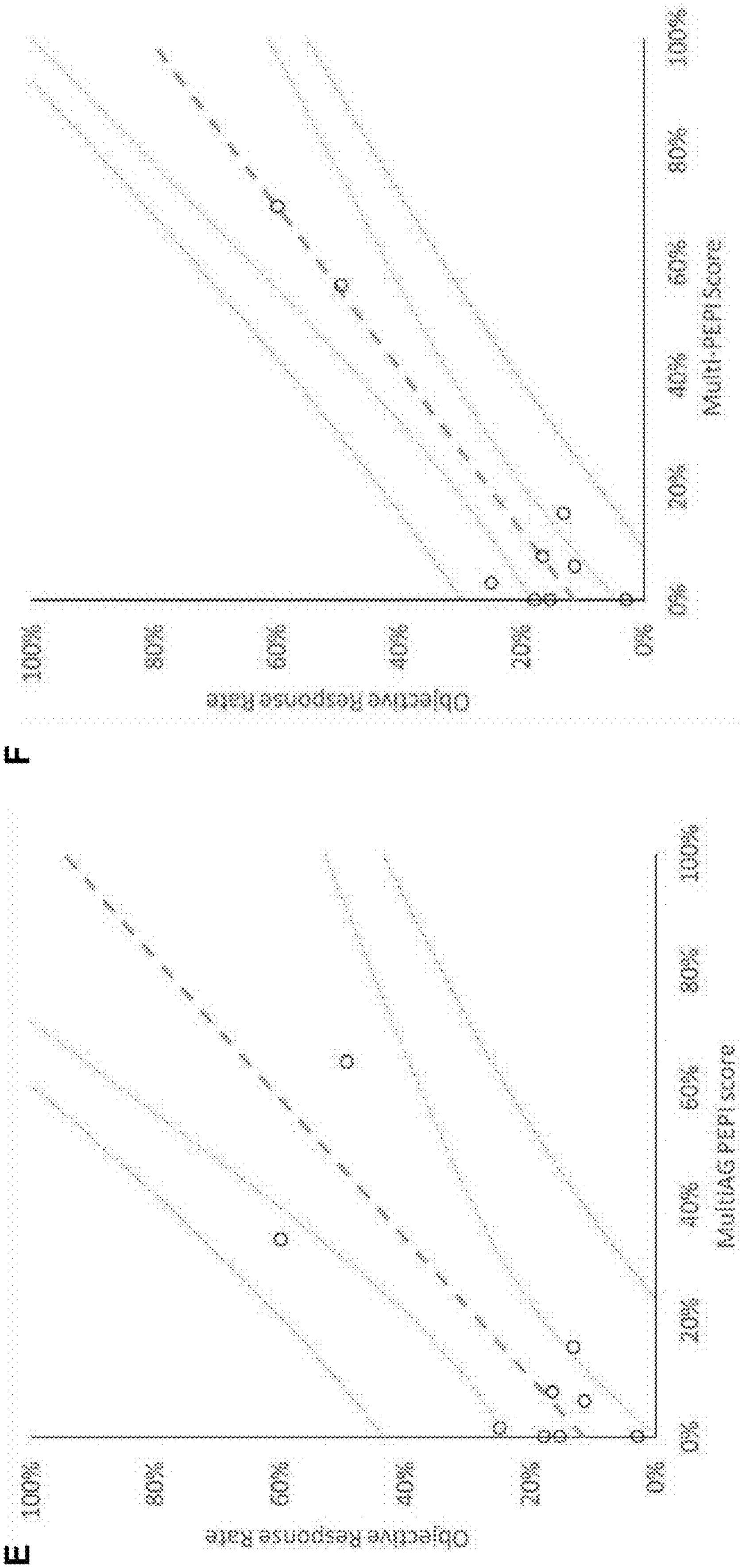
Figure 10:
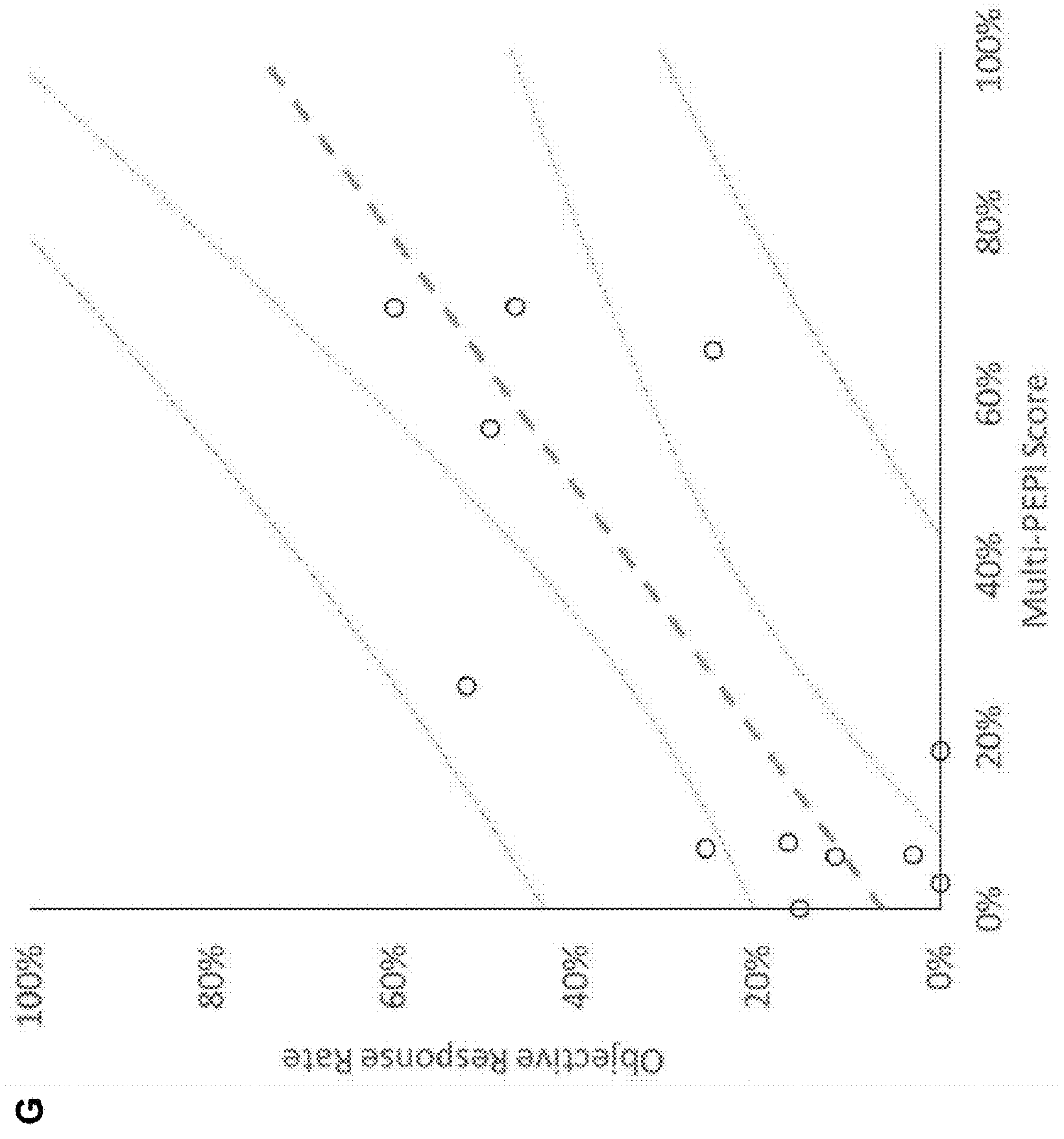

We investigated the correlation between ≥1 PEPI3+ Score and immune response rate in a previous study of 12 peptide vaccines derived from cancer antigens that induced T cell responses in a subpopulation of 172 subjects from 19 clinical trials, that were identified from peer reviewed publications. The experimentally determined response rates reported from the trials were compared with the ≥1 PEPI3+ Scores and linear correlation between ≥1 PEPI3+ Score and response rate ($R^2$=0.70) was found (p=0.001) (FIG. 10A). The correlation between ≥1 PEPI3+ Score and immune response rate was then confirmed by the analysis of 59 clinical trials involving 1,343 subjects who were treated with 40 different vaccines. Each vaccine was analyzed by comparing the published IRR from the clinical trial to the PEPI Score from the model population. (FIG. 10B). The correlation between the IRR and PEPI Score was significant ($r^2$=0.465 and p=0.001). This result demonstrated that the PEPI Score determined by in silico trials in the MP accurately predicts the IRRs observed in clinical trials.

To test whether polyclonal T cell response increases the likelihood of tumor shrinkage, ORR and MultiPEPI Score were compared. Preliminary experiments analyzed the relationship between clinical response (either ORR or DCR) and MultiPEPI Score in 17 clinical trials conducted with peptide- and DNA-based immunotherapy vaccines. The results from these experiments demonstrated a significant correlation between clinical response rate and MultiPEPI Score ($r^2$=0.75, p<0.001). To confirm these findings, ORR data from 27 clinical trials with 21 different vaccines, involving 600 subjects, were collected and analyzed (FIG. 10C). The MultiPEPI Score was calculated as the percentage of subjects in the model population with multiple PEPIs from the study vaccine. The results from this experiment demonstrated that ORR does not correlate with MultiPEPI Score (FIG. 10D).

Results from previous studies suggested that T cell responses against multiple antigens were associated with longer progression free- and overall survival. Consequently, we hypothesized that the induction of T cell responses against multiple tumor antigens increases the likelihood of tumor shrinkage. To test this hypothesis, ORR data from 10 clinical trials conducted with 9 different vaccines, involving 263 subjects, that were treated with multiantigen-targeting vaccine were collected and analyzed. The MultiAg PEPI Score was calculated as the percentage of subjects with vaccine-specific PEPIs on at least two antigens. The results from this experiment demonstrated a significant correlation between ORR and MultiAg PEPI Score ($r^2$=0.64; p=0.01), and ORR and MultiPEPI Score ($r^2$=0.88 and p=0.001) (FIGS. 10E and F, respectively). These results suggest that T cell responses against multiple tumor antigens may recognize a larger tumor cell population, thereby increasing the likelihood of tumor shrinkage.

The next analysis explored whether PEPI-specific T cell responses against antigens expressed in the tumor of interest, increase the likelihood of tumor shrinkage. A total of 15 clinical trials enrolled subjects with target antigen positive disease and 11 clinical trials had no subject preselection based on antigen expression. The proportion of subjects with objective response was significantly higher in CTs with target antigen-positive subjects compared with CTs without target pre-selection (21.0% vs 3.6%, respectively, p=0.03).

The correlation between ORR and MultiPEPI Score was statistically significant in subjects with confirmed expression of target antigens ($r^2$=0.56, p=0.005) (FIG. 10G). These results emphasize the importance of the presence of cognate PEPI in the tumor, and also that the presence of the cognate PEPI in the tumor increases the likelihood of tumor shrinkage.

This study demonstrated that the link between a subject's HLA genotype and PEPI is the most important factor in predicting clinical response to a vaccine. This study also showed that the PEPI Score can predict the clinical outcome of therapeutic vaccines.

Figure 11:
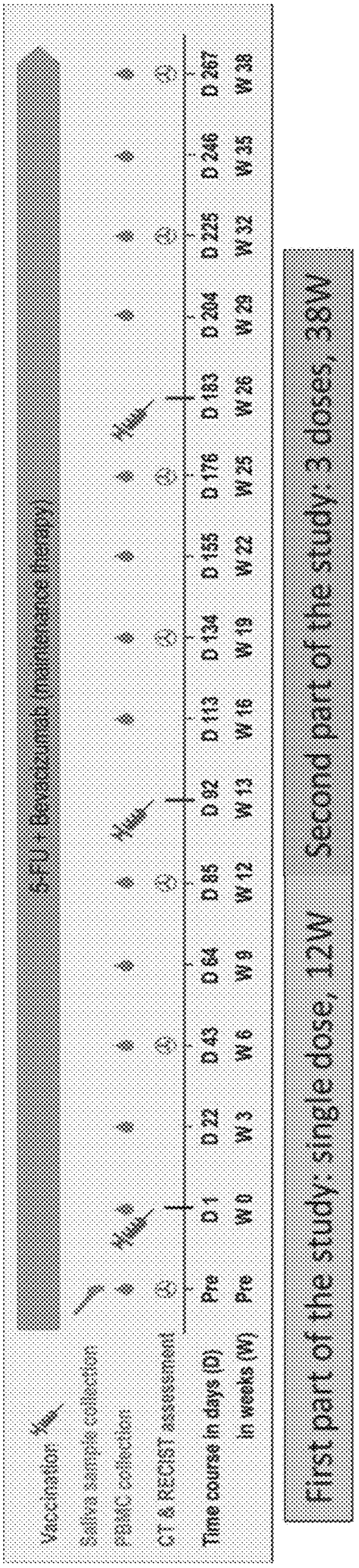

Example 12—Study Design of OBERTO Phase I/II Clinical Trial and Preliminary Safety Data OBERTO trial is a Phase I/II trial of PolyPEPI1018 Vaccine and CDx for the Treatment of Metastatic Colorectal Cancer (NCT03391232). Study design is shown in FIG. 11.

Enrollment Criteria

- Histologically confirmed metastatic adenocarcinoma originating from the colon or the rectum
- Presence of at least 1 measurable reference lesion according to RECIST 1.1
- PR or stable disease during first-line treatment with a systemic chemotherapy regimen and 1 biological therapy regimen
- Maintenance therapy with a fluoropyrimidine (5-fluorouracil or capecitabine) plus the same biologic agent (bevacizumab, cetuximab or panitumumab) used during induction, scheduled to initiate prior to the first day of treatment with the study drug
- Last CT scan at 3 weeks or less before the first day of treatment Subject Withdrawal and Discontinuation.

- During the initial study period (12W), if a patient experiences disease progression and needs to start a second-line therapy, the patient will be withdrawn from the study.
- During the second part of the study (after 2nd dose) if a patient experiences disease progression and needs to start a second-line therapy, the patient will remain in the study, receive the third vaccination as scheduled and complete follow-up.
- Transient local erythema and edema at the site of vaccination were observed as expected, as well as a flu-like syndrome with minor fever and fatigue. These reactions are already well-known for peptide vaccination and usually are associated with the mechanism of action, because fever and flu-like syndrome might be the consequence and sign for the induction of immune responses (this is known as typical vaccine reactions for childhood vaccinations).
- Only one serious adverse event (SAE) "possibly related" to the vaccine was recorded (Table 17).
- One dose limiting toxicity (DLT) not related to the vaccine occurred (syncope).

Safety results are summarized in Table 17.

TABLE 17

Serious adverse events reported in the OBERTO clinical trial. No related SAE occurred (only 1 "possibly related").

| Patient ID | SAE | Relatedness |
|---|---|---|
| 010001 | Death due to disease progression | Unrelated |
| 010004 | Embolism | Unlikely Related |
| 010004 | Abdominal pain | Unrelated |
| 010007 | Bowel Obstruction | Unrelated |
| 020004 | Non-Infectious Acute Encephalitis | Possibly Related |

Example 13—Expression Frequency Based Target Antigen Selection During Vaccine Design and It's Clinical Validation for mCRC Shared tumor antigens enable precise targeting of all tumor types—including the ones with low mutational burden. Population expression data collected previously from 2,391 CRC biopsies represents the variability of antigen expression in CRC patients worldwide (FIG. 12A).

PolyPEPI1018 is a peptide vaccine we designed to contain 12 unique epitopes derived from 7 conserved testis specific antigens (TSAs) frequently expressed in mCRC. In our model we supposed, that by selecting the TSA frequently expressed in CRC, the target identification will be correct and will eliminate the need for tumor biopsy. We have calculated that the probability of 3 out of 7 TSAs being expressed in each tumor is greater than 95%. (FIG. 12B)

In a phase I study we evaluated the safety, tolerability and immunogenicity of PolyPEPI1018 as an add-on to maintenance therapy in subjects with metastatic colorectal cancer (mCRC) (NCT03391232) (See also in Example 4).

Immunogenicity measurements proved pre-existing immune responses and indirectly confirmed target antigen expression in the patients. Immunogenicity was measured with enriched Fluorospot assay (ELISPOT) from PBMC samples isolated prior to vaccination and in different time points following a following single immunization with PolyPEPI1018 to confirm vaccine-induced T cell responses; PBMC samples were in vitro stimulated with vaccine-specific peptides (9mers and 30mers) to determine vaccine-induced T cell responses above baseline. In average 4, at least 2 patients had pre-existing CD8 T cell responses against each target antigen (FIG. 12C). 7 out of 10 patients had pre-existing immune responses against at least 1 antigen (average 3) (FIG. 12D). These results provide proof for the proper target selection, because CD8+ T cell response for a CRC specific target TSA prior to vaccination with PolyPEPI1018 vaccine confirms the expression of that target antigen in the analyzed patient. Targeting the real (expressed) TSAs is the prerequisite for an effective tumor vaccine.

Figure 12:
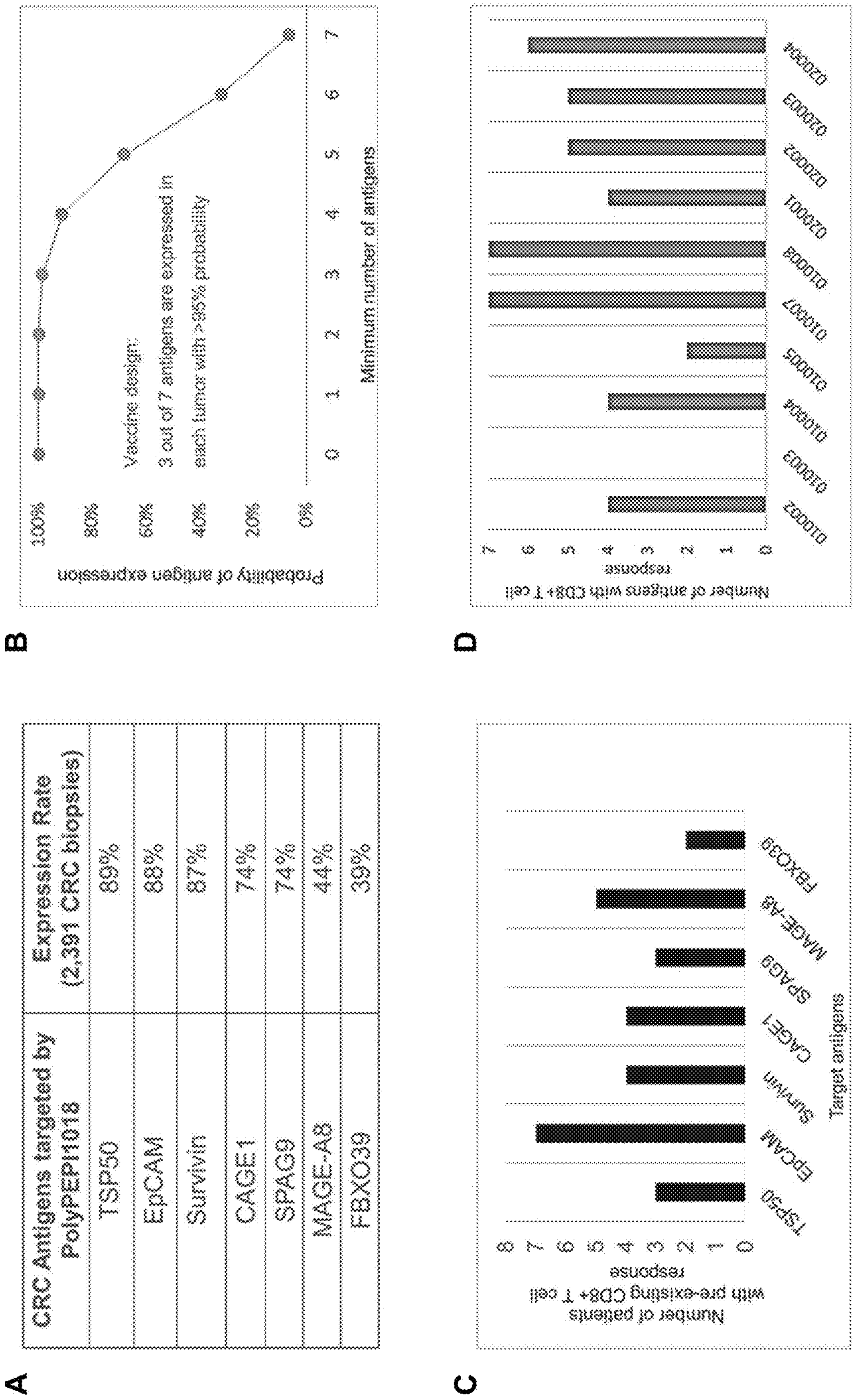

Example 14—Pre-Clinical and Clinical Immunogenicity of PolyPEPI1018 Vaccine Proves Proper Peptide Selection PolyPEPI1018 vaccine contains six 30mer peptides, each designed by joining two immunogenic 15mer fragments (each involving a 9mer PEPI, consequently there are 2 PEPIs in each 30mer by design) derived from 7 TSAs (FIG. 13). These antigens are frequently expressed in CRC tumors based on analysis of 2,391 biopsies (FIG. 12).

Preclinical immunogenicity results calculated for the Model Population (n=433) and for a CRC cohort (n=37) resulted in 98% and 100% predicted immunogenicity based on PEPI test predictions and this was clinically proved in the OBERTO trial (n=10), with immune responses measured for at least one antigen in 90% of patients. More interestingly, 90% of patients had vaccine peptide specific immune responses against at least 2 antigens and 80% had CD8+ T cell response against 3 or more different vaccine antigens, showing evidence for appropriate target antigen selection during the design of PolyPEPI1018. CD4+ T cell specific and CD8+ T cell specific clinical immunogenicity is detailed in Table 18.

TABLE 18

Clinical immunogenicity results for PolyPEPI1018 in mCRC.

| Immunological responses | % Patients (n) |
|---|---|
| CD4+ T cell responses | 100% (10/10) |
| CD8+ T cell responses against ≥3 antigens | 80% (8/10) |
| Both CD8+ and CD4+ T cell responses | 90% (9/10) |
| Ex vivo detected CD8+ T cell response | 71% (5/7) |
| Ex vivo detected CD4+ T cell response | 86% (6/7) |
| Average increase of the fraction of polyfunctional (IFN-γ and TNF-α positive) CD8+ T cells compared to pre-vaccination | 0.39% |
| Average increase of the fraction of polyfunctional (IL-2 and TNF-α positive) CD4+ T cells compared to pre-vaccination | 0.066% |

High immune response rates were found for both effector and memory effector T cells, both for CD4+ and CD8+ T cells, and 9 of 10 patients' immune responses were boosted or de novo induced by the vaccine. Also, the fractions of CRC-reactive, polyfunctional CD8+ and CD4+ T cells have been increased in patient's PBMC after vaccination by 2.5- and 13-fold, respectively.

Example 15—Clinical Response for PolyPEPI1018 Treatment

Figure 14A:
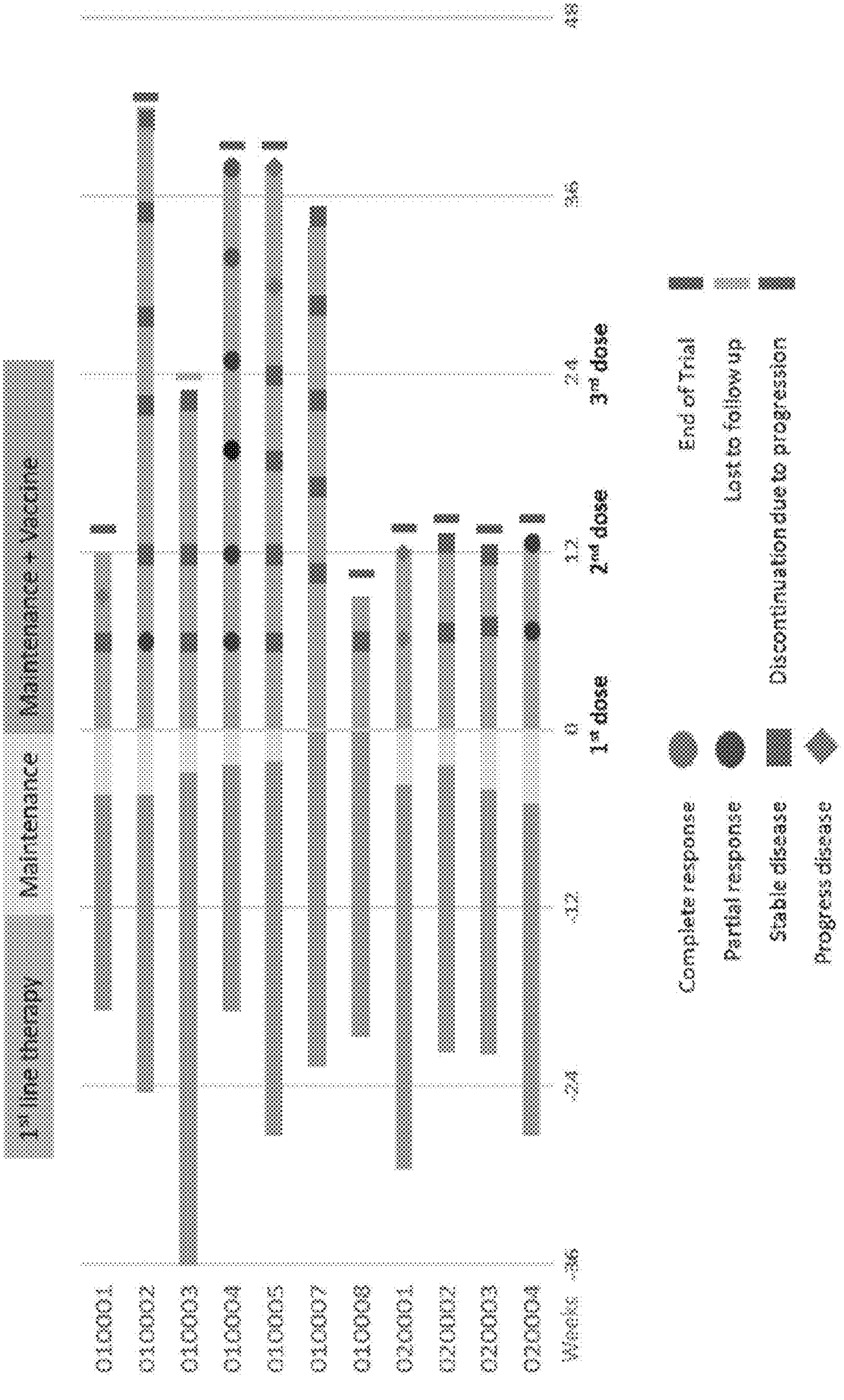
Figure 14B:
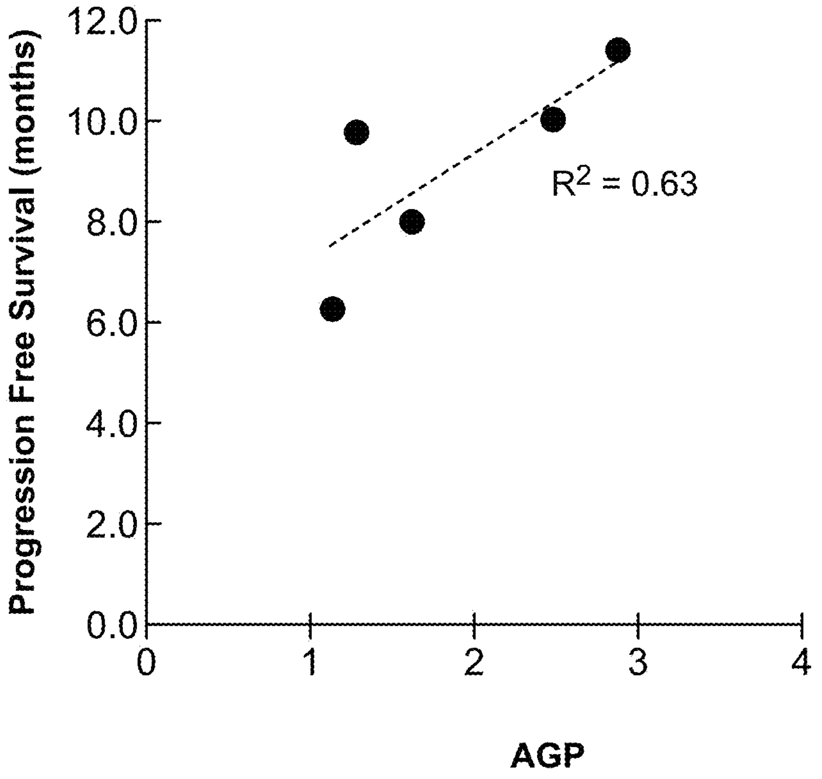
Figure 14C:
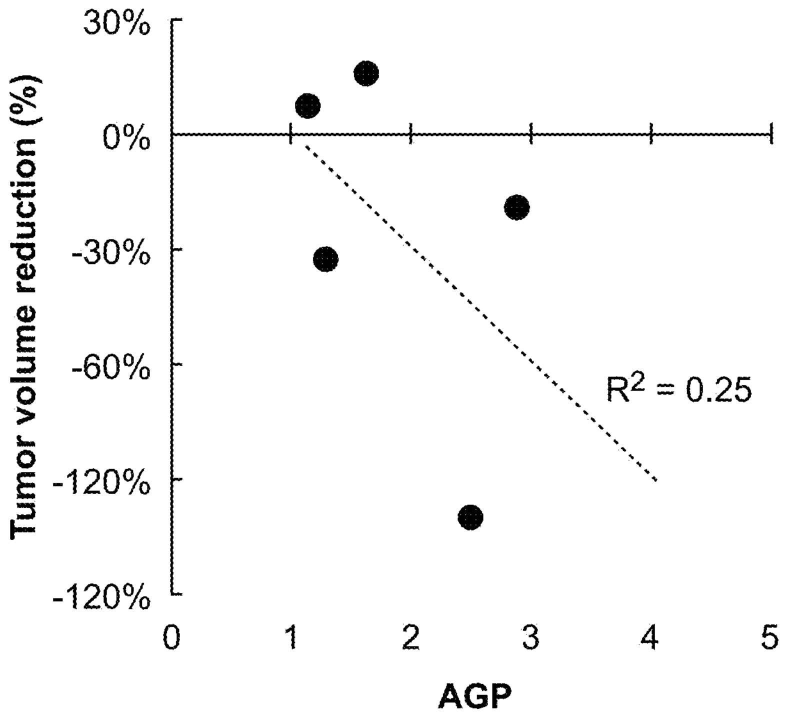

The OBERTO clinical trial (NCT03391232), that has been further described in Examples 4, 12, 13 and 14 was analyzed for preliminary objective tumor response rates (RECIST 1.1) (FIGS. 14A-C). Of the eleven vaccinated patients on maintenance therapy, 5 had stable disease (SD) at the time point of the preliminary analysis (12 weeks), 3 experienced unexpected tumor responses (partial response, PR) observed on treatment (maintenance therapy+ vaccination) and 3 had progressed disease (PD) according to RECIST 1.1 criteria. Stable disease as best response was achieved in 69% of patients on maintenance therapy (capecitabine and bevacizumab). Patient 020004 had durable treatment effect after 12 weeks, and patient 010004 had long lasting treatment effect, qualified for curative surgery. Following the 3r d vaccination this patient had no evidence of disease thus being complete responder, as shown on the swimmer plot on FIGS. 14A-C.

After one vaccination, ORR was 27%, DCR was 63%, and in patients receiving at least 2 doses (out of the 3 doses), 2 of 5 had ORR (40%) and DCR was as high as 80% (SD+PR+CR in 4 out of 5 patients) (Table 19).

TABLE 19

Clinical response for PolyPEPI1018 treatment after ≥ 1 and ≥ 2 vaccination dose

| Number of vaccination dose | Objective Response Rate (CR + PR) | Disease Control Rate (SD + PR + CR) |
|---|---|---|
| ≥1 | 27% (3/11) | 63% (7/11) |
| ≥2 | 40% (2/5) | 80% (4/5) |

Based on the data of the 5 patients receiving multiple doses of PolyPEPI1018 vaccine in the OBERTO-101 clinical trial, preliminary data suggests that higher AGP count (>2) is associated with longer PFS and elevated tumor size reduction (FIGS. 14B and C).

Example 16—Gastric Cancer Peptide Vaccine Design for Large Population

The PEPI3+ Test described above was used to design peptides for use in gastric cancer vaccines that are effective in a large percentage of patients, taking into account the heterogeneities of both tumour antigens and patients' HLAs.

Gastric cancer CTAs were identified and ranked based on the overall expression frequencies of antigens found in gastric cancer tumor samples as reported in peer reviewed publications.

Figure 16:
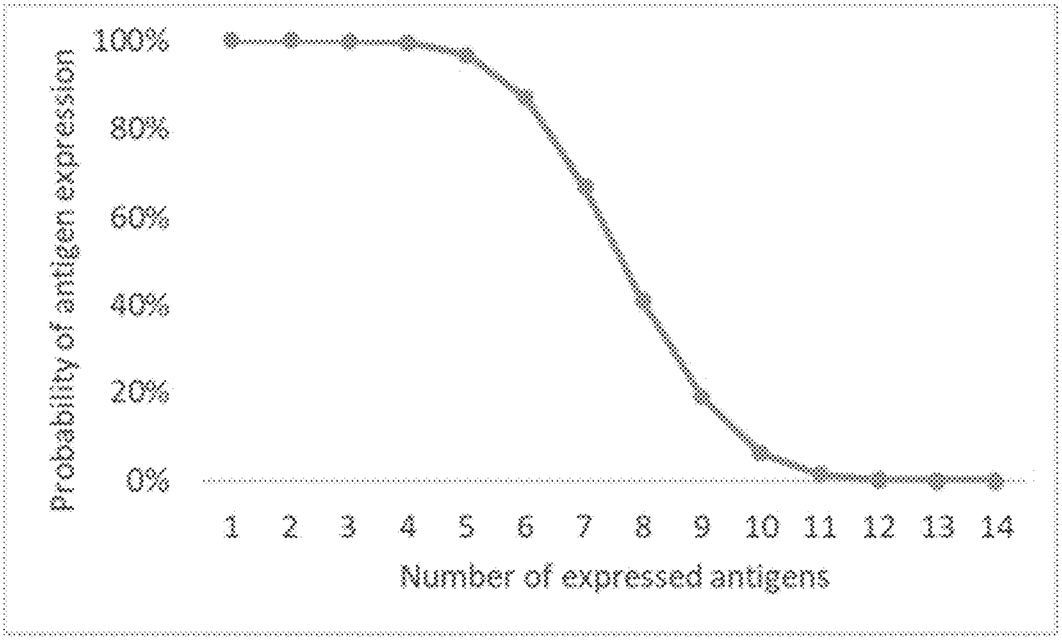

Based on the ranked expression rate the most frequently expressed CTA were selected as target antigens for gastric cancer vaccine. The expression rates of the selected gastric cancer, specific CTAs are illustrated in FIG. 16.

Figure 15:
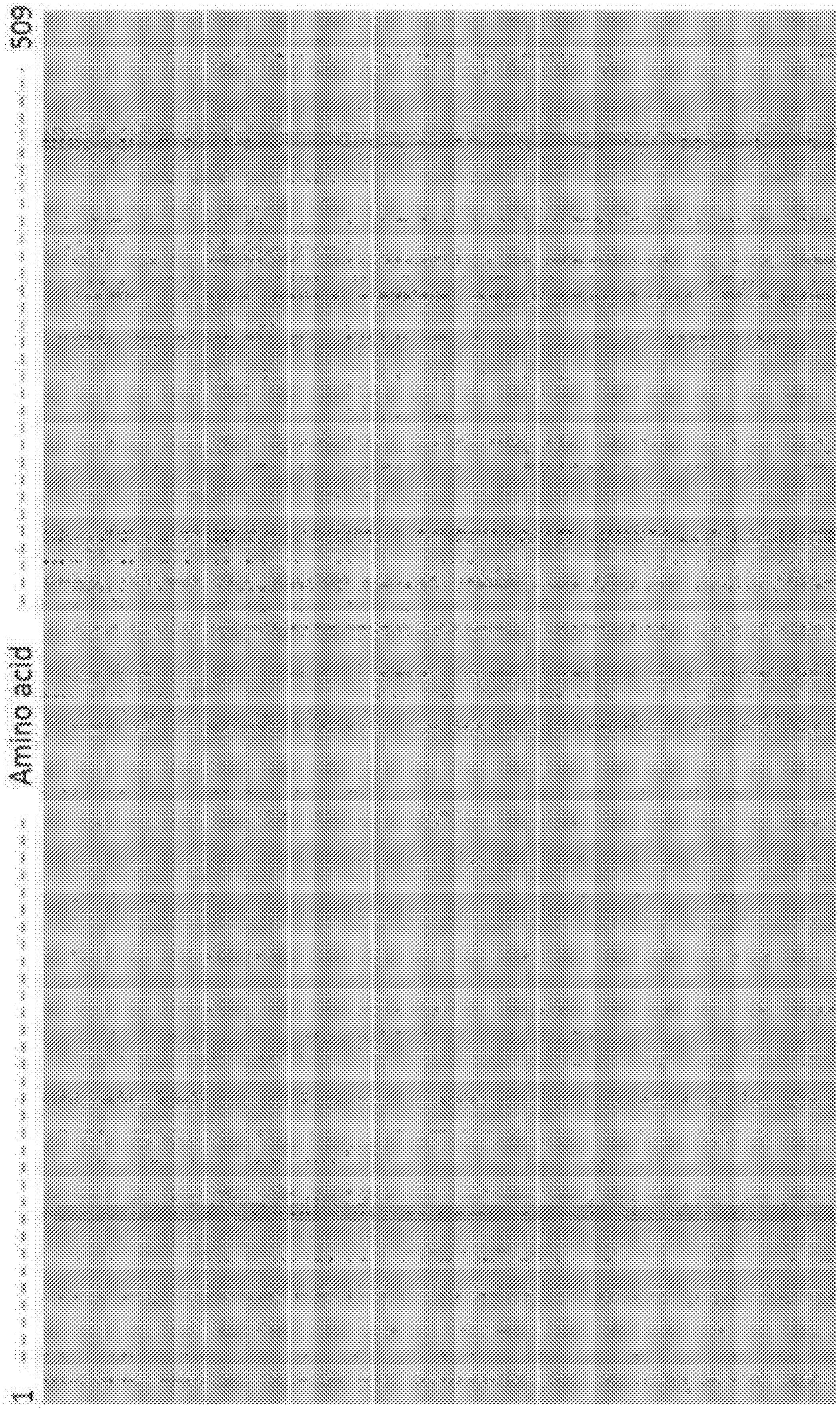

To select immunogenic peptides from the target CTAs, the PEPI3+ Test and the Model Population described in Example 8 were used to identify the 9 mer epitopes (PEPI3+ s) that are most frequently presented by at least 3 HLAs of the individuals in the Model Population. These epitopes are referred to herein as "bestEPIs". An illustrative example of the "PEPI3+ hotspot" analysis and bestEPI identification is shown in FIG. 15 for the PRAME antigen.

The reported expression frequency for each CTA was multiplied by the frequency of the PEPI3+ hotspots in the Model Population to identify the T cell epitopes (9 mers) that will induce a cytotoxic T cell response against gastric cancer antigens in the highest proportion of individuals (Table 20a). 15 mers were then selected encompassing each of the selected 9 mers (Table 20a). The 15 mers were selected to bind to most HLA class II alleles of most subjects. These 15 mers can induce both CTL and T helper responses in the highest proportion of subjects.

TABLE 20a

BestEPI list (9-mers underlined) for selecting gastric cancer peptides for vaccine composition.

| SEQ ID NO. 9 mer | SEQ ID NO. 15 mer | Antigen | N % | BestEPIs and Optimized 15 mer: Opt. 15 mer | Opt. Position | B % | HLAII** (CD4) | B % * N % |
|---|---|---|---|---|---|---|---|---|
| 1 | 31 | DPPA2 | 100% | KRNKKMMKRLMTVEK | 284 | 43% | 12% | 43% |
| 2 | 32 | CAGE-1 | 77% | ASQLASKMHSLLALM | 610 | 42% | 94% | 33% |
| 3 | 33 | TSP50 | 57% | GFSYEQDPTLRDPEA | 105 | 51% | 0% | 29% |
| 4 | 34 | DPPA2 | 100% | KIEVYLRLHRHAYPE | 115 | 28% | 98% | 28% |
| 5 | 35 | HIWI | 76% | GFTTSILQYENSIML | 251 | 37% | 86% | 28% |
| 6 | 36 | SURVIVIN | 100% | AKKVRRAIEQLAAMD | 128 | 26% | 25% | 26% |
| 7 | 37 | HIWI | 76% | SIAGFVASINEGMTR | 643 | 28% | 44% | 21% |
| 8 | 38 | TSP50 | 57% | STTMETQFPVSEGKV | 84 | 36% | 0% | 21% |
| 9 | 39 | 5T4 | 52% | RLELASNHFLYLPRD | 214 | 40% | 97% | 21% |
| 10 | 40 | 5T4 | 52% | SNHFLYLPRDVLAQL | 219 | 40% | 100% | 21% |
| 11 | 41 | 5T4 | 52% | SSASSFSSSAPFLAS | 36 | 33% | 88% | 17% |
| 12 | 42 | MAGE-A2 | 31% | REDSVFAHPRKLLMQ | 234 | 55% | 74% | 17% |
| 13 | 43 | KK-LC-1 | 80% | RNTGEMSSNSTALAL | 26 | 21% | 0% | 17% |
| 14 | 44 | CAGE-1 | 77% | NIENYSTNALIQPVD | 97 | 21% | 14% | 16% |
| 15 | 45 | SURVIVIN | 100% | KDHRISTFKNWPFLE | 15 | 15% | 83% | 15% |
| 16 | 46 | MAGE-A2 | 31% | SFSTTINYTLWRQSD | 70 | 37% | 65% | 12% |
| 17 | 47 | KK-LC-1 | 80% | SRDILNNFPHSIARQ | 63 | 13% | 11% | 11% |
| 18 | 48 | MAGE-A3 | 37% | LTQHFVQENYLEYRQ | 246 | 27% | 56% | 10% |
| 19 | 49 | LAGE-1 | 14% | ITMPFSSPMEAELVR | 92 | 65% | 8% | 9% |
| 20 | 50 | MAGE-A3 | 37% | KASSSLQLVFGIELM | 153 | 23% | 58% | 9% |
| 21 | 51 | MAGE-A10 | 30% | RNYEDHFPLLFSEAS | 166 | 27% | 26% | 8% |
| 22 | 52 | MAGE-A1 | 31% | ETSYVKVLEYVIKVS | 273 | 26% | 85% | 8% |
| 23 | 53 | MAGE-A3 | 37% | QAALSRKVAELVHFL | 106 | 21% | 45% | 8% |
| 24 | 54 | KK-LC-1 | 80% | SNTDNNLAVYDLSRD | 51 | 10% | 0% | 8% |
| 25 | 55 | PRAME | 20% | RHSQTLKAMVQAWPF | 64 | 37% | 38% | 7% |
| 26 | 56 | MAGE-A2 | 31% | SKASEYLQLVFGIEV | 152 | 24% | 69% | 7% |
| 27 | 57 | MAGE-A1 | 31% | SAFPTTINFTRQRQP | 62 | 24% | 0% | 7% |

TABLE 20a-continued

BestEPI list (9-mers underlined) for selecting gastric cancer peptides for vaccine composition.

| SEQ ID NO. 9 mer | SEQ ID NO. 15 mer | Antigen | N % | Opt. 15 mer | Opt. Position | B % | HLAII** (CD4) | B % * N % |
|---|---|---|---|---|---|---|---|---|
| 28 | 58 | SSX1 | 13% | QVEHPQMTFGRLHRI | 93 | 55% | 20% | 7% |
| 29 | 59 | MAGE-A1 | 31% | PRALAETSYVKVLEY | 268 | 16% | 39% | 5% |
| 30 | 60 | PRAME | 20% | DQLLRHVMNPLETLS | 314 | 22% | 63% | 4% |

N %: Antigen expression frequency in gastric cancers;
B %: bestEPI frequency, ie the percentage of individuals with epitopes binding to at least 3 HLA class I of subjects in the model population (433 subjects);
HLAII**: Percentage of individuals having CD4+ T cell specific PEPI4+ within normal donors (n = 400);
N % * B %: N % multiplied by B %.

Fifteen 30 mer peptides were then designed (Table 21a). The 30 mers may each consist of two optimized 15 mer fragments, generally from different frequent CTAs, arranged end to end, each fragment comprising one of the 9 mers (BestEPIs) from Table 2-a.

TABLE 21a 30 mer gastric cancer vaccine peptides of composition PolyPEPI1311

| SEQID | TREOSID | Source Antigen | Peptide (30 mer) | HLAI* (CD8) | HLAH** (CD4) |
|---|---|---|---|---|---|
| 61 | GC1311-01 | CAGE-1/DPPA2 | ASQLASKMHSLLALMKRNKKMMKRLMTVEK | 64% | 94% |
| 62 | GC1311-02 | HIWI/MAGE-A10 | GFTTSILQYENSIMLRNYEDHFPLLFSEAS | 62% | 86% |
| 63 | GC1311-03 | MAGE-A2/SURVIVIN | SFSTTINYTLWRQSDAKKVRRAIEQLAAMD | 49% | 69% |
| 64 | GC1311-04 | KK-LC-1/SURVMN | RNTGEMSSNSTALALKDHRISTFKNWPFLE | 39% | 83% |
| 65 | GC1311-05 | KK-LC-1/HIWI | SRDILNNFPHSIARQSIAGFVASINEGMTR | 36% | 45% |
| 66 | GC1311-06 | MAGE-A2/PRAME | REDSVFAHPRKLLMQDQLLRHVMNPLETLS | 64% | 91% |
| 67 | GC1311-07 | 5T4/5T4 | RLELASNHFLYLPRDSNHFLYLPRDVLAQL | 65% | 100% |
| 68 | GC1311-08 | 5T4/TSP50 | SSASSFSSSAPFLASSTTMETQFPVSEGKV | 55% | 88% |
| 69 | GC1311-09 | TSP50/MAGE-A1 | GFSYEQDPTLRDPEAPRALAETSYVKVLEY | 67% | 39% |
| 70 | GC1311-10 | KK-LC-1/SSX1 | SNTDNNLAVYDLSRDQVEHPQMTFGRLHRI | 58% | 20% |
| 71 | GC1311-11 | DPPA2/LAGE-1 | KIEVYLRLHRHAYPEITMPFSSPMEAELVR | 82% | 99% |
| 72 | GC1311-12 | MAGE-A1/MAGE-A3 | ETSYVKVLEYVIKVSLTQHFVQENYLEYRQ | 41% | 91% |
| 73 | GC1311-13 | MAGE-A3/CAGE-1 | QAALSRKVAELVHFLNIENYSTNALIQPVD | 30% | 49% |
| 74 | GC1311-14 | PRAME/MAGE-A3 | RHSQTLKAMVQAWPFKASSSLQLVFGIELM | 53% | 77% |
| 75 | GC1311-15 | MAGE-A2/MAGE-A1 | SKASEYLQLVFGIEVSAFPTTINFTRQRQP | 41% | 69% |

*Percentage of individuals having CD8+ T cell specific PEPI3+ within the HLA class I Model Population (n = 433).
**Percentage of individuals having CD4+ T cell specific PEPI4+ within the normal donors(n = 400).

Characterization of PolyPEPI131

Tumor heterogeneity can be addressed by including peptide sequences that target multiple CTAs in a vaccine or immunotherapy regime. The PolyPEPI1311, composition targets 14 different CTAs. Based on the antigen expression rates for these 14 CTAs, we modelled the predicted average number of expressed antigens (AG50) and the minimum number of expressed antigens with 95% likelihood (AG95) in the cancer cells. 95% of individuals expressed minimum of the 14 target antigens (AG95=5) as shown by the antigen expression curve in FIG. 17.

The AG values described above characterize a vaccine independently from the target patient population. They can be used to predict the likelihood that a specific cancer (e.g. gastric cancer) expresses antigens targeted by a specific vaccine or immunotherapy composition. AG values are based on known tumor heterogeneity, but do not take HLA heterogeneity into account.

HLA heterogeneity of a certain population can be characterised from the viewpoint of an immunotherapy or vaccine composition by the number of antigens representing PEPI3+. These are the vaccine-specific CTA antigens for which ≥1 PEPI3+ is predicted, referred to herein as the "AP". The average number of antigens with PEPI3+(AP50) shows how the vaccine can induce immune response against the antigens targeted by the composition (gastric cancer vaccine specific immune response). The PolyPEPI1311 composition can induce immune response against an average of 8 vaccine antigens (AP50=7.98) and 95% of the Model Population can induce immune response against at least three vaccine antigens (AP95=3)(FIG. 18).

Vaccines can be further characterized by AGP values that refers to antigens with PEPIs". This parameter is the combination of the previous two parameters: (1) AG is depending on the antigen expression frequencies in the specific tumor type but not on the HLA genotype of individuals in the population, and (2) AP is depending on the HLA genotype of individuals in a population without taking account the expression frequencies of the antigen. The AGP is depending on both, the expression frequencies of vaccine antigens in the disease and the HLA genotype of individuals in a population.

Combining the data of AG of gastric cancer and AP in the Model Population we determined the AGP value of PolyPEPI1311 that represents the probability distribution of vaccine antigens that induce immune responses against antigens expressed in gastric tumors. For PolyPEPI1311, the AGP50 value in the Model Population is 3.86. The AGP95=1, means that 95% of the subjects in the Model Population induce immune responses against at least one expressed vaccine antigen (FIG. 19).

Example 17—Patient Selection Using Companion Diagnostic for Gastric Cancer, Lung Cancer, Melanoma and Bladder Cancer Vaccine The likelihood that a specific patient will have an immune response or a clinical response to treatment with one or more cancer vaccine peptides, for example as described above, can be determined based on (i) the identification of PEPI3+ within the vaccine peptide(s) (9 mer epitopes capable of binding at least three HLA of the patient); and/or (ii) a determination of target antigen expression in cancer cells of the patient, for example as measured in a tumour biopsy. Ideally both parameters are determined and the optimal combination of vaccine peptides is selected for use in treatment of the patient. However, PEPI3+ analysis alone may be used if a determination of the expressed tumour antigens, for example by biopsy, is not possible, not advised, or unreliable due to biopsy error (i.e. biopsy tissue samples taken from a small portion of the tumor or metastasised tumors do not represent the complete repertoire of CTAs expressed in the patient).

Example 18—Lung Cancer Peptide Vaccine Design for Large Population

Figure 20:
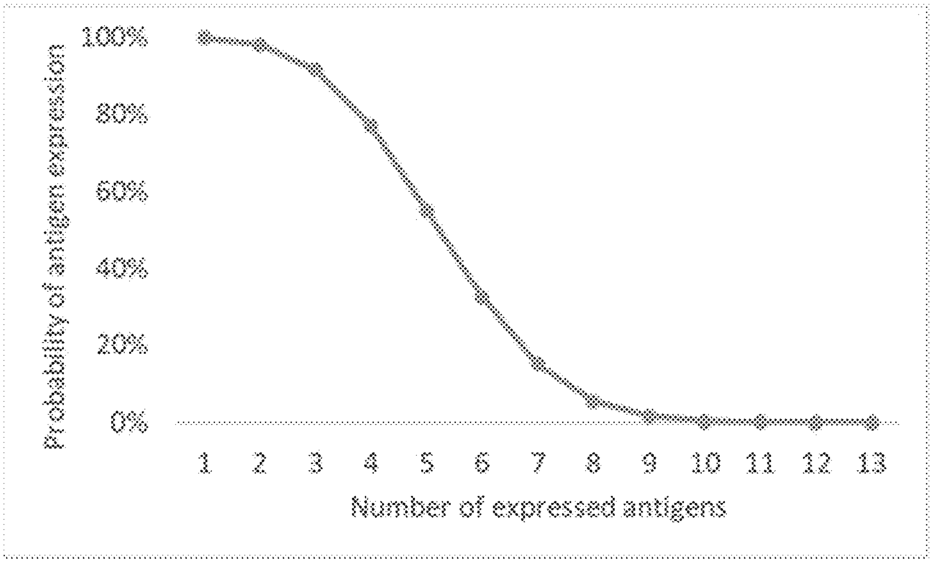

The PEPI3+ Test described above was used to design 9-mer and 15-mer peptides for use in lung cancer vaccines, using the same method described in Example 16 above for gastric cancer (Tables 20b, 21b). The expression rates of the selected gastric cancer, specific CTAs are illustrated in FIG. 20.

TABLE 20b

BestEPI list (9-mers underlined) for selecting lung cancer peptides for vaccine composition.

| SEQ ID NO. | SEQ ID NO. | Antigen | | BestEPIs and Optimized 15 mer | | | | |
|---|---|---|---|---|---|---|---|---|
| 9 mer | 15 mer | Antigen | N % | Antigen | N % | Antigen | N % | Antigen |
| 90 | 120 | BRDT | 48% | DAYKFAADVRLMFMN | 333 | 58% | 100% | 28% |
| 91 | 121 | PRAME | 63% | RHSQTLKAMVQAWPF | 64 | 37% | 38% | 23% |
| 92 | 122 | BRDT | 48% | DLWKHSFSWPFQRPV | 42 | 43% | 88% | 21% |
| 93 | 123 | NALP4 | 38% | QSTTSVYSSFVFNLF | 366 | 50% | 75% | 19% |
| 94 | 124 | NALP4 | 38% | KRAMEAFNLVRESEQ | 319 | 48% | 67% | 18% |
| 95 | 125 | NALP4 | 38% | FVIDSFEELQGGLNE | 228 | 46% | 47% | 17% |
| 96 | 126 | MAGE-A12 | 36% | QVALSRKMAELVHFL | 106 | 48% | 63% | 17% |
| 97 | 127 | MAGE-A2 | 27% | REDSVFAHPRKLLMQ | 234 | 55% | 74% | 15% |
| 98 | 128 | SURVIVIN | 57% | AKKVRRAIEQLAAMD | 128 | 26% | 25% | 15% |
| 99 | 129 | PRAME | 63% | KEEQYIAQFTSQFLS | 280 | 23% | 99% | 14% |
| 100 | 130 | PRAME | 63% | DQLLRHVMNPLETLS | 314 | 22% | 63% | 14% |
| 101 | 131 | MAGE-A12 | 36% | RNFQDFFPVIFSKAS | 141 | 37% | 90% | 13% |
| 102 | 132 | PRAME | 63% | RGRLDQLLRHVMNPL | 310 | 21% | 65% | 13% |
| 103 | 133 | DPPA2 | 30% | KRNKKMMKRLMTVEK | 284 | 43% | 12% | 13% |
| 104 | 134 | NY-SAR-35 | 28% | SSYFVLANGHILPNS | 94 | 42% | 85% | 12% |
| 105 | 135 | BRDT | 48% | ILKEMLAKKHFSYAW | 279 | 23% | 55% | 11% |
| 106 | 136 | LDHC | 29% | SVMDLVGSILKNLRR | 255 | 38% | 85% | 11% |

TABLE 20b-continued

BestEPI list (9-mers underlined) for selecting lung cancer peptides for vaccine composition.

| SEQ ID NO. | SEQ ID NO. | Antigen | | BestEPIs and Optimized 15 mer | | | | |
|---|---|---|---|---|---|---|---|---|
| 9 mer | 15 mer | Antigen | N % | Antigen | N % | Antigen | N % | Antigen |
| 107 | 137 | LDHC | 29% | KLKGEMMDLQHGSLF | 57 | 37% | 1% | 11% |
| 108 | 138 | MAGE-A2 | 27% | SSFSTTINYTLWRQS | 69 | 37% | 74% | 10% |
| 109 | 139 | MAGE-C2 | 24% | MASESLSVMSSNVSF | 357 | 40% | 15% | 10% |
| 110 | 140 | MAGE-C2 | 24% | EHFVYGEPRELLTKV | 263 | 40% | 60% | 10% |
| 111 | 141 | MAGE-C2 | 24% | SESLSVMSSNVSFSE | 359 | 38% | 33% | 9% |
| 112 | 142 | MAGE-A3 | 33% | LTQHFVQENYLEYRQ | 246 | 27% | 56% | 9% |
| 113 | 143 | MAGE-A12 | 36% | SKASEYLQLVFGIEV | 152 | 24% | 69% | 9% |
| 114 | 144 | SURVIVIN | 57% | KDHRISTFKNWPFLE | 15 | 15% | 83% | 9% |
| 115 | 145 | DPPA2 | 30% | KIEVYLRLHRHAYPE | 115 | 28% | 98% | 9% |
| 116 | 146 | MAGE-A3 | 33% | KASSSLQLVFGIELM | 153 | 23% | 58% | 8% |
| 117 | 147 | KK-LC-1 | 35% | RNTGEMSSNSTALAL | 26 | 21% | 0% | 7% |
| 118 | 148 | MAGE-C2 | 24% | SSFSTSSSLILGGPE | 53 | 30% | 44% | 7% |
| 119 | 149 | MAGE-A1 | 28% | PRALAETSYVKVLEY | 268 | 16% | 39% | 5% |

N %: Antigen expression frequency in lung cancers;

B %: bestEPI frequency, i.e. the percentage of individuals with epitopes binding to at least 3 HLA class 1 of subjects in the model population (433 subjects);

HLAII**: Percentage of individuals having CD4+ T cell specific PEPI4+ within normal donors (n = 400);

N % * B %: N % multiplied by B %.

TABLE 21b 30 mer lung cancer vaccine peptides of composition PolyPEPI821

| SEQID | TREOSID | Source Antigen | Peptide (30 mer) | HLAI* (CD8) | HLAH** (CD4) |
|---|---|---|---|---|---|
| 150 | LC821-01 | BRDT/SURVIVIN | DAYKFAADVRLMFMNAKKVRRAIEQLAAMD | 64% | 100% |
| 151 | LC821-02 | PRAME/MAGE-A2 | RHSQTLKAMVQAWPFREDSVFAHPRKLLMQ | 67% | 78% |
| 152 | LC821-03 | BRDT/MAGE-A12 | DLWKHSFSWPFQRPVSKASEYLQLVFGIEV | 57% | 91% |
| 153 | LC821-04 | PRAME/LDHC | DQLLRHVMNPLETLSSVMDLVGSILKNLRR | 53% | 94% |
| 154 | LC821-05 | NALP4/SURVIVIN | QSTTSVYSSFVFNLFKDHRISTFKNWPFLE | 55% | 92% |
| 155 | LC821-06 | MAGE-C2/NALP4 | SSFSTSSSLILGGPEFVIDSFEELQGGLNE | 60% | 80% |
| 156 | LC821-07 | MAGE-A2/NALP4 | SSFSTTINYTLWRQSKRAMEAFNLVRESEQ | 70% | 90% |
| 157 | LC821-08 | NY-SAR-35/MAGE-A12 | SSYFVLANGHILPNSRNFQDFFPVIESKAS | 67% | 98% |
| 158 | LC821-09 | MAGE-C2/PRAME | MASESLSVMSSNVSFKEEQYIAQFTSQFLS | 51% | 99% |
| 159 | LC821-10 | PRAME/MAGE-A3 | RGRLDQLLRHVMNPLLTQHFVQENYLEYRQ | 42% | 85% |
| 160 | LC821-11 | MAGE-C2/LDHC | SESLSVMSSNVSFSEKLKGEMMDLQHGSLF | 67% | 33% |
| 161 | LC821-12 | MAGE-A12/MAGE-A1 | QVALSRKMAELVHFLPRALAETSYVKVLEY | 63% | 72% |
| 162 | LC821-13 | MAGE-C2/BRDT | EHFVYGEPRELLTKVILKEMLAKKHFSYAW | 59% | 75% |

TABLE 21b-continued

| 30 mer lung cancer vaccine peptides of composition PolyPEPI821 | | | | | |
|---|---|---|---|---|---|
| SEQID | TREOSID | Source Antigen | Peptide (30 mer) | HLAI* (CD8) | HLAII** (CD4) |
| 163 | LC821-14 | DPPA2/MAGE-A3 | KIEVYLRLHRHAYPEKASSSLQLVFGIELM | 53% | 99% |
| 164 | LC821-15 | KK-LC-1/DPPA2 | RNTGEMSSNSTALALKRNKKMMKRLMTVEK | 60% | 12% |

*Percentage of individuals having CD8+ T cell specific PEPI3+ within the HLA class I Model Population (n = 433).
**Percentage of individuals having CD4+ T cell specific PEPI4+ within the normal donors (n = 400).

Characterization of PolyPEPI821

Figure 21:
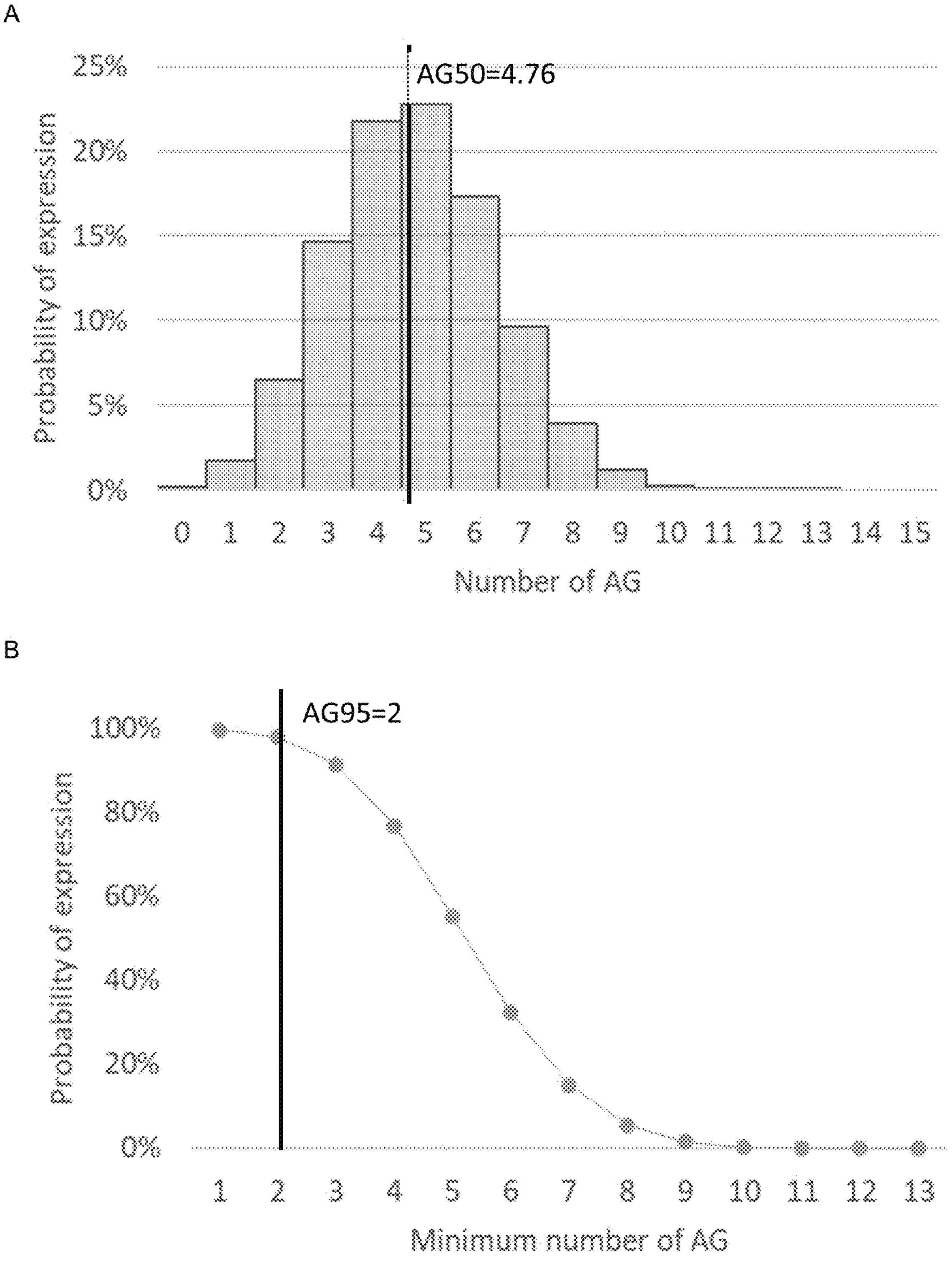

The PolyPEPI821 composition targets 13 different CTAs. Based on the antigen expression rates for these 13 CTAs, we modelled the predicted average number of expressed antigens (AG50) and the minimum number of expressed antigens with 95% likelihood (AG95) in the cancer cells. 95% of individuals expressed minimum 2 of the 10 target antigens (AG95=2) as shown by the antigen expression curve in FIG. 21.

Figure 22:
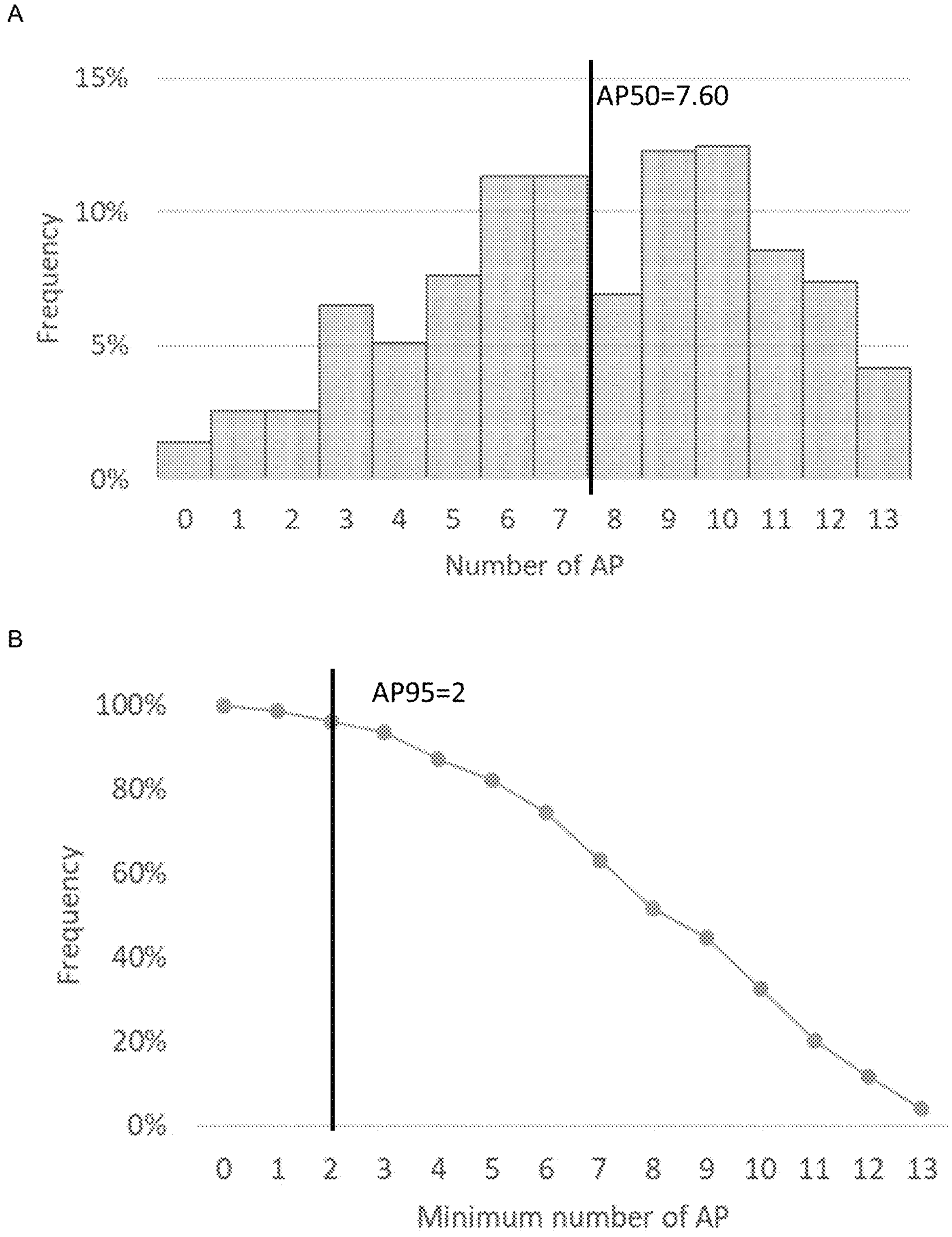

The PolyPEPI821 composition can induce immune response against an average of approaching 8 vaccine antigens (AP50=7.60) and 95% of the Model Population can induce immune response against at least two vaccine antigens (AP95=2)(FIG. 22).

Figure 23:
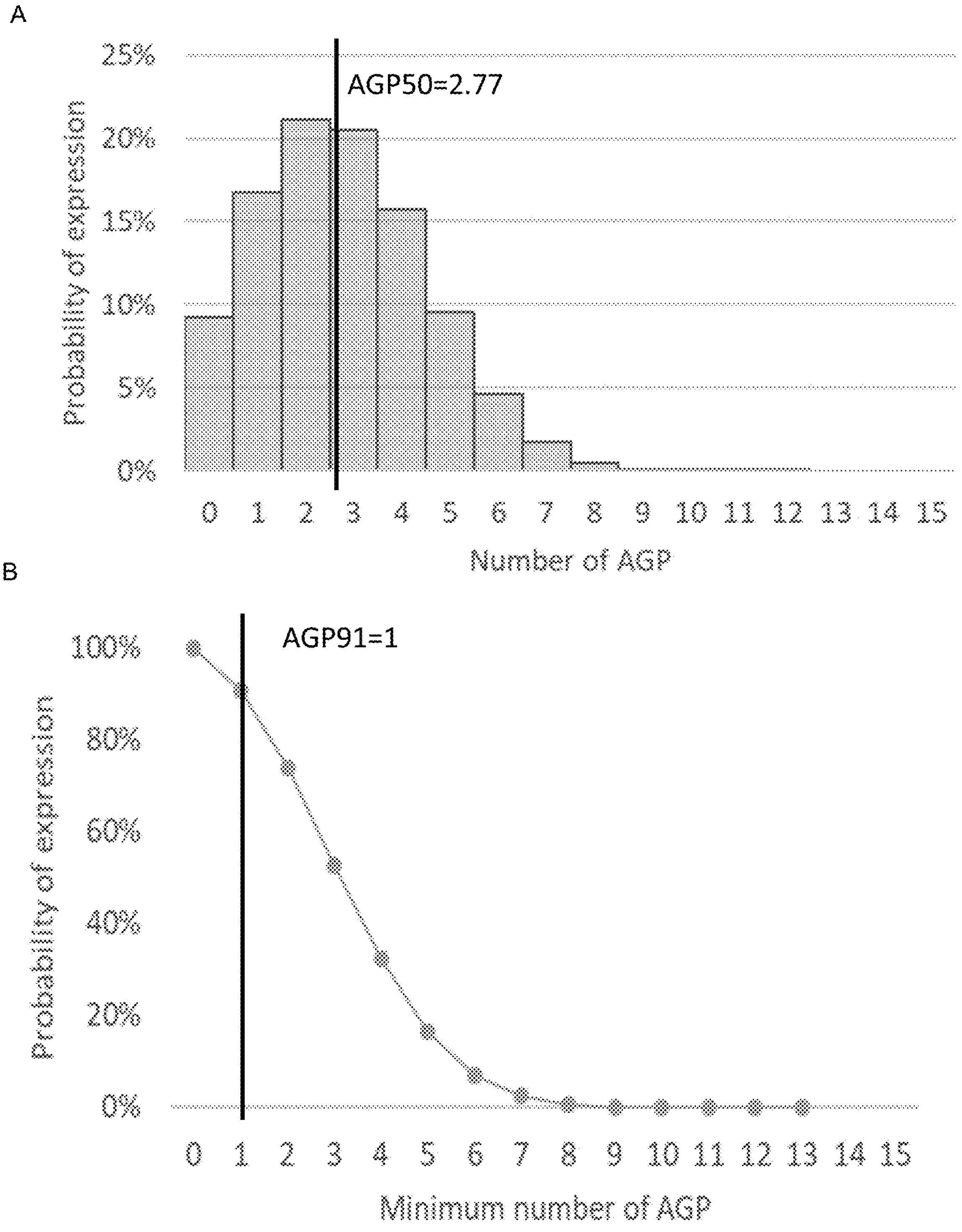

For PolyPEPI821, the AGP50 value in the Model Population is 2.77. The AGP91=1, means that 91% of the subjects in the Model Population induce immune responses against at least one expressed vaccine antigen (FIG. 23).

Example 19—Melanoma Peptide Vaccine Design for Large Population

Figure 24:
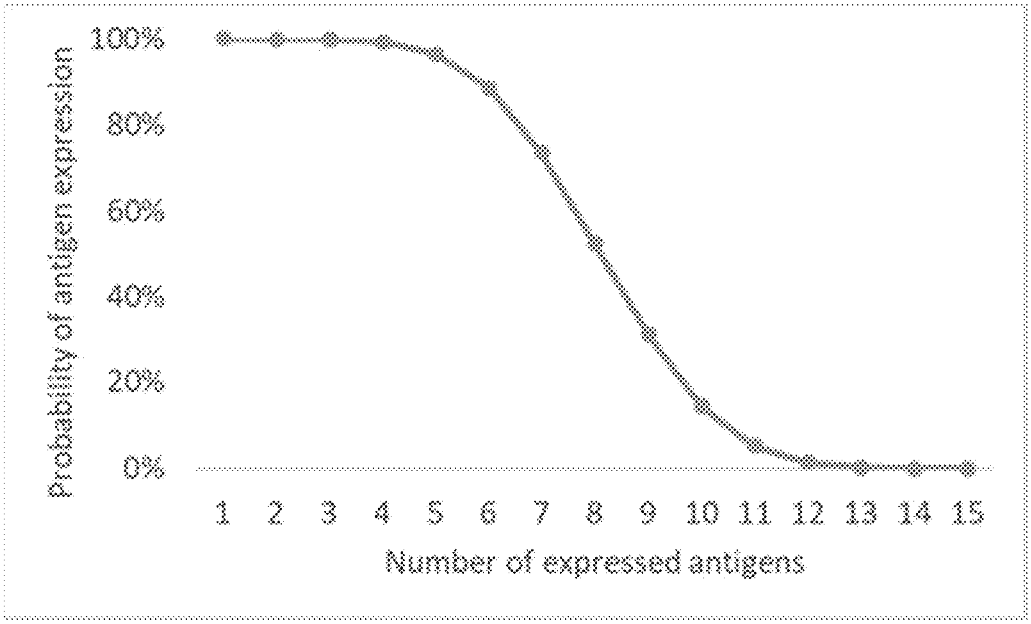

The PEPI3+ Test described above was used to design 9-mer and 15-mer peptides for use in melanoma vaccines, using the same method described in Example 16 above for gastric cancer (Tables 20c, 21c). The expression rates of the selected gastric cancer, specific CTAs are illustrated in FIG. 24.

TABLE 20c

BestEPI list (9-mers underlined) for selecting melanoma peptides for vaccine composition.

| SEQ ID NO. 9 mer | SEQ ID NO. 15 mer | Antigen | N % | BestEPIs and Optimized 15 mer: Opt. 15 mer | Opt. Position | B % | HLAII** (CD4) | B % * N % |
|---|---|---|---|---|---|---|---|---|
| 178 | 208 | PRAME | 90% | LERLAYLHARLRELL | 457 | 52% | 100% | 47% |
| 179 | 209 | MAGE-A2 | 61% | EDSVFAHPRKLLMQD | 235 | 55% | 43% | 34% |
| 180 | 210 | PRAME | 90% | RHSQTLKAMVQAWPF | 64 | 37% | 38% | 33% |
| 181 | 211 | MAGE-C1 | 45% | SFSYTLLSLFQSSPE | 450 | 57% | 99% | 26% |
| 182 | 212 | Survivin | 96% | TAKKVRRAIEQLAAM | 127 | 26% | 26% | 25% |
| 183 | 213 | MAGE-C1 | 45% | SPSFSSTLVSLFQSS | 273 | 53% | 97% | 24% |
| 184 | 214 | MAGE-A2 | 61% | SSFSTTINYTLWRQS | 69 | 37% | 74% | 23% |
| 185 | 215 | MAGE-A12 | 45% | QVALSRKMAELVHFL | 106 | 48% | 63% | 22% |
| 186 | 216 | MAGE-C1 | 45% | DDSYVFVNTLDLTSE | 971 | 48% | 99% | 22% |
| 187 | 217 | MAGE-C1 | 45% | FSYTLASLLQSSHES | 783 | 47% | 100% | 21% |
| 188 | 218 | PRAME | 90% | KEEQYIAQFTSQFLS | 280 | 23% | 99% | 20% |
| 189 | 219 | MAGE-C1 | 45% | QIPMTSSFSSTLLSI | 339 | 45% | 65% | 20% |
| 190 | 220 | PRAME | 90% | DQLLRHVMNPLETLS | 314 | 22% | 63% | 20% |
| 191 | 221 | Ny-ESO-1 | 38% | RGPESRLLEFYLAMP | 81 | 52% | 65% | 20% |
| 192 | 222 | MAGE-C2 | 45% | MASESLSVMSSNVSF | 357 | 40% | 15% | 18% |
| 193 | 223 | MAGE-C2 | 45% | REHFVYGEPRELLTK | 262 | 40% | 74% | 18% |
| 194 | 224 | MAGE-A6 | 62% | QYFVQENYLEYRQVP | 248 | 27% | 93% | 17% |
| 195 | 225 | BORIS | 27% | MFTSSRMSSFNRHMK | 263 | 57% | 66% | 15% |

TABLE 20c-continued

BestEPI list (9-mers underlined) for selecting melanoma peptides for vaccine composition.

| SEQ ID NO. 9 mer | SEQ ID NO. 15 mer | Antigen | N % | BestEPIs and Optimized 15 mer: Opt. 15 mer | Opt. Position | B % | HLAII** (CD4) | B % * N % |
|---|---|---|---|---|---|---|---|---|
| 196 | 226 | LAGE-1 | 35% | DFTVSGNLLFMSVRD | 125 | 43% | 82% | 15% |
| 197 | 227 | MAGE-A2 | 61% | SKASEYLQLVFGIEV | 152 | 24% | 69% | 15% |
| 198 | 228 | Survivin | 96% | KDHRISTFKNWPFLE | 15 | 15% | 83% | 14% |
| 199 | 229 | MAGE-A11 | 54% | SHSYVLVTSLNLSYD | 286 | 26% | 100% | 14% |
| 200 | 230 | SSX-1 | 25% | QVEHPQMTFGRLHRI | 93 | 55% | 20% | 14% |
| 201 | 231 | MAGE-A3 | 59% | KASSSLQLVFGIELM | 153 | 23% | 58% | 14% |
| 202 | 232 | MAGE-C2 | 45% | SSFSTSSSLILGGPE | 53 | 30% | 44% | 13% |
| 203 | 233 | MAGE-A3 | 59% | QAALSRKVAELVHFL | 106 | 21% | 45% | 12% |
| 204 | 234 | MAGE-A11 | 54% | SPTAMDAIFGSLSDE | 181 | 23% | 0% | 12% |
| 205 | 235 | MAGE-A10 | 44% | RNYEDHFPLLFSEAS | 166 | 27% | 26% | 12% |
| 206 | 236 | MAGE-A11 | 54% | YAGREHFLFGEPKRL | 344 | 18% | 71% | 9% |
| 207 | 237 | MAGE-A1 | 37% | PRALAETSYVKVLEY | 268 | 16% | 39% | 6% |

N %: Antigen expression frequency in melanomas;
B %: bestEPI frequency, i.e. the percentage of individuals with epitopes binding to at least 3 HLA class 1 of subjects in the model population (433 subjects);
HLAII**: Percentage of individuals having CD4+ T cell specific PEPI4+ within normal donors (n = 400);
N % * B %: N % multiplied by B %.

Fifteen 30 mer peptides were then designed (Table 21c). The 30 mers may each consist of two optimized 15 mer fragments, generally from different frequent CTAs, arranged end to end, each fragment comprising one of the 9 mers (BestEPIs) from Table 20c.

TABLE 21c 30 mer melanoma vaccine peptides of composition PolyPEPI621

| SEQID | TREOSID | Source Antigen | Peptide (30 mer) | HLAI* (CD8) | HLAI** (CD4) |
|---|---|---|---|---|---|
| 238 | MC621-01 | PRAME/PRAME | LERLAYLHARLRELLDQLLRHVMNPLETLS | 58% | 100% |
| 239 | MC621-02 | Survivin/MAGE-A2 | TAKKVRRAIEQLAAMEDSVFAHPRKLLMQD | 65% | 54% |
| 240 | MC621-03 | PRAME/MAGE-A3 | RHSQTLKAMVQAWPFKASSSLQLVFGIELM | 53% | 77% |
| 241 | MC621-04 | MAGE-C1/MAGE-A2 | DDSYVFVNTLDLTSESSFSTTINYTLWRQS | 70% | 99% |
| 242 | MC621-05 | MAGE-C1/MAGE-A2 | SFSYTLLSLFQSSPESKASEYLQLVFGIEV | 64% | 99% |
| 243 | MC621-06 | MAGE-A11/MAGE-C1 | SHSYVLVTSLNLSYDSPSFSSTLVSLFQSS | 73% | 100% |
| 244 | MC621-07 | LAGE-1/MAGE-C2 | DFTVSGNLLFMSVRDMASESLSVMSSNVSF | 60% | 83% |
| 245 | MC621-08 | BORIS/MAGE-A12 | MFTSSRMSSFNRHMKQVALSRKMAELVHFL | 74% | 81% |
| 246 | MC621-09 | MAGE-C2/MAGE-C1 | SSFSTSSSLILGGPEFSYTLASLLQSSHES | 54% | 100% |
| 247 | MC621-10 | Survivin/MAGE-C1 | KDHRISTFKNWPFLEQIPMTSSFSSTLLSI | 51% | 89% |
| 248 | MC621-11 | Ny-ESO-1/MAGE-A10 | RGPESRLLEFYLAMPRNYEDHFPLLFSEAS | 73% | 66% |
| 249 | MC621-12 | MAGE-A3 /MAGE-A6 | QAALSRKVAELVHFLQYFVQENYLEYRQVP | 48% | 97% |
| 250 | MC621-13 | MAGE-A11/MAGE-A1 | SPTAMDAIFGSLSDEPRALAETSYVKVLEY | 53% | 39% |

TABLE 21c-continued 30 mer melanoma vaccine peptides of composition PolyPEPI621

| SEQID | TREOSID | Source Antigen | Peptide (30 mer) | HLAI* (CD8) | HLAI** (CD4) |
|---|---|---|---|---|---|
| 251 | MC621-14 | MAGE-C2/MAGE-A11 | REHFVYGEPRELLTKYAGREHFLFGEPKRL | 57% | 83% |
| 252 | MC621-15 | SSX-1/PRAME | QVEHPQMTFGRLHRIKEEQYIAQFTSQFLS | 67% | 99% |

*Percentage of individuals having CD8+ T cell specific PEPI3+ within the HLA class I Model Population (n = 433).
**Percentage of individuals having CD4+ T cell specific PEPI4+ within the normal donors (n = 400)

Characterization of PolyPEPI621

The PolyPEPI621 composition targets 15 different CTAs. Based on the antigen expression rates for these 15 CTAs, we modelled the predicted average number of expressed antigens (AG50) and the minimum number of expressed antigens with 95% likelihood (AG95) in the cancer cells. 95% of individuals expressed minimum 5 of the 15 target antigens (AG95=5) as shown by the antigen expression curve in FIG. 25.

The PolyPEPI621 composition can induce immune response against an average of 8 vaccine antigens (AP50=8.29) and 95% of the Model Population can induce immune response against at least three vaccine antigens (AP95=2)(FIG. 26).

Figure 27:
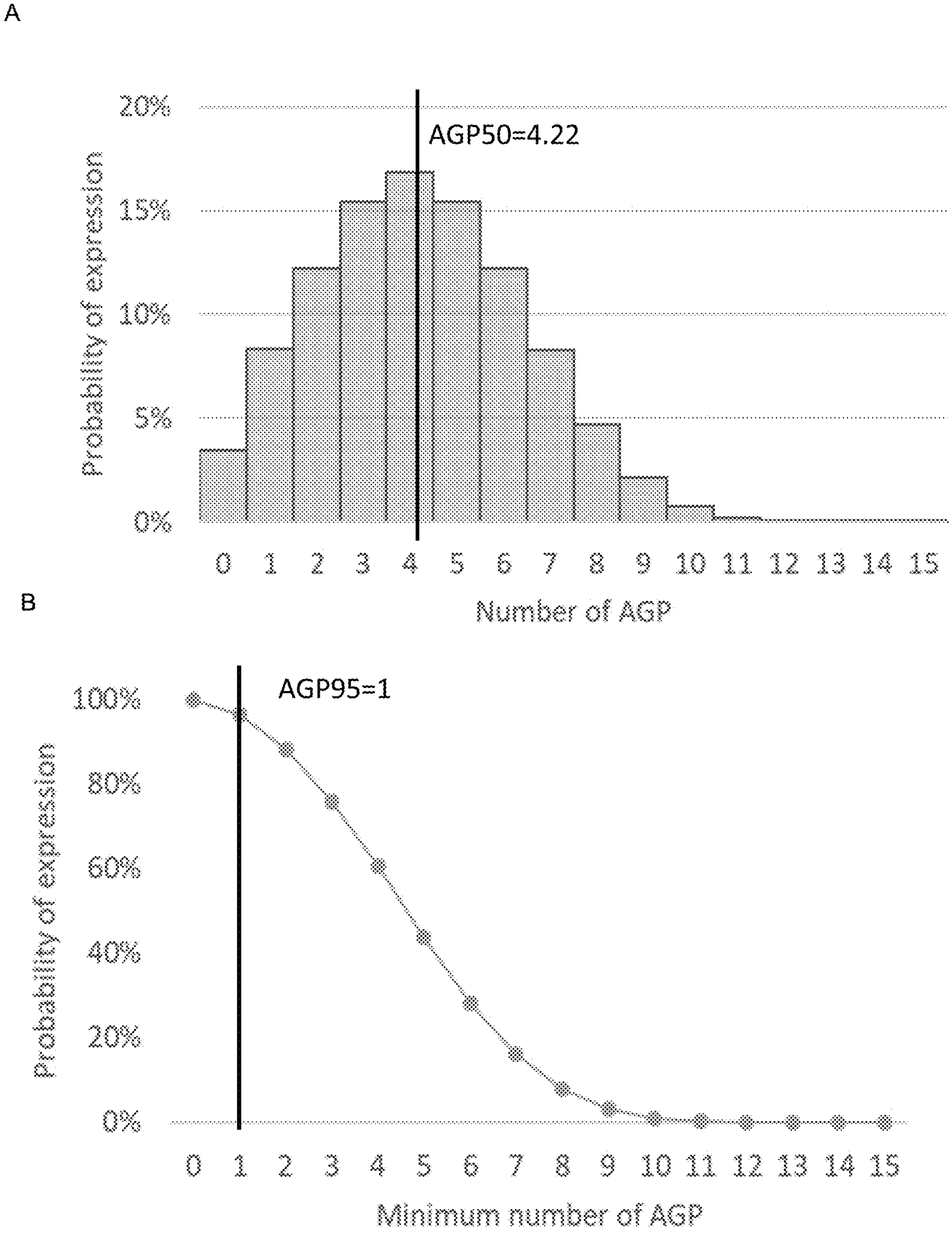

Combining the data of AG of melanoma and AP in the Model Population we determined the AGP value of PolyPEPI621 that represents the probability distribution of vaccine antigens that induce immune responses against antigens expressed in gastric tumors. For PolyPEPI621, the AGP50 value in the Model Population is 2.77. The AGP95=1, means that 95% of the subjects in the Model Population induce immune responses against at least one expressed vaccine antigen (FIG. 27).

Example 20—Bladder Cancer Peptide Vaccine Design for Large Population

Figure 28:
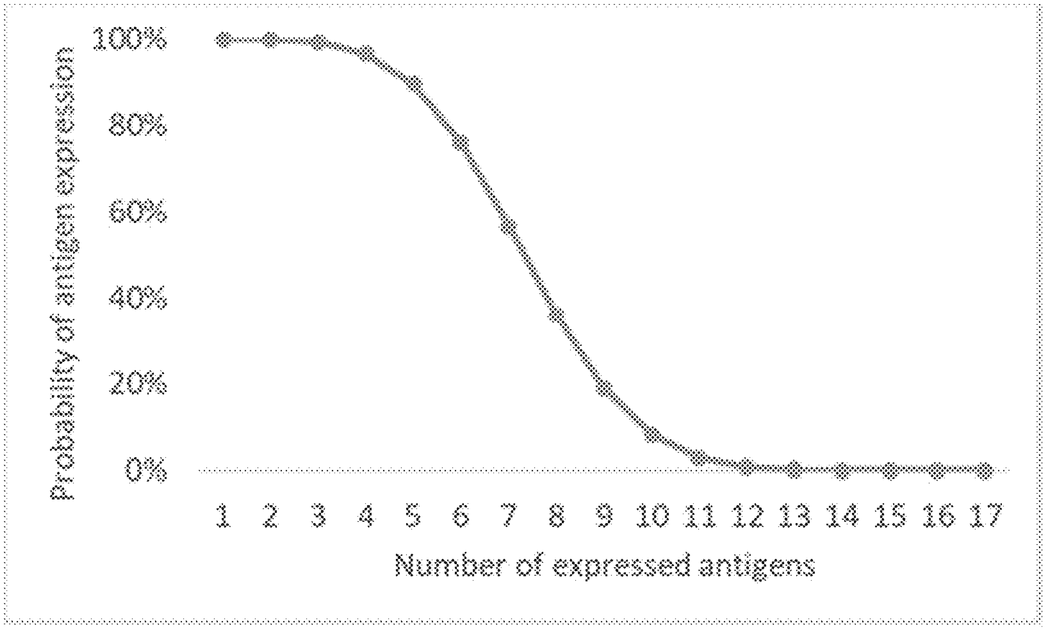

The PEPI3+ Test described above was used to design 9-mer and 15-mer peptides for use in bladder cancer vaccines, using the same method described in Example 16 above for gastric cancer (Tables 120d, 21d). The expression rates of the selected gastric cancer, specific CTAs are illustrated in FIG. 28.

TABLE 20d

BestEPI list (9-mers underlined) for selecting bladder cancer peptides for vaccine composition.

| SEQ ID NO. 9 mer | SEQ ID NO. 15 mer | Antigen: Antigen | Antigen: N % | BestEPIs and Optimized 15 mer: Opt. 15 mer | Opt. Position | B % | HLAI** (CD4) | B % * N % |
|---|---|---|---|---|---|---|---|---|
| 268 | 298 | PIWIL2 | 82% | FVASINLTLTKWYSR | 760 | 67% | 93% | 55% |
| 269 | 299 | PIWIL2 | 82% | RNFYDPTSAMVLQQH | 341 | 60% | 49% | 49% |
| 270 | 300 | PIWIL2 | 82% | YSRVVFQMPHQEIVD | 772 | 40% | 77% | 33% |
| 271 | 301 | CTAGE1 | 53% | QNYIDQFLLTSFPTF | 33 | 59% | 90% | 31% |
| 272 | 302 | MAGE-A9 | 61% | EFMFQEALKLKVAEL | 101 | 49% | 100% | 30% |
| 273 | 303 | EpCAM | 54% | RTYWIIIELKHKARE | 140 | 51% | 100% | 28% |
| 274 | 304 | OY-TES-1 | 28% | ESTPMIMENIQELIR | 276 | 67% | 82% | 19% |
| 275 | 305 | MAGE-A9 | 61% | SSISVYYTLWSQFDE | 67 | 30% | 97% | 19% |
| 276 | 306 | NY-ESO-1 | 31% | RGPESRLLEFYLAMP | 81 | 52% | 65% | 16% |
| 277 | 307 | SURVIVIN | 62% | AKKVRRAIEQLAAMD | 128 | 26% | 25% | 16% |
| 278 | 308 | MAGE-C1 | 27% | SSFSYTLLSLFQSSP | 449 | 57% | 98% | 16% |
| 279 | 309 | CTAGE1 | 53% | SFVLFLFGGNNFIQN | 14 | 29% | 85% | 15% |
| 280 | 310 | EpCAM | 54% | QTLIYYVDEKAPEFS | 246 | 28% | 34% | 15% |
| 281 | 311 | MAGE-A2 | 25% | REDSVFAHPRKLLMQ | 234 | 55% | 74% | 14% |
| 282 | 312 | MAGE-C1 | 27% | DDSYVFVNTLDLTSE | 971 | 48% | 99% | 13% |
| 283 | 313 | LAGE-1 | 30% | DFTVSGNLLFMSVRD | 125 | 43% | 82% | 13% |

TABLE 20d-continued

BestEPI list (9-mers underlined) for selecting bladder cancer peptides for vaccine composition.

| SEQ ID NO. 9 mer | SEQ ID NO. 15 mer | Antigen | N % | BestEPIs and Optimized 15 mer: Opt. 15 mer | Opt. Position | B % | HLAI** (CD4) | B % * N % |
|---|---|---|---|---|---|---|---|---|
| 284 | 314 | MAGE-A3 | 42% | LTQHFVQENYLEYRQ | 246 | 27% | 56% | 11% |
| 285 | 315 | MAGE-A8 | 57% | EEAIWEALSVMGLYD | 221 | 20% | 78% | 11% |
| 286 | 316 | HAGE | 24% | NDLQMSNFVNLKNIT | 377 | 43% | 67% | 10% |
| 287 | 317 | MAGE-A8 | 57% | EKVAELVRFLLRKYQ | 114 | 18% | 99% | 10% |
| 288 | 318 | MAGE-A3 | 42% | KASSSLQLVFGIELM | 153 | 23% | 58% | 10% |
| 289 | 319 | SURVIVIN | 62% | KDHRISTFKNWPFLE | 15 | 15% | 83% | 9% |
| 290 | 320 | MAGE-A2 | 25% | SSFSTTINYTLWRQS | 69 | 37% | 74% | 9% |
| 291 | 321 | MAGE-A3 | 42% | QAALSRKVAELVHFL | 106 | 21% | 45% | 9% |
| 292 | 322 | MAGE-A1 | 34% | ETSYVKVLEYVIKVS | 273 | 26% | 85% | 9% |
| 293 | 323 | MAGE-C2 | 19% | MASESLSVMSSNVSF | 357 | 40% | 15% | 8% |
| 294 | 324 | MAGE-C2 | 19% | REHFVYGEPRELLTK | 262 | 40% | 74% | 8% |
| 295 | 325 | MAGE-A10 | 28% | RNYEDHFPLLFSEAS | 166 | 27% | 26% | 7% |
| 296 | 326 | MAGE-A12 | 29% | KASEYLQLVFGIEW | 153 | 24% | 83% | 7% |
| 297 | 327 | LAGE-1 | 30% | DSRLLQLHITMPFSS | 84 | 20% | 99% | 6% |

N %: Antigen expression frequency in bladder cancers;
B %: bestEPI frequency, ie the percentage of individuals with epitopes binding to at least 3 HLA class I of subjects in the model population (433 subjects);
HLAII**: Percentage of individuals having CD4+ T cell specific PEPI4+ within normal donors (n = 400);
N % * B %: N % multiplied by B %.

Fifteen 30 mer peptides were then designed (Table 21d). The 30 mers may each consist of two optimized 15 mer fragments, generally from different frequent CTAs, arranged end to end, each fragment comprising one of the 9 mers (BestEPIs) from Table 20d.

TABLE 21d 30 mer bladder cancer vaccine peptides of composition PolyPEPI1411

| SEQID | TREOSID | Source Antigen | Peptide (30 mer) | HLAI* (CD8) | HLAH** (CD4) |
|---|---|---|---|---|---|
| 328 | BLV1411-01 | MAGE-C1/PIWIL2 | DDSYVFVNTLDLTSERNFYDPTSAMVLQQH | 81% | 99% |
| 329 | BLV1411-02 | MAGE-A9/OY-TES-1 | EFMFQEALKLKVAELESTPMIMENIQELIR | 77% | 100% |
| 330 | BLV1411-03 | PIWIL2/MAGE-A1 | YSRVVFQMPHQEIVDETSYVKVLEYVIKVS | 54% | 93% |
| 331 | BLV1411-04 | CTAGE1/MAGE-A2 | QNYIDQFLLTSFPTFREDSVFAHPRKLLMQ | 82% | 100% |
| 332 | BLV1411-05 | HAGE/EpCAM | NDLQMSNFVNLKNITRTYWIIIELKHKARE | 66% | 100% |
| 333 | BLV1411-06 | MAGE-A9/MAGE-A8 | SSISVYYTLWSQFDEEKVAELVRFLLRKYQ | 42% | 100% |
| 334 | BLV1411-07 | NY-ESO-1/MAGE-A10 | RGPESRLLEFYLAMPRNYEDHFPLLFSEAS | 73% | 66% |
| 335 | BLV1411-08 | CTAGE1/MAGE-A8 | SFVLFLFGGNNFIQNEEAIWEALSVMGLYD | 46% | 94% |
| 336 | BLV1411-09 | EpCAM/MAGE-C2 | QTLIYYVDEKAPEFSREHFVYGEPRELLTK | 64% | 80% |
| 337 | BLV1411-10 | MAGE-C1/MAGE-A12 | SSFSYTLLSLFQSSPKASEYLQLVFGIEVV | 64% | 98% |
| 338 | BLV1411-11 | PIWIL2/LAGE-1 | FVASINLTLTKWYSRDFTVSGNLLFMSVRD | 76% | 94% |

TABLE 21d-continued

| 30 mer bladder cancer vaccine peptides of composition PolyPEPI1411 | | | | | |
|---|---|---|---|---|---|
| SEQID | TREOSID | Source Antigen | Peptide (30 mer) | HLAI* (CD8) | HLAH** (CD4) |
| 339 | BLV1411-12 | MAGE-A3/MAGE-A3 | LTQHFVQENYLEYRQKASSSLQLVFGIELM | 47% | 71% |
| 340 | BLV1411-13 | MAGE-A2/LAGE-1 | SSFSTTINYTLWRQSDSRLLQLHITMPFSS | 61% | 99% |
| 341 | BLV1411-14 | SURVIVIN/MAGE-C2 | AKKVRRAIEQLAAMDMASESLSVMSSNVSF | 52% | 28% |
| 342 | BLV1411-15 | MAGE-A3/SURVIVIN | QAALSRKVAELVHFLKDHRISTFKNWPFLE | 30% | 90% |

*Percentage of individuals having CD8+ T cell specific PEPI3+ within the HLA class I Model Population (n = 433).
**Percentage of individuals having CD4+ T cell specific PEPI4+ within the normal donors (n = 400).

Characterization of PolyPEPI1411

Figure 29:
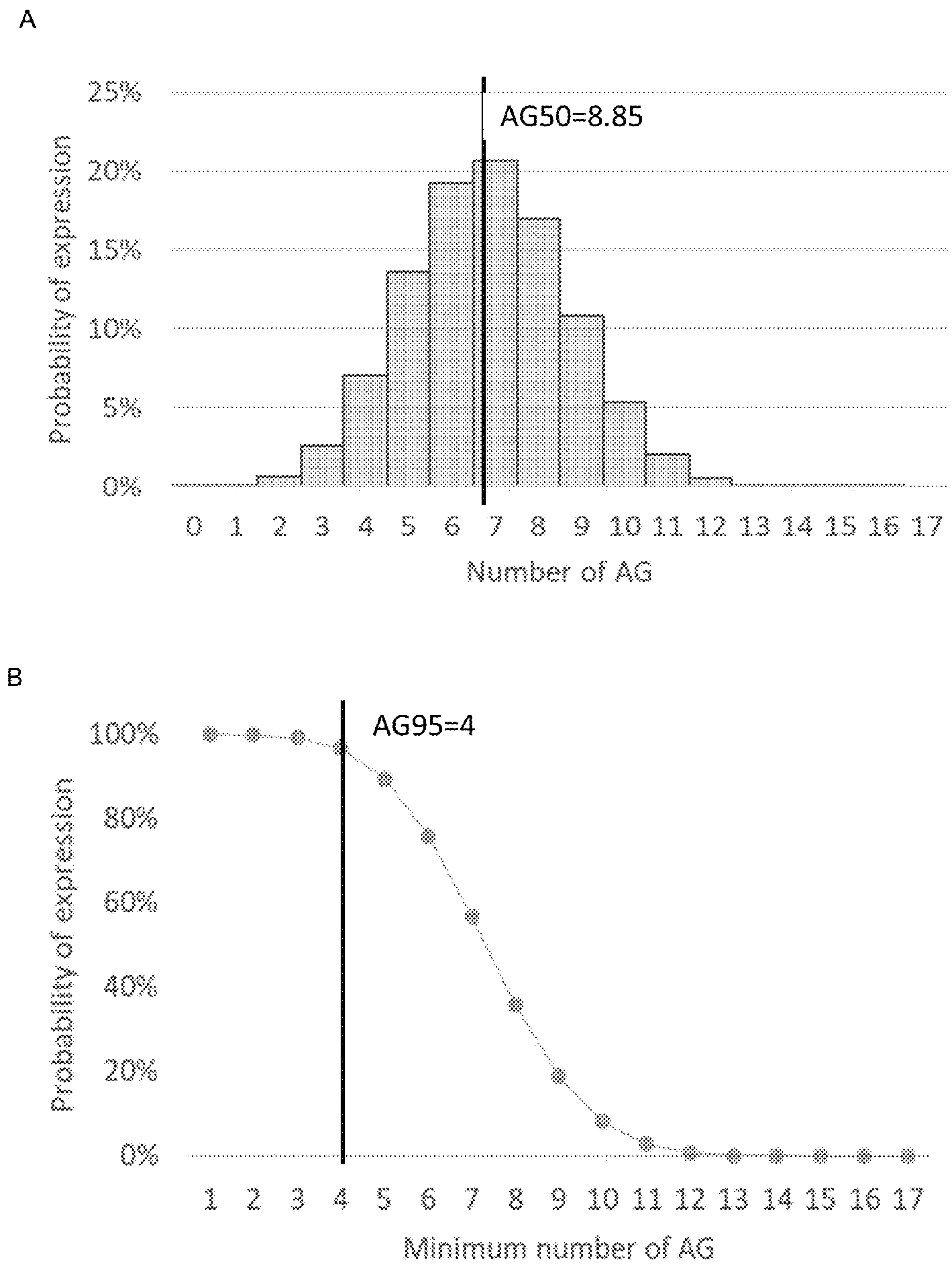

The PolyPEPI1411 composition targets 17 different CTAs. Based on the antigen expression rates for these 17 CTAs, we modelled the predicted average number of expressed antigens (AG50) and the minimum number of expressed antigens with 95% likelihood (AG95) in the cancer cells. 95% of individuals expressed minimum 4 of the 17 target antigens (AG95=4) as shown by the antigen expression curve in FIG. 29.

The PolyPEPI1411 composition can induce immune response against an average of 9 vaccine antigens (AP50=9.44) and 95% of the Model Population can induce immune response against at least three vaccine antigens (AP95=3)(FIG. 30).

Combining the data of AG of bladder cancer and AP in the Model Population we determined the AGP value of PolyPEPI1411 that represents the probability distribution of vaccine antigens that induce immune responses against antigens expressed in bladder tumors. For PolyPEPI1411, the AGP50 value in the Model Population is 3.90. The AGP95=1, means that 95% of the subjects in the Model Population induce immune responses against at least one expressed vaccine antigen (FIG. 31).

Example 21—Personalised Immunotherapy (PIT) Design and Treatment for Ovarian-, Breast- and Colorectal Cancer This Example provides proof of concept data from 4 metastatic cancer patients treated with personalized immunotherapy vaccine compositions to support the principals of binding of epitopes by multiple HLAs of a subject to induce cytotoxic T cell responses, on which the present disclosure is partly based on.

Composition for Treatment of Ovarian Cancer with P0001—PIT (Patient A)

This example describes the treatment of an ovarian cancer patient with a personalised immunotherapy composition, wherein the composition was specifically designed for the patient based on her HLA genotype based on the disclosure described herein.

The HLA class I and class II genotype of a metastatic ovarian adenocarcinoma cancer patient (Patient-A) was determined from a saliva sample.

To make a personalized pharmaceutical composition for Patient-A thirteen peptides were selected, each of which met the following two criteria: (i) derived from an antigen that is expressed in ovarian cancers, as reported in peer reviewed scientific publications; and (ii) comprises a fragment that is a T cell epitope capable of binding to at least three HLA class I of Patient-A (Table 22). In addition, each peptide is optimized to bind the maximum number of HLA class II of the patient.

TABLE 22

| Personalized vaccine of Patient-A. | | | | | |
|---|---|---|---|---|---|
| POC01 vaccine for Patient-A | Target Antigen | Antigen Expression | 20 mer peptides | MAX HLA class I | MAX HLA class II |
| POC01_P1 | AKAP4 | 89% | NSLQKQLQAVLQWIAASQFN | 3 | 5 |
| POC01_P2 | BORIS | 82% | SGDERSDEIVLTVSNSNVEE | 4 | 2 |
| POC01_P3 | SPAG9 | 76% | VQKEDGRVQAFGWSLPQKYK | 3 | 3 |
| POC01_P4 | OY-TES-1 | 75% | EVESTPMIMENIQELIRSAQ | 3 | 4 |
| POC01_P5 | SP17 | 69% | AYFESLLEKREKTNFDPAEW | 3 | 1 |
| POC01_P6 | WT1 | 63% | PSQASSGQARMFPNAPYLPS | 4 | 1 |
| POC01_P7 | HIWI | 63% | RRSIAGFVASINEGMTRWFS | 3 | 4 |
| POC01_P8 | PRAME | 60% | MQDIKMILKMVQLDSIEDLE | 3 | 4 |
| POC01_P9 | AKAP-3 | 58% | ANSVVSDMMVSIMKTLKIQV | 3 | 4 |
| POC01_P10 | MAGE-A4 | 37% | REALSNKVDELAHFLLRKYR | 3 | 2 |

TABLE 22-continued

Personalized vaccine of Patient-A.

| POC01 vaccine for Patient-A | Target Antigen | Antigen Expression | 20 mer peptides | MAX HLA class I | MAX HLA class II |
|---|---|---|---|---|---|
| POC01_P11 | MAGE-A9 | 37% | ETSYEKVINYLVMLNAREPI | 3 | 4 |
| POC01_P12a | MAGE-A10 | 52% | DVKEVDPTGHSFVLVTSLGL | 3 | 4 |
| POC01_P12b | BAGE | 30% | SAQLLQARLMKEESPVVSWR | 3 | 2 |

Eleven PEPI3 peptides in this immunotherapy composition can induce T cell responses in Patient-A with 84% probability and the two PEPI4 peptides (P0001-P2 and P0001-P5) with 98% probability, according to the validation of the PEPI test shown in Table 3. T cell responses target 13 antigens expressed in ovarian cancers. Expression of these cancer antigens in patient-A was not tested. Instead the probability of successful killing of cancer cells was determined based on the probability of antigen expression in the patient's cancer cells and the positive predictive value of the ≥1 PEPI3+ test (AGP count). AGP count predicts the effectiveness of a vaccine in a subject: Number of vaccine antigens expressed in the patient's tumor (ovarian adenocarcinoma) with PEPI. The AGP count indicates the number of tumor antigens that the vaccine recognizes and induces a T cell response against the patient's tumor (hit the target). The AGP count depends on the vaccine-antigen expression rate in the subject's tumor and the HLA genotype of the subject. The correct value is between 0 (no PEPI presented by any expressed antigen) and maximum number of antigens (all antigens are expressed and present a PEPI).

Figure 32:
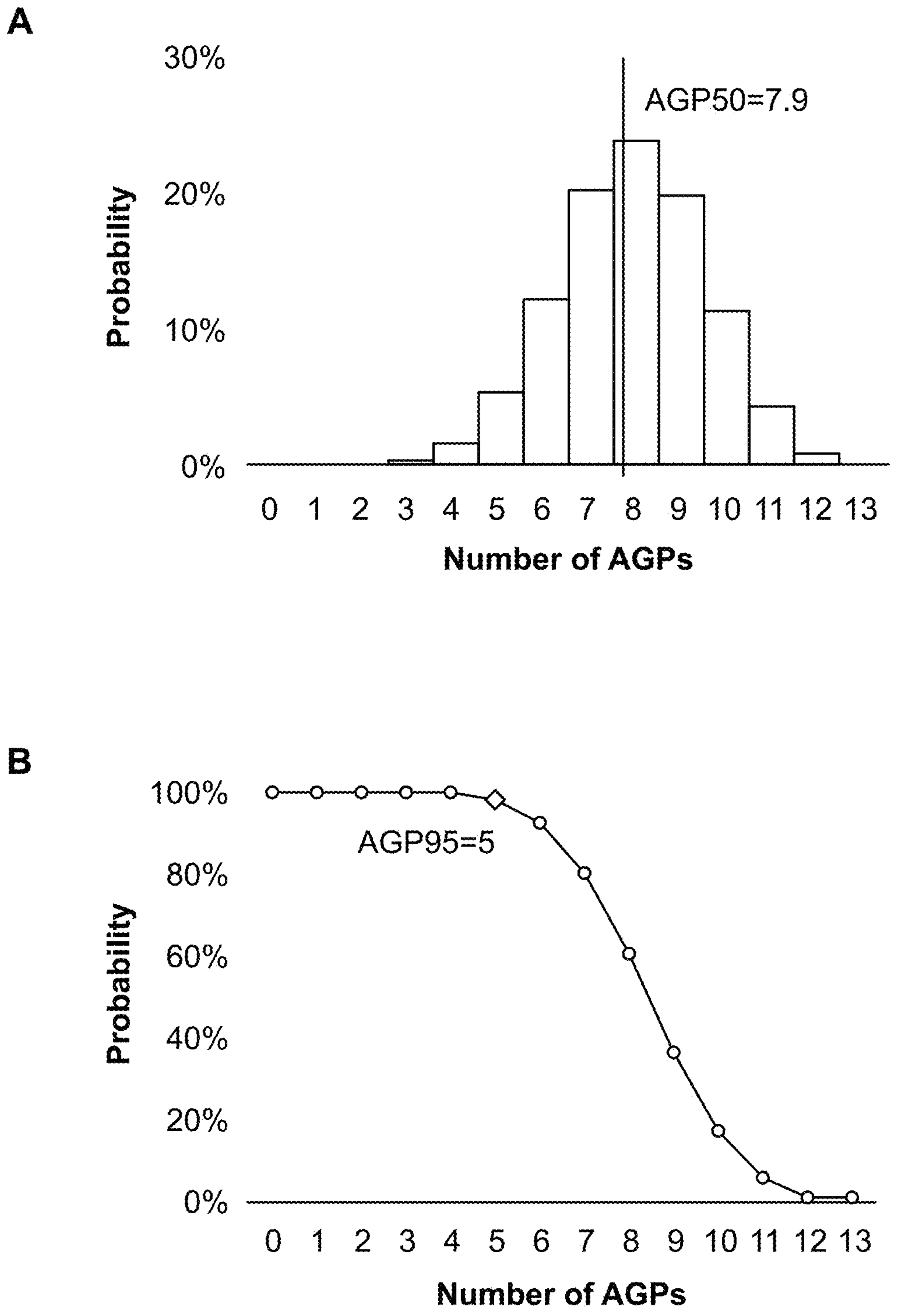

The probability that Patient-A will express one or more of the 13 antigens is shown in FIG. 32. AGP95 (AGP with 95% probability)=5, AGP50 (the mean—expected value—of the discrete probability distribution)=7.9, mAGP (probability that AGP is at least 2)=100%, AP=13.

A pharmaceutical composition for Patient-A may be comprised of at least 2 from the 13 peptides (Table 22), because the presence in a vaccine or immunotherapy composition of at least two polypeptide fragments (epitopes) that can bind to at least three HLAs of an individual (≥2 PEPI3+) was determined to be predictive for a clinical response. The peptides are synthetized, dissolved in a pharmaceutically acceptable solvent and mixed with an adjuvant prior to injection. It is desirable for the patient to receive personalized immunotherapy with at least two peptide vaccines, but preferable more to increase the probability of killing cancer cells and decrease the chance of relapse.

For treatment of Patient-A the 13 peptides were formulated as 4×3 or 4 peptide (P0001/1, P0001/2, P0001/3, P0001/4). One treatment cycle is defined as administration of all 13 peptides within 30 days.

Patient History:

Diagnosis: Metastatic ovarian adenocarcinoma

Age: 51

Family anamnesis: colon and ovary cancer (mother) breast cancer (grandmother)

Tumor Pathology:

2011: first diagnosis of ovarian adenocarcinoma; Wertheim operation and chemotherapy; lymph node removal 2015: metastasis in pericardial adipose tissue, excised 2016: hepatic metastases 2017: retroperitoneal and mesenteric lymph nodes have progressed; incipient peritoneal carcinosis with small accompanying ascites Prior Therapy:

2012: Paclitaxel-carboplatin (6×)

2014: Caelyx-carboplatin (1×)

2016-2017 (9 months): Lymparza (Olaparib) 2×400 mg/day, oral

2017: Hycamtin inf. 5×2.5 mg (3× one seria/month)

Figure 33:
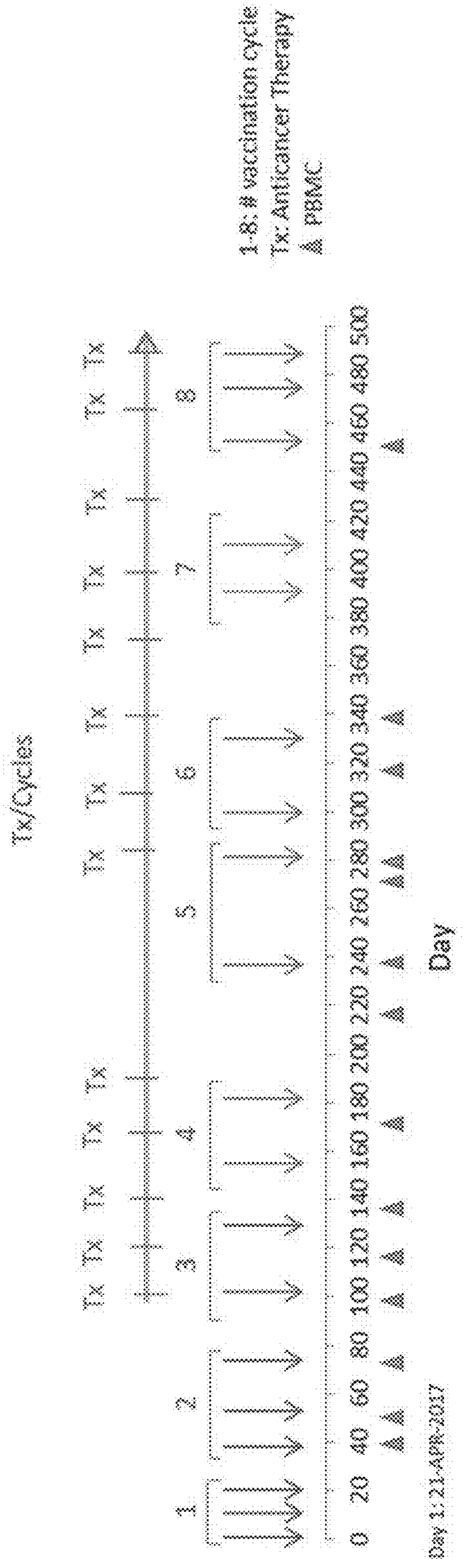

PIT vaccine treatment began on 21 Apr. 2017. FIG. 33.

2017-2018: Patient-A received 8 cycles of vaccination as add-on therapy, and lived 17 months (528 days) after start of the treatment. During this interval, after the 3$^{rd}$ and 4$^{th}$ vaccine treatment she experienced partial response as best response. She died in October 2018.

An interferon (IFN)-γ ELISPOT bioassay confirmed the predicted T cell responses of Patient-A to the 13 peptides. Positive T cell responses (defined as >5 fold above control, or >3 fold above control and >50 spots) were detected for all 13 20-mer peptides and all 13 9-mer peptides having the sequence of the PEPI of each peptide capable of binding to the maximum HLA class I alleles of Patient-A (FIG. 34).

Figure 35:
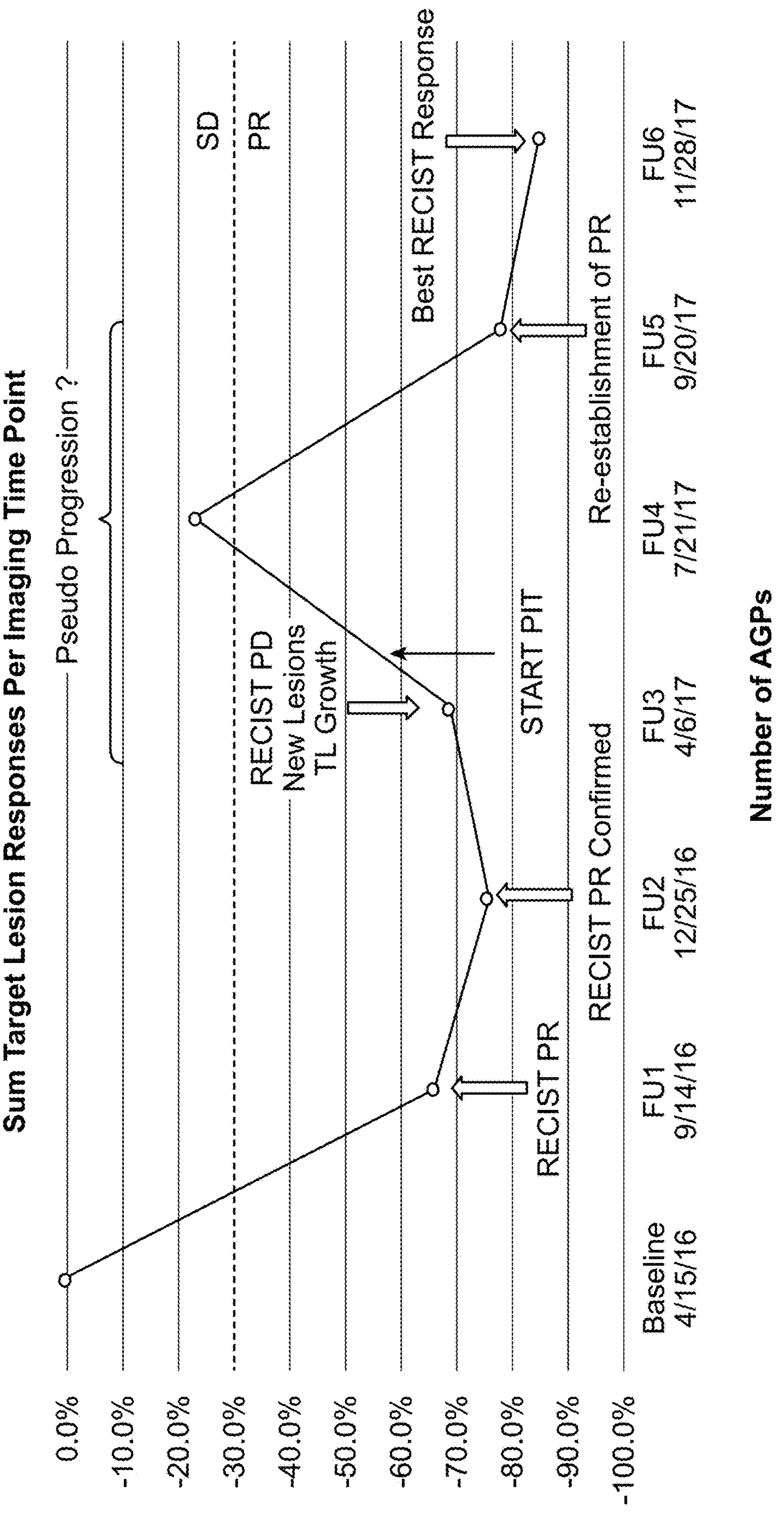

Patient's tumor MRI findings (Baseline Apr. 15, 2016) (BL: baseline for tumor response evaluation on FIG. 35)

Disease was confined primarily to liver and lymph nodes. The use of MRI limits detection of lung (pulmonary) metastasis May 2016-January 2017: Olaparib treatment (FU1: follow up 1 on FIG. 35) Dec. 25, 2016 (before PIT vaccine treatment) There was dramatic reduction in tumor burden with confirmation of response obtained at (FU2: follow up 2 on FIG. 35)

January-March 2017—TOPO protocol (topoisomerase)

Apr. 6, 2017 (FU3 on FIG. 35) demonstrated regrowth of existing lesions and appearance of new lesions leading to disease progression. Peritoneal carcinomatosis with increased amount of ascites. Progressive hepatic tumor and lymph node Apr. 21, 2017 START PIT Jul. 26, 2017 (after the 2n d Cycle of PIT): (FU4 on FIG. 35) Progression/Pseudo-Progression Rapid progression in lymph nodes, hepatic, retroperitoneal and thoracic areas, significant pleural fluid and ascites. Initiate Carboplatin, Gemcitabine, Avastin.

Sep. 20, 2017 (after 3 Cycles of PIT): (FU5 on FIG. 35) Partial Response

Complete remission in the pleural region/fluid and ascites

Remission in hepatic, retroperitoneal area and lymph nodes

The findings suggest pseudo progression.

Nov. 28, 2017 (after 4 Cycles of PIT): (FU6 on FIG. 35) Partial Response

Complete remission in the thoracic region. Remission in hepatic, retroperitoneal area and lymph nodes Apr. 13, 2018: Progression Complete remission in the thoracic and retroperitoneal regions. Progression in hepatic centers and lymph nodes Jun. 12, 2018: Stable disease Complete remission in the thoracic and retroperitoneal regions. Minimal regression in hepatic centers and lymph nodes July 2018: Progression October 2018: Patient-A died Partial MRI data for Patient-A is shown in Table 23 and FIG. 35.

TABLE 23

Summary Table of Lesions Responses

| Lesion/ Time Point | Baseline (% Δ from BL) | FU1 (% Δ from BL) | FU2 (% Δ from BL) | FU3 (% Δ from BL) | FU4 (% Δ from BL) | FU5 (% Δ from BL) | FU6 (% Δ from BL) | Best Response Cycle | PD Time Point |
|---|---|---|---|---|---|---|---|---|---|
| TL1 | NA | −56.1 | −44.4 | −44.8 | +109.3 | −47.8 | −67.3 | FU6 | FU4 |
| TL2 | NA | −100.0 | −100.0 | −47.1 | −13.1 | −100.0 | −100.0 | FU1 | FU3 |
| TL3 | NA | −59.4 | −62.3 | −62.0 | −30.9 | −66.7 | −75.9 | FU6 | FU4 |
| TL4 | NA | −65.8 | −100.0 | −100.0 | −100.0 | −100.0 | −100.0 | FU2 | NA |
| SUM | NA | −66.3 | −76.0 | −68.9 | −23.5 | −78.2 | −85.2 | FU6 | FU4 |

Design, Safety and Immunogenicity of Personalised Immunotherapy Composition (PBRC01) for Treatment of Metastatic Breast Cancer (Patient-B) PT9

Figure 36:
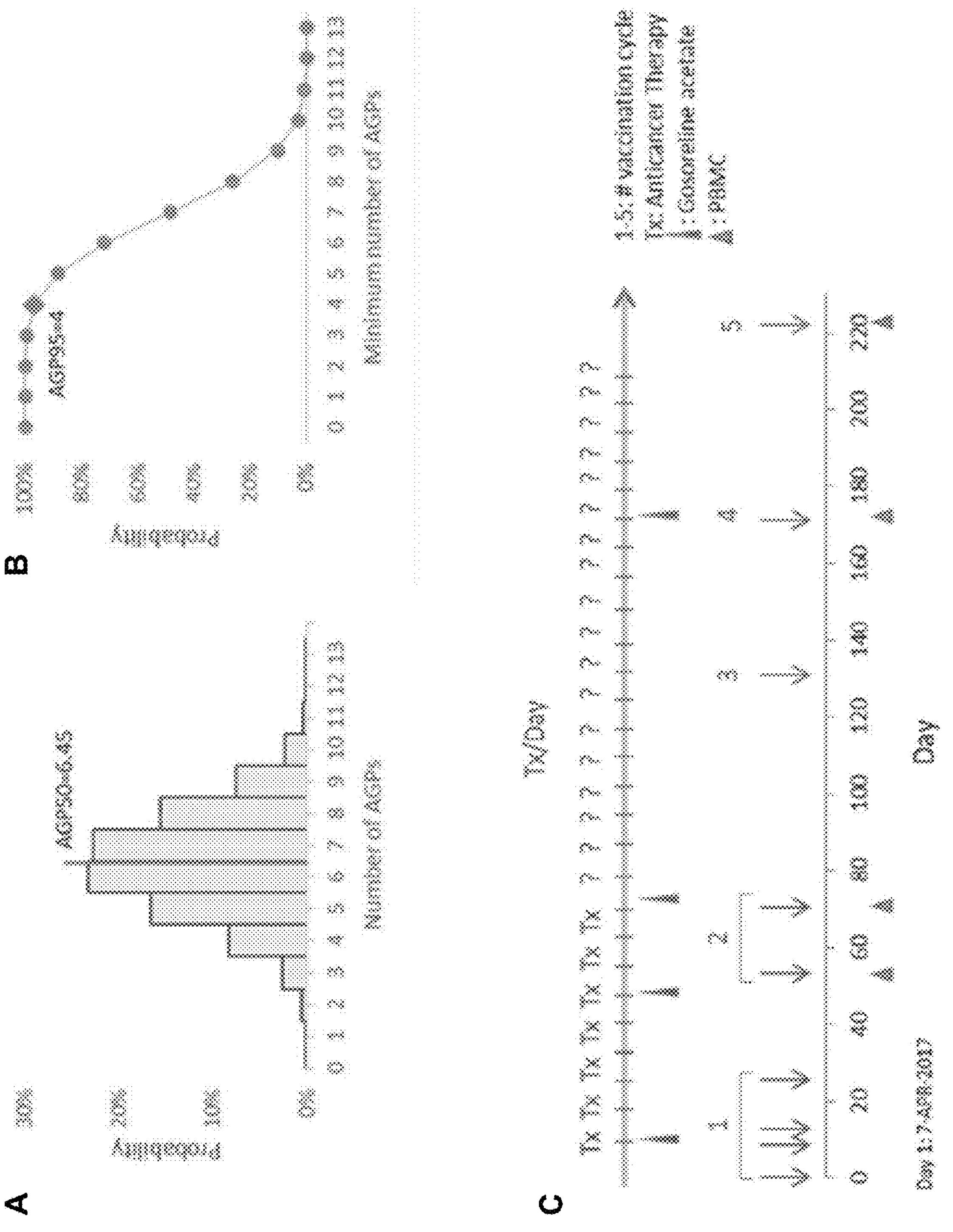

The HLA class I and class II genotype of metastatic breast cancer Patient-B was determined from a saliva sample. To make a personalized pharmaceutical composition for Patient-B twelve peptides were selected, each of which met the following two criteria: (i) derived from an antigen that is expressed in breast cancers, as reported in peer reviewed scientific publications; and (ii) comprises a fragment that is a T cell epitope capable of binding to at least three HLA class I of Patient-B (Table 24). In addition, each peptide is optimized to bind the maximum number of HLA class II of the patient. The twelve peptides target twelve breast cancer antigens. The probability that Patient-B will express one or more of the 12 antigens is shown in FIG. 36.

TABLE 24

12 peptides for Patient-B breast cancer patient

| BRC01 vaccine peptides | Target Antigen | Antigen Expression | 20 mer peptide | MAX HLA Class I | MAX HLA Class II |
|---|---|---|---|---|---|
| PBRC01_cP1 | FSIP1 | 49% | ISDTKDYFMSKTLGIGRLKR | 3 | 6 |
| PBRC01_cP2 | SPAG9 | 88% | FDRNTESLFEELSSAGSGLI | 3 | 2 |
| PBRC01_cP3 | AKAP4 | 85% | SQKMDMSNIVLMLIQKLLNE | 3 | 6 |
| PBRC01_cP4 | BORIS | 71% | SAVFHERYALIQHQKTHKNE | 3 | 6 |
| PBRC01_cP5 | MAGE-A11 | 59% | DVKEVDPTSHSYVLVTSLNL | 3 | 4 |
| PBRC01_cP6 | NY-SAR-35 | 49% | ENAHGQSLEEDSALEALLNF | 3 | 2 |
| PBRC01_cP7 | HOM-TES-85 | 47% | MASFRKLTLSEKVPPNHPSR | 3 | 5 |
| PBRC01_cP8 | NY-BR-1 | 47% | KRASQYSGQLKVLIAENTML | 3 | 6 |
| PBRC01_cP9 | MAGE-A9 | 44% | VDPAQLEFMFQEALKLKVAE | 3 | 8 |
| PBRC01_cP10 | SCP-1 | 38% | EYEREETRQVYMDLNNNIEK | 3 | 3 |
| PBRC01_cP11 | MAGE-A1 | 37% | PEIFGKASESLQLVFGIDVK | 3 | 3 |
| PBRC01_cP12 | MAGE-C2 | 21% | DSESSFTYTLDEKVAELVEF | 4 | 2 |

Predicted efficacy: AGP95=4; 95% likelihood that the PIT Vaccine induces CTL responses against 4 TSAs expressed in the breast cancer cells of BRC09. Additional efficacy parameters: AGP50=6.45, mAGP=100%, AP=12.

For treatment of Patient-B the 12 peptides were formulated as 4×3 peptide (PBR01/1, PBR01/2, PBR01/3, PBR01/4). One treatment cycle is defined as administration of all 12 different peptide vaccines within 30 days (FIG. 36C).

Patient History:

- 2013: Diagnosis: breast carcinoma diagnosis; CT scan and bone scan ruled out metastatic disease.
- 2014: bilateral mastectomy, postoperative chemotherapy
- 2016: extensive metastatic disease with nodal involvement both above and below the diaphragm.
- Multiple liver and pulmonary metastases.

Therapy:

- 2011.3-2014: Adriamycin-Cyclophosphamide and Paclitaxel
- 2017: Letrozole, Palbociclib and Gosorelin and PIT vaccine
- 2018: Worsening conditions, patient died in January
  - PIT vaccine treatment began on 7 Apr. 2017. Patient-B's treatment schedule and main characteristics of disease are shown in Table 25.

TABLE 25

Treatment and response of Patient-B

| Treatment regimen | Mar. | May | Jun. | Sep. | Nov. | Dec. |
|---|---|---|---|---|---|---|
| | Date (2017) | | | | | |
| | PIT Vaccine | | | | | |
| | Palbocyclib Letrozole Gosorelin | | Anticancer drug treatment interruption | | | |
| Neutrophils (1.7-3.5/mm$^3$) | ND | 1.1 | 4.5 | 3.4 | 2.4 | 3 |
| CEA (<5.0 ng/ml) | 99 | 65 | 23 | 32 | 128 | 430 |
| CA 15-3 (<31.3 U/ml) | 322 | 333 | 138 | 76 | 272 | 230 |
| T1: Right axillar lymph node | 15 mm & 11.6 SUV$_{max}$ | 9 mm & 2.0 SUV$_{max}$ | nd* | nd | nd | 6 mm & 0 SUVmax |
| T2: Right lung metastasis | 10 mm & 4.8 SUV$_{max}$ | 7 mm & 0 SUV$_{max}$ | nd | nd | nd | 4 mm & 0 SUV$_{max}$ |
| Left iliac bone metastasis | Non measurable &4.0 SUV$_{max}$ | Regression &O SUV$_{max}$ | nd | nd | nd | Regression & 0 SUV$_{max}$ |
| Multiple liver metastases | Non measurable & 11.5 SUV$_{max}$ | Partial regression &6.1 SUV$_{max}$ | nd | nd | nd | Progression & 16.8 SUV$_{max}$ |

*no data

Figure 37:
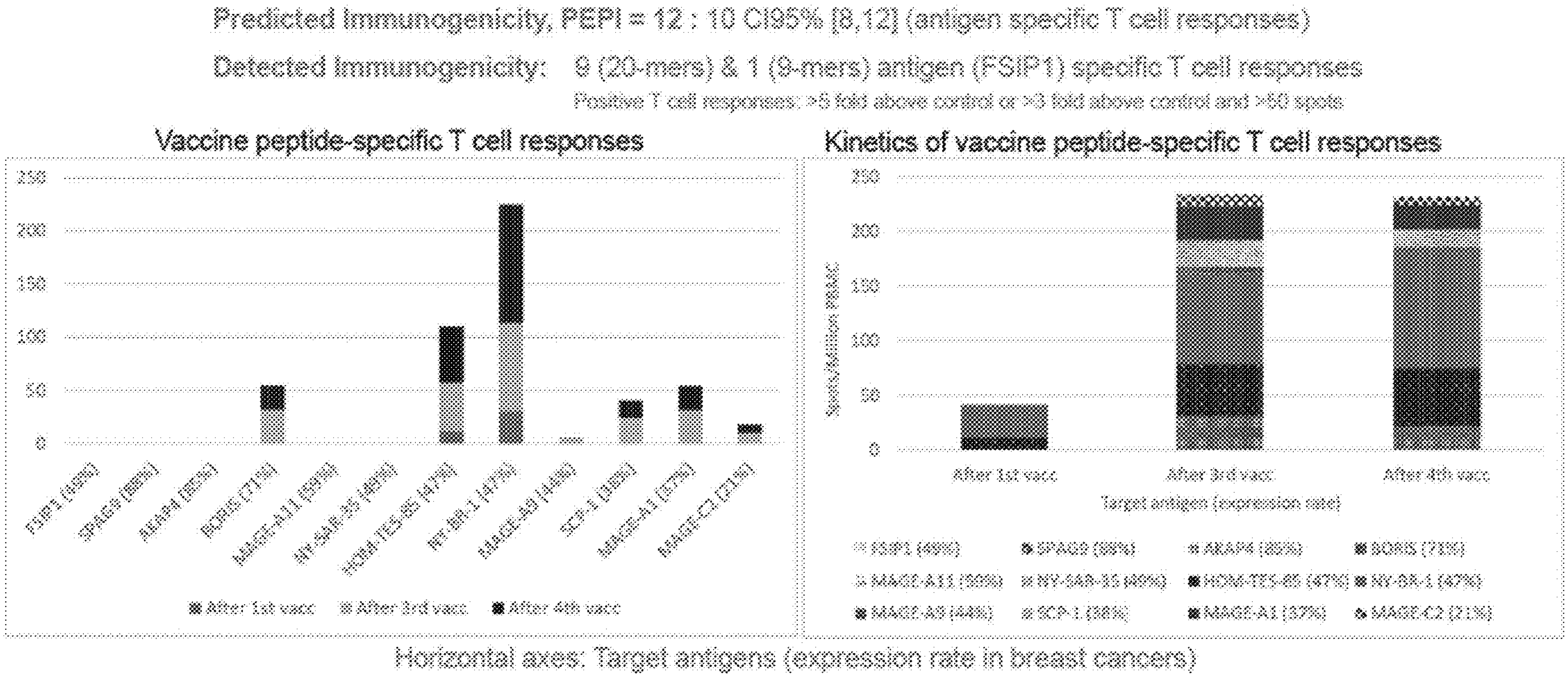

It was predicted with 95% confidence that 8-12 vaccine peptides would induce T cell responses in Patient-B. Peptide-specific T cell responses were measured in all available PBMC samples using an interferon (IFN)-γ ELISPOT bioassay (FIG. 37). The results confirmed the prediction: Nine peptides reacted positive demonstrating that T cells can recognize Patient-B's tumor cells expressing FISP1, BORIS, MAGE-A11, HOM-TES-85, NY-BR-1, MAGE-A9, SCP1, MAGE-A1 and MAGE-C2 antigens. Some tumor specific T cells were present after the 1$^{st}$ vaccination and boosted with additional treatments (e.g. MAGE-A1) others induced after boosting (e.g. MAGE-A9). Such broad tumor specific T cell responses are remarkable in a late stage cancer patient.

Patient-B History and Results

- Mar. 7, 2017: Prior PIT Vaccine treatment
- Hepatic multi-metastatic disease with truly extrinsic compression of the origin of the choledochal duct and massive dilatation of the entire intrahepatic biliary tract. Celiac, hepatic hilar and retroperitoneal adenopathy
- March 2017: Treatment initiation—Letrozole, Palbociclib, Gosorelin & PIT Vaccine
- May 2017: Drug interruption
- May 26, 2017: After 1 cycle of PIT
- 83% reduction of tumor metabolic activity (PET CT) liver, lung lymph nodes and other metastases.
- June 2017: Normalized Neutrophils values indicate Palbociclib interruption as affirmed by the patient 4 Months Delayed Rebound of Tumor Markers

- March to May 2017: CEA and CA remained elevated consistently with the outcome of her anti-cancer treatment (Ban, Future Oncol 2018)
- June to September 2017: CEA and CA decreased consistently with the delayed responses to immunotherapies Quality of Life

- February to March 2017: Poor, hospitalized with jaundice
- April to October 2017: Excellent
- November 2017: (Worsening conditions (tumor escape?)
- January 2018: Patient-B died.

Immunogenicity results are summarized in FIG. 37.

Clinical outcome measurements of the patient: One month prior to the initiation of PIT vaccine treatment PET CT documented extensive DFG avid disease with nodal involvement both above and below the diaphragm (Table 25). She had progressive multiple hepatic, multifocal osseous and pulmonary metastases and retroperitoneal adenopathy. Her intrahepatic enzymes were elevated consistent with the damage caused by her liver metastases with elevated bilirubin and jaundice. She accepted Letrozole, Palbociclib and Gosorelin as anti-cancer treatment. Two month after initiation of PIT vaccinations the patient felt very well and her quality of life normalized. In fact, her PET CT showed a significant morphometabolic regression in the liver, lung, bone and lymph node metastases. No metabolic adenopathy was identifiable at the supra-diaphragmatic stage.

The combination of Pablocyclib and the personalised vaccine was likely to have been responsible for the remarkable early response observed following administration of the vaccine. Palbocyclib has been shown to improve the activity of immunotherapies by increases CTA presentation by HLAs and decreasing the proliferation of Tregs: (Goel et al. Nature. 2017:471-475). The results of Patient-B's treatment suggest that PIT vaccine may be used as add-on to the state-of-art therapy to obtain maximal efficacy.

Patient-B's tumor biomarkers were followed to disentangle the effects of state-of-art therapy from those of PIT vaccine. Tumor markers were unchanged during the initial 2-3 months of treatment then sharply dropped suggesting of a delayed effect, typical of immunotherapies (Table 25). Moreover, at the time the tumor biomarkers dropped the patient had already voluntarily interrupted treatment and confirmed by the increase in neutrophil counts.

After the 5$^{th}$ PIT treatment the patient experienced symptoms. The levels of tumor markers and liver enzymes were increased again. 33 days after the last PIT vaccination, her PET CT showed significant metabolic progression in the liver, peritoneal, skeletal and left adrenal site confirming the laboratory findings. The discrete relapse in the distant metastases could be due to potential immune resistance; perhaps caused by downregulation of both HLA expression that impairs the recognition of the tumor by PIT induced T cells. However, the PET CT had detected complete regression of the metabolic activity of all axillary and mediastinal axillary supra-diaphragmatic targets (Table 25). These localized tumor responses may be accounted to the known delayed and durable responses to immunotherapy, as it is unlikely that after anti-cancer drug treatment interruption these tumor sites would not relapse.

Personalised Immunotherapy Composition for Treatment of Patient with Metastatic Breast Carcinoma (Patient-C) PT13

Figure 38:
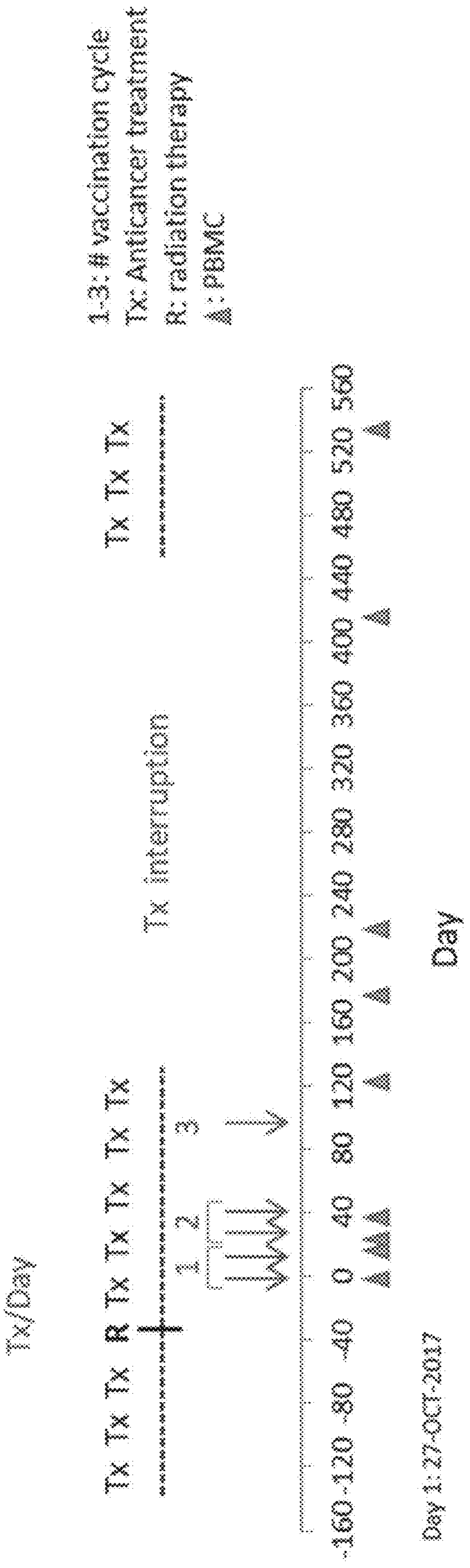

PIT vaccine similar in design to that described for Patient-A and Patient-B was prepared for the treatment of a patient (Patient-C) with metastatic breast carcinoma. PIT vaccine contained 12 PEPIs. The PIT vaccine has a predicted efficacy of AGP=4. The patient's treatment schedule is shown in FIG. 38.

Tumor Pathology

2011 Original tumor: HER2−, ER+, sentinel lymph node negative

2017 Multiple bone metastases: ER+, cytokeratin 7+, cytokeratin 20−, CA125−, TTF1−, CDX2−

Treatments

2011 Wide local resection, sentinel lymph nodes negative; radiotherapy

2017—Anti-cancer therapy (Tx): Letrozole (2.5 mg/day), Denosumab;

Radiation (Rx): one bone

PIT vaccine (3 cycles) as add-on to standard of care

Figure 39:
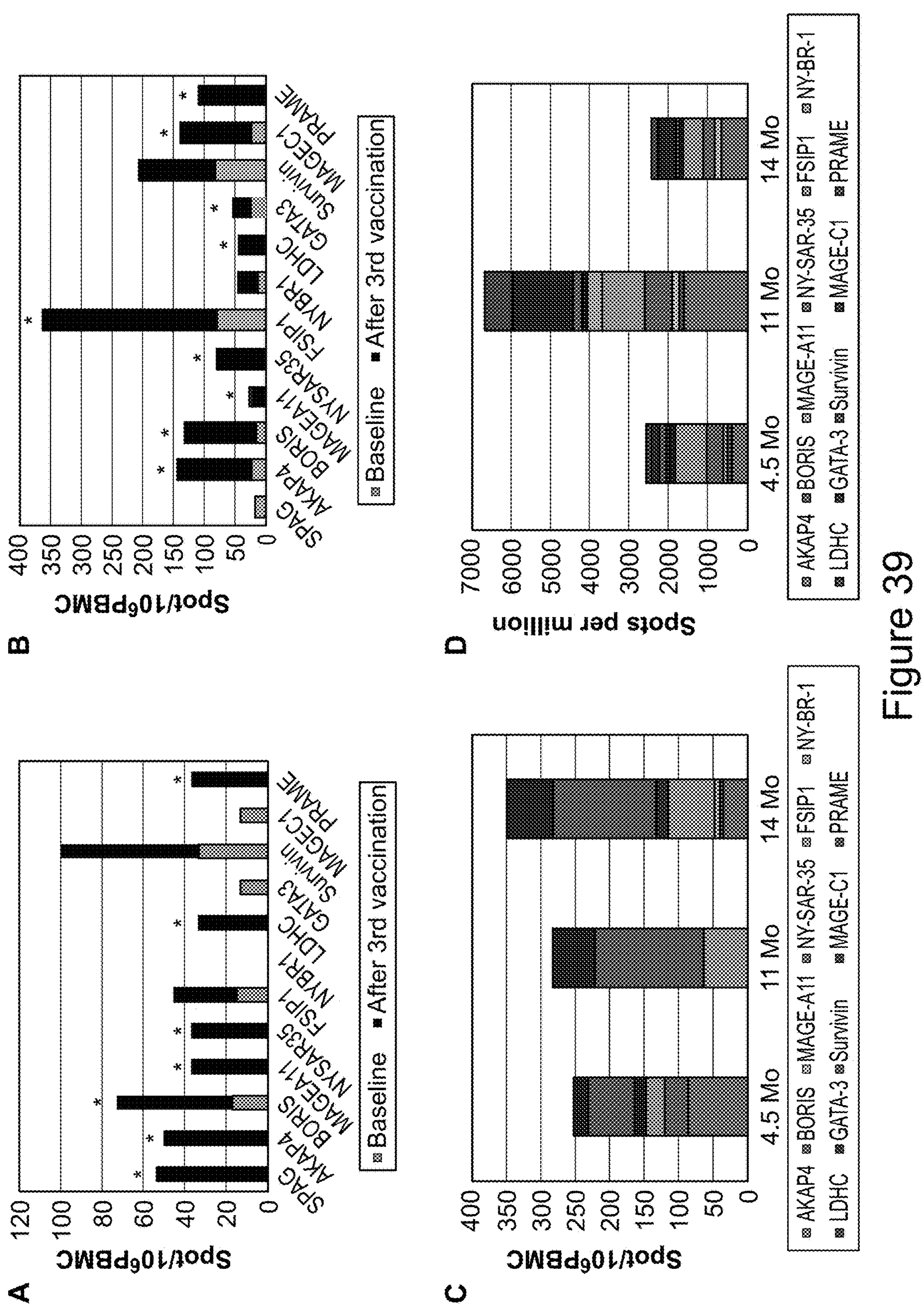

Bioassay confirmed positive T cell responses (defined as >5 fold above control, or >3 fold above control and >50 spots) to 11 out of the 12 20-mer peptides of the PIT vaccine and 11 out of 12 9-mer peptides having the sequence of the PEPI of each peptide capable of binding to the maximum HLA class I alleles of the patient (FIG. 39).

Long-lasting memory T-cell responses were detected after 14 months of the last vaccination (FIG. 24C-D).

Treatment Outcome

Clinical results of treatment of Patient-C are shown in Table 26. Patient-C has partial response and signs of healing bone metastases.

TABLE 26

Clinical results of treatment of breast cancer Patient-C

| | Before PIT | +70 days * (10 w) | +150 days * (21 w) | +388 days* (55 w) |
|---|---|---|---|---|
| Bone Biopsy | Met. breast Cancer DCIS | Not done | RIB5 is negative | Not done |
| PET CT | Multiple metastases | Only RIB5 is DFG avid | Not done | Not done |
| CT | Multiple metastases | Not done | Not done | Healing bone mets (sclerotic foci) |
| CA-15-3 | 87 | 50 | 32 | 24 |

* After 3rd cycle of PIT vaccination

Immune responses are shown on FIG. 39. Predicted Immunogenicity, PEPI=12 (CI95% [8, 12]

Detected Immunogenicity: 11 (20-mers) & 11 (9-mers) antigen specific T cell responses following 3 PIT vaccinations (FIG. 39A, B). After 4.5, 11 or 14 months of the last vaccination, PIT vaccine-specific immune response could still be detected (FIG. 39C, D).

Personalised Immunotherapy Composition for Treatment of Patient with Metastatic Colorectal Cancer (Patient-D) PT16

Tumor Pathology 2017 (February) mCRC (MSS) with liver metastases, surgery of primer tumor (in sigmoid colon). pT3 pN2b (8/16) M1. KRAS G12D, TP53-C135Y, KDR-Q472H, MET-T1010I mutations. SATB2 expression. EGFR wt, PIK3CA-1391M (non-driver).

2017 (June) Partial liver resection: KRAS-G12D (35G>A) NRAS wt, 2018 (May) 2nd resection: SATB2 expression, lung metastases 3→21

Treatments

2017 FOLFOX-4 (oxaliplatin, Ca-folinate, 5-FU)→allergic reaction during 2nd treatment DeGramont (5-FU+Ca-folinate)

2018 (June)→FOLFIRI plus ramucirumab, biweekly; chemoembolization 2018 (October) PIT vaccination (13 patient-specific peptides, 4 doses) as add-on to standard of care.

Figure 40:
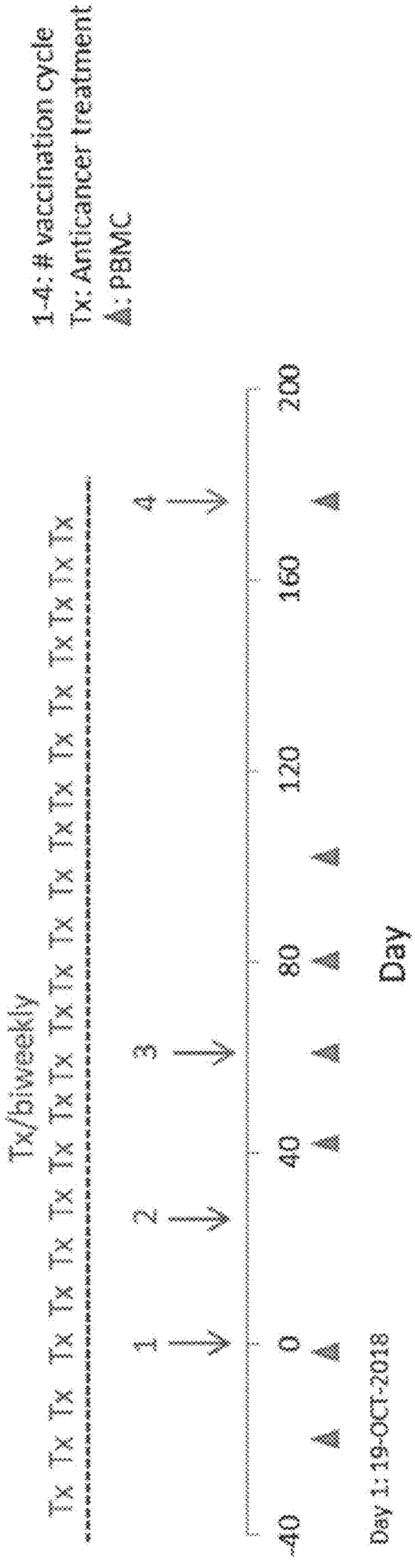

The patient's treatment schedule is shown in FIG. 40.

Treatment Outcome

Patient in good overall condition, disease progression in lungs after 8 months confirmed by CT.

Figure 41:
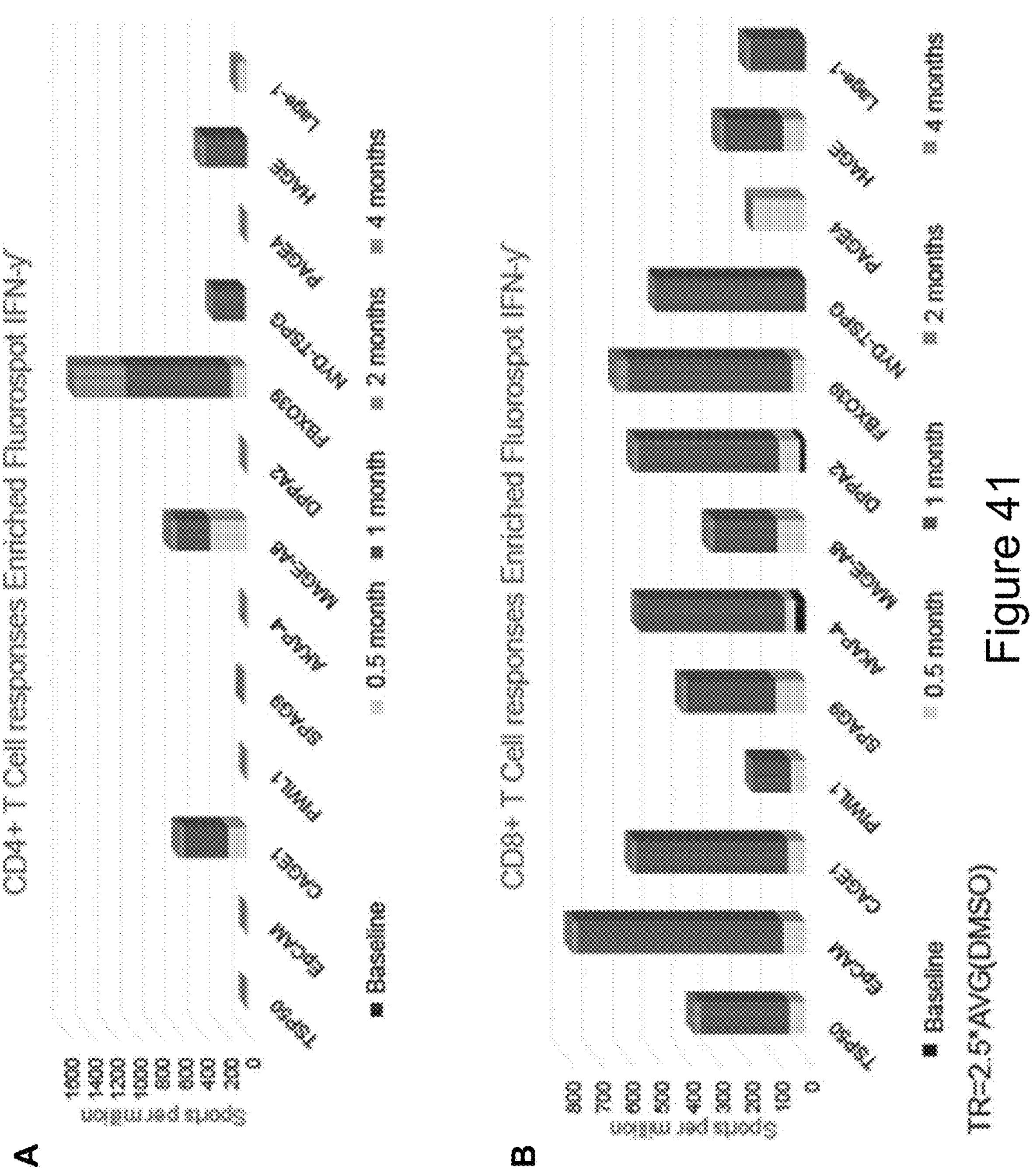

Both PIT induced and pre-existing T cell responses were measured by enriched Fluorospot from PBMC, using 9mer and 20mer peptides for stimulation (FIG. 41).

Summary of immune response rate and immunogenicity results prove the proper design for target antigen selection as well as for the induction of multi-peptide targeting immune responses, both CD4+ and CD8+ specific ones.

TABLE 27

Summary table of immunological analysis of Patient A-D

| | Measured immunogenicity for the different vaccine peptides* | |
|---|---|---|
| Patient ID | CD4+ T cells | CD8+ T cells |
| Patient-A | 13/13 (100%) | 13/13 (100%) |
| Patient-B | 9/12 (75%) | 1/12 (8%) |
| Patient-C | 11/12 (92%) | 11/12 (92%) |
| Patient-D | 7/13 (54%) | 13/13 (100%) |
| IRR (ratio of immune responder patients) | 4/4 | 4/4 |
| Ratio of immunogenic peptides (median) | 10/12-13 | 10/12-13 |

*Following 1-3 cycles of vaccination

SEQUENCE LISTING

```
Sequence total quantity: 394
SEQ ID NO: 1            moltype = AA  length = 9
FEATURE                 Location/Qualifiers
source                  1..9
                        mol_type = protein
                        organism = synthetic construct
                        note = MAGE-C1 9mer
SEQUENCE: 1
KMMKRLMTV                                                              9
```

```
SEQ ID NO: 2            moltype = AA  length = 9
FEATURE                 Location/Qualifiers
source                  1..9
                        mol_type = protein
                        organism = synthetic construct
                        note = CAGE-1  9mer
SEQUENCE: 2
KMHSLLALM                                                          9

SEQ ID NO: 3            moltype = AA  length = 9
FEATURE                 Location/Qualifiers
source                  1..9
                        mol_type = protein
                        organism = synthetic construct
                        note = TSP50  9mer
SEQUENCE: 3
FSYEQDPTL                                                          9

SEQ ID NO: 4            moltype = AA  length = 9
FEATURE                 Location/Qualifiers
source                  1..9
                        mol_type = protein
                        organism = synthetic construct
                        note = DPPA2 9mer
SEQUENCE: 4
YLRLHRHAY                                                          9

SEQ ID NO: 5            moltype = AA  length = 9
FEATURE                 Location/Qualifiers
source                  1..9
                        mol_type = protein
                        organism = synthetic construct
                        note = HIWI 9mer
SEQUENCE: 5
LQYENSIML                                                          9

SEQ ID NO: 6            moltype = AA  length = 9
FEATURE                 Location/Qualifiers
source                  1..9
                        mol_type = protein
                        organism = synthetic construct
                        note = SURVIVIN 9mer
SEQUENCE: 6
RAIEQLAAM                                                          9

SEQ ID NO: 7            moltype = AA  length = 9
FEATURE                 Location/Qualifiers
source                  1..9
                        mol_type = protein
                        organism = synthetic construct
                        note = HIWI 9mer
SEQUENCE: 7
FVASINEGM                                                          9

SEQ ID NO: 8            moltype = AA  length = 9
FEATURE                 Location/Qualifiers
source                  1..9
                        mol_type = protein
                        organism = synthetic construct
                        note = TSP50 9mer
SEQUENCE: 8
TTMETQFPV                                                          9

SEQ ID NO: 9            moltype = AA  length = 9
FEATURE                 Location/Qualifiers
source                  1..9
                        mol_type = protein
                        organism = synthetic construct
                        note = 5T4 9mer
SEQUENCE: 9
LASNHFLYL                                                          9

SEQ ID NO: 10           moltype = AA  length = 9
FEATURE                 Location/Qualifiers
source                  1..9
                        mol_type = protein
                        organism = synthetic construct
                        note = 5T4 9mer
```

-continued

```
SEQUENCE: 10
FLYLPRDVL                                                           9

SEQ ID NO: 11          moltype = AA  length = 9
FEATURE                Location/Qualifiers
source                 1..9
                       mol_type = protein
                       organism = synthetic construct
                       note = 5T4 9mer
SEQUENCE: 11
SSFSSSAPF                                                           9

SEQ ID NO: 12          moltype = AA  length = 9
FEATURE                Location/Qualifiers
source                 1..9
                       mol_type = protein
                       organism = synthetic construct
                       note = MAGE-A2 9mer
SEQUENCE: 12
FAHPRKLLM                                                           9

SEQ ID NO: 13          moltype = AA  length = 9
FEATURE                Location/Qualifiers
source                 1..9
                       mol_type = protein
                       organism = synthetic construct
                       note = KK-LC-1 9mer
SEQUENCE: 13
SSNSTALAL                                                           9

SEQ ID NO: 14          moltype = AA  length = 9
FEATURE                Location/Qualifiers
source                 1..9
                       mol_type = protein
                       organism = synthetic construct
                       note = CAGE-1 9mer
SEQUENCE: 14
STNALIQPV                                                           9

SEQ ID NO: 15          moltype = AA  length = 9
FEATURE                Location/Qualifiers
source                 1..9
                       mol_type = protein
                       organism = synthetic construct
                       note = SURVIVIN 9mer
SEQUENCE: 15
STFKNWPFL                                                           9

SEQ ID NO: 16          moltype = AA  length = 9
FEATURE                Location/Qualifiers
source                 1..9
                       mol_type = protein
                       organism = synthetic construct
                       note = MAGE-A2 9mer
SEQUENCE: 16
FSTTINYTL                                                           9

SEQ ID NO: 17          moltype = AA  length = 9
FEATURE                Location/Qualifiers
source                 1..9
                       mol_type = protein
                       organism = synthetic construct
                       note = KK-LC-1 9mer
SEQUENCE: 17
ILNNFPHSI                                                           9

SEQ ID NO: 18          moltype = AA  length = 9
FEATURE                Location/Qualifiers
source                 1..9
                       mol_type = protein
                       organism = synthetic construct
                       note = MAGE-A3 9mer
SEQUENCE: 18
FVQENYLEY                                                           9

SEQ ID NO: 19          moltype = AA  length = 9
FEATURE                Location/Qualifiers
source                 1..9
                       mol_type = protein
```

```
                         organism = synthetic construct
                         note = LAGE-1 9mer
SEQUENCE: 19
ITMPFSSPM                                                                9

SEQ ID NO: 20            moltype = AA  length = 9
FEATURE                  Location/Qualifiers
source                   1..9
                         mol_type = protein
                         organism = synthetic construct
                         note = MAGE-A3 9mer
SEQUENCE: 20
ASSSLQLVF                                                                9

SEQ ID NO: 21            moltype = AA  length = 9
FEATURE                  Location/Qualifiers
source                   1..9
                         mol_type = protein
                         organism = synthetic construct
                         note = MAGE-A10 9mer
SEQUENCE: 21
YEDHFPLLF                                                                9

SEQ ID NO: 22            moltype = AA  length = 9
FEATURE                  Location/Qualifiers
source                   1..9
                         mol_type = protein
                         organism = synthetic construct
                         note = MAGE-A1 9mer
SEQUENCE: 22
TSYVKVLEY                                                                9

SEQ ID NO: 23            moltype = AA  length = 9
FEATURE                  Location/Qualifiers
source                   1..9
                         mol_type = protein
                         organism = synthetic construct
                         note = MAGE-A3 9mer
SEQUENCE: 23
KVAELVHFL                                                                9

SEQ ID NO: 24            moltype = AA  length = 9
FEATURE                  Location/Qualifiers
source                   1..9
                         mol_type = protein
                         organism = synthetic construct
                         note = KK-LC-1 9mer
SEQUENCE: 24
NTDNNLAVY                                                                9

SEQ ID NO: 25            moltype = AA  length = 9
FEATURE                  Location/Qualifiers
source                   1..9
                         mol_type = protein
                         organism = synthetic construct
                         note = PRAME 9mer
SEQUENCE: 25
KAMVQAWPF                                                                9

SEQ ID NO: 26            moltype = AA  length = 9
FEATURE                  Location/Qualifiers
source                   1..9
                         mol_type = protein
                         organism = synthetic construct
                         note = MAGE-A2 9mer
SEQUENCE: 26
KASEYLQLV                                                                9

SEQ ID NO: 27            moltype = AA  length = 9
FEATURE                  Location/Qualifiers
source                   1..9
                         mol_type = protein
                         organism = synthetic construct
                         note = MAGE-A1 9mer
SEQUENCE: 27
SAFPTTINF                                                                9

SEQ ID NO: 28            moltype = AA  length = 9
FEATURE                  Location/Qualifiers
```

```
source                  1..9
                        mol_type = protein
                        organism = synthetic construct
                        note = SSX1 9mer
SEQUENCE: 28
MTFGRLHRI                                                           9

SEQ ID NO: 29           moltype = AA  length = 9
FEATURE                 Location/Qualifiers
source                  1..9
                        mol_type = protein
                        organism = synthetic construct
                        note = MAGE-A1 9mer
SEQUENCE: 29
RALAETSYV                                                           9

SEQ ID NO: 30           moltype = AA  length = 9
FEATURE                 Location/Qualifiers
source                  1..9
                        mol_type = protein
                        organism = synthetic construct
                        note = PRAME 9mer
SEQUENCE: 30
HVMNPLETL                                                           9

SEQ ID NO: 31           moltype = AA  length = 15
FEATURE                 Location/Qualifiers
source                  1..15
                        mol_type = protein
                        organism = synthetic construct
                        note = DPPA2 15mer
SEQUENCE: 31
KRNKKMMKRL MTVEK                                                    15

SEQ ID NO: 32           moltype = AA  length = 15
FEATURE                 Location/Qualifiers
source                  1..15
                        mol_type = protein
                        organism = synthetic construct
                        note = CAGE-1 15mer
SEQUENCE: 32
ASQLASKMHS LLALM                                                    15

SEQ ID NO: 33           moltype = AA  length = 15
FEATURE                 Location/Qualifiers
source                  1..15
                        mol_type = protein
                        organism = synthetic construct
                        note = TSP50 15mer
SEQUENCE: 33
GFSYEQDPTL RDPEA                                                    15

SEQ ID NO: 34           moltype = AA  length = 15
FEATURE                 Location/Qualifiers
source                  1..15
                        mol_type = protein
                        organism = synthetic construct
                        note = DPPA2 15mer
SEQUENCE: 34
KIEVYLRLHR HAYPE                                                    15

SEQ ID NO: 35           moltype = AA  length = 15
FEATURE                 Location/Qualifiers
source                  1..15
                        mol_type = protein
                        organism = synthetic construct
                        note = HIWI 15mer
SEQUENCE: 35
GFTTSILQYE NSIML                                                    15

SEQ ID NO: 36           moltype = AA  length = 15
FEATURE                 Location/Qualifiers
source                  1..15
                        mol_type = protein
                        organism = synthetic construct
                        note = SURVIVIN 15mer
SEQUENCE: 36
AKKVRRAIEQ LAAMD                                                    15
```

-continued

```
SEQ ID NO: 37          moltype = AA  length = 15
FEATURE                Location/Qualifiers
source                 1..15
                       mol_type = protein
                       organism = synthetic construct
                       note = HIWI 15mer
SEQUENCE: 37
SIAGFVASIN EGMTR                                                15

SEQ ID NO: 38          moltype = AA  length = 15
FEATURE                Location/Qualifiers
source                 1..15
                       mol_type = protein
                       organism = synthetic construct
                       note = TSP50 15mer
SEQUENCE: 38
STTMETQFPV SEGKV                                                15

SEQ ID NO: 39          moltype = AA  length = 15
FEATURE                Location/Qualifiers
source                 1..15
                       mol_type = protein
                       organism = synthetic construct
                       note = 5T4 15mer
SEQUENCE: 39
RLELASNHFL YLPRD                                                15

SEQ ID NO: 40          moltype = AA  length = 15
FEATURE                Location/Qualifiers
source                 1..15
                       mol_type = protein
                       organism = synthetic construct
                       note = 5T4 15mer
SEQUENCE: 40
SNHFLYLPRD VLAQL                                                15

SEQ ID NO: 41          moltype = AA  length = 15
FEATURE                Location/Qualifiers
source                 1..15
                       mol_type = protein
                       organism = synthetic construct
                       note = 5T4 15mer
SEQUENCE: 41
SSASSFSSSA PFLAS                                                15

SEQ ID NO: 42          moltype = AA  length = 15
FEATURE                Location/Qualifiers
source                 1..15
                       mol_type = protein
                       organism = synthetic construct
                       note = MAGE-A215mer
SEQUENCE: 42
REDSVFAHPR KLLMQ                                                15

SEQ ID NO: 43          moltype = AA  length = 15
FEATURE                Location/Qualifiers
source                 1..15
                       mol_type = protein
                       organism = synthetic construct
                       note = KK-LC-1 15mer
SEQUENCE: 43
RNTGEMSSNS TALAL                                                15

SEQ ID NO: 44          moltype = AA  length = 15
FEATURE                Location/Qualifiers
source                 1..15
                       mol_type = protein
                       organism = synthetic construct
                       note = CAGE-1 15mer
SEQUENCE: 44
NIENYSTNAL IQPVD                                                15

SEQ ID NO: 45          moltype = AA  length = 15
FEATURE                Location/Qualifiers
source                 1..15
                       mol_type = protein
                       organism = synthetic construct
                       note = SURVIVIN 15mer
SEQUENCE: 45
```

```
KDHRISTFKN WPFLE                                                    15

SEQ ID NO: 46           moltype = AA  length = 15
FEATURE                 Location/Qualifiers
source                  1..15
                        mol_type = protein
                        organism = synthetic construct
                        note = MAGE-A215mer
SEQUENCE: 46
SFSTTINYTL WRQSD                                                    15

SEQ ID NO: 47           moltype = AA  length = 15
FEATURE                 Location/Qualifiers
source                  1..15
                        mol_type = protein
                        organism = synthetic construct
                        note = KK-LC-1 15mer
SEQUENCE: 47
SRDILNNFPH SIARQ                                                    15

SEQ ID NO: 48           moltype = AA  length = 15
FEATURE                 Location/Qualifiers
source                  1..15
                        mol_type = protein
                        organism = synthetic construct
                        note = MAGE-A315mer
SEQUENCE: 48
LTQHFVQENY LEYRQ                                                    15

SEQ ID NO: 49           moltype = AA  length = 15
FEATURE                 Location/Qualifiers
source                  1..15
                        mol_type = protein
                        organism = synthetic construct
                        note = LAGE-1 15mer
SEQUENCE: 49
ITMPFSSPME AELVR                                                    15

SEQ ID NO: 50           moltype = AA  length = 15
FEATURE                 Location/Qualifiers
source                  1..15
                        mol_type = protein
                        organism = synthetic construct
                        note = MAGE-A315mer
SEQUENCE: 50
KASSSLQLVF GIELM                                                    15

SEQ ID NO: 51           moltype = AA  length = 15
FEATURE                 Location/Qualifiers
source                  1..15
                        mol_type = protein
                        organism = synthetic construct
                        note = MAGE-A10 15mer
SEQUENCE: 51
RNYEDHFPLL FSEAS                                                    15

SEQ ID NO: 52           moltype = AA  length = 15
FEATURE                 Location/Qualifiers
source                  1..15
                        mol_type = protein
                        organism = synthetic construct
                        note = MAGE-A115mer
SEQUENCE: 52
ETSYVKVLEY VIKVS                                                    15

SEQ ID NO: 53           moltype = AA  length = 15
FEATURE                 Location/Qualifiers
source                  1..15
                        mol_type = protein
                        organism = synthetic construct
                        note = MAGE-A315mer
SEQUENCE: 53
QAALSRKVAE LVHFL                                                    15

SEQ ID NO: 54           moltype = AA  length = 15
FEATURE                 Location/Qualifiers
```

-continued

```
source                  1..15
                        mol_type = protein
                        organism = synthetic construct
                        note = KK-LC-1 15mer
SEQUENCE: 54
SNTDNNLAVY DLSRD                                                  15

SEQ ID NO: 55           moltype = AA  length = 15
FEATURE                 Location/Qualifiers
source                  1..15
                        mol_type = protein
                        organism = synthetic construct
                        note = PRAME 15mer
SEQUENCE: 55
RHSQTLKAMV QAWPF                                                  15

SEQ ID NO: 56           moltype = AA  length = 15
FEATURE                 Location/Qualifiers
source                  1..15
                        mol_type = protein
                        organism = synthetic construct
                        note = MAGE-A215mer
SEQUENCE: 56
SKASEYLQLV FGIEV                                                  15

SEQ ID NO: 57           moltype = AA  length = 15
FEATURE                 Location/Qualifiers
source                  1..15
                        mol_type = protein
                        organism = synthetic construct
                        note = MAGE-A115mer
SEQUENCE: 57
SAFPTTINFT RQRQP                                                  15

SEQ ID NO: 58           moltype = AA  length = 15
FEATURE                 Location/Qualifiers
source                  1..15
                        mol_type = protein
                        organism = synthetic construct
                        note = SSX1 15mer
SEQUENCE: 58
QVEHPQMTFG RLHRI                                                  15

SEQ ID NO: 59           moltype = AA  length = 15
FEATURE                 Location/Qualifiers
source                  1..15
                        mol_type = protein
                        organism = synthetic construct
                        note = MAGE-A115mer
SEQUENCE: 59
PRALAETSYV KVLEY                                                  15

SEQ ID NO: 60           moltype = AA  length = 15
FEATURE                 Location/Qualifiers
source                  1..15
                        mol_type = protein
                        organism = synthetic construct
                        note = PRAME 15mer
SEQUENCE: 60
DQLLRHVMNP LETLS                                                  15

SEQ ID NO: 61           moltype = AA  length = 30
FEATURE                 Location/Qualifiers
source                  1..30
                        mol_type = protein
                        organism = synthetic construct
                        note = GC1311-01 CAGE-1/DPPA2
SEQUENCE: 61
ASQLASKMHS LLALMKRNKK MMKRLMTVEK                                  30

SEQ ID NO: 62           moltype = AA  length = 30
FEATURE                 Location/Qualifiers
source                  1..30
                        mol_type = protein
                        organism = synthetic construct
                        note = GC1311-02 HIWI/MAGE-A10
SEQUENCE: 62
GFTTSILQYE NSIMLRNYED HFPLLFSEAS                                  30
```

-continued

```
SEQ ID NO: 63          moltype = AA  length = 30
FEATURE                Location/Qualifiers
source                 1..30
                       mol_type = protein
                       organism = synthetic construct
                       note = GC1311-03 MAGE-A2/SURVIVIN
SEQUENCE: 63
SFSTTINYTL WRQSDAKKVR RAIEQLAAMD                                    30

SEQ ID NO: 64          moltype = AA  length = 30
FEATURE                Location/Qualifiers
source                 1..30
                       mol_type = protein
                       organism = synthetic construct
                       note = GC1311-04 KK-LC-1/SURVIVIN
SEQUENCE: 64
RNTGEMSSNS TALALKDHRI STFKNWPFLE                                    30

SEQ ID NO: 65          moltype = AA  length = 30
FEATURE                Location/Qualifiers
source                 1..30
                       mol_type = protein
                       organism = synthetic construct
                       note = GC1311-05 KK-LC-1/HIWI
SEQUENCE: 65
SRDILNNFPH SIARQSIAGF VASINEGMTR                                    30

SEQ ID NO: 66          moltype = AA  length = 30
FEATURE                Location/Qualifiers
source                 1..30
                       mol_type = protein
                       organism = synthetic construct
                       note = GC1311-06 MAGE-A2/PRAME
SEQUENCE: 66
REDSVFAHPR KLLMQDQLLR HVMNPLETLS                                    30

SEQ ID NO: 67          moltype = AA  length = 30
FEATURE                Location/Qualifiers
source                 1..30
                       mol_type = protein
                       organism = synthetic construct
                       note = GC1311-07 5T4/5T4
SEQUENCE: 67
RLELASNHFL YLPRDSNHFL YLPRDVLAQL                                    30

SEQ ID NO: 68          moltype = AA  length = 30
FEATURE                Location/Qualifiers
source                 1..30
                       mol_type = protein
                       organism = synthetic construct
                       note = GC1311-08 5T4/TSP50
SEQUENCE: 68
SSASSFSSSA PFLASSTTME TQFPVSEGKV                                    30

SEQ ID NO: 69          moltype = AA  length = 30
FEATURE                Location/Qualifiers
source                 1..30
                       mol_type = protein
                       organism = synthetic construct
                       note = GC1311-09 TSP50/MAGE-A1
SEQUENCE: 69
GFSYEQDPTL RDPEAPRALA ETSYVKVLEY                                    30

SEQ ID NO: 70          moltype = AA  length = 30
FEATURE                Location/Qualifiers
source                 1..30
                       mol_type = protein
                       organism = synthetic construct
                       note = GC1311-10 KK-LC-1/SSX1
SEQUENCE: 70
SNTDNNLAVY DLSRDQVEHP QMTFGRLHRI                                    30

SEQ ID NO: 71          moltype = AA  length = 30
FEATURE                Location/Qualifiers
source                 1..30
                       mol_type = protein
                       organism = synthetic construct
                       note = GC1311-11 DPPA2/LAGE-1
```

```
SEQUENCE: 71
KIEVYLRLHR HAYPEITMPF SSPMEAELVR                                30

SEQ ID NO: 72          moltype = AA  length = 30
FEATURE                Location/Qualifiers
source                 1..30
                       mol_type = protein
                       organism = synthetic construct
                       note = GC1311-12 MAGE-A1/MAGE-A3
SEQUENCE: 72
ETSYVKVLEY VIKVSLTQHF VQENYLEYRQ                                30

SEQ ID NO: 73          moltype = AA  length = 30
FEATURE                Location/Qualifiers
source                 1..30
                       mol_type = protein
                       organism = synthetic construct
                       note = GC1311-13 MAGE-A3/CAGE-1
SEQUENCE: 73
QAALSRKVAE LVHFLNIENY STNALIQPVD                                30

SEQ ID NO: 74          moltype = AA  length = 30
FEATURE                Location/Qualifiers
source                 1..30
                       mol_type = protein
                       organism = synthetic construct
                       note = GC1311-14 PRAME/MAGE-A3
SEQUENCE: 74
RHSQTLKAMV QAWPFKASSS LQLVFGIELM                                30

SEQ ID NO: 75          moltype = AA  length = 30
FEATURE                Location/Qualifiers
source                 1..30
                       mol_type = protein
                       organism = synthetic construct
                       note = GC1311-15 MAGE-A2/MAGE-A1
SEQUENCE: 75
SKASEYLQLV FGIEVSAFPT TINFTRQRQP                                30

SEQ ID NO: 76          moltype = AA  length = 298
FEATURE                Location/Qualifiers
source                 1..298
                       mol_type = protein
                       organism = Homo sapiens
SEQUENCE: 76
MSDANLDSSK KNFLEGEVDD EESVILTLVP VKDDANMEQM EPSVSSTSDV KLEKPKKYNP  60
GHLLQTNEQF TAPQKARCKI PALPLPTILP PINKVCRDTL RDWCQQLGLS TNGKKIEVYL  120
RLHRHAYPEQ RQDMPEMSQE TRLQRCSRKR KAVTKRARLQ RSYEMNERAE ETNTVEVITS  180
APGAMLASWA RIAARAVQPK ALNSCSIPVS VEAFLMQASG VRWCVVHGRL LSADTKGWVR  240
LQFHAGQAWV PTTHRRMISL FLLPACIFPS PGIEDNMLCP DCAKRNKKMM KRLMTVEK    298

SEQ ID NO: 77          moltype = AA  length = 777
FEATURE                Location/Qualifiers
source                 1..777
                       mol_type = protein
                       organism = Homo sapiens
SEQUENCE: 77
MNKDYQKFWS SPSDPVHFEV DTSHEKVESM SESDTMNVSN LSQGVMLSHS PICMETTGTT  60
CDLPQNEIKN FERENEYEST LCEDAYGTLD NLLNDNNIEN YSTNALIQPV DTISISSLRQ  120
FETVCKFHWV EAFDDEMTEK PEFQSQVYNY AKDNNIKQDS FKEENPMETS VSANTDQLGN  180
EYFRQPPPRS PPLIHCSGEM LKFTEKSLAK SIAKESALNP SQPPSFLCKT AVPSKEIQNY  240
GEIPEMSVSY EKEVTAEGVE RPEIVSTWSS AGISWRSEAC RENCEMPDWE QSAESLQPVQ  300
EDMALNEVLQ KLKHTNRKQE VRIQELQCSN LYLEKRVKEL QMKITKQQVF IDVINKLKEN  360
VEELIEDKYK IILEKNDTKK TLQNLEEVLA NTQKHLQESR NDKEMLQLQF KKIKANYVCL  420
QERYMTEMQQ KNKSVSQYLE MDKTLSKKEE EVERLQQLKK ELEKATASAL DLLKREKEAQ  480
EQEFLSLQEE FQKLEKENLE ERQKLKSRLE KLLTQVRNLQ FMSENERTKN IKLQQQINEV  540
KNENAKLKQQ VARSEEQNYV PKFETAQLKD QLEEVLKSDI TKDTKTTHSN LLPDCSPCEE  600
RLNPADIKRA SQLASKMHSL LALMVGLLTC QDIINSDAEH FKESEKVSDI MLQKLKSLHL  660
KKKTLDKEVI DCDSDEAKSI RDVPTLLGAK LDKYHSLNEE LDFLVTSYEE IIECADQRLA  720
ISHSQIAHLE ERNKHLEDLI RKPREKARKP RSKSLENHPK SMTMMPALFK ENRNDLD     777

SEQ ID NO: 78          moltype = AA  length = 385
FEATURE                Location/Qualifiers
source                 1..385
                       mol_type = protein
                       organism = Homo sapiens
SEQUENCE: 78
MGRWCQTVAR GQRPRTSAPS RAGALLLLLL LLRSAGCWGA GEAPGALSTA DPADQSVQCV  60
PKATCPSSRP RLLWQTPTTQ TLPSTTMETQ FPVSEGKVDP YRSCGFSYEQ DPTLRDPEAV  120
```

```
ARRWPWMVSV RANGTHICAG TIIASQWVLT VAHCLIWRDV IYSVRVGSPW IDQMTQTASD  180
VPVLQVIMHS RYRAQRFWSW VGQANDIGLL KLKQELKYSN YVRPICLPGT DYVLKDHSRC  240
TVTGWGLSKA DGMWPQFRTI QEKEVIILNN KECDNFYHNF TKIPTLVQII KSQMMCAEDT  300
HREKFCYELT GEPLVCSMEG TWYLVGLVSW GAGCQKSEAP PIYLQVSSYQ HWIWDCLNGQ  360
ALALPAPSRT LLLALPLPLS LLAAL                                        385

SEQ ID NO: 79          moltype = AA  length = 861
FEATURE                Location/Qualifiers
source                 1..861
                       mol_type = protein
                       organism = Homo sapiens
SEQUENCE: 79
MTGRARARAR GRARGQETAQ LVGSTASQQP GYIQPRPQPP PAEGELFGRG RQRGTAGGTA  60
KSQGLQISAG FQELSLAERG GRRRDFHDLG VNTRQNLDHV KESKTGSSGI IVRLSTNHFR  120
LTSRPQWALY QYHIDYNPLM EARRLRSALL FQHEDLIGKC HAFDGTILFL PKRLQQKVTE  180
VFSKTRNGED VRITITLTNE LPPTSPTCLQ FYNIIFRRLL KIMNLQQIGR NYYNPNDPID  240
IPSHRLVIWP GFTTSILQYE NSIMLCTDVS HKVLRSETVL DFMFNFYHQT EEHKFQEQVS  300
KELIGLVVLT KYNNKTYRVD DIDWDQNPKS TFKKADGSEV SFLEYYRKQY NQEITDLKQP  360
VLVSQPKRRR GPGGTLPGPA MLIPELCYLT GLTDKMRNDF NVMKDLAVHT RLTPEQRQRE  420
VGRLIDYIHK NDNVQRELRD WGLSFDSNLL SFSGRILQTE KIHQGGKTFD YNPQFADWSK  480
ETRGAPLISV KPLDNWLLIY TRRNYEAANS LIQNLFKVTP AMGMQMRKAI MIEVDDRTEA  540
YLRVLQQKVT ADTQIVVCLL SSNRKDKYDA IKKYLCTDCP TPSQCVVART LGKQQTVMAI  600
ATKIALQMNC KMGGELWRVD IPLKLVMIVG IDCYHDMTAG RRSIAGFVAS INEGMTRWFS  660
RCIFQDRGQE LVDGLKVCLQ AALRAWNSCN EYMPSRIIVY RDGVGDGQLK TLVNYEVPQF  720
LDCLKSIGRG YNPRLTVIVV KKRVNTRFFA QSGGRLQNPL PGTVIDVEVT RPEWYDFFIV  780
SQAVRSGSVS PTHYNVIYDN SGLKPDHIQR LTYKLCHIYY NWPGVIRVPA PCQYAHKLAF  840
LVGQSIHREP NLSLSNRLYY L                                            861

SEQ ID NO: 80          moltype = AA  length = 142
FEATURE                Location/Qualifiers
source                 1..142
                       mol_type = protein
                       organism = Homo sapiens
SEQUENCE: 80
MGAPTLPPAW QPFLKDHRIS TFKNWPFLEG CACTPERMAE AGFIHCPTEN EPDLAQCFFC  60
FKELEGWEPD DDPIEEHKKH SSGCAFLSVK KQFEELTLGE FLKLDRERAK NKIAKETNNK  120
KKEFEETAKK VRRAIEQLAA MD                                           142

SEQ ID NO: 81          moltype = AA  length = 420
FEATURE                Location/Qualifiers
source                 1..420
                       mol_type = protein
                       organism = Homo sapiens
SEQUENCE: 81
MPGGCSRGPA AGDGRLRLAR LALVLLGWVS SSSPTSSASS FSSSAPFLAS AVSAQPPLPD  60
QCPALCECSE AARTVKCVNR NLTEVPTDLP AYVRNLFLTG NQLAVLPAGA FARRPPLAEL  120
AALNLSGSRL DEVRAGAFEH LPSLRQLDLS HNPLADLSPF AFSGSNASVS APSPLVELIL  180
NHIVPPEDER QNRSFEGMVV AALLAGRALQ GLRRLELASN HFLYLPRDVL AQLPSLRHLD  240
LSNNSLVSLT YVSFRNLTHL ESLHLEDNAL KVLHNGTLAE LQGLPHIRVF LDNNPWVCDC  300
HMADMVTWLK ETEVVQGKDR LTCAYPEKMR NRVLLELNSA DLDCDPILPP SLQTSYVFLG  360
IVLALIGAIF LLVLYLNRKG IKKWMHNIRD ACRDHMEGYH YRYEINADPR LTNLSSNSDV  420

SEQ ID NO: 82          moltype = AA  length = 509
FEATURE                Location/Qualifiers
source                 1..509
                       mol_type = protein
                       organism = Homo sapiens
SEQUENCE: 82
MERRRLWGSI QSRYISMSVW TSPRRLVELA GQSLLKDEAL AIAALELLPR ELFPPLFMAA  60
FDGRHSQTLK AMVQAWPFTC LPLGVLMKGQ HLHLETFKAV LDGLDVLLAQ EVRPRRWKLQ  120
VLDLRKNSHQ DFWTVWSGNR ASLYSFPEPE AAQPMTKKRK VDGLSTEAEQ PFIPVEVLVD  180
LFLKEGACDE LFSYLIEKVK RKKNVLRLCC KKLKIFAMPM QDIKMILKMV QLDSIEDLEV  240
TCTWKLPTLA KFSPYLGQMI NLRRLLLSHI HASSYISPEK EEQYIAQFTS QFLSLQCLQA  300
LYVDSLFFLR GRLDQLLRHV MNPLETLSIT NCRLSEGDVM HLSQSPSVSQ LSVLSLSGVM  360
LTDVSPEPLQ ALLERASATL QDLVFDECGI TDDQLLALLP SLSHCSQLTT LSFYGNSISI  420
SALQSLLQHL IGLSNLTHVL YPVPLESYED IHGTLHLERL AYLHARLREL LCELGRPSMV  480
WLSANPCPHC GDRTFYDPEP ILCPCFMPN                                    509

SEQ ID NO: 83          moltype = AA  length = 113
FEATURE                Location/Qualifiers
source                 1..113
                       mol_type = protein
                       organism = Homo sapiens
SEQUENCE: 83
MNFYLLLASS ILCALIVFWK YRRFQRNTGE MSSNSTALAL VRPSSSGLIN SNTDNNLAVY  60
DLSRDILNNF PHSIARQKRI LVNLSMVENK LVELEHTLLS KGFRGASPHR KST         113

SEQ ID NO: 84          moltype = AA  length = 314
FEATURE                Location/Qualifiers
```

```
source                  1..314
                        mol_type = protein
                        organism = Homo sapiens
SEQUENCE: 84
MPLEQRSQHC KPEEGLEARG EALGLVGAQA PATEEQQTAS SSSTLVEVTL GEVPAADSPS  60
PPHSPQGASS FSTTINYTLW RQSDEGSSNQ EEEGPRMFPD LESEFQAAIS RKMVELVHFL  120
LLKYRAREPV TKAEMLESVL RNCQDFFPVI FSKASEYLQL VFGIEVVEVV PISHLYILVT  180
CLGLSYDGLL GDNQVMPKTG LLIIVLAIIA IEGDCAPEEK IWEELSMLEV FEGREDSVFA  240
HPRKLLMQDL VQENYLEYRQ VPGSDPACYE FLWGPRALIE TSYVKVLHHT LKIGGEPHIS  300
YPPLHERALR EGEE                                                  314

SEQ ID NO: 85           moltype = AA  length = 314
FEATURE                 Location/Qualifiers
source                  1..314
                        mol_type = protein
                        organism = Homo sapiens
SEQUENCE: 85
MPLEQRSQHC KPEEGLEARG EALGLVGAQA PATEEQEAAS SSSTLVEVTL GEVPAAESPD  60
PPQSPQGASS LPTTMNYPLW SQSYEDSSNQ EEEGPSTFPD LESEFQAALS RKVAELVHFL  120
LLKYRAREPV TKAEMLGSVV GNWQYFFPVI FSKASSSLQL VFGIELMEVD PIGHLYIFAT  180
CLGLSYDGLL GDNQIMPKAG LLIIVLAIIA REGDCAPEEK IWEELSVLEV FEGREDSILG  240
DPKKLLTQHF VQENYLEYRQ VPGSDPACYE FLWGPRALVE TSYVKVLHHM VKISGGPHIS  300
YPPLHEWVLR EGEE                                                  314

SEQ ID NO: 86           moltype = AA  length = 210
FEATURE                 Location/Qualifiers
source                  1..210
                        mol_type = protein
                        organism = Homo sapiens
SEQUENCE: 86
MQAEGQGTGG STGDADGPGG PGIPDGPGGN AGGPGEAGAT GGRGPRGAGA ARASGPRGGA  60
PRGPHGGAAS AQDGRCPCGA RRPDSRLLQL HITMPFSSPM EAELVRRILS RDAAPLPRPG  120
AVLKDFTVSG NLLFMSVRDQ DREGAGRMRV VGWGLGSASP EGQKARDLRT PKHKVSEQRP  180
GTPGPPPPEG AQGDGCRGVA FNVMFSAPHI                                  210

SEQ ID NO: 87           moltype = AA  length = 369
FEATURE                 Location/Qualifiers
source                  1..369
                        mol_type = protein
                        organism = Homo sapiens
SEQUENCE: 87
MPRAPKRQRC MPEEDLQSQS ETQGLEGAQA PLAVEEDASS STSTSSSFPS SFPSSSSSSS  60
SSCYPLIPST PEEVSADDET PNPPQSAQIA CSSPSVVASL PLDQSDEGSS SQKEESPSTL  120
QVLPDSESLP RSEIDEKVTD LVQFLLFKYQ MKEPITKAEI LESVIRNYED HFPLLFSEAS  180
ECMLLVFGID VKEVDPTGHS FVLVTSLGLT YDGMLSDVQS MPKTGILILI LSIIFIEGYC  240
TPEEVIWEAL NMMGLYDGME HLIYGEPRKL LTQDWVQENY LEYRQVPGSD PARYEFLWGP  300
RAHAEIRKMS LLKFLAKVNG SDPRSFPLWY EEALKDEEER AQDRIATTDD TTAMASASSS  360
ATGSFSYPE                                                        369

SEQ ID NO: 88           moltype = AA  length = 309
FEATURE                 Location/Qualifiers
source                  1..309
                        mol_type = protein
                        organism = Homo sapiens
SEQUENCE: 88
MSLEQRSLHC KPEEALEAQQ EALGLVCVQA ATSSSSPLVL GTLEEVPTAG STDPPQSPQG  60
ASAFPTTINF TRQRQPSEGS SSREEEGPST SCILESLFRA VITKKVADLV GFLLLKYRAR  120
EPVTKAEMLE SVIKNYKHCF PEIFGKASES LQLVFGIDVK EADPTGHSYV LVTCLGLSYD  180
GLLGDNQIMP KTGFLIIVLV MIAMEGGHAP EEEIWEELSV MEVYDGREHS AYGEPRKLLT  240
QDLVQEKYLE YRQVPDSDPA RYEFLWGPRA LAETSYVKVL EYVIKVSARV RFFFPSLREA  300
ALREEEEGV                                                        309

SEQ ID NO: 89           moltype = AA  length = 188
FEATURE                 Location/Qualifiers
source                  1..188
                        mol_type = protein
                        organism = Homo sapiens
SEQUENCE: 89
MNGDDTFAKR PRDDAKASEK RSKAFDDIAT YFSKKEWKKM KYSEKISYVY MKRNYKAMTK  60
LGFKVTLPPF MCNKQATDFQ GNDFDNDHNR RIQVEHPQMT FGRLHRIIPK IMPKKPAEDE  120
NDSKGVSEAS GPQNDGKQLH PPGKANISEK INKRSGPKRG KHAWTHRLRE RKQLVIYEEI  180
SDPEEDDE                                                         188

SEQ ID NO: 90           moltype = AA  length = 9
FEATURE                 Location/Qualifiers
source                  1..9
                        mol_type = protein
                        organism = synthetic construct
                        note = BRDT 9mer
```

-continued

```
SEQUENCE: 90
FAADVRLMF                                                          9

SEQ ID NO: 91          moltype = AA  length = 9
FEATURE                Location/Qualifiers
source                 1..9
                       mol_type = protein
                       organism = synthetic construct
                       note = PRAME 9mer
SEQUENCE: 91
KAMVQAWPF                                                          9

SEQ ID NO: 92          moltype = AA  length = 9
FEATURE                Location/Qualifiers
source                 1..9
                       mol_type = protein
                       organism = synthetic construct
                       note = BRDT 9mer
SEQUENCE: 92
FSWPFQRPV                                                          9

SEQ ID NO: 93          moltype = AA  length = 9
FEATURE                Location/Qualifiers
source                 1..9
                       mol_type = protein
                       organism = synthetic construct
                       note = NALP4 9mer
SEQUENCE: 93
YSSFVFNLF                                                          9

SEQ ID NO: 94          moltype = AA  length = 9
FEATURE                Location/Qualifiers
source                 1..9
                       mol_type = protein
                       organism = synthetic construct
                       note = NALP4 9mer
SEQUENCE: 94
RAMEAFNLV                                                          9

SEQ ID NO: 95          moltype = AA  length = 9
FEATURE                Location/Qualifiers
source                 1..9
                       mol_type = protein
                       organism = synthetic construct
                       note = NALP4 9mer
SEQUENCE: 95
FVIDSFEEL                                                          9

SEQ ID NO: 96          moltype = AA  length = 9
FEATURE                Location/Qualifiers
source                 1..9
                       mol_type = protein
                       organism = synthetic construct
                       note = MAGE-A12 9mer
SEQUENCE: 96
KMAELVHFL                                                          9

SEQ ID NO: 97          moltype = AA  length = 9
FEATURE                Location/Qualifiers
source                 1..9
                       mol_type = protein
                       organism = synthetic construct
                       note = MAGE-A2 9mer
SEQUENCE: 97
FAHPRKLLM                                                          9

SEQ ID NO: 98          moltype = AA  length = 9
FEATURE                Location/Qualifiers
source                 1..9
                       mol_type = protein
                       organism = synthetic construct
                       note = SURVIVIN 9mer
SEQUENCE: 98
RAIEQLAAM                                                          9

SEQ ID NO: 99          moltype = AA  length = 9
FEATURE                Location/Qualifiers
```

-continued

```
source                  1..9
                        mol_type = protein
                        organism = synthetic construct
                        note = PRAME 9mer
SEQUENCE: 99
YIAQFTSQF                                                                  9

SEQ ID NO: 100          moltype = AA  length = 9
FEATURE                 Location/Qualifiers
source                  1..9
                        mol_type = protein
                        organism = synthetic construct
                        note = PRAME 9mer
SEQUENCE: 100
HVMNPLETL                                                                  9

SEQ ID NO: 101          moltype = AA  length = 9
FEATURE                 Location/Qualifiers
source                  1..9
                        mol_type = protein
                        organism = synthetic construct
                        note = MAGE-A12 9mer
SEQUENCE: 101
FQDFFPVIF                                                                  9

SEQ ID NO: 102          moltype = AA  length = 9
FEATURE                 Location/Qualifiers
source                  1..9
                        mol_type = protein
                        organism = synthetic construct
                        note = PRAME 9mer
SEQUENCE: 102
LLRHVMNPL                                                                  9

SEQ ID NO: 103          moltype = AA  length = 9
FEATURE                 Location/Qualifiers
source                  1..9
                        mol_type = protein
                        organism = synthetic construct
                        note = DPPA2 9mer
SEQUENCE: 103
KMMKRLMTV                                                                  9

SEQ ID NO: 104          moltype = AA  length = 9
FEATURE                 Location/Qualifiers
source                  1..9
                        mol_type = protein
                        organism = synthetic construct
                        note = NY-SAR-35 9mer
SEQUENCE: 104
FVLANGHIL                                                                  9

SEQ ID NO: 105          moltype = AA  length = 9
FEATURE                 Location/Qualifiers
source                  1..9
                        mol_type = protein
                        organism = synthetic construct
                        note = BRDT 9mer
SEQUENCE: 105
MLAKKHFSY                                                                  9

SEQ ID NO: 106          moltype = AA  length = 9
FEATURE                 Location/Qualifiers
source                  1..9
                        mol_type = protein
                        organism = synthetic construct
                        note = LDHC 9mer
SEQUENCE: 106
SVMDLVGSI                                                                  9

SEQ ID NO: 107          moltype = AA  length = 9
FEATURE                 Location/Qualifiers
source                  1..9
                        mol_type = protein
                        organism = synthetic construct
                        note = LDHC 9mer
SEQUENCE: 107
MMDLQHGSL                                                                  9
```

-continued

```
SEQ ID NO: 108          moltype = AA  length = 9
FEATURE                 Location/Qualifiers
source                  1..9
                        mol_type = protein
                        organism = synthetic construct
                        note = MAGE-A2 9mer
SEQUENCE: 108
FSTTINYTL                                                     9

SEQ ID NO: 109          moltype = AA  length = 9
FEATURE                 Location/Qualifiers
source                  1..9
                        mol_type = protein
                        organism = synthetic construct
                        note = MAGE-C2 9mer
SEQUENCE: 109
MASESLSVM                                                     9

SEQ ID NO: 110          moltype = AA  length = 9
FEATURE                 Location/Qualifiers
source                  1..9
                        mol_type = protein
                        organism = synthetic construct
                        note = MAGE-C2 9mer
SEQUENCE: 110
FVYGEPREL                                                     9

SEQ ID NO: 111          moltype = AA  length = 9
FEATURE                 Location/Qualifiers
source                  1..9
                        mol_type = protein
                        organism = synthetic construct
                        note = MAGE-C2 9mer
SEQUENCE: 111
SVMSSNVSF                                                     9

SEQ ID NO: 112          moltype = AA  length = 9
FEATURE                 Location/Qualifiers
source                  1..9
                        mol_type = protein
                        organism = synthetic construct
                        note = MAGE-A3 9mer
SEQUENCE: 112
FVQENYLEY                                                     9

SEQ ID NO: 113          moltype = AA  length = 9
FEATURE                 Location/Qualifiers
source                  1..9
                        mol_type = protein
                        organism = synthetic construct
                        note = MAGE-A12 9mer
SEQUENCE: 113
KASEYLQLV                                                     9

SEQ ID NO: 114          moltype = AA  length = 9
FEATURE                 Location/Qualifiers
source                  1..9
                        mol_type = protein
                        organism = synthetic construct
                        note = SURVIVIN 9mer
SEQUENCE: 114
STFKNWPFL                                                     9

SEQ ID NO: 115          moltype = AA  length = 9
FEATURE                 Location/Qualifiers
source                  1..9
                        mol_type = protein
                        organism = synthetic construct
                        note = DPPA2 9mer
SEQUENCE: 115
YLRLHRHAY                                                     9

SEQ ID NO: 116          moltype = AA  length = 9
FEATURE                 Location/Qualifiers
source                  1..9
                        mol_type = protein
                        organism = synthetic construct
                        note = MAGE-A3 9mer
SEQUENCE: 116
```

-continued

```
ASSSLQLVF                                                             9

SEQ ID NO: 117          moltype = AA  length = 9
FEATURE                 Location/Qualifiers
source                  1..9
                        mol_type = protein
                        organism = synthetic construct
                        note = KK-LC-1 9mer
SEQUENCE: 117
SSNSTALAL                                                             9

SEQ ID NO: 118          moltype = AA  length = 9
FEATURE                 Location/Qualifiers
source                  1..9
                        mol_type = protein
                        organism = synthetic construct
                        note = MAGE-C2 9mer
SEQUENCE: 118
FSTSSSLIL                                                             9

SEQ ID NO: 119          moltype = AA  length = 9
FEATURE                 Location/Qualifiers
source                  1..9
                        mol_type = protein
                        organism = synthetic construct
                        note = MAGE-A1 9mer
SEQUENCE: 119
RALAETSYV                                                             9

SEQ ID NO: 120          moltype = AA  length = 15
FEATURE                 Location/Qualifiers
source                  1..15
                        mol_type = protein
                        organism = synthetic construct
                        note = BRDT 15mer
SEQUENCE: 120
DAYKFAADVR LMFMN                                                      15

SEQ ID NO: 121          moltype = AA  length = 15
FEATURE                 Location/Qualifiers
source                  1..15
                        mol_type = protein
                        organism = synthetic construct
                        note = PRAME 15mer
SEQUENCE: 121
RHSQTLKAMV QAWPF                                                      15

SEQ ID NO: 122          moltype = AA  length = 15
FEATURE                 Location/Qualifiers
source                  1..15
                        mol_type = protein
                        organism = synthetic construct
                        note = BRDT 15mer
SEQUENCE: 122
DLWKHSFSWP FQRPV                                                      15

SEQ ID NO: 123          moltype = AA  length = 15
FEATURE                 Location/Qualifiers
source                  1..15
                        mol_type = protein
                        organism = synthetic construct
                        note = NALP4 15mer
SEQUENCE: 123
QSTTSVYSSF VFNLF                                                      15

SEQ ID NO: 124          moltype = AA  length = 15
FEATURE                 Location/Qualifiers
source                  1..15
                        mol_type = protein
                        organism = synthetic construct
                        note = NALP4 15mer
SEQUENCE: 124
KRAMEAFNLV RESEQ                                                      15

SEQ ID NO: 125          moltype = AA  length = 15
FEATURE                 Location/Qualifiers
```

```
source                  1..15
                        mol_type = protein
                        organism = synthetic construct
                        note = NALP4 15mer
SEQUENCE: 125
FVIDSFEELQ GGLNE                                                    15

SEQ ID NO: 126          moltype = AA  length = 15
FEATURE                 Location/Qualifiers
source                  1..15
                        mol_type = protein
                        organism = synthetic construct
                        note = MAGE-A12 15mer
SEQUENCE: 126
QVALSRKMAE LVHFL                                                    15

SEQ ID NO: 127          moltype = AA  length = 15
FEATURE                 Location/Qualifiers
source                  1..15
                        mol_type = protein
                        organism = synthetic construct
                        note = MAGE-A215mer
SEQUENCE: 127
REDSVFAHPR KLLMQ                                                    15

SEQ ID NO: 128          moltype = AA  length = 15
FEATURE                 Location/Qualifiers
source                  1..15
                        mol_type = protein
                        organism = synthetic construct
                        note = SURVIVIN 15mer
SEQUENCE: 128
AKKVRRAIEQ LAAMD                                                    15

SEQ ID NO: 129          moltype = AA  length = 15
FEATURE                 Location/Qualifiers
source                  1..15
                        mol_type = protein
                        organism = synthetic construct
                        note = PRAME 15mer
SEQUENCE: 129
KEEQYIAQFT SQFLS                                                    15

SEQ ID NO: 130          moltype = AA  length = 15
FEATURE                 Location/Qualifiers
source                  1..15
                        mol_type = protein
                        organism = synthetic construct
                        note = PRAME 15mer
SEQUENCE: 130
DQLLRHVMNP LETLS                                                    15

SEQ ID NO: 131          moltype = AA  length = 15
FEATURE                 Location/Qualifiers
source                  1..15
                        mol_type = protein
                        organism = synthetic construct
                        note = MAGE-A12 15mer
SEQUENCE: 131
RNFQDFFPVI FSKAS                                                    15

SEQ ID NO: 132          moltype = AA  length = 15
FEATURE                 Location/Qualifiers
source                  1..15
                        mol_type = protein
                        organism = synthetic construct
                        note = PRAME 15mer
SEQUENCE: 132
RGRLDQLLRH VMNPL                                                    15

SEQ ID NO: 133          moltype = AA  length = 15
FEATURE                 Location/Qualifiers
source                  1..15
                        mol_type = protein
                        organism = synthetic construct
                        note = DPPA2 15mer
SEQUENCE: 133
KRNKKMMKRL MTVEK                                                    15
```

```
SEQ ID NO: 134          moltype = AA  length = 15
FEATURE                 Location/Qualifiers
source                  1..15
                        mol_type = protein
                        organism = synthetic construct
                        note = NY-SAR-35 15mer
SEQUENCE: 134
SSYFVLANGH ILPNS                                                      15

SEQ ID NO: 135          moltype = AA  length = 15
FEATURE                 Location/Qualifiers
source                  1..15
                        mol_type = protein
                        organism = synthetic construct
                        note = BRDT 15mer
SEQUENCE: 135
ILKEMLAKKH FSYAW                                                      15

SEQ ID NO: 136          moltype = AA  length = 15
FEATURE                 Location/Qualifiers
source                  1..15
                        mol_type = protein
                        organism = synthetic construct
                        note = LDHC 15mer
SEQUENCE: 136
SVMDLVGSIL KNLRR                                                      15

SEQ ID NO: 137          moltype = AA  length = 15
FEATURE                 Location/Qualifiers
source                  1..15
                        mol_type = protein
                        organism = synthetic construct
                        note = LDHC 15mer
SEQUENCE: 137
KLKGEMMDLQ HGSLF                                                      15

SEQ ID NO: 138          moltype = AA  length = 15
FEATURE                 Location/Qualifiers
source                  1..15
                        mol_type = protein
                        organism = synthetic construct
                        note = MAGE-A215mer
SEQUENCE: 138
SSFSTTINYT LWRQS                                                      15

SEQ ID NO: 139          moltype = AA  length = 15
FEATURE                 Location/Qualifiers
source                  1..15
                        mol_type = protein
                        organism = synthetic construct
                        note = MAGE-C215mer
SEQUENCE: 139
MASESLSVMS SNVSF                                                      15

SEQ ID NO: 140          moltype = AA  length = 15
FEATURE                 Location/Qualifiers
source                  1..15
                        mol_type = protein
                        organism = synthetic construct
                        note = MAGE-C215mer
SEQUENCE: 140
EHFVYGEPRE LLTKV                                                      15

SEQ ID NO: 141          moltype = AA  length = 15
FEATURE                 Location/Qualifiers
source                  1..15
                        mol_type = protein
                        organism = synthetic construct
                        note = MAGE-C215mer
SEQUENCE: 141
SESLSVMSSN VSFSE                                                      15

SEQ ID NO: 142          moltype = AA  length = 15
FEATURE                 Location/Qualifiers
source                  1..15
                        mol_type = protein
                        organism = synthetic construct
                        note = MAGE-A315mer
```

-continued

```
SEQUENCE: 142
LTQHFVQENY LEYRQ                                                    15

SEQ ID NO: 143          moltype = AA  length = 15
FEATURE                 Location/Qualifiers
source                  1..15
                        mol_type = protein
                        organism = synthetic construct
                        note = MAGE-A12 15mer
SEQUENCE: 143
SKASEYLQLV FGIEV                                                    15

SEQ ID NO: 144          moltype = AA  length = 15
FEATURE                 Location/Qualifiers
source                  1..15
                        mol_type = protein
                        organism = synthetic construct
                        note = SURVIVIN 15mer
SEQUENCE: 144
KDHRISTFKN WPFLE                                                    15

SEQ ID NO: 145          moltype = AA  length = 15
FEATURE                 Location/Qualifiers
source                  1..15
                        mol_type = protein
                        organism = synthetic construct
                        note = DPPA2 15mer
SEQUENCE: 145
KIEVYLRLHR HAYPE                                                    15

SEQ ID NO: 146          moltype = AA  length = 15
FEATURE                 Location/Qualifiers
source                  1..15
                        mol_type = protein
                        organism = synthetic construct
                        note = MAGE-A315mer
SEQUENCE: 146
KASSSLQLVF GIELM                                                    15

SEQ ID NO: 147          moltype = AA  length = 15
FEATURE                 Location/Qualifiers
source                  1..15
                        mol_type = protein
                        organism = synthetic construct
                        note = KK-LC-1 15mer
SEQUENCE: 147
RNTGEMSSNS TALAL                                                    15

SEQ ID NO: 148          moltype = AA  length = 15
FEATURE                 Location/Qualifiers
source                  1..15
                        mol_type = protein
                        organism = synthetic construct
                        note = MAGE-C215mer
SEQUENCE: 148
SSFSTSSSLI LGGPE                                                    15

SEQ ID NO: 149          moltype = AA  length = 15
FEATURE                 Location/Qualifiers
source                  1..15
                        mol_type = protein
                        organism = synthetic construct
                        note = MAGE-A115mer
SEQUENCE: 149
PRALAETSYV KVLEY                                                    15

SEQ ID NO: 150          moltype = AA  length = 30
FEATURE                 Location/Qualifiers
source                  1..30
                        mol_type = protein
                        organism = synthetic construct
                        note = LC821-01BRDT/SURVIVIN
SEQUENCE: 150
DAYKFAADVR LMFMNAKKVR RAIEQLAAMD                                    30

SEQ ID NO: 151          moltype = AA  length = 30
FEATURE                 Location/Qualifiers
```

```
source                  1..30
                        mol_type = protein
                        organism = synthetic construct
                        note = LC821-02PRAME/MAGE-A2
SEQUENCE: 151
RHSQTLKAMV QAWPFREDSV FAHPRKLLMQ                                    30

SEQ ID NO: 152          moltype = AA  length = 30
FEATURE                 Location/Qualifiers
source                  1..30
                        mol_type = protein
                        organism = synthetic construct
                        note = LC821-03BRDT/MAGE-A12
SEQUENCE: 152
DLWKHSFSWP FQRPVSKASE YLQLVFGIEV                                    30

SEQ ID NO: 153          moltype = AA  length = 30
FEATURE                 Location/Qualifiers
source                  1..30
                        mol_type = protein
                        organism = synthetic construct
                        note = LC821-04PRAME/LDHC
SEQUENCE: 153
DQLLRHVMNP LETLSSVMDL VGSILKNLRR                                    30

SEQ ID NO: 154          moltype = AA  length = 30
FEATURE                 Location/Qualifiers
source                  1..30
                        mol_type = protein
                        organism = synthetic construct
                        note = LC821-05NALP4/SURVIVIN
SEQUENCE: 154
QSTTSVYSSF VFNLFKDHRI STFKNWPFLE                                    30

SEQ ID NO: 155          moltype = AA  length = 30
FEATURE                 Location/Qualifiers
source                  1..30
                        mol_type = protein
                        organism = synthetic construct
                        note = LC821-06 MAGE-C2/NALP4
SEQUENCE: 155
SSFSTSSSLI LGGPEFVIDS FEELQGGLNE                                    30

SEQ ID NO: 156          moltype = AA  length = 30
FEATURE                 Location/Qualifiers
source                  1..30
                        mol_type = protein
                        organism = synthetic construct
                        note = LC821-07 MAGE-A2/NALP4
SEQUENCE: 156
SSFSTTINYT LWRQSKRAME AFNLVRESEQ                                    30

SEQ ID NO: 157          moltype = AA  length = 30
FEATURE                 Location/Qualifiers
source                  1..30
                        mol_type = protein
                        organism = synthetic construct
                        note = LC821-08 NY-SAR-35/MAGE-A12
SEQUENCE: 157
SSYFVLANGH ILPNSRNFQD FFPVIFSKAS                                    30

SEQ ID NO: 158          moltype = AA  length = 30
FEATURE                 Location/Qualifiers
source                  1..30
                        mol_type = protein
                        organism = synthetic construct
                        note = LC821-09 MAGE-C2/PRAME
SEQUENCE: 158
MASESLSVMS SNVSFKEEQY IAQFTSQFLS                                    30

SEQ ID NO: 159          moltype = AA  length = 30
FEATURE                 Location/Qualifiers
source                  1..30
                        mol_type = protein
                        organism = synthetic construct
                        note = LC821-10 PRAME/MAGE-A3
SEQUENCE: 159
RGRLDQLLRH VMNPLLTQHF VQENYLEYRQ                                    30
```

```
SEQ ID NO: 160          moltype = AA  length = 30
FEATURE                 Location/Qualifiers
source                  1..30
                        mol_type = protein
                        organism = synthetic construct
                        note = LC821-11 MAGE-C2/LDHC
SEQUENCE: 160
SESLSVMSSN VSFSEKLKGE MMDLQHGSLF                                    30

SEQ ID NO: 161          moltype = AA  length = 30
FEATURE                 Location/Qualifiers
source                  1..30
                        mol_type = protein
                        organism = synthetic construct
                        note = LC821-12 MAGE-A12/MAGE-A1
SEQUENCE: 161
QVALSRKMAE LVHFLPRALA ETSYVKVLEY                                    30

SEQ ID NO: 162          moltype = AA  length = 30
FEATURE                 Location/Qualifiers
source                  1..30
                        mol_type = protein
                        organism = synthetic construct
                        note = LC821-13 MAGE-C2/BRDT
SEQUENCE: 162
EHFVYGEPRE LLTKVILKEM LAKKHFSYAW                                    30

SEQ ID NO: 163          moltype = AA  length = 30
FEATURE                 Location/Qualifiers
source                  1..30
                        mol_type = protein
                        organism = synthetic construct
                        note = LC821-14 DPPA2/MAGE-A3
SEQUENCE: 163
KIEVYLRLHR HAYPEKASSS LQLVFGIELM                                    30

SEQ ID NO: 164          moltype = AA  length = 30
FEATURE                 Location/Qualifiers
source                  1..30
                        mol_type = protein
                        organism = synthetic construct
                        note = LC821-15 KK-LC-1/DPPA2
SEQUENCE: 164
RNTGEMSSNS TALALKRNKK MMKRLMTVEK                                    30

SEQ ID NO: 165          moltype = AA  length = 947
FEATURE                 Location/Qualifiers
source                  1..947
                        mol_type = protein
                        organism = Homo sapiens
SEQUENCE: 165
MSLPSRQTAI IVNPPPPEYI NTKKNGRLTN QLQYLQKVVL KDLWKHSFSW PFQRPVDAVK  60
LQLPDYYTII KNPMDLNTIK KRLENKYYAK ASECIEDFNT MFSNCYLYNK PGDDIVLMAQ  120
ALEKLFMQKL SQMPQEEQVV GVKERIKKGT QQNIAVSSAK EKSSPSATEK VFKQQEIPSV  180
FPKTSISPLN VVQGASVNSS SQTAAQVTKG VKRKADTTTP ATSAVKASSE FSPTFTEKSV  240
ALPPIKENMP KNVLPDSQQQ YNVVKTVKVT EQLRHCSEIL KEMLAKKHFS YAWPFYNPVD  300
VNALGLHNYY DVVKNPMDLG TIKEKMDNQE YKDAYKFAAD VRLMFMNCYK YNPPDHEVVT  360
MARMLQDVFE THFSKIPIEP VESMPLCYIK TDITETTGRE NTNEASSEGN SSDDSEDERV  420
KRLAKLQEQL KAVHQQLQVL SQVPFRKLNK KKEKSKKEKK KEKVNNSNEN PRKMCEQMRL  480
KEKSKRNQPK KRKQQFIGLK SEDEDNAKPM NYDEKRQLSL NINKLPGDKL GRVVHIIQSR  540
EPSLSNSNPD EIEIDFETLK ASTLRELEKY VSACLRKRPL KPPAKKIMMS KEELHSQKKQ  600
ELEKRLLDVN NQLNSRKRQT KSDKTQPSKA VENVSRLSES SSSSSSSSES ESSSSDLSSS  660
DSSDSESEMF PKFTEVKPND SPSKENVKKM KNECIPPEGR TGVTQIGYCV QDTTSANTTL  720
VHQTTPSHVM PPNHHQLAFN YQELEHLQTV KNISPLQILP PSGDSEQLSN GITVMHPSGD  780
SDTTMLESEC QAPVQKDIKI KNADSWKSLG KPVKPSGVMK SSDELFNQFR KAAIEKEVKA  840
RTQELIRKHL EQNTKELKAS QENQRDLGNG LTVESFSNKI QNKCSGEEQK EHQQSSEAQD  900
KSKLWLLKDR DLARQKEQER RRREAMVGTI DMTLQSDIMT MFENNFD                 947

SEQ ID NO: 166          moltype = AA  length = 509
FEATURE                 Location/Qualifiers
source                  1..509
                        mol_type = protein
                        organism = Homo sapiens
SEQUENCE: 166
MERRRLWGSI QSRYISMSVW TSPRRLVELA GQSLLKDEAL AIAALELLPR ELFPPLFMAA  60
FDGRHSQTLK AMVQAWPFTC LPLGVLMKGQ HLHLETFKAV LDGLDVLLAQ EVRPRRWKLQ  120
VLDLRKNSHQ DFWTVWSGNR ASLYSFPEPE AAQPMTKKRK VDGLSTEAEQ PFIPVEVLVD  180
LFLKEGACDE LFSYLIEKVK RKKNVLRLCC KKLKIFAMPM QDIKMILKMV QLDSIEDLEV  240
TCTWKLPTLA KFSPYLGQMI NLRRLLLSHI HASSYISPEK EEQYIAQFTS QFLSLQCLQA  300
```

-continued

```
LYVDSLFFLR GRLDQLLRHV MNPLETLSIT NCRLSEGDVM HLSQSPSVSQ LSVLSLSGVM  360
LTDVSPEPLQ ALLERASATL QDLVFDECGI TDDQLLALLP SLSHCSQLTT LSFYGNSISI  420
SALQSLLQHL IGLSNLTHVL YPVPLESYED IHGTLHLERL AYLHARLREL LCELGRPSMV  480
WLSANPCPHC GDRTFYDPEP ILCPCFMPN                                   509

SEQ ID NO: 167         moltype = AA  length = 994
FEATURE                Location/Qualifiers
source                 1..994
                       mol_type = protein
                       organism = Homo sapiens
SEQUENCE: 167
MAASFFSDFG LMWYLEELKK EEFRKFKEHL KQMTLQLELK QIPWTEVKKA SREELANLLI  60
KHYEEQQAWN ITLRIFQKMD RKDLCMKVMR ERTGYTKTYQ AHAKQKFSRL WSSKSVTEIH  120
LYFEEEVKQE ECDHLDRLFA PKEAGKQPRT VIIQGPQGIG KTTLLMKLMM AWSDNKIFRD  180
RFLYTFYFCC RELRELPPTS LADLISREWP DPAAPITEIV SQPERLLFVI DSFEELQGGL  240
NEPDSDLCGD LMEKRPVQVL LSSLLRKKML PEASLLIAIK PVCPKELRDQ VTISEIYQPR  300
GFNESDRLVY FCCFFKDPKR AMEAFNLVRE SEQLFSICQI PLLCWILCTS LKQEMQKGKD  360
LALTCQSTTS VYSSFVFNLF TPEGAEGPTP QTQHQLKALC SLAAEGMWTD TFEFCEDDLR  420
RNGVVDADIP ALLGTKILLK YGERESSYVF LHVCIQEFCA ALFYLLKSHL DHPHPAVRCV  480
QELLVANFEK ARRAHWIFLG CFLTGLLNKK EQEKLDAFFG FQLSQEIKQQ IHQCLKSLGE  540
RGNPQGQVDS LAIFYCLFEM QDPAFVKQAV NLLQEANFHI IDNVDLVVSA YCLKYCSSLR  600
KLCFSVQNVF KKEDEHSSTS DYSLICWHHI CSVLTTSGHL RELQVQDSTL SESTFVTWCN  660
QLRHPSCRLQ KLGINNVSFS GQSVLLFEVL FYQPDLKYLS FTLTKLSRDD IRSLCDALNY  720
PAGNVKELAL VNCHLSPIDC EVLAGLLTNN KKLTYLNVSC NQLDTGVPLL CEALCSPDTV  780
LVYLMLAFCH LSEQCCEYIS EMLLRNKSVR YLDLSANVLK DEGLKTLCEA LKHPDCCLDS  840
LCLVKCFITA AGCEDLASAL ISNQNLKILQ IGCNEIGDVG VQLLCRALTH TDCRLEILGL  900
EECGLTSTCC KDLASVLTCS KTLQQLNLTL NTLDHTGVVV LCEALRHPEC ALQVLGLRKT  960
DFDEETQALL TAEEERNPNL TITDDCDTIT RVEI                             994

SEQ ID NO: 168         moltype = AA  length = 314
FEATURE                Location/Qualifiers
source                 1..314
                       mol_type = protein
                       organism = Homo sapiens
SEQUENCE: 168
MPLEQRSQHC KPEEGLEAQG EALGLVGAQA PATEEQETAS SSSTLVEVTL REVPAAESPS  60
PPHSPQGAST LPTTINYTLW SQSDEGSSNE EQEGPSTFPD LETSFQVALS RKMAELVHFL  120
LLKYRAREPF TKAEMLGSVI RNFQDFFPVI FSKASEYLQL VFGIEVVEVV RIGHLYILVT  180
CLGLSYDGLL GDNQIVPKTG LLIIVLAIIA KEGDCAPEEK IWEELSVLEA SDGREDSVFA  240
HPRKLLTQDL VQENYLEYRQ VPGSDPACYE FLWGPRALVE TSYVKVLHHL LKISGGPHIS  300
YPPLHEWAFR EGEE                                                   314

SEQ ID NO: 169         moltype = AA  length = 314
FEATURE                Location/Qualifiers
source                 1..314
                       mol_type = protein
                       organism = Homo sapiens
SEQUENCE: 169
MPLEQRSQHC KPEEGLEARG EALGLVGAQA PATEEQQTAS SSSTLVEVTL GEVPAADSPS  60
PPHSPQGASS FSTTINYTLW RQSDEGSSNQ EEEGPRMFPD LESEFQAAIS RKMVELVHFL  120
LLKYRAREPV TKAEMLESVL RNCQDFFPVI FSKASEYLQL VFGIEVVEVV PISHLYILVT  180
CLGLSYDGLL GDNQVMPKTG LLIIVLAIIA IEGDCAPEEK IWEELSMLEV FEGREDSVFA  240
HPRKLLMQDL VQENYLEYRQ VPGSDPACYE FLWGPRALIE TSYVKVLHHT LKIGGEPHIS  300
YPPLHERALR EGEE                                                   314

SEQ ID NO: 170         moltype = AA  length = 142
FEATURE                Location/Qualifiers
source                 1..142
                       mol_type = protein
                       organism = Homo sapiens
SEQUENCE: 170
MGAPTLPPAW QPFLKDHRIS TFKNWPFLEG CACTPERMAE AGFIHCPTEN EPDLAQCFFC  60
FKELEGWEPD DDPIEEHKKH SSGCAFLSVK KQFEELTLGE FLKLDRERAK NKIAKETNNK  120
KKEFEETAKK VRRAIEQLAA MD                                          142

SEQ ID NO: 171         moltype = AA  length = 298
FEATURE                Location/Qualifiers
source                 1..298
                       mol_type = protein
                       organism = Homo sapiens
SEQUENCE: 171
MSDANLDSSK KNFLEGEVDD EESVILTLVP VKDDANMEQM EPSVSSTSDV KLEKPKKYNP  60
GHLLQTNEQF TAPQKARCKI PALPLPTILP PINKVCRDTL RDWCQQLGLS TNGKKIEVYL  120
RLHRHAYPEQ RQDMPEMSQE TRLQRCSRKR KAVTKRARLQ RSYEMNERAE ETNTVEVITS  180
APGAMLASWA RIAARAVQPK ALNSCSIPVS VEAFLMQASG VRWCVVHGRL LSADTKGWVR  240
LQFHAGQAWV PTTHRRMISL FLLPACIFPS PGIEDNMLCP DCAKRNKKMM KRLMTVEK   298

SEQ ID NO: 172         moltype = AA  length = 255
FEATURE                Location/Qualifiers
```

-continued

```
source                1..255
                      mol_type = protein
                      organism = Homo sapiens
SEQUENCE: 172
MSSHRRKAKG RNRRSHRAMR VAHLELATYE LAATESNPES SHPGYEAAMA DRPQPGWRES  60
LKMRVSKPFG MLMLSIWILL FVCYYLSYYL CSGSSYFVLA NGHILPNSEN AHGQSLEEDS  120
ALEALLNFFF PTTCNLRENQ VAKPCNELQD LSESECLRHK CCFSSSGTTS FKCFAPFRDV  180
PKQMMQMFGL GAISLILVCL PIYCRSLFWR SEPADDLQRQ DNRVVTGLKK QRRKRKRKSE  240
MLQKAARGRE EHGDE                                                  255

SEQ ID NO: 173        moltype = AA  length = 332
FEATURE               Location/Qualifiers
source                1..332
                      mol_type = protein
                      organism = Homo sapiens
SEQUENCE: 173
MSTVKEQLIE KLIEDDENSQ CKITIVGTGA VGMACAISIL LKDLADELAL VDVALDKLKG  60
EMMDLQHGSL FFSTSKITSG KDYSVSANSR IVIVTAGARQ QEGETRLALV QRNVAIMKSI  120
IPAIVHYSPD CKILVVSNPV DILTYIVWKI SGLPVTRVIG SGCNLDSARF RYLIGEKLGV  180
HPTSCHGWII GEHGDSSVPL WSGVNVAGVA LKTLDPKLGT DSDKEHWKNI HKQVIQSAYE  240
IIKLKGYTSW AIGLSVMDLV GSILKNLRRV HPVSTMVKGL YGIKEELFLS IPCVLGRNGV  300
SDVVKINLNS EEEALFKKSA ETLWNIQKDL IF                               332

SEQ ID NO: 174        moltype = AA  length = 373
FEATURE               Location/Qualifiers
source                1..373
                      mol_type = protein
                      organism = Homo sapiens
SEQUENCE: 174
MPPVPGVPFR NVDNDSPTSV ELEDWVDAQH PTDEEEEEAS SASSTLYLVF SPSSFSTSSS  60
LILGGPEEEE VPSGVIPNLT ESIPSSPPQG PPQGPSQSPL SSCCSSFSWS SFSEESSSQK  120
GEDTGTCQGL PDSESSFTYT LDEKVAELVE FLLLKYEAEE PVTEAEMLMI VIKYKDYFPV  180
ILKRAREFME LLFGLALIEV GPDHFCVFAN TVGLTDEGSD DEGMPENSLL IIILSVIFIK  240
GNCASEEVIW EVLNAVGVYA GREHFVYGEP RELLTKVWVQ GHYLEYREVP HSSPPYYEFL  300
WGPRAHSESI KKKVLEFLAK LNNTVPSSFP SWYKDALKDV EERVQATIDT ADDATVMASE  360
SLSVMSSNVS FSE                                                    373

SEQ ID NO: 175        moltype = AA  length = 314
FEATURE               Location/Qualifiers
source                1..314
                      mol_type = protein
                      organism = Homo sapiens
SEQUENCE: 175
MPLEQRSQHC KPEEGLEARG EALGLVGAQA PATEEQEAAS SSSTLVEVTL GEVPAAESPD  60
PPQSPQGASS LPTTMNYPLW SQSYEDSSNQ EEEGPSTFPD LESEFQAALS RKVAELVHFL  120
LLKYRAREPV TKAEMLGSVV GNWQYFFPVI FSKASSSLQL VFGIELMEVD PIGHLYIFAT  180
CLGLSYDGLL GDNQIMPKAG LLIIVLAIIA REGDCAPEEK IWEELSVLEV FEGREDSILG  240
DPKKLLTQHF VQENYLEYRQ VPGSDPACYE FLWGPRALVE TSYVKVLHHM VKISGGPHIS  300
YPPLHEWVLR EGEE                                                   314

SEQ ID NO: 176        moltype = AA  length = 113
FEATURE               Location/Qualifiers
source                1..113
                      mol_type = protein
                      organism = Homo sapiens
SEQUENCE: 176
MNFYLLLASS ILCALIVFWK YRRFQRNTGE MSSNSTALAL VRPSSSGLIN SNTDNNLAVY  60
DLSRDILNNF PHSIARQKRI LVNLSMVENK LVELEHTLLS KGFRGASPHR KST        113

SEQ ID NO: 177        moltype = AA  length = 309
FEATURE               Location/Qualifiers
source                1..309
                      mol_type = protein
                      organism = Homo sapiens
SEQUENCE: 177
MSLEQRSLHC KPEEALEAQQ EALGLVCVQA ATSSSSPLVL GTLEEVPTAG STDPPQSPQG  60
ASAFPTTINF TRQRQPSEGS SSREEEGPST SCILESLFRA VITKKVADLV GFLLLKYRAR  120
EPVTKAEMLE SVIKNYKHCF PEIFGKASES LQLVFGIDVK EADPTGHSYV LVTCLGLSYD  180
GLLGDNQIMP KTGFLIIVLV MIAMEGGHAP EEEIWEELSV MEVYDGREHS AYGEPRKLLT  240
QDLVQEKYLE YRQVPDSDPA RYEFLWGPRA LAETSYVKVL EYVIKVSARV RFFFPSLREA  300
ALREEEEGV                                                         309

SEQ ID NO: 178        moltype = AA  length = 9
FEATURE               Location/Qualifiers
source                1..9
                      mol_type = protein
                      organism = synthetic construct
                      note = PRAME 9mer
SEQUENCE: 178
```

-continued

```
YLHARLREL                                                                 9

SEQ ID NO: 179          moltype = AA  length = 9
FEATURE                 Location/Qualifiers
source                  1..9
                        mol_type = protein
                        organism = synthetic construct
                        note = MAGE-A2 9mer
SEQUENCE: 179
FAHPRKLLM                                                                 9

SEQ ID NO: 180          moltype = AA  length = 9
FEATURE                 Location/Qualifiers
source                  1..9
                        mol_type = protein
                        organism = synthetic construct
                        note = PRAME 9mer
SEQUENCE: 180
KAMVQAWPF                                                                 9

SEQ ID NO: 181          moltype = AA  length = 9
FEATURE                 Location/Qualifiers
source                  1..9
                        mol_type = protein
                        organism = synthetic construct
                        note = MAGE-C1 9mer
SEQUENCE: 181
FSYTLLSLF                                                                 9

SEQ ID NO: 182          moltype = AA  length = 9
FEATURE                 Location/Qualifiers
source                  1..9
                        mol_type = protein
                        organism = synthetic construct
                        note = Survivin 9mer
SEQUENCE: 182
RAIEQLAAM                                                                 9

SEQ ID NO: 183          moltype = AA  length = 9
FEATURE                 Location/Qualifiers
source                  1..9
                        mol_type = protein
                        organism = synthetic construct
                        note = MAGE-C1 9mer
SEQUENCE: 183
FSSTLVSLF                                                                 9

SEQ ID NO: 184          moltype = AA  length = 9
FEATURE                 Location/Qualifiers
source                  1..9
                        mol_type = protein
                        organism = synthetic construct
                        note = MAGE-A2 9mer
SEQUENCE: 184
FSTTINYTL                                                                 9

SEQ ID NO: 185          moltype = AA  length = 9
FEATURE                 Location/Qualifiers
source                  1..9
                        mol_type = protein
                        organism = synthetic construct
                        note = MAGE-A12 9mer
SEQUENCE: 185
KMAELVHFL                                                                 9

SEQ ID NO: 186          moltype = AA  length = 9
FEATURE                 Location/Qualifiers
source                  1..9
                        mol_type = protein
                        organism = synthetic construct
                        note = MAGE-C1 9mer
SEQUENCE: 186
YVFVNTLDL                                                                 9

SEQ ID NO: 187          moltype = AA  length = 9
FEATURE                 Location/Qualifiers
```

```
source                  1..9
                        mol_type = protein
                        organism = synthetic construct
                        note = MAGE-C1 9mer
SEQUENCE: 187
FSYTLASLL                                                         9

SEQ ID NO: 188          moltype = AA  length = 9
FEATURE                 Location/Qualifiers
source                  1..9
                        mol_type = protein
                        organism = synthetic construct
                        note = PRAME 9mer
SEQUENCE: 188
YIAQFTSQF                                                         9

SEQ ID NO: 189          moltype = AA  length = 9
FEATURE                 Location/Qualifiers
source                  1..9
                        mol_type = protein
                        organism = synthetic construct
                        note = MAGE-C1 9mer
SEQUENCE: 189
MTSSFSSTL                                                         9

SEQ ID NO: 190          moltype = AA  length = 9
FEATURE                 Location/Qualifiers
source                  1..9
                        mol_type = protein
                        organism = synthetic construct
                        note = PRAME 9mer
SEQUENCE: 190
HVMNPLETL                                                         9

SEQ ID NO: 191          moltype = AA  length = 9
FEATURE                 Location/Qualifiers
source                  1..9
                        mol_type = protein
                        organism = synthetic construct
                        note = Ny-ESO-1 9mer
SEQUENCE: 191
RLLEFYLAM                                                         9

SEQ ID NO: 192          moltype = AA  length = 9
FEATURE                 Location/Qualifiers
source                  1..9
                        mol_type = protein
                        organism = synthetic construct
                        note = MAGE-C2 9mer
SEQUENCE: 192
MASESLSVM                                                         9

SEQ ID NO: 193          moltype = AA  length = 9
FEATURE                 Location/Qualifiers
source                  1..9
                        mol_type = protein
                        organism = synthetic construct
                        note = MAGE-C2 9mer
SEQUENCE: 193
FVYGEPREL                                                         9

SEQ ID NO: 194          moltype = AA  length = 9
FEATURE                 Location/Qualifiers
source                  1..9
                        mol_type = protein
                        organism = synthetic construct
                        note = MAGE-A6 9mer
SEQUENCE: 194
FVQENYLEY                                                         9

SEQ ID NO: 195          moltype = AA  length = 9
FEATURE                 Location/Qualifiers
source                  1..9
                        mol_type = protein
                        organism = synthetic construct
                        note = BORIS 9mer
SEQUENCE: 195
FTSSRMSSF                                                         9
```

```
SEQ ID NO: 196          moltype = AA  length = 9
FEATURE                 Location/Qualifiers
source                  1..9
                        mol_type = protein
                        organism = synthetic construct
                        note = LAGE-1 9mer
SEQUENCE: 196
FTVSGNLLF                                                           9

SEQ ID NO: 197          moltype = AA  length = 9
FEATURE                 Location/Qualifiers
source                  1..9
                        mol_type = protein
                        organism = synthetic construct
                        note = MAGE-A2 9mer
SEQUENCE: 197
KASEYLQLV                                                           9

SEQ ID NO: 198          moltype = AA  length = 9
FEATURE                 Location/Qualifiers
source                  1..9
                        mol_type = protein
                        organism = synthetic construct
                        note = Survivin 9mer
SEQUENCE: 198
STFKNWPFL                                                           9

SEQ ID NO: 199          moltype = AA  length = 9
FEATURE                 Location/Qualifiers
source                  1..9
                        mol_type = protein
                        organism = synthetic construct
                        note = MAGE-A11 9mer
SEQUENCE: 199
HSYVLVTSL                                                           9

SEQ ID NO: 200          moltype = AA  length = 9
FEATURE                 Location/Qualifiers
source                  1..9
                        mol_type = protein
                        organism = synthetic construct
                        note = SSX-1 9mer
SEQUENCE: 200
MTFGRLHRI                                                           9

SEQ ID NO: 201          moltype = AA  length = 9
FEATURE                 Location/Qualifiers
source                  1..9
                        mol_type = protein
                        organism = synthetic construct
                        note = MAGE-A3 9mer
SEQUENCE: 201
ASSSLQLVF                                                           9

SEQ ID NO: 202          moltype = AA  length = 9
FEATURE                 Location/Qualifiers
source                  1..9
                        mol_type = protein
                        organism = synthetic construct
                        note = MAGE-C2 9mer
SEQUENCE: 202
FSTSSSLIL                                                           9

SEQ ID NO: 203          moltype = AA  length = 9
FEATURE                 Location/Qualifiers
source                  1..9
                        mol_type = protein
                        organism = synthetic construct
                        note = MAGE-A3 9mer
SEQUENCE: 203
KVAELVHFL                                                           9

SEQ ID NO: 204          moltype = AA  length = 9
FEATURE                 Location/Qualifiers
source                  1..9
                        mol_type = protein
                        organism = synthetic construct
                        note = MAGE-A11 9mer
```

```
SEQUENCE: 204
AMDAIFGSL                                                   9

SEQ ID NO: 205          moltype = AA  length = 9
FEATURE                 Location/Qualifiers
source                  1..9
                        mol_type = protein
                        organism = synthetic construct
                        note = MAGE-A10 9mer
SEQUENCE: 205
YEDHFPLLF                                                   9

SEQ ID NO: 206          moltype = AA  length = 9
FEATURE                 Location/Qualifiers
source                  1..9
                        mol_type = protein
                        organism = synthetic construct
                        note = MAGE-A11 9mer
SEQUENCE: 206
YAGREHFLF                                                   9

SEQ ID NO: 207          moltype = AA  length = 9
FEATURE                 Location/Qualifiers
source                  1..9
                        mol_type = protein
                        organism = synthetic construct
                        note = MAGE-A1 9mer
SEQUENCE: 207
RALAETSYV                                                   9

SEQ ID NO: 208          moltype = AA  length = 15
FEATURE                 Location/Qualifiers
source                  1..15
                        mol_type = protein
                        organism = synthetic construct
                        note = PRAME 15mer
SEQUENCE: 208
LERLAYLHAR LRELL                                            15

SEQ ID NO: 209          moltype = AA  length = 15
FEATURE                 Location/Qualifiers
source                  1..15
                        mol_type = protein
                        organism = synthetic construct
                        note = PRAME 15mer
SEQUENCE: 209
EDSVFAHPRK LLMQD                                            15

SEQ ID NO: 210          moltype = AA  length = 15
FEATURE                 Location/Qualifiers
source                  1..15
                        mol_type = protein
                        organism = synthetic construct
                        note = MAGE-C115mer
SEQUENCE: 210
RHSQTLKAMV QAWPF                                            15

SEQ ID NO: 211          moltype = AA  length = 15
FEATURE                 Location/Qualifiers
source                  1..15
                        mol_type = protein
                        organism = synthetic construct
                        note = MAGE-C115mer
SEQUENCE: 211
SFSYTLLSLF QSSPE                                            15

SEQ ID NO: 212          moltype = AA  length = 15
FEATURE                 Location/Qualifiers
source                  1..15
                        mol_type = protein
                        organism = synthetic construct
                        note = Survivin 15mer
SEQUENCE: 212
TAKKVRRAIE QLAAM                                            15

SEQ ID NO: 213          moltype = AA  length = 15
FEATURE                 Location/Qualifiers
```

```
source                  1..15
                        mol_type = protein
                        organism = synthetic construct
                        note = MAGE-C115mer
SEQUENCE: 213
SPSFSSTLVS LFQSS                                                           15

SEQ ID NO: 214          moltype = AA  length = 15
FEATURE                 Location/Qualifiers
source                  1..15
                        mol_type = protein
                        organism = synthetic construct
                        note = MAGE-A215mer
SEQUENCE: 214
SSFSTTINYT LWRQS                                                           15

SEQ ID NO: 215          moltype = AA  length = 15
FEATURE                 Location/Qualifiers
source                  1..15
                        mol_type = protein
                        organism = synthetic construct
                        note = MAGE-A12 15mer
SEQUENCE: 215
QVALSRKMAE LVHFL                                                           15

SEQ ID NO: 216          moltype = AA  length = 15
FEATURE                 Location/Qualifiers
source                  1..15
                        mol_type = protein
                        organism = synthetic construct
                        note = MAGE-C115mer
SEQUENCE: 216
DDSYVFVNTL DLTSE                                                           15

SEQ ID NO: 217          moltype = AA  length = 15
FEATURE                 Location/Qualifiers
source                  1..15
                        mol_type = protein
                        organism = synthetic construct
                        note = MAGE-C115mer
SEQUENCE: 217
FSYTLASLLQ SSHES                                                           15

SEQ ID NO: 218          moltype = AA  length = 15
FEATURE                 Location/Qualifiers
source                  1..15
                        mol_type = protein
                        organism = synthetic construct
                        note = PRAME 15mer
SEQUENCE: 218
KEEQYIAQFT SQFLS                                                           15

SEQ ID NO: 219          moltype = AA  length = 15
FEATURE                 Location/Qualifiers
source                  1..15
                        mol_type = protein
                        organism = synthetic construct
                        note = MAGE-C115mer
SEQUENCE: 219
QIPMTSSFSS TLLSI                                                           15

SEQ ID NO: 220          moltype = AA  length = 15
FEATURE                 Location/Qualifiers
source                  1..15
                        mol_type = protein
                        organism = synthetic construct
                        note = PRAME 15mer
SEQUENCE: 220
DQLLRHVMNP LETLS                                                           15

SEQ ID NO: 221          moltype = AA  length = 15
FEATURE                 Location/Qualifiers
source                  1..15
                        mol_type = protein
                        organism = synthetic construct
                        note = Ny-ESO-1 15mer
SEQUENCE: 221
RGPESRLLEF YLAMP                                                           15
```

-continued

```
SEQ ID NO: 222          moltype = AA  length = 15
FEATURE                 Location/Qualifiers
source                  1..15
                        mol_type = protein
                        organism = synthetic construct
                        note = MAGE-C2 15mer
SEQUENCE: 222
MASESLSVMS SNVSF                                                       15

SEQ ID NO: 223          moltype = AA  length = 15
FEATURE                 Location/Qualifiers
source                  1..15
                        mol_type = protein
                        organism = synthetic construct
                        note = MAGE-C2 15mer
SEQUENCE: 223
REHFVYGEPR ELLTK                                                       15

SEQ ID NO: 224          moltype = AA  length = 15
FEATURE                 Location/Qualifiers
source                  1..15
                        mol_type = protein
                        organism = synthetic construct
                        note = MAGE-A6 15mer
SEQUENCE: 224
QYFVQENYLE YRQVP                                                       15

SEQ ID NO: 225          moltype = AA  length = 15
FEATURE                 Location/Qualifiers
source                  1..15
                        mol_type = protein
                        organism = synthetic construct
                        note = BORIS 15mer
SEQUENCE: 225
MFTSSRMSSF NRHMK                                                       15

SEQ ID NO: 226          moltype = AA  length = 15
FEATURE                 Location/Qualifiers
source                  1..15
                        mol_type = protein
                        organism = synthetic construct
                        note = LAGE-115mer
SEQUENCE: 226
DFTVSGNLLF MSVRD                                                       15

SEQ ID NO: 227          moltype = AA  length = 15
FEATURE                 Location/Qualifiers
source                  1..15
                        mol_type = protein
                        organism = synthetic construct
                        note = MAGE-A215mer
SEQUENCE: 227
SKASEYLQLV FGIEV                                                       15

SEQ ID NO: 228          moltype = AA  length = 15
FEATURE                 Location/Qualifiers
source                  1..15
                        mol_type = protein
                        organism = synthetic construct
                        note = Survivin 15mer
SEQUENCE: 228
KDHRISTFKN WPFLE                                                       15

SEQ ID NO: 229          moltype = AA  length = 15
FEATURE                 Location/Qualifiers
source                  1..15
                        mol_type = protein
                        organism = synthetic construct
                        note = MAGE-A11 15mer
SEQUENCE: 229
SHSYVLVTSL NLSYD                                                       15

SEQ ID NO: 230          moltype = AA  length = 15
FEATURE                 Location/Qualifiers
source                  1..15
                        mol_type = protein
                        organism = synthetic construct
                        note = SSX-1 15mer
```

```
SEQUENCE: 230
QVEHPQMTFG RLHRI                                                15

SEQ ID NO: 231          moltype = AA  length = 15
FEATURE                 Location/Qualifiers
source                  1..15
                        mol_type = protein
                        organism = synthetic construct
                        note = MAGE-A315mer
SEQUENCE: 231
KASSSLQLVF GIELM                                                15

SEQ ID NO: 232          moltype = AA  length = 15
FEATURE                 Location/Qualifiers
source                  1..15
                        mol_type = protein
                        organism = synthetic construct
                        note = MAGE-C2 15mer
SEQUENCE: 232
SSFSTSSSLI LGGPE                                                15

SEQ ID NO: 233          moltype = AA  length = 15
FEATURE                 Location/Qualifiers
source                  1..15
                        mol_type = protein
                        organism = synthetic construct
                        note = MAGE-A315mer
SEQUENCE: 233
QAALSRKVAE LVHFL                                                15

SEQ ID NO: 234          moltype = AA  length = 15
FEATURE                 Location/Qualifiers
source                  1..15
                        mol_type = protein
                        organism = synthetic construct
                        note = MAGE-A11 15mer
SEQUENCE: 234
SPTAMDAIFG SLSDE                                                15

SEQ ID NO: 235          moltype = AA  length = 15
FEATURE                 Location/Qualifiers
source                  1..15
                        mol_type = protein
                        organism = synthetic construct
                        note = MAGE-A10 15mer
SEQUENCE: 235
RNYEDHFPLL FSEAS                                                15

SEQ ID NO: 236          moltype = AA  length = 15
FEATURE                 Location/Qualifiers
source                  1..15
                        mol_type = protein
                        organism = synthetic construct
                        note = MAGE-A11 15mer
SEQUENCE: 236
YAGREHFLFG EPKRL                                                15

SEQ ID NO: 237          moltype = AA  length = 15
FEATURE                 Location/Qualifiers
source                  1..15
                        mol_type = protein
                        organism = synthetic construct
                        note = MAGE-A115mer
SEQUENCE: 237
PRALAETSYV KVLEY                                                15

SEQ ID NO: 238          moltype = AA  length = 30
FEATURE                 Location/Qualifiers
source                  1..30
                        mol_type = protein
                        organism = synthetic construct
                        note = MC621-01 PRAME/PRAME
SEQUENCE: 238
LERLAYLHAR LRELLDQLLR HVMNPLETLS                                30

SEQ ID NO: 239          moltype = AA  length = 30
FEATURE                 Location/Qualifiers
```

```
source                  1..30
                        mol_type = protein
                        organism = synthetic construct
                        note = MC621-02 Survivin/MAGE-A2
SEQUENCE: 239
TAKKVRRAIE QLAAMEDSVF AHPRKLLMQD                                    30

SEQ ID NO: 240          moltype = AA  length = 30
FEATURE                 Location/Qualifiers
source                  1..30
                        mol_type = protein
                        organism = synthetic construct
                        note = MC621-03 PRAME/MAGE-A3
SEQUENCE: 240
RHSQTLKAMV QAWPFKASSS LQLVFGIELM                                    30

SEQ ID NO: 241          moltype = AA  length = 30
FEATURE                 Location/Qualifiers
source                  1..30
                        mol_type = protein
                        organism = synthetic construct
                        note = MC621-04 MAGE-C1 /MAGE-A2
SEQUENCE: 241
DDSYVFVNTL DLTSESSFST TINYTLWRQS                                    30

SEQ ID NO: 242          moltype = AA  length = 30
FEATURE                 Location/Qualifiers
source                  1..30
                        mol_type = protein
                        organism = synthetic construct
                        note = MC621-05 MAGE-C1 /MAGE-A2
SEQUENCE: 242
SFSYTLLSLF QSSPESKASE YLQLVFGIEV                                    30

SEQ ID NO: 243          moltype = AA  length = 30
FEATURE                 Location/Qualifiers
source                  1..30
                        mol_type = protein
                        organism = synthetic construct
                        note = MC621-06 MAGE-A11/MAGE-C1
SEQUENCE: 243
SHSYVLVTSL NLSYDSPSFS STLVSLFQSS                                    30

SEQ ID NO: 244          moltype = AA  length = 30
FEATURE                 Location/Qualifiers
source                  1..30
                        mol_type = protein
                        organism = synthetic construct
                        note = MC621-07 LAGE-1 /MAGE-C2
SEQUENCE: 244
DFTVSGNLLF MSVRDMASES LSVMSSNVSF                                    30

SEQ ID NO: 245          moltype = AA  length = 30
FEATURE                 Location/Qualifiers
source                  1..30
                        mol_type = protein
                        organism = synthetic construct
                        note = MC621-08 BORIS/MAGE-A12
SEQUENCE: 245
MFTSSRMSSF NRHMKQVALS RKMAELVHFL                                    30

SEQ ID NO: 246          moltype = AA  length = 30
FEATURE                 Location/Qualifiers
source                  1..30
                        mol_type = protein
                        organism = synthetic construct
                        note = MC621-09 MAGE-C2/MAGE-C1
SEQUENCE: 246
SSFSTSSSLI LGGPEFSYTL ASLLQSSHES                                    30

SEQ ID NO: 247          moltype = AA  length = 30
FEATURE                 Location/Qualifiers
source                  1..30
                        mol_type = protein
                        organism = synthetic construct
                        note = MC621-10 Survivin/MAGE-C1
SEQUENCE: 247
KDHRISTFKN WPFLEQIPMT SSFSSTLLSI                                    30
```

-continued

```
SEQ ID NO: 248         moltype = AA  length = 30
FEATURE                Location/Qualifiers
source                 1..30
                       mol_type = protein
                       organism = synthetic construct
                       note = MC621-11 Ny-ESO-1/MAGE-A10
SEQUENCE: 248
RGPESRLLEF YLAMPRNYED HFPLLFSEAS                                    30

SEQ ID NO: 249         moltype = AA  length = 30
FEATURE                Location/Qualifiers
source                 1..30
                       mol_type = protein
                       organism = synthetic construct
                       note = MC621-12 MAGE-A3 /MAGE-A6
SEQUENCE: 249
QAALSRKVAE LVHFLQYFVQ ENYLEYRQVP                                    30

SEQ ID NO: 250         moltype = AA  length = 30
FEATURE                Location/Qualifiers
source                 1..30
                       mol_type = protein
                       organism = synthetic construct
                       note = MC621-13 MAGE-A11 /MAGE-A1
SEQUENCE: 250
SPTAMDAIFG SLSDEPRALA ETSYVKVLEY                                    30

SEQ ID NO: 251         moltype = AA  length = 30
FEATURE                Location/Qualifiers
source                 1..30
                       mol_type = protein
                       organism = synthetic construct
                       note = MC621-14 MAGE-C2/MAGE-A11
SEQUENCE: 251
REHFVYGEPR ELLTKYAGRE HFLFGEPKRL                                    30

SEQ ID NO: 252         moltype = AA  length = 30
FEATURE                Location/Qualifiers
source                 1..30
                       mol_type = protein
                       organism = synthetic construct
                       note = MC621-15 SSX-1/PRAME
SEQUENCE: 252
QVEHPQMTFG RLHRIKEEQY IAQFTSQFLS                                    30

SEQ ID NO: 253         moltype = AA  length = 509
FEATURE                Location/Qualifiers
source                 1..509
                       mol_type = protein
                       organism = Homo sapiens
SEQUENCE: 253
MERRRLWGSI QSRYISMSVW TSPRRLVELA GQSLLKDEAL AIAALELLPR ELFPPLFMAA  60
FDGRHSQTLK AMVQAWPFTC LPLGVLMKGQ HLHLETFKAV LDGLDVLLAQ EVRPRRWKLQ  120
VLDLRKNSHQ DFWTVWSGNR ASLYSFPEPE AAQPMTKKRK VDGLSTEAEQ PFIPVEVLVD  180
LFLKEGACDE LFSYLIEKVK RKKNVLRLCC KKLKIFAMPM QDIKMILKMV QLDSIEDLEV  240
TCTWKLPTLA KFSPYLGQMI NLRRLLLSHI HASSYISPEK EEQYIAQFTS QFLSLQCLQA  300
LYVDSLFFLR GRLDQLLRHV MNPLETLSIT NCRLSEGDVM HLSQSPSVSQ LSVLSLSGVM  360
LTDVSPEPLQ ALLERASATL QDLVFDECGI TDDQLLALLP SLSHCSQLTT LSFYGNSISI  420
SALQSLLQHL IGLSNLTHVL YPVPLESYED IHGTLHLERL AYLHARLREL LCELGRPSMV  480
WLSANPCPHC GDRTFYDPEP ILCPCFMPN                                     509

SEQ ID NO: 254         moltype = AA  length = 314
FEATURE                Location/Qualifiers
source                 1..314
                       mol_type = protein
                       organism = Homo sapiens
SEQUENCE: 254
MPLEQRSQHC KPEEGLEARG EALGLVGAQA PATEEQQTAS SSSTLVEVTL GEVPAADSPS  60
PPHSPQGASS FSTTINYTLW RQSDEGSSNQ EEEGPRMFPD LESEFQAAIS RKMVELVHFL  120
LLKYRAREPV TKAEMLESVL RNCQDFFPVI FSKASEYLQL VFGIEVVEVV PISHLYILVT  180
CLGLSYDGLL GDNQVMPKTG LLIIVLAIIA IEGDCAPEEK IWEELSMLEV FEGREDSVFA  240
HPRKLLMQDL VQENYLEYRQ VPGSDPACYE FLWGPRALIE TSYVKVLHHT LKIGGEPHIS  300
YPPLHERALR EGEE                                                     314

SEQ ID NO: 255         moltype = AA  length = 1142
FEATURE                Location/Qualifiers
source                 1..1142
                       mol_type = protein
                       organism = Homo sapiens
```

```
SEQUENCE: 255
MGDKDMPTAG MPSLLQSSSE SPQSCPEGED SQSPLQIPQS SPESDDTLYP LQSPQSRSEG  60
EDSSDPLQRP PEGKDSQSPL QIPQSSPEGD DTQSPLQNSQ SSPEGKDSLS PLEISQSPPE  120
GEDVQSPLQN PASSFFSSAL LSIFQSSPES TQSPFEGFPQ SVLQIPVSAA SSSTLVSIFQ  180
SSPESTQSPF EGFPQSPLQI PVSRSFSSTL LSIFQSSPER TQSTFEGFAQ SPLQIPVSPS  240
SSSTLLSLFQ SFSERTQSTF EGFAQSSLQI PVSPSFSSTL VSLFQSSPER TQSTFEGFPQ  300
SPLQIPVSSS SSSTLLSLFQ SSPERTHSTF EGFPQSLLQI PMTSSFSSTL LSIFQSSPES  360
AQSTFEGFPQ SPLQIPGSPS FSSTLLSLFQ SSPERTHSTF EGFPQSPLQI PMTSSFSSTL  420
LSILQSSPES AQSAFEGFPQ SPLQIPVSSS FSYTLLSLFQ SSPERTHSTF EGFPQSPLQI  480
PVSSSSSSST LLSLFQSSPE CTQSTFEGFP QSPLQIPQSP PEGENTHSPL QIVPSLPEWE  540
DSLSPHYFPQ SPPQGEDSLS PHYFPQSPPQ GEDSLSPHYF PQSPQGEDSL SPHYFPQSPP  600
QGEDSMSPLY FPQSPLQGEE FQSSLQSPVS ICSSSTPSSL PQSFPESSQS PPEGPVQSPL  660
HSPQSPPEGM HSQSPLQSPE SAPEGEDSLS PLQIPQSPLE GEDSLSSLHF PQSPPEWEDS  720
LSPLHFPQFP PQGEDFQSSL QSPVSICSSS TSLSLPQSFP ESPQSPPEGP AQSPLQRPVS  780
SFFSYTLASL LQSSHESPQS PPEGPAQSPL QSPVSSFPSS TSSSLSQSSP VSSFPSSTSS  840
SLSKSSPESP LQSPVISFSS STSLSPFSEE SSSPVDEYTS SSDTLLESDS LTDSESLIES  900
EPLFTYTLDE KVDELARFLL LKYQVKQPIT KAEMLTNVIS RYTGYFPVIF RKAREFIEIL  960
FGISLREVDP DDSYVFVNTL DLTSEGCLSD EQGMSQNRLL ILILSIIFIK GTYASEEVIW  1020
DVLSGIGVRA GREHFAFGEP RELLTKVWVQ EHYLEYREVP NSSPPRYEFL WGPRAHSEVI  1080
KRKVVEFLAM LKNTVPITFP SSYKDALKDV EERAQAIIDT TDDSTATESA SSSVMSPSFS  1140
SE                                                                1142

SEQ ID NO: 256         moltype = AA  length = 142
FEATURE                Location/Qualifiers
source                 1..142
                       mol_type = protein
                       organism = Homo sapiens
SEQUENCE: 256
MGAPTLPPAW QPFLKDHRIS TFKNWPFLEG CACTPERMAE AGFIHCPTEN EPDLAQCFFC  60
FKELEGWEPD DDPIEEHKKH SSGCAFLSVK KQFEELTLGE FLKLDRERAK NKIAKETNNK  120
KKEFEETAKK VRRAIEQLAA MD                                          142

SEQ ID NO: 257         moltype = AA  length = 314
FEATURE                Location/Qualifiers
source                 1..314
                       mol_type = protein
                       organism = Homo sapiens
SEQUENCE: 257
MPLEQRSQHC KPEEGLEAQG EALGLVGAQA PATEEQETAS SSSTLVEVTL REVPAAESPS  60
PPHSPQGAST LPTTINYTLW SQSDEGSSNE EQEGPSTFPD LETSFQVALS RKMAELVHFL  120
LLKYRAREPF TKAEMLGSVI RNFQDFFPVI FSKASEYLQL VFGIEVVEVV RIGHLYILVT  180
CLGLSYDGLL GDNQIVPKTG LLIIVLAIIA KEGDCAPEEK IWEELSVLEA SDGREDSVFA  240
HPRKLLTQDL VQENYLEYRQ VPGSDPACYE FLWGPRALVE TSYVKVLHHL LKISGGPHIS  300
YPPLHEWAFR EGEE                                                   314

SEQ ID NO: 258         moltype = AA  length = 180
FEATURE                Location/Qualifiers
source                 1..180
                       mol_type = protein
                       organism = Homo sapiens
SEQUENCE: 258
MQAEGRGTGG STGDADGPGG PGIPDGPGGN AGGPGEAGAT GGRGPRGAGA ARASGPGGGA  60
PRGPHGGAAS GLNGCCRCGA RGPESRLLEF YLAMPFATPM EAELARRSLA QDAPPLPVPG  120
VLLKEFTVSG NILTIRLTAA DHRQLQLSIS SCLQQLSLLM WITQCFLPVF LAQPPSGQRR  180

SEQ ID NO: 259         moltype = AA  length = 373
FEATURE                Location/Qualifiers
source                 1..373
                       mol_type = protein
                       organism = Homo sapiens
SEQUENCE: 259
MPPVPGVPFR NVDNDSPTSV ELEDWVDAQH PTDEEEEEAS SASSTLYLVF SPSSFSTSSS  60
LILGGPEEEE VPSGVIPNLT ESIPSSPPQG PPQGPSQSPL SSCCSSFSWS SFSEESSSQK  120
GEDTGTCQGL PDSESSFTYT LDEKVAELVE FLLLKYEAEE PVTEAEMLMI VIKYKDYFPV  180
ILKRAREFME LLFGLALIEV GPDHFCVFAN TVGLTDEGSD DEGMPENSLL IIILSVIFIK  240
GNCASEEVIW EVLNAVGVYA GREHFVYGEP RELLTKVWVQ GHYLEYREVP HSSPPYYEFL  300
WGPRAHSESI KKKVLEFLAK LNNTVPSSFP SWYKDALKDV EERVQATIDT ADDATVMASE  360
SLSVMSSNVS FSE                                                    373

SEQ ID NO: 260         moltype = AA  length = 314
FEATURE                Location/Qualifiers
source                 1..314
                       mol_type = protein
                       organism = Homo sapiens
SEQUENCE: 260
MPLEQRSQHC KPEEGLEARG EALGLVGAQA PATEEQEAAS SSSTLVEVTL GEVPAAESPD  60
PPQSPQGASS LPTTMNYPLW SQSYEDSSNQ EEEGPSTFPD LESEFQAALS RKVAKLVHFL  120
LLKYRAREPV TKAEMLGSVV GNWQYFFPVI FSKASDSLQL VFGIELMEVD PIGHVYIFAT  180
CLGLSYDGLL GDNQIMPKTG FLIIILAIIA KEGDCAPEEK IWEELSVLEV FEGREDSIFG  240
```

-continued

```
DPKKLLTQYF VQENYLEYRQ VPGSDPACYE FLWGPRALIE TSYVKVLHHM VKISGGPRIS  300
YPLLHEWALR EGEE                                                    314

SEQ ID NO: 261          moltype = AA  length = 663
FEATURE                 Location/Qualifiers
source                  1..663
                        mol_type = protein
                        organism = Homo sapiens
SEQUENCE: 261
MAATEISVLS EQFTKIKELE LMPEKGLKEE EKDGVCREKD HRSPSELEAE RTSGAFQDSV  60
LEEEVELVLA PSEESEKYIL TLQTVHFTSE AVELQDMSLL SIQQQEGVQV VVQQPGPGLL  120
WLEEGPRQSL QQCVAISIQQ ELYSPQEMEV LQFHALEENV MVASEDSKLA VSLAETTGLI  180
KLEEEQEKNQ LLAERTKEQL FFVETMSGDE RSDEIVLTVS NSNVEEQEDQ PTAGQADAEK  240
AKSTKNQRKT KGAKGTFHCD VCMFTSSRMS SFNRHMKTHT SEKPHLCHLC LKTFRTVTLL  300
RNHVNTHTGT RPYKCNDCNM AFVTSGELVR HRRYKHTHEK PFKCSMCKYA SVEASKLKRH  360
VRSHTGERPF QCCQCSYASR DTYKLKRHMR THSGEKPYEC HICHTRFTQS GTMKIHILQK  420
HGENVPKYQC PHCATIIARK SDLRVHMRNL HAYSAAELKC RYCSAVFHER YALIQHQKTH  480
KNEKRFKCKH CSYACKQERH MTAHIRTHTG EKPFTCLSCN KCFRQKQLLN AHFRKYHDAN  540
FIPTVYKCSK CGKGFSRWIN LHRHSEKCGS GEAKSAASGK GRRTRKRKQT ILKEATKGQK  600
EAAKGWKEAA NGDEAAAEEA STTKGEQFPG EMFPVACRET TARVKEEVDE GVTCEMLLNT  660
MDK                                                                663

SEQ ID NO: 262          moltype = AA  length = 210
FEATURE                 Location/Qualifiers
source                  1..210
                        mol_type = protein
                        organism = Homo sapiens
SEQUENCE: 262
MQAEGQGTGG STGDADGPGG PGIPDGPGGN AGGPGEAGAT GGRGPRGAGA ARASGPRGGA  60
PRGPHGGAAS AQDGRCPCGA RRPDSRLLQL HITMPFSSPM EAELVRRILS RDAAPLPRPG  120
AVLKDFTVSG NLLFMSVRDQ DREGAGRMRV VGWGLGSASP EGQKARDLRT PKHKVSEQRP  180
GTPGPPPPEG AQGDGCRGVA FNVMFSAPHI                                   210

SEQ ID NO: 263          moltype = AA  length = 429
FEATURE                 Location/Qualifiers
source                  1..429
                        mol_type = protein
                        organism = Homo sapiens
SEQUENCE: 263
METQFRRGGL GCSPASIKRK KKREDSGDFG LQVSTMFSED DFQSTERAPY GPQLQWSQDL  60
PRVQVFREQA NLEDRSPRRT QRITGGEQVL WGPITQIFPT VRPADLTRVI MPLEQRSQHC  120
KPEEGLQAQE EDLGLVGAQA LQAEEQEAAF FSSTLNVGTL EELPAAESPS PPQSPQEESF  180
SPTAMDAIFG SLSDEGSGSQ EKEGPSTSPD LIDPESFSQD ILHDKIIDLV HLLLRKYRVK  240
GLITKAEMLG SVIKNYEDYF PEIFREASVC MQLLFGIDVK EVDPTSHSYV LVTSLNLSYD  300
GIQCNEQSMP KSGLLIIVLG VIFMEGNCIP EEVMWEVLSI MGVYAGREHF LFGEPKRLLT  360
QNWVQEKYLV YRQVPGTDPA CYEFLWGPRA HAETSKMKVL EYIANANGRD PTSYPSLYED  420
ALREEGEGV                                                          429

SEQ ID NO: 264          moltype = AA  length = 188
FEATURE                 Location/Qualifiers
source                  1..188
                        mol_type = protein
                        organism = Homo sapiens
SEQUENCE: 264
MNGDDTFAKR PRDDAKASEK RSKAFDDIAT YFSKKEWKKM KYSEKISYVY MKRNYKAMTK  60
LGFKVTLPPF MCNKQATDFQ GNDFDNDHNR RIQVEHPQMT FGRLHRIIPK IMPKKPAEDE  120
NDSKGVSEAS GPQNDGKQLH PPGKANISEK INKRSGPKRG KHAWTHRLRE RKQLVIYEEI  180
SDPEEDDE                                                           188

SEQ ID NO: 265          moltype = AA  length = 314
FEATURE                 Location/Qualifiers
source                  1..314
                        mol_type = protein
                        organism = Homo sapiens
SEQUENCE: 265
MPLEQRSQHC KPEEGLEARG EALGLVGAQA PATEEQEAAS SSSTLVEVTL GEVPAAESPD  60
PPQSPQGASS LPTTMNYPLW SQSYEDSSNQ EEEGPSTFPD LESEFQAALS RKVAELVHFL  120
LLKYRAREPV TKAEMLGSVV GNWQYFFPVI FSKASSSLQL VFGIELMEVD PIGHLYIFAT  180
CLGLSYDGLL GDNQIMPKAG LLIIVLAIIA REGDCAPEEK IWEELSVLEV FEGREDSILG  240
DPKKLLTQHF VQENYLEYRQ VPGSDPACYE FLWGPRALVE TSYVKVLHHM VKISGGPHIS  300
YPPLHEWVLR EGEE                                                    314

SEQ ID NO: 266          moltype = AA  length = 369
FEATURE                 Location/Qualifiers
source                  1..369
                        mol_type = protein
                        organism = Homo sapiens
```

-continued

```
SEQUENCE: 266
MPRAPKRQRC MPEEDLQSQS ETQGLEGAQA PLAVEEDASS STSTSSSFPS SFPSSSSSSS  60
SSCYPLIPST PEEVSADDET PNPPQSAQIA CSSPSVVASL PLDQSDEGSS SQKEESPSTL  120
QVLPDSESLP RSEIDEKVTD LVQFLLFKYQ MKEPITKAEI LESVIRNYED HFPLLFSEAS  180
ECMLLVFGID VKEVDPTGHS FVLVTSLGLT YDGMLSDVQS MPKTGILILI LSIIFIEGYC  240
TPEEVIWEAL NMMGLYDGME HLIYGEPRKL LTQDWVQENY LEYRQVPGSD PARYEFLWGP  300
RAHAEIRKMS LLKFLAKVNG SDPRSFPLWY EEALKDEEER AQDRIATTDD TTAMASASSS  360
ATGSFSYPE                                                         369

SEQ ID NO: 267         moltype = AA  length = 309
FEATURE                Location/Qualifiers
source                 1..309
                       mol_type = protein
                       organism = Homo sapiens
SEQUENCE: 267
MSLEQRSLHC KPEEALEAQQ EALGLVCVQA ATSSSSPLVL GTLEEVPTAG STDPPQSPQG  60
ASAFPTTINF TRQRQPSEGS SSREEEGPST SCILESLFRA VITKKVADLV GFLLLKYRAR  120
EPVTKAEMLE SVIKNYKHCF PEIFGKASES LQLVFGIDVK EADPTGHSYV LVTCLGLSYD  180
GLLGDNQIMP KTGFLIIVLV MIAMEGGHAP EEEIWEELSV MEVYDGREHS AYGEPRKLLT  240
QDLVQEKYLE YRQVPDSDPA RYEFLWGPRA LAETSYVKVL EYVIKVSARV RFFFPSLREA  300
ALREEEEGV                                                         309

SEQ ID NO: 268         moltype = AA  length = 9
FEATURE                Location/Qualifiers
source                 1..9
                       mol_type = protein
                       organism = synthetic construct
                       note = PIWIL2 9mer
SEQUENCE: 268
FVASINLTL                                                         9

SEQ ID NO: 269         moltype = AA  length = 9
FEATURE                Location/Qualifiers
source                 1..9
                       mol_type = protein
                       organism = synthetic construct
                       note = PIWIL2 9mer
SEQUENCE: 269
FYDPTSAMV                                                         9

SEQ ID NO: 270         moltype = AA  length = 9
FEATURE                Location/Qualifiers
source                 1..9
                       mol_type = protein
                       organism = synthetic construct
                       note = PIWIL2 9mer
SEQUENCE: 270
FQMPHQEIV                                                         9

SEQ ID NO: 271         moltype = AA  length = 9
FEATURE                Location/Qualifiers
source                 1..9
                       mol_type = protein
                       organism = synthetic construct
                       note = CTAGE1 9mer
SEQUENCE: 271
FLLTSFPTF                                                         9

SEQ ID NO: 272         moltype = AA  length = 9
FEATURE                Location/Qualifiers
source                 1..9
                       mol_type = protein
                       organism = synthetic construct
                       note = MAGE-A9 9mer
SEQUENCE: 272
FMFQEALKL                                                         9

SEQ ID NO: 273         moltype = AA  length = 9
FEATURE                Location/Qualifiers
source                 1..9
                       mol_type = protein
                       organism = synthetic construct
                       note = EpCAM 9mer
SEQUENCE: 273
RTYWIIIEL                                                         9

SEQ ID NO: 274         moltype = AA  length = 9
FEATURE                Location/Qualifiers
```

```
source                  1..9
                        mol_type = protein
                        organism = synthetic construct
                        note = OY-TES-1 9mer
SEQUENCE: 274
MIMENIQEL                                                               9

SEQ ID NO: 275          moltype = AA  length = 9
FEATURE                 Location/Qualifiers
source                  1..9
                        mol_type = protein
                        organism = synthetic construct
                        note = MAGE-A9 9mer
SEQUENCE: 275
SSISVYYTL                                                               9

SEQ ID NO: 276          moltype = AA  length = 9
FEATURE                 Location/Qualifiers
source                  1..9
                        mol_type = protein
                        organism = synthetic construct
                        note = NY-ESO-1 9mer
SEQUENCE: 276
RLLEFYLAM                                                               9

SEQ ID NO: 277          moltype = AA  length = 9
FEATURE                 Location/Qualifiers
source                  1..9
                        mol_type = protein
                        organism = synthetic construct
                        note = SURVIVIN 9mer
SEQUENCE: 277
RAIEQLAAM                                                               9

SEQ ID NO: 278          moltype = AA  length = 9
FEATURE                 Location/Qualifiers
source                  1..9
                        mol_type = protein
                        organism = synthetic construct
                        note = MAGE-C1 9mer
SEQUENCE: 278
FSYTLLSLF                                                               9

SEQ ID NO: 279          moltype = AA  length = 9
FEATURE                 Location/Qualifiers
source                  1..9
                        mol_type = protein
                        organism = synthetic construct
                        note = CTAGE1 9mer
SEQUENCE: 279
FLFGGNNFI                                                               9

SEQ ID NO: 280          moltype = AA  length = 9
FEATURE                 Location/Qualifiers
source                  1..9
                        mol_type = protein
                        organism = synthetic construct
                        note = EpCAM 9mer
SEQUENCE: 280
YVDEKAPEF                                                               9

SEQ ID NO: 281          moltype = AA  length = 9
FEATURE                 Location/Qualifiers
source                  1..9
                        mol_type = protein
                        organism = synthetic construct
                        note = MAGE-A2 9mer
SEQUENCE: 281
FAHPRKLLM                                                               9

SEQ ID NO: 282          moltype = AA  length = 9
FEATURE                 Location/Qualifiers
source                  1..9
                        mol_type = protein
                        organism = synthetic construct
                        note = MAGE-C1 9mer
SEQUENCE: 282
YVFVNTLDL                                                               9
```

```
SEQ ID NO: 283          moltype = AA  length = 9
FEATURE                 Location/Qualifiers
source                  1..9
                        mol_type = protein
                        organism = synthetic construct
                        note = LAGE-1 9mer
SEQUENCE: 283
FTVSGNLLF                                                                    9

SEQ ID NO: 284          moltype = AA  length = 9
FEATURE                 Location/Qualifiers
source                  1..9
                        mol_type = protein
                        organism = synthetic construct
                        note = MAGE-A3 9mer
SEQUENCE: 284
FVQENYLEY                                                                    9

SEQ ID NO: 285          moltype = AA  length = 9
FEATURE                 Location/Qualifiers
source                  1..9
                        mol_type = protein
                        organism = synthetic construct
                        note = MAGE-A8 9mer
SEQUENCE: 285
AIWEALSVM                                                                    9

SEQ ID NO: 286          moltype = AA  length = 9
FEATURE                 Location/Qualifiers
source                  1..9
                        mol_type = protein
                        organism = synthetic construct
                        note = HAGE 9mer
SEQUENCE: 286
LQMSNFVNL                                                                    9

SEQ ID NO: 287          moltype = AA  length = 9
FEATURE                 Location/Qualifiers
source                  1..9
                        mol_type = protein
                        organism = synthetic construct
                        note = MAGE-A8 9mer
SEQUENCE: 287
KVAELVRFL                                                                    9

SEQ ID NO: 288          moltype = AA  length = 9
FEATURE                 Location/Qualifiers
source                  1..9
                        mol_type = protein
                        organism = synthetic construct
                        note = MAGE-A3 9mer
SEQUENCE: 288
ASSSLQLVF                                                                    9

SEQ ID NO: 289          moltype = AA  length = 9
FEATURE                 Location/Qualifiers
source                  1..9
                        mol_type = protein
                        organism = synthetic construct
                        note = SURVIVIN 9mer
SEQUENCE: 289
STFKNWPFL                                                                    9

SEQ ID NO: 290          moltype = AA  length = 9
FEATURE                 Location/Qualifiers
source                  1..9
                        mol_type = protein
                        organism = synthetic construct
                        note = MAGE-A2 9mer
SEQUENCE: 290
FSTTINYTL                                                                    9

SEQ ID NO: 291          moltype = AA  length = 9
FEATURE                 Location/Qualifiers
source                  1..9
                        mol_type = protein
                        organism = synthetic construct
                        note = MAGE-A3 9mer
```

-continued

```
SEQUENCE: 291
KVAELVHFL                                                    9

SEQ ID NO: 292          moltype = AA  length = 9
FEATURE                 Location/Qualifiers
source                  1..9
                        mol_type = protein
                        organism = synthetic construct
                        note = MAGE-A1 9mer
SEQUENCE: 292
TSYVKVLEY                                                    9

SEQ ID NO: 293          moltype = AA  length = 9
FEATURE                 Location/Qualifiers
source                  1..9
                        mol_type = protein
                        organism = synthetic construct
                        note = MAGE-C2 9mer
SEQUENCE: 293
MASESLSVM                                                    9

SEQ ID NO: 294          moltype = AA  length = 9
FEATURE                 Location/Qualifiers
source                  1..9
                        mol_type = protein
                        organism = synthetic construct
                        note = MAGE-C2 9mer
SEQUENCE: 294
FVYGEPREL                                                    9

SEQ ID NO: 295          moltype = AA  length = 9
FEATURE                 Location/Qualifiers
source                  1..9
                        mol_type = protein
                        organism = synthetic construct
                        note = MAGE-A10 9mer
SEQUENCE: 295
YEDHFPLLF                                                    9

SEQ ID NO: 296          moltype = AA  length = 9
FEATURE                 Location/Qualifiers
source                  1..9
                        mol_type = protein
                        organism = synthetic construct
                        note = MAGE-A12 9mer
SEQUENCE: 296
KASEYLQLV                                                    9

SEQ ID NO: 297          moltype = AA  length = 9
FEATURE                 Location/Qualifiers
source                  1..9
                        mol_type = protein
                        organism = synthetic construct
                        note = LAGE-1 9mer
SEQUENCE: 297
LQLHITMPF                                                    9

SEQ ID NO: 298          moltype = AA  length = 15
FEATURE                 Location/Qualifiers
source                  1..15
                        mol_type = protein
                        organism = synthetic construct
                        note = PIWIL2 15mer
SEQUENCE: 298
FVASINLTLT KWYSR                                             15

SEQ ID NO: 299          moltype = AA  length = 15
FEATURE                 Location/Qualifiers
source                  1..15
                        mol_type = protein
                        organism = synthetic construct
                        note = PIWIL2 15mer
SEQUENCE: 299
RNFYDPTSAM VLQQH                                             15

SEQ ID NO: 300          moltype = AA  length = 15
FEATURE                 Location/Qualifiers
```

```
source                  1..15
                        mol_type = protein
                        organism = synthetic construct
                        note = PIWIL2 15mer
SEQUENCE: 300
YSRVVFQMPH QEIVD                                                          15

SEQ ID NO: 301          moltype = AA  length = 15
FEATURE                 Location/Qualifiers
source                  1..15
                        mol_type = protein
                        organism = synthetic construct
                        note = CTAGE1 15mer
SEQUENCE: 301
QNYIDQFLLT SFPTF                                                          15

SEQ ID NO: 302          moltype = AA  length = 15
FEATURE                 Location/Qualifiers
source                  1..15
                        mol_type = protein
                        organism = synthetic construct
                        note = MAGE-A9 15mer
SEQUENCE: 302
EFMFQEALKL KVAEL                                                          15

SEQ ID NO: 303          moltype = AA  length = 15
FEATURE                 Location/Qualifiers
source                  1..15
                        mol_type = protein
                        organism = synthetic construct
                        note = EpCAM 15mer
SEQUENCE: 303
RTYWIIIELK HKARE                                                          15

SEQ ID NO: 304          moltype = AA  length = 15
FEATURE                 Location/Qualifiers
source                  1..15
                        mol_type = protein
                        organism = synthetic construct
                        note = OY-TES-1 15mer
SEQUENCE: 304
ESTPMIMENI QELIR                                                          15

SEQ ID NO: 305          moltype = AA  length = 15
FEATURE                 Location/Qualifiers
source                  1..15
                        mol_type = protein
                        organism = synthetic construct
                        note = MAGE-A9 15mer
SEQUENCE: 305
SSISVYYTLW SQFDE                                                          15

SEQ ID NO: 306          moltype = AA  length = 15
FEATURE                 Location/Qualifiers
source                  1..15
                        mol_type = protein
                        organism = synthetic construct
                        note = NY-ESO-1 15mer
SEQUENCE: 306
RGPESRLLEF YLAMP                                                          15

SEQ ID NO: 307          moltype = AA  length = 15
FEATURE                 Location/Qualifiers
source                  1..15
                        mol_type = protein
                        organism = synthetic construct
                        note = SURVIVIN 15mer
SEQUENCE: 307
AKKVRRAIEQ LAAMD                                                          15

SEQ ID NO: 308          moltype = AA  length = 15
FEATURE                 Location/Qualifiers
source                  1..15
                        mol_type = protein
                        organism = synthetic construct
                        note = MAGE-C1 15mer
SEQUENCE: 308
SSFSYTLLSL FQSSP                                                          15
```

-continued

```
SEQ ID NO: 309          moltype = AA  length = 15
FEATURE                 Location/Qualifiers
source                  1..15
                        mol_type = protein
                        organism = synthetic construct
                        note = CTAGE1 15mer
SEQUENCE: 309
SFVLFLFGGN NFIQN                                                   15

SEQ ID NO: 310          moltype = AA  length = 15
FEATURE                 Location/Qualifiers
source                  1..15
                        mol_type = protein
                        organism = synthetic construct
                        note = EpCAM 15mer
SEQUENCE: 310
QTLIYYVDEK APEFS                                                   15

SEQ ID NO: 311          moltype = AA  length = 15
FEATURE                 Location/Qualifiers
source                  1..15
                        mol_type = protein
                        organism = synthetic construct
                        note = MAGE-A2 15mer
SEQUENCE: 311
REDSVFAHPR KLLMQ                                                   15

SEQ ID NO: 312          moltype = AA  length = 15
FEATURE                 Location/Qualifiers
source                  1..15
                        mol_type = protein
                        organism = synthetic construct
                        note = MAGE-C1 15mer
SEQUENCE: 312
DDSYVFVNTL DLTSE                                                   15

SEQ ID NO: 313          moltype = AA  length = 15
FEATURE                 Location/Qualifiers
source                  1..15
                        mol_type = protein
                        organism = synthetic construct
                        note = LAGE-1 15mer
SEQUENCE: 313
DFTVSGNLLF MSVRD                                                   15

SEQ ID NO: 314          moltype = AA  length = 15
FEATURE                 Location/Qualifiers
source                  1..15
                        mol_type = protein
                        organism = synthetic construct
                        note = MAGE-A3 15mer
SEQUENCE: 314
LTQHFVQENY LEYRQ                                                   15

SEQ ID NO: 315          moltype = AA  length = 15
FEATURE                 Location/Qualifiers
source                  1..15
                        mol_type = protein
                        organism = synthetic construct
                        note = MAGE-A8 15mer
SEQUENCE: 315
EEAIWEALSV MGLYD                                                   15

SEQ ID NO: 316          moltype = AA  length = 15
FEATURE                 Location/Qualifiers
source                  1..15
                        mol_type = protein
                        organism = synthetic construct
                        note = HAGE 15mer
SEQUENCE: 316
NDLQMSNFVN LKNIT                                                   15

SEQ ID NO: 317          moltype = AA  length = 15
FEATURE                 Location/Qualifiers
source                  1..15
                        mol_type = protein
                        organism = synthetic construct
                        note = MAGE-A8 15mer
```

-continued

```
SEQUENCE: 317
EKVAELVRFL LRKYQ                                                    15

SEQ ID NO: 318          moltype = AA  length = 15
FEATURE                 Location/Qualifiers
source                  1..15
                        mol_type = protein
                        organism = synthetic construct
                        note = MAGE-A3 15mer
SEQUENCE: 318
KASSSLQLVF GIELM                                                    15

SEQ ID NO: 319          moltype = AA  length = 15
FEATURE                 Location/Qualifiers
source                  1..15
                        mol_type = protein
                        organism = synthetic construct
                        note = SURVIVIN 15mer
SEQUENCE: 319
KDHRISTFKN WPFLE                                                    15

SEQ ID NO: 320          moltype = AA  length = 15
FEATURE                 Location/Qualifiers
source                  1..15
                        mol_type = protein
                        organism = synthetic construct
                        note = MAGE-A2 15mer
SEQUENCE: 320
SSFSTTINYT LWRQS                                                    15

SEQ ID NO: 321          moltype = AA  length = 15
FEATURE                 Location/Qualifiers
source                  1..15
                        mol_type = protein
                        organism = synthetic construct
                        note = MAGE-A3 15mer
SEQUENCE: 321
QAALSRKVAE LVHFL                                                    15

SEQ ID NO: 322          moltype = AA  length = 15
FEATURE                 Location/Qualifiers
source                  1..15
                        mol_type = protein
                        organism = synthetic construct
                        note = MAGE-A1 15mer
SEQUENCE: 322
ETSYVKVLEY VIKVS                                                    15

SEQ ID NO: 323          moltype = AA  length = 15
FEATURE                 Location/Qualifiers
source                  1..15
                        mol_type = protein
                        organism = synthetic construct
                        note = MAGE-C2 15mer
SEQUENCE: 323
MASESLSVMS SNVSF                                                    15

SEQ ID NO: 324          moltype = AA  length = 15
FEATURE                 Location/Qualifiers
source                  1..15
                        mol_type = protein
                        organism = synthetic construct
                        note = MAGE-C2 15mer
SEQUENCE: 324
REHFVYGEPR ELLTK                                                    15

SEQ ID NO: 325          moltype = AA  length = 15
FEATURE                 Location/Qualifiers
source                  1..15
                        mol_type = protein
                        organism = synthetic construct
                        note = MAGE-A10 15mer
SEQUENCE: 325
RNYEDHFPLL FSEAS                                                    15
```

```
SEQ ID NO: 326          moltype = AA  length = 15
FEATURE                 Location/Qualifiers
source                  1..15
                        mol_type = protein
                        organism = synthetic construct
                        note = MAGE-A12 15mer
SEQUENCE: 326
KASEYLQLVF GIEVV                                                    15

SEQ ID NO: 327          moltype = AA  length = 15
FEATURE                 Location/Qualifiers
source                  1..15
                        mol_type = protein
                        organism = synthetic construct
                        note = LAGE-1 15mer
SEQUENCE: 327
DSRLLQLHIT MPFSS                                                    15

SEQ ID NO: 328          moltype = AA  length = 30
FEATURE                 Location/Qualifiers
source                  1..30
                        mol_type = protein
                        organism = synthetic construct
                        note = BLV1411-01 MAGE-C1/PIWIL2
SEQUENCE: 328
DDSYVFVNTL DLTSERNFYD PTSAMVLQQH                                    30

SEQ ID NO: 329          moltype = AA  length = 30
FEATURE                 Location/Qualifiers
source                  1..30
                        mol_type = protein
                        organism = synthetic construct
                        note = BLV1411-02 MAGE-A9/OY-TES-1
SEQUENCE: 329
EFMFQEALKL KVAELESTPM IMENIQELIR                                    30

SEQ ID NO: 330          moltype = AA  length = 30
FEATURE                 Location/Qualifiers
source                  1..30
                        mol_type = protein
                        organism = synthetic construct
                        note = BLV1411-03 PIWIL2/MAGE-A1
SEQUENCE: 330
YSRVVFQMPH QEIVDETSYV KVLEYVIKVS                                    30

SEQ ID NO: 331          moltype = AA  length = 30
FEATURE                 Location/Qualifiers
source                  1..30
                        mol_type = protein
                        organism = synthetic construct
                        note = BLV1411-04 CTAGE1/MAGE-A2
SEQUENCE: 331
QNYIDQFLLT SFPTFREDSV FAHPRKLLMQ                                    30

SEQ ID NO: 332          moltype = AA  length = 30
FEATURE                 Location/Qualifiers
source                  1..30
                        mol_type = protein
                        organism = synthetic construct
                        note = BLV1411-05 HAGE/EpCAM
SEQUENCE: 332
NDLQMSNFVN LKNITRTYWI IIELKHKARE                                    30

SEQ ID NO: 333          moltype = AA  length = 30
FEATURE                 Location/Qualifiers
source                  1..30
                        mol_type = protein
                        organism = synthetic construct
                        note = BLV1411-06 MAGE-A9/MAGE-A8
SEQUENCE: 333
SSISVYYTLW SQFDEEKVAE LVRFLLRKYQ                                    30

SEQ ID NO: 334          moltype = AA  length = 30
FEATURE                 Location/Qualifiers
source                  1..30
                        mol_type = protein
                        organism = synthetic construct
                        note = BLV1411-07 NY-ESO-1/MAGE-A10
```

-continued

```
SEQUENCE: 334
RGPESRLLEF YLAMPRNYED HFPLLFSEAS                                    30

SEQ ID NO: 335          moltype = AA  length = 30
FEATURE                 Location/Qualifiers
source                  1..30
                        mol_type = protein
                        organism = synthetic construct
                        note = BLV1411-08 CTAGE1/MAGE-A8
SEQUENCE: 335
SFVLFLFGGN NFIQNEEAIW EALSVMGLYD                                    30

SEQ ID NO: 336          moltype = AA  length = 30
FEATURE                 Location/Qualifiers
source                  1..30
                        mol_type = protein
                        organism = synthetic construct
                        note = BLV1411-09 EpCAM/MAGE-C2
SEQUENCE: 336
QTLIYYVDEK APEFSREHFV YGEPRELLTK                                    30

SEQ ID NO: 337          moltype = AA  length = 30
FEATURE                 Location/Qualifiers
source                  1..30
                        mol_type = protein
                        organism = synthetic construct
                        note = BLV1411-10 MAGE-C1/MAGE-A12
SEQUENCE: 337
SSFSYTLLSL FQSSPKASEY LQLVFGIEVV                                    30

SEQ ID NO: 338          moltype = AA  length = 30
FEATURE                 Location/Qualifiers
source                  1..30
                        mol_type = protein
                        organism = synthetic construct
                        note = BLV1411-11 PIWIL2/LAGE-1
SEQUENCE: 338
FVASINLTLT KWYSRDFTVS GNLLFMSVRD                                    30

SEQ ID NO: 339          moltype = AA  length = 30
FEATURE                 Location/Qualifiers
source                  1..30
                        mol_type = protein
                        organism = synthetic construct
                        note = BLV1411-12 MAGE-A3/MAGE-A3
SEQUENCE: 339
LTQHFVQENY LEYRQKASSS LQLVFGIELM                                    30

SEQ ID NO: 340          moltype = AA  length = 30
FEATURE                 Location/Qualifiers
source                  1..30
                        mol_type = protein
                        organism = synthetic construct
                        note = BLV1411-13 MAGE-A2/LAGE-1
SEQUENCE: 340
SSFSTTINYT LWRQSDSRLL QLHITMPFSS                                    30

SEQ ID NO: 341          moltype = AA  length = 30
FEATURE                 Location/Qualifiers
source                  1..30
                        mol_type = protein
                        organism = synthetic construct
                        note = BLV1411-14 SURVIVIN/MAGE-C2
SEQUENCE: 341
AKKVRRAIEQ LAAMDMASES LSVMSSNVSF                                    30

SEQ ID NO: 342          moltype = AA  length = 30
FEATURE                 Location/Qualifiers
source                  1..30
                        mol_type = protein
                        organism = synthetic construct
                        note = BLV1411-15 MAGE-A3/SURVIVIN
SEQUENCE: 342
QAALSRKVAE LVHFLKDHRI STFKNWPFLE                                    30

SEQ ID NO: 343          moltype = AA  length = 973
FEATURE                 Location/Qualifiers
```

```
source                  1..973
                        mol_type = protein
                        organism = Homo sapiens
SEQUENCE: 343
MDPFRPSFRG QSPIHPSQCQ AVRMPGCWPQ ASKPLDPALG RGAPAGRGHV FGKPEEPSTQ  60
RGPAQRESVG LVSMFRGLGI ETVSKTPLKR EMLPSGRGIL GRGLSANLVR KDREELSPTF  120
WDPKVLAAGD SKMAETSVGW SRTLGRGSSD ASLLPLGRAA GGISREVDKP PCTFSTPSRG  180
PPQLSSPPAL PQSPLHSPDR PLVLTVEHKE KELIVKQGSK GTPQSLGLNL VKIQCHNEAV  240
YQYHVTFSPN VECKSMRFGM LKDHQAVTGN VTAFDGSILY LPVKLQQVLE LKSQRKTDSA  300
EISIKIQMTK ILEPCSDLCI PFYNVVFRRV MKLLDMKLVG RNFYDPTSAM VLQQHRLQIW  360
PGYAASIRRT DGGLFLLADV SHKVIRNDCV LDVMHAIYQQ NKEHFQDECT KLLVGNIVIT  420
RYNNRTYRID DVDWNKTPKD SFTMSDGKEI TFLEYYSKNY GITVKEEDQP LLIHRPSERQ  480
DNHGMLLKGE ILLLPELSFM TGIPEKMKKD FRAMKDLAQQ INLSPKQHHS ALECLLQRIA  540
KNEAATNELM RWGLRLQKDV HKIEGRVLPM ERINLKNTSF ITSQELNWVK EVTRDPSILT  600
IPMHFWALFY PKRAMDQARE LVNMLEKIAG PIGMRMSPPA WVELKDDRIE TYVRTIQSTL  660
GAEGKIQMVV CIIMGPRDDL YGAIKKLCCV QSPVPSQVVN VRTIGQPTRL RSVAQKILLQ  720
INCKLGGELW GVDIPLKQLM VIGMDVYHDP SRGMRSVVGF VASINLTLTK WYSRVVFQMP  780
HQEIVDSLKL CLVGSLKKFY EVNHCLPEKI VVYRDGVSDG QLKTVANYEI PQLQKCFEAF  840
ENYQPKMVVF VVQKKISTNL YLAAPQNFVT PTPGTVVDHT ITSCEWVDFY LLAHHVRQGC  900
GIPTHYVCVL NTANLSPDHM QRLTFKLCHM YWNWPGTIRV PAPCKYAHKL AFLSGHILHH  960
EPAIQLCENL FFL                                                   973

SEQ ID NO: 344          moltype = AA  length = 74
FEATURE                 Location/Qualifiers
source                  1..74
                        mol_type = protein
                        organism = Homo sapiens
SEQUENCE: 344
MFVIISLHNC VVISFVLFLF GGNNFIQNFY LPQNYIDQFL LTSFPTFTSV GVLIVLVLCS  60
AFLLLWQGEG VNLR                                                  74

SEQ ID NO: 345          moltype = AA  length = 315
FEATURE                 Location/Qualifiers
source                  1..315
                        mol_type = protein
                        organism = Homo sapiens
SEQUENCE: 345
MSLEQRSPHC KPDEDLEAQG EDLGLMGAQE PTGEEEETTS SSDSKEEEVS AAGSSSPPQS  60
PQGGASSSIS VYYTLWSQFD EGSSSQEEEE PSSSVDPAQL EFMFQEALKL KVAELVHFLL  120
HKYRVKEPVT KAEMLESVIK NYKRYFPVIF GKASEFMQVI FGTDVKEVDP AGHSYILVTA  180
LGLSCDSMLG DGHSMPKAAL LIIVLGVILT KDNCAPEEVI WEALSVMGVY VGKEHMFYGE  240
PRKLLTQDWV QENYLEYRQV PGSDPAHYEF LWGSKAHAET SYEKVINYLV MLNAREPICY  300
PSLYEEVLGE EQEGV                                                 315

SEQ ID NO: 346          moltype = AA  length = 314
FEATURE                 Location/Qualifiers
source                  1..314
                        mol_type = protein
                        organism = Homo sapiens
SEQUENCE: 346
MAPPQVLAFG LLLAAATATF AAAQEECVCE NYKLAVNCFV NNNRQCQCTS VGAQNTVICS  60
KLAAKCLVMK AEMNGSKLGR RAKPEGALQN NDGLYDPDCD ESGLFKAKQC NGTSMCWCVN  120
TAGVRRTDKD TEITCSERVR TYWIIIELKH KAREKPYDSK SLRTALQKEI TTRYQLDPKF  180
ITSILYENNV ITIDLVQNSS QKTQNDVDIA DVAYYFEKDV KGESLFHSKK MDLTVNGEQL  240
DLDPGQTLIY YVDEKAPEFS MQGLKAGVIA VIVVVVIAVV AGIVVLVISR KKRMAKYEKA  300
EIKEMGEMHR ELNA                                                  314

SEQ ID NO: 347          moltype = AA  length = 543
FEATURE                 Location/Qualifiers
source                  1..543
                        mol_type = protein
                        organism = Homo sapiens
SEQUENCE: 347
MRKPAAGFLP SLLKVLLLPL APAAAQDSTQ ASTPGSPLSP TEYERFFALL TPTWKAETTC  60
RLRATHGCRN PTLVQLDQYE NHGLVPDGAV CSNLPYASWF ESFCQFTHYR CSNHVYYAKR  120
VLCSQPVSIL SPNTLKEIEA SAEVSPTTMT SPISPHFTVT ERQTFQPWPE RLSNNVEELL  180
QSSLSLGGQE QAPEHKQEQG VEHRQEPTQE HKQEEGQKQE EQEEEQEEEG KQEEGQGTKE  240
GREAVSQLQT DSEPKFHSES LSSNPSSFAP RVREVESTPM IMENIQELIR SAQEIDEMNE  300
IYDENSYWRN QNPGSLLQLP HTEALLVLCY SIVENTCIIT PTAKAWKYME EEILGFGKSV  360
CDSLGRRHMS TCALCDFCSL KLEQCHSEAS LQRQQCDTSH KTPFVSPLLA SQSLSIGNQV  420
GSPESGRFYG LDLYGGLHMD FWCARLATKG CEDVRVSGWL QTEFLSFQDG DFPTKICDTD  480
YIQYPNYCSF KSQQCLMRNR NRKVSRMRCL QNETYSALSP GKSEDVVLRW SQEFSTLTLG  540
QFG                                                              543

SEQ ID NO: 348          moltype = AA  length = 180
FEATURE                 Location/Qualifiers
source                  1..180
                        mol_type = protein
                        organism = Homo sapiens
```

SEQUENCE: 348
MQAEGRGTGG STGDADGPGG PGIPDGPGGN AGGPGEAGAT GGRGPRGAGA ARASGPGGGA 60
PRGPHGGAAS GLNGCCRCGA RGPESRLLEF YLAMPFATPM EAELARRSLA QDAPPLPVPG 120
VLLKEFTVSG NILTIRLTAA DHRQLQLSIS SCLQQLSLLM WITQCFLPVF LAQPPSGQRR 180

SEQ ID NO: 349 moltype = AA length = 142
FEATURE Location/Qualifiers
source 1..142
mol_type = protein
organism = Homo sapiens
SEQUENCE: 349
MGAPTLPPAW QPFLKDHRIS TFKNWPFLEG CACTPERMAE AGFIHCPTEN EPDLAQCFFC 60
FKELEGWEPD DDPIEEHKKH SSGCAFLSVK KQFEELTLGE FLKLDRERAK NKIAKETNNK 120
KKEFEETAKK VRRAIEQLAA MD 142

SEQ ID NO: 350 moltype = AA length = 1142
FEATURE Location/Qualifiers
source 1..1142
mol_type = protein
organism = Homo sapiens
SEQUENCE: 350
MGDKDMPTAG MPSLLQSSSE SPQSCPEGED SQSPLQIPQS SPESDDTLYP LQSPQSRSEG 60
EDSSDPLQRP PEGKDSQSPL QIPQSSPEGD DTQSPLQNSQ SSPEGKDSLS PLEISQSPPE 120
GEDVQSPLQN PASSFFSSAL LSIFQSSPES TQSPFEGFPQ SVLQIPVSAA SSSTLVSIFQ 180
SSPESTQSPF EGFPQSPLQI PVSRSFSSTL LSIFQSSPER TQSTFEGFAQ SPLQIPVSPS 240
SSSTLLSLFQ SFSERTQSTF EGFAQSSLQI PVSPSFSSTL VSLFQSSPER TQSTFEGFPQ 300
SPLQIPVSSS SSSTLLSLFQ SSPERTHSTF EGFPQSLLQI PMTSSFSSTL LSIFQSSPES 360
AQSTFEGFPQ SPLQIPGSPS FSSTLLSLFQ SSPERTHSTF EGFPQSPLQI PMTSSFSSTL 420
LSILQSSPES AQSAFEGFPQ SPLQIPVSSS FSYTLLSLFQ SSPERTHSTF EGFPQSPLQI 480
PVSSSSSSST LLSLFQSSPE CTQSTFEGFP QSPLQIPQSP PEGENTHSPL QIVPSLPEWE 540
DSLSPHYFPQ SPPQGEDSLS PHYFPQSPPQ GEDSLSPHYF PQSPQGEDSL SPHYFPQSPP 600
QGEDSMSPLY FPQSPLQGEE FQSSLQSPVS ICSSSTPSSL PQSFPESSQS PPEGPVQSPL 660
HSPQSPPEGM HSQSPLQSPE SAPEGEDSLS PLQIPQSPLE GEDSLSSLHF PQSPPEWEDS 720
LSPLHFPQFP PQGEDFQSSL QSPVSICSSS TSLSLPQSFP ESPQSPPEGP AQSPLQRPVS 780
SFFSYTLASL LQSSHESPQS PPEGPAQSPL QSPVSSFPSS TSSSLSQSSP VSSFPSSTSS 840
SLSKSSPESP LQSPVISFSS STSLSPFSEE SSSPVDEYTS SSDTLLESDS LTDSESLIES 900
EPLFTYTLDE KVDELARFLL LKYQVKQPIT KAEMLTNVIS RYTGYFPVIF RKAREFIEIL 960
FGISLREVDP DDSYVFVNTL DLTSEGCLSD EQGMSQNRLL ILILSIIFIK GTYASEEVIW 1020
DVLSGIGVRA GREHFAFGEP RELLTKVWVQ EHYLEYREVP NSSPPRYEFL WGPRAHSEVI 1080
KRKVVEFLAM LKNTVPITFP SSYKDALKDV EERAQAIIDT TDDSTATESA SSSVMSPSFS 1140
SE 1142

SEQ ID NO: 351 moltype = AA length = 314
FEATURE Location/Qualifiers
source 1..314
mol_type = protein
organism = Homo sapiens
SEQUENCE: 351
MPLEQRSQHC KPEEGLEARG EALGLVGAQA PATEEQQTAS SSSTLVEVTL GEVPAADSPS 60
PPHSPQGASS FSTTINYTLW RQSDEGSSNQ EEEGPRMFPD LESEFQAAIS RKMVELVHFL 120
LLKYRAREPV TKAEMLESVL RNCQDFFPVI FSKASEYLQL VFGIEVVEVV PISHLYILVT 180
CLGLSYDGLL GDNQVMPKTG LLIIVLAIIA IEGDCAPEEK IWEELSMLEV FEGREDSVFA 240
HPRKLLMQDL VQENYLEYRQ VPGSDPACYE FLWGPRALIE TSYVKVLHHT LKIGGEPHIS 300
YPPLHERALR EGEE 314

SEQ ID NO: 352 moltype = AA length = 210
FEATURE Location/Qualifiers
source 1..210
mol_type = protein
organism = Homo sapiens
SEQUENCE: 352
MQAEGQGTGG STGDADGPGG PGIPDGPGGN AGGPGEAGAT GGRGPRGAGA ARASGPRGGA 60
PRGPHGGAAS AQDGRCPCGA RRPDSRLLQL HITMPFSSPM EAELVRRILS RDAAPLPRPG 120
AVLKDFTVSG NLLFMSVRDQ DREGAGRMRV VGWGLGSASP EGQKARDLRT PKHKVSEQRP 180
GTPGPPPPEG AQGDGCRGVA FNVMFSAPHI 210

SEQ ID NO: 353 moltype = AA length = 314
FEATURE Location/Qualifiers
source 1..314
mol_type = protein
organism = Homo sapiens
SEQUENCE: 353
MPLEQRSQHC KPEEGLEARG EALGLVGAQA PATEEQEAAS SSSTLVEVTL GEVPAAESPD 60
PPQSPQGASS LPTTMNYPLW SQSYEDSSNQ EEEGPSTFPD LESEFQAALS RKVAELVHFL 120
LLKYRAREPV TKAEMLGSVV GNWQYFFPVI FSKASSSLQL VFGIELMEVD PIGHLYIFAT 180
CLGLSYDGLL GDNQIMPKAG LLIIVLAIIA REGDCAPEEK IWEELSVLEV FEGREDSILG 240
DPKKLLTQHF VQENYLEYRQ VPGSDPACYE FLWGPRALVE TSYVKVLHHM VKISGGPHIS 300
YPPLHEWVLR EGEE 314

-continued

```
SEQ ID NO: 354         moltype = AA  length = 318
FEATURE                Location/Qualifiers
source                 1..318
                       mol_type = protein
                       organism = Homo sapiens
SEQUENCE: 354
MLLGQKSQRY KAEEGLQAQG EAPGLMDVQI PTAEEQKAAS SSSTLIMGTL EEVTDSGSPS  60
PPQSPEGASS SLTVTDSTLW SQSDEGSSSN EEEGPSTSPD PAHLESLFRE ALDEKVAELV  120
RFLLRKYQIK EPVTKAEMLE SVIKNYKNHF PDIFSKASEC MQVIFGIDVK EVDPAGHSYI  180
LVTCLGLSYD GLLGDDQSTP KTGLLIIVLG MILMEGSRAP EEAIWEALSV MGLYDGREHS  240
VYWKLRKLLT QEWVQENYLE YRQAPGSDPV RYEFLWGPRA LAETSYVKVL EHVVRVNARV  300
RISYPSLHEE ALGEEKGV                                              318

SEQ ID NO: 355         moltype = AA  length = 648
FEATURE                Location/Qualifiers
source                 1..648
                       mol_type = protein
                       organism = Homo sapiens
SEQUENCE: 355
MSHHGGAPKA STWVVASRRS STVSRAPERR PAEELNRTGP EGYSVGRGGR WRGTSRPPEA  60
VAAGHEELPL CFALKSHFVG AVIGRGGSKI KNIQSTTNTT IQIIQEQPES LVKIFGSKAM  120
QTKAKAVIDN FVKKLEENYN SECGIDTAFQ PSVGKDGSTD NNVVAGDRPL IDWDQIREEG  180
LKWQKTKWAD LPPIKKNFYK ESTATSAMSK VEADSWRKEN FNITWDDLKD GEKRPIPNPT  240
CTFDDAFQCY PEVMENIKKA GFQKPTPIQS QAWPIVLQGI DLIGVAQTGT GKTLCYLMPG  300
FIHLVLQPSL KGQRNRPGML VLTPTRELAL QVEGECCKYS YKGLRSVCVY GGGNRDEQIE  360
ELKKGVDIII ATPGRLNDLQ MSNFVNLKNI TYLVLDEADK MLDMGFEPQI MKILLDVRPD  420
RQTVMTSATW PHSVHRLAQS YLKEPMIVYV GTLDLVAVSS VKQNIIVTTE EEKWSHMQTF  480
LQSMSSTDKV IVFVSRKAVA DHLSSDLILG NISVESLHGD REQRDREKAL ENFKTGKVRI  540
LIATDLASRG LDVHDVTHVY NFDFPRNIEE YVHRIGRTGR AGRTGVSITT LTRNDWRVAS  600
ELINILERAN QSIPEELVSM AERFKAHQQK REMERKMERP QGRPKKFH              648

SEQ ID NO: 356         moltype = AA  length = 309
FEATURE                Location/Qualifiers
source                 1..309
                       mol_type = protein
                       organism = Homo sapiens
SEQUENCE: 356
MSLEQRSLHC KPEEALEAQQ EALGLVCVQA ATSSSSPLVL GTLEEVPTAG STDPPQSPQG  60
ASAFPTTINF TRQRQPSEGS SSREEEGPST SCILESLFRA VITKKVADLV GFLLLKYRAR  120
EPVTKAEMLE SVIKNYKHCF PEIFGKASES LQLVFGIDVK EADPTGHSYV LVTCLGLSYD  180
GLLGDNQIMP KTGFLIIVLV MIAMEGGHAP EEEIWEELSV MEVYDGREHS AYGEPRKLLT  240
QDLVQEKYLE YRQVPDSDPA RYEFLWGPRA LAETSYVKVL EYVIKVSARV RFFFPSLREA  300
ALREEEEGV                                                        309

SEQ ID NO: 357         moltype = AA  length = 373
FEATURE                Location/Qualifiers
source                 1..373
                       mol_type = protein
                       organism = Homo sapiens
SEQUENCE: 357
MPPVPGVPFR NVDNDSPTSV ELEDWVDAQH PTDEEEEEAS SASSTLYLVF SPSSFSTSSS  60
LILGGPEEEE VPSGVIPNLT ESIPSSPPQG PPQGPSQSPL SSCCSSFSWS SFSEESSSQK  120
GEDTGTCQGL PDSESSFTYT LDEKVAELVE FLLLKYEAEE PVTEAEMLMI VIKYKDYFPV  180
ILKRAREFME LLFGLALIEV GPDHFCVFAN TVGLTDEGSD DEGMPENSLL IIILSVIFIK  240
GNCASEEVIW EVLNAVGVYA GREHFVYGEP RELLTKVWVQ GHYLEYREVP HSSPPYYEFL  300
WGPRAHSESI KKKVLEFLAK LNNTVPSSFP SWYKDALKDV EERVQATIDT ADDATVMASE  360
SLSVMSSNVS FSE                                                   373

SEQ ID NO: 358         moltype = AA  length = 369
FEATURE                Location/Qualifiers
source                 1..369
                       mol_type = protein
                       organism = Homo sapiens
SEQUENCE: 358
MPRAPKRQRC MPEEDLQSQS ETQGLEGAQA PLAVEEDASS STSTSSSFPS SFPSSSSSSS  60
SSCYPLIPST PEEVSADDET PNPPQSAQIA CSSPSVVASL PLDQSDEGSS SQKEESPSTL  120
QVLPDSESLP RSEIDEKVTD LVQFLLFKYQ MKEPITKAEI LESVIRNYED HFPLLFSEAS  180
ECMLLVFGID VKEVDPTGHS FVLVTSLGLT YDGMLSDVQS MPKTGILILI LSIIFIEGYC  240
TPEEVIWEAL NMMGLYDGME HLIYGEPRKL LTQDWVQENY LEYRQVPGSD PARYEFLWGP  300
RAHAEIRKMS LLKFLAKVNG SDPRSFPLWY EEALKDEEER AQDRIATTDD TTAMASASSS  360
ATGSFSYPE                                                        369

SEQ ID NO: 359         moltype = AA  length = 314
FEATURE                Location/Qualifiers
source                 1..314
                       mol_type = protein
                       organism = Homo sapiens
```

```
SEQUENCE: 359
MPLEQRSQHC KPEEGLEAQG EALGLVGAQA PATEEQETAS SSSTLVEVTL REVPAAESPS  60
PPHSPQGAST LPTTINYTLW SQSDEGSSNE EQEGPSTFPD LETSFQVALS RKMAELVHFL  120
LLKYRAREPF TKAEMLGSVI RNFQDFFPVI FSKASEYLQL VFGIEVVEVV RIGHLYILVT  180
CLGLSYDGLL GDNQIVPKTG LLIIVLAIIA KEGDCAPEEK IWEELSVLEA SDGREDSVFA  240
HPRKLLTQDL VQENYLEYRQ VPGSDPACYE FLWGPRALVE TSYVKVLHHL LKISGGPHIS  300
YPPLHEWAFR EGEE                                                    314

SEQ ID NO: 360          moltype = AA  length = 20
FEATURE                 Location/Qualifiers
source                  1..20
                        mol_type = protein
                        organism = synthetic construct
                        note = POC01_P1 AKAP4
SEQUENCE: 360
NSLQKQLQAV LQWIAASQFN                                              20

SEQ ID NO: 361          moltype = AA  length = 20
FEATURE                 Location/Qualifiers
source                  1..20
                        mol_type = protein
                        organism = synthetic construct
                        note = POC01_P2 BORIS
SEQUENCE: 361
SGDERSDEIV LTVSNSNVEE                                              20

SEQ ID NO: 362          moltype = AA  length = 20
FEATURE                 Location/Qualifiers
source                  1..20
                        mol_type = protein
                        organism = synthetic construct
                        note = POC01_P3 SPAG9
SEQUENCE: 362
VQKEDGRVQA FGWSLPQKYK                                              20

SEQ ID NO: 363          moltype = AA  length = 20
FEATURE                 Location/Qualifiers
source                  1..20
                        mol_type = protein
                        organism = synthetic construct
                        note = POC01_P4 OY-TES-1
SEQUENCE: 363
EVESTPMIME NIQELIRSAQ                                              20

SEQ ID NO: 364          moltype = AA  length = 20
FEATURE                 Location/Qualifiers
source                  1..20
                        mol_type = protein
                        organism = synthetic construct
                        note = POC01_P5 SP17
SEQUENCE: 364
AYFESLLEKR EKTNFDPAEW                                              20

SEQ ID NO: 365          moltype = AA  length = 20
FEATURE                 Location/Qualifiers
source                  1..20
                        mol_type = protein
                        organism = synthetic construct
                        note = POC01_P6 WT1
SEQUENCE: 365
PSQASSGQAR MFPNAPYLPS                                              20

SEQ ID NO: 366          moltype = AA  length = 20
FEATURE                 Location/Qualifiers
source                  1..20
                        mol_type = protein
                        organism = synthetic construct
                        note = POC01_P7 HIWI
SEQUENCE: 366
RRSIAGFVAS INEGMTRWFS                                              20

SEQ ID NO: 367          moltype = AA  length = 20
FEATURE                 Location/Qualifiers
source                  1..20
                        mol_type = protein
                        organism = synthetic construct
                        note = POC01_P8 PRAME
SEQUENCE: 367
MQDIKMILKM VQLDSIEDLE                                              20
```

```
SEQ ID NO: 368          moltype = AA  length = 20
FEATURE                 Location/Qualifiers
source                  1..20
                        mol_type = protein
                        organism = synthetic construct
                        note = POC01_P9 AKAP-3
SEQUENCE: 368
ANSVVSDMMV SIMKTLKIQV                                        20

SEQ ID NO: 369          moltype = AA  length = 20
FEATURE                 Location/Qualifiers
source                  1..20
                        mol_type = protein
                        organism = synthetic construct
                        note = POC01_P10 MAGE-A4
SEQUENCE: 369
REALSNKVDE LAHFLLRKYR                                        20

SEQ ID NO: 370          moltype = AA  length = 20
FEATURE                 Location/Qualifiers
source                  1..20
                        mol_type = protein
                        organism = synthetic construct
                        note = POC01_P11 MAGE-A9
SEQUENCE: 370
ETSYEKVINY LVMLNAREPI                                        20

SEQ ID NO: 371          moltype = AA  length = 20
FEATURE                 Location/Qualifiers
source                  1..20
                        mol_type = protein
                        organism = synthetic construct
                        note = POC01_P12a MAGE-A10
SEQUENCE: 371
DVKEVDPTGH SFVLVTSLGL                                        20

SEQ ID NO: 372          moltype = AA  length = 20
FEATURE                 Location/Qualifiers
source                  1..20
                        mol_type = protein
                        organism = synthetic construct
                        note = POC01_P12b BAGE
SEQUENCE: 372
SAQLLQARLM KEESPVVSWR                                        20

SEQ ID NO: 373          moltype = AA  length = 20
FEATURE                 Location/Qualifiers
source                  1..20
                        mol_type = protein
                        organism = synthetic construct
                        note = PBRC01_cP1 FSIP1
SEQUENCE: 373
ISDTKDYFMS KTLGIGRLKR                                        20

SEQ ID NO: 374          moltype = AA  length = 20
FEATURE                 Location/Qualifiers
source                  1..20
                        mol_type = protein
                        organism = synthetic construct
                        note = PBRC01_cP2 SPAG9
SEQUENCE: 374
FDRNTESLFE ELSSAGSGLI                                        20

SEQ ID NO: 375          moltype = AA  length = 20
FEATURE                 Location/Qualifiers
source                  1..20
                        mol_type = protein
                        organism = synthetic construct
                        note = PBRC01_cP3 AKAP4
SEQUENCE: 375
SQKMDMSNIV LMLIQKLLNE                                        20

SEQ ID NO: 376          moltype = AA  length = 20
FEATURE                 Location/Qualifiers
source                  1..20
                        mol_type = protein
                        organism = synthetic construct
                        note = PBRC01_cP4 BORIS
```

```
SEQUENCE: 376
SAVFHERYAL IQHQKTHKNE                                         20

SEQ ID NO: 377          moltype = AA  length = 20
FEATURE                 Location/Qualifiers
source                  1..20
                        mol_type = protein
                        organism = synthetic construct
                        note = PBRC01_cP5 MAGE-A11
SEQUENCE: 377
DVKEVDPTSH SYVLVTSLNL                                         20

SEQ ID NO: 378          moltype = AA  length = 20
FEATURE                 Location/Qualifiers
source                  1..20
                        mol_type = protein
                        organism = synthetic construct
                        note = PBRC01_cP6 NY-SAR-35
SEQUENCE: 378
ENAHGQSLEE DSALEALLNF                                         20

SEQ ID NO: 379          moltype = AA  length = 20
FEATURE                 Location/Qualifiers
source                  1..20
                        mol_type = protein
                        organism = synthetic construct
                        note = PBRC01_cP7 HOM-TES-85
SEQUENCE: 379
MASFRKLTLS EKVPPNHPSR                                         20

SEQ ID NO: 380          moltype = AA  length = 20
FEATURE                 Location/Qualifiers
source                  1..20
                        mol_type = protein
                        organism = synthetic construct
                        note = PBRC01_cP8 NY-BR-1
SEQUENCE: 380
KRASQYSGQL KVLIAENTML                                         20

SEQ ID NO: 381          moltype = AA  length = 20
FEATURE                 Location/Qualifiers
source                  1..20
                        mol_type = protein
                        organism = synthetic construct
                        note = PBRC01_cP9 MAGE-A9
SEQUENCE: 381
VDPAQLEFMF QEALKLKVAE                                         20

SEQ ID NO: 382          moltype = AA  length = 20
FEATURE                 Location/Qualifiers
source                  1..20
                        mol_type = protein
                        organism = synthetic construct
                        note = PBRC01_cP10 SCP-1
SEQUENCE: 382
EYEREETRQV YMDLNNNIEK                                         20

SEQ ID NO: 383          moltype = AA  length = 20
FEATURE                 Location/Qualifiers
source                  1..20
                        mol_type = protein
                        organism = synthetic construct
                        note = PBRC01_cP11 MAGE-A1
SEQUENCE: 383
PEIFGKASES LQLVFGIDVK                                         20

SEQ ID NO: 384          moltype = AA  length = 20
FEATURE                 Location/Qualifiers
source                  1..20
                        mol_type = protein
                        organism = synthetic construct
                        note = PBRC01_cP12 MAGE-C2
SEQUENCE: 384
DSESSFTYTL DEKVAELVEF                                         20

SEQ ID NO: 385          moltype = AA  length = 30
FEATURE                 Location/Qualifiers
```

```
source                 1..30
                       mol_type = protein
                       organism = synthetic construct
                       note = crc_P3 peptide 30aa
SEQUENCE: 385
YVDEKAPEFS MQGLKDEKVA ELVRFLLRKY                        30

SEQ ID NO: 386         moltype = AA  length = 9
FEATURE                Location/Qualifiers
source                 1..9
                       mol_type = protein
                       organism = Homo sapiens
SEQUENCE: 386
SVASTITGV                                               9

SEQ ID NO: 387         moltype = AA  length = 9
FEATURE                Location/Qualifiers
source                 1..9
                       mol_type = protein
                       organism = Homo sapiens
SEQUENCE: 387
VMAGDIYSV                                               9

SEQ ID NO: 388         moltype = AA  length = 9
FEATURE                Location/Qualifiers
source                 1..9
                       mol_type = protein
                       organism = Homo sapiens
SEQUENCE: 388
ALADGVQKV                                               9

SEQ ID NO: 389         moltype = AA  length = 9
FEATURE                Location/Qualifiers
source                 1..9
                       mol_type = protein
                       organism = Homo sapiens
SEQUENCE: 389
LLGATCMFV                                               9

SEQ ID NO: 390         moltype = AA  length = 9
FEATURE                Location/Qualifiers
source                 1..9
                       mol_type = protein
                       organism = Homo sapiens
SEQUENCE: 390
SVFAGVVGV                                               9

SEQ ID NO: 391         moltype = AA  length = 9
FEATURE                Location/Qualifiers
source                 1..9
                       mol_type = protein
                       organism = Homo sapiens
SEQUENCE: 391
ALFDGDPHL                                               9

SEQ ID NO: 392         moltype = AA  length = 9
FEATURE                Location/Qualifiers
source                 1..9
                       mol_type = protein
                       organism = Homo sapiens
SEQUENCE: 392
YVDPVITSI                                               9

SEQ ID NO: 393         moltype = AA  length = 9
FEATURE                Location/Qualifiers
source                 1..9
                       mol_type = protein
                       organism = Homo sapiens
SEQUENCE: 393
STAPPVHNV                                               9

SEQ ID NO: 394         moltype = AA  length = 9
FEATURE                Location/Qualifiers
source                 1..9
                       mol_type = protein
                       organism = Homo sapiens
SEQUENCE: 394
LAALPHSCL                                               9
```

The invention claimed is:

1. A composition comprising (i) a polypeptide having an amino acid sequence comprising any of SEQ ID NOs: 150-164; and (ii) an adjuvant.

2. The composition of claim 1, further comprising at least one additional polypeptide having at least 15 consecutive amino acids from an antigen or fragment thereof selected from: BRDT, PRAME, NALP4, MAGE-A12, MAGE-A2, SURVIVIN, DPPA2, NY-SAR-35, LDHC, MAGE-C2, MAGE-A3, KK-LC-1, and MAGE-A1.

3. The composition of claim 1, further comprising at least one additional polypeptide, wherein the amino acid sequence of the additional polypeptide comprises any of SEQ ID NOs: 150-164.

4. The composition of claim 3, further comprising at least two additional polypeptides, wherein the amino acid sequence of the at least two additional polypeptides comprises any of SEQ ID NOs: 150-164.

5. The composition of claim 3, further comprising at least 13 additional polypeptides, wherein the amino acid sequence of each additional polypeptide is selected from any of SEQ ID NOs: 150-164.

6. A method of providing immunotherapy to an individual having or suspected of having lung cancer, comprising administering to the individual the composition of claim 1.

7. The method of claim 6, further comprising administering at least one checkpoint inhibitor, wherein the checkpoint inhibitor is administered prior to, concomitant with, or after administration of the composition.

* * * * *